US012742189B2

(12) United States Patent
Naesby

(10) Patent No.: US 12,742,189 B2
(45) Date of Patent: Sep. 22, 2026

(54) RECOMBINANT HOST CELLS WITH IMPROVED PRODUCTION OF TETRAKETIDE DERIVATIVES

(71) Applicants: IPTECTOR ASSETS APS, Lynge (DK); Michael Naesby, Huningue (FR)

(72) Inventor: Michael Naesby, Huningue (FR)

(73) Assignees: Michael Naesby, Huningue (FR); IPTECTOR ASSETS APS, Lynge (DK)

( * ) Notice: Subject to any disclaimer, the term of this patent is extended or adjusted under 35 U.S.C. 154(b) by 510 days.

(21) Appl. No.: 17/420,990

(22) PCT Filed: Jan. 6, 2020

(86) PCT No.: PCT/EP2020/050150
§ 371 (c)(1),
(2) Date: Jul. 6, 2021

(87) PCT Pub. No.: WO2020/141230
PCT Pub. Date: Jul. 9, 2020

(65) Prior Publication Data

US 2024/0263203 A1 Aug. 8, 2024

(30) Foreign Application Priority Data

Jan. 6, 2019 (EP) .................................... 19150443
Apr. 5, 2019 (EP) .................................... 19167702
Jun. 27, 2019 (EP) .................................... 19182812

(51) Int. Cl.
*C12P 17/06* (2006.01)
*C12N 9/00* (2006.01)
*C12N 9/02* (2006.01)
*C12N 9/04* (2006.01)
*C12N 9/10* (2006.01)
*C12N 9/88* (2006.01)
*C12N 15/52* (2006.01)

(52) U.S. Cl.
CPC ............ *C12P 17/06* (2013.01); *C12N 9/0006* (2013.01); *C12N 9/001* (2013.01); *C12N 9/0042* (2013.01); *C12N 9/0071* (2013.01); *C12N 9/0093* (2013.01); *C12N 9/1088* (2013.01); *C12N 9/88* (2013.01); *C12N 9/93* (2013.01); *C12N 15/52* (2013.01); *C12Y 101/01219* (2013.01); *C12Y 103/01074* (2013.01); *C12Y 106/02004* (2013.01); *C12Y 114/11022* (2013.01); *C12Y 114/11023* (2013.01); *C12Y 117/01003* (2013.01); *C12Y 205/01018* (2013.01); *C12Y 402/01105* (2013.01); *C12Y 403/01024* (2013.01); *C12Y 403/01025* (2013.01); *C12Y 602/01012* (2013.01)

(58) Field of Classification Search
None
See application file for complete search history.

(56) References Cited

U.S. PATENT DOCUMENTS

2006/0019334 A1* 1/2006 Koffas ................ C12N 9/0006
435/41

FOREIGN PATENT DOCUMENTS

WO 2006010117 A2 1/2006

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Zhaonan, et al., "Noncatylitic chalcone isomerase-fold proteins in Humulus lupulus are auxiliary components in prenylated flavonoid biosynthesis", Proceedings of the National Academy of Sciences, vol. 115, No. 22, May 14, 2018, 10 pgs.
Wenbo, et al., "Role of a chalcone isomerase-like protein in flavonoid biosynthesis in *Arabidopsis thaliana*", Journal of Experimental Botany, vol. 66, No. 22, Sep. 7, 2015, 15 pgs.
Kang, et al., "The flavonoid biosynthesis enzyme chalcone isomerase modulates terpenoid production in glandular trichomes of tomato", Plant Physiology, vol. 164, No. 3, Jan. 14, 2014, 14 pgs.
Yan, et al., "Biosynthesis of Natural Flavanones in *Saccharomyces cerevisiae*", Applied and Environmental Microbiology, vol. 71, No. 9, Sep. 2009, 6 pgs.
Ralston, et al. "Partial reconstruction of flavonoid and isoflavonoid biosynthesis in yeast using soybean type I and type II chalcone isomerases", Plant Physioloy, American Society of Plant Physiologists, vol. 137, No. 4, Apr. 2005, 14 pgs.
International Search Report issued in PCT/EP2020/050150 mailed Mar. 4, 2020; 7 pgs.
Written Opinion of the International Searching Authority issued in PCT/EP2020/050150, 6 pgs.

* cited by examiner

*Primary Examiner* — Christian L Fronda
(74) *Attorney, Agent, or Firm* — HOLLAND & HART LLP

(57) ABSTRACT

The present invention relates to a recombinant microbial host cell producing a tetraketide or derivatives thereof from one or more substrates selected from cinnamoyl-CoA, p-Coumaroyl-CoA, Caffeoyl-CoA, Feruloyl-CoA, malonyl-CoA, sinapoyl-CoA and dihydro derivatives thereof, comprising an operative biosynthetic metabolic pathway for the tetraketide or derivatives thereof comprising a chalcone isomerase-like (CHIL) polypeptide heterologous to the host cell and a Type 3 polyketide synthase (PKS).

19 Claims, 4 Drawing Sheets

Figure 1:
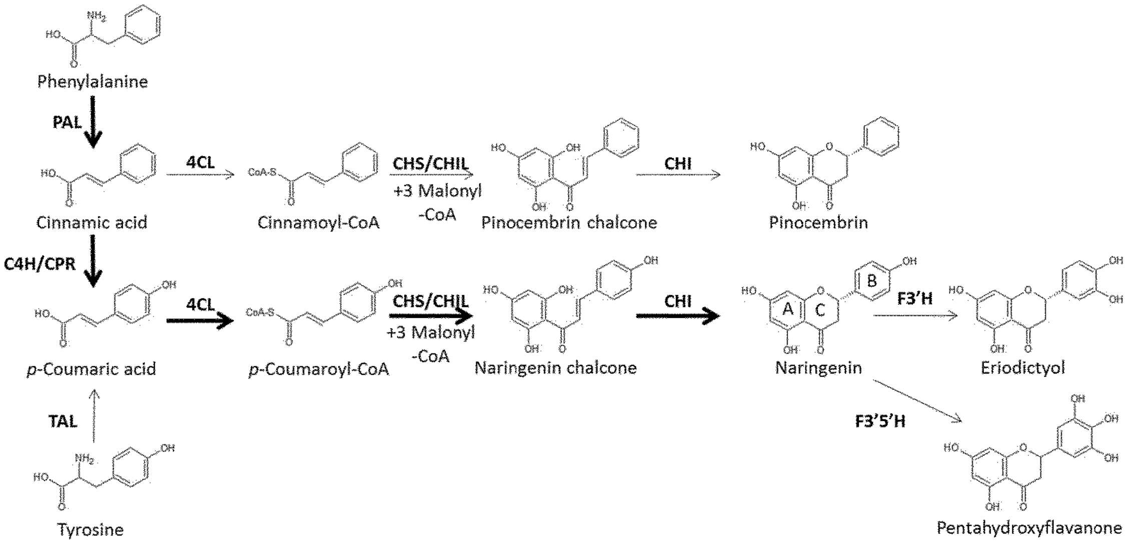

Specification includes a Sequence Listing.

Phenylalanine
Cinnamic acid
Cinnamoyl-CoA
Pinosylvin
*p*-Coumaric acid
*p*-Coumaroyl-CoA
Resveratrol
Tyrosine Phenylalanine
Cinnamic acid
Cinnamoyl-CoA
*p*-Coumaric acid
*p*-Coumaroyl-CoA
*p*-Dihydrocoumaroyl-CoA
Dihydroresveratrol
Tyrosine
Phloretic acid
Phloretin
Nothofagin
Phlorizin Naringenin
Dihydro kaempferol
Leuco-pelargonidin
Pelargonidin
(-)-Epiafzelechin
Pelargonidin -3-O-glucoside
Kaempferol
(+)-Afzelechin

SEQUENCE LISTING

```
<160> NUMBER OF SEQ ID NOS: 125

<210> SEQ ID NO 1
<211> LENGTH: 2154
<212> TYPE: DNA
<213> ORGANISM: Arabidopsis thaliana

<400> SEQUENCE: 1

atggaccaaa ttgaagcaat gctatgcggt ggtggtgaaa agaccaaggt ggccgtaacg      60

acaaaaactc ttgcagatcc tttgaattgg ggtctggcag ctgaccagat gaaaggtagc     120

catctggatg aagttaagaa gatggttgag gaatacagaa gaccagtcgt aaatctaggc     180

ggcgagacat tgacgatagg acaggtagct gctatttcga ccgttggcgg ttcagtgaag     240
```

```
gtagaacttg cagaaacaag tagagccgga gttaaggctt catcagattg ggtcatggaa    300
agtatgaaca agggcacaga ttcctatggc gttaccacag gctttggtgc tacctctcat    360
agaagaacta aaaatggcac tgctttgcaa acagaactga tcagattcct taacgccggt    420
attttcggta atacaaagga aacttgccat acattacccc aatcggcaac aagagctgct    480
atgcttgtta gggtgaacac tttgttgcaa ggttactctg gaataaggtt tgaaattctt    540
gaggccatca cttcactatt gaaccacaac atttctcctt cgttgccctt aagaggaaca    600
ataactgcca gcggtgattt ggttcccctt tcatatatcg caggcttatt aacgggaaga    660
cctaattcaa aggccactgg tccagacgga gaatccttaa ccgctaagga agcatttgag    720
aaagctggta tttcaactgg tttctttgat ttgcaaccca aggaaggttt agccctggtg    780
aatggcaccg ctgtcggcag cggtatggca tccatggtgt tgtttgaagc taacgtacaa    840
gcagttttgg ccgaagtttt gtccgcaatt tttgccgaag tcatgagtgg aaaacctgag    900
tttactgatc acttgaccca caggttaaaa catcacccag gacaaattga agcagcagct    960
atcatggagc acattttgga cggctctagc tacatgaagt tagcccagaa ggttcatgaa   1020
atggaccctt tgcaaaaacc caaacaagat agatatgctt taaggacatc cccacaatgg   1080
cttggccctc aaattgaagt aattagacaa gctacaaagt ctatagaaag agagatcaac   1140
tctgttaacg ataatccact tattgatgtg tcgaggaata aggcaataca tggaggcaat   1200
ttccagggta cacccatagg agtcagtatg gataatacca ggcttgccat agccgcaatt   1260
ggcaaattaa tgtttgccca attttctgaa ttggtcaatg acttctacaa taacggtttg   1320
ccttcgaatc tgaccgcatc ttctaaccct agtcttgatt atggtttcaa aggtgctgag   1380
atagcaatgg caagctattg ttcagagctg caatatctag ccaacccagt aacctctcat   1440
gtacaatcag ccgaacaaca caatcaggat gttaattctt tgggcctgat ttcatcaaga   1500
aaaacaagcg aggccgttga tatccttaaa ttaatgtcca caacattttt agtgggtata   1560
tgccaggccg tagatttgag acacttggaa gagaatttga gacagacagt gaaaaatacc   1620
gtatcacagg ttgcaaaaaa ggttctaact acaggtatca atggtgaatt gcacccatca   1680
agattctgtg aaaaagattt attaaaagtt gtagatagag aacaagtatt tacttacgtt   1740
gacgatccat gtagcgctac ttatccattg atgcagagat tgagacaagt tattgtagat   1800
cacgctttat ccaatggtga aactgagaaa aatgccgtta cttcaatatt ccaaaagata   1860
ggtgcctttg aagaagaact gaaggcagtt ttaccaaagg aagtcgaagc tgctagagcc   1920
gcatacggaa atggtactgc ccctatacca aatagaatca aagagtgtag gtcgtaccct   1980
ttgtacagat tcgttagaga agagttggga accaaattac taactggtga aaaagtcgtt   2040
agcccaggtg aagaatttga caaggtattc acagctatgt gcgagggaaa gttgatagat   2100
ccacttatgg attgcttgaa agagtggaat ggtgcaccta ttccaatctg ctaa         2154
```

<210> SEQ ID NO 2
<211> LENGTH: 717
<212> TYPE: PRT
<213> ORGANISM: Arabidopsis thaliana

<400> SEQUENCE: 2

```
Met Asp Gln Ile Glu Ala Met Leu Cys Gly Gly Gly Glu Lys Thr Lys
1               5                   10                  15

Val Ala Val Thr Thr Lys Thr Leu Ala Asp Pro Leu Asn Trp Gly Leu
            20                  25                  30
```

-continued

```
Ala Ala Asp Gln Met Lys Gly Ser His Leu Asp Glu Val Lys Lys Met
        35                  40                  45

Val Glu Glu Tyr Arg Arg Pro Val Val Asn Leu Gly Gly Glu Thr Leu
    50                  55                  60

Thr Ile Gly Gln Val Ala Ala Ile Ser Thr Val Gly Gly Ser Val Lys
65                  70                  75                  80

Val Glu Leu Ala Glu Thr Ser Arg Ala Gly Val Lys Ala Ser Ser Asp
                85                  90                  95

Trp Val Met Glu Ser Met Asn Lys Gly Thr Asp Ser Tyr Gly Val Thr
            100                 105                 110

Thr Gly Phe Gly Ala Thr Ser His Arg Arg Thr Lys Asn Gly Thr Ala
        115                 120                 125

Leu Gln Thr Glu Leu Ile Arg Phe Leu Asn Ala Gly Ile Phe Gly Asn
    130                 135                 140

Thr Lys Glu Thr Cys His Thr Leu Pro Gln Ser Ala Thr Arg Ala Ala
145                 150                 155                 160

Met Leu Val Arg Val Asn Thr Leu Leu Gln Gly Tyr Ser Gly Ile Arg
                165                 170                 175

Phe Glu Ile Leu Glu Ala Ile Thr Ser Leu Leu Asn His Asn Ile Ser
            180                 185                 190

Pro Ser Leu Pro Leu Arg Gly Thr Ile Thr Ala Ser Gly Asp Leu Val
        195                 200                 205

Pro Leu Ser Tyr Ile Ala Gly Leu Leu Thr Gly Arg Pro Asn Ser Lys
    210                 215                 220

Ala Thr Gly Pro Asp Gly Glu Ser Leu Thr Ala Lys Glu Ala Phe Glu
225                 230                 235                 240

Lys Ala Gly Ile Ser Thr Gly Phe Phe Asp Leu Gln Pro Lys Glu Gly
                245                 250                 255

Leu Ala Leu Val Asn Gly Thr Ala Val Gly Ser Gly Met Ala Ser Met
            260                 265                 270

Val Leu Phe Glu Ala Asn Val Gln Ala Val Leu Ala Glu Val Leu Ser
        275                 280                 285

Ala Ile Phe Ala Glu Val Met Ser Gly Lys Pro Glu Phe Thr Asp His
    290                 295                 300

Leu Thr His Arg Leu Lys His His Pro Gly Gln Ile Glu Ala Ala Ala
305                 310                 315                 320

Ile Met Glu His Ile Leu Asp Gly Ser Ser Tyr Met Lys Leu Ala Gln
                325                 330                 335

Lys Val His Glu Met Asp Pro Leu Gln Lys Pro Lys Gln Asp Arg Tyr
            340                 345                 350

Ala Leu Arg Thr Ser Pro Gln Trp Leu Gly Pro Gln Ile Glu Val Ile
        355                 360                 365

Arg Gln Ala Thr Lys Ser Ile Glu Arg Glu Ile Asn Ser Val Asn Asp
    370                 375                 380

Asn Pro Leu Ile Asp Val Ser Arg Asn Lys Ala Ile His Gly Gly Asn
385                 390                 395                 400

Phe Gln Gly Thr Pro Ile Gly Val Ser Met Asp Asn Thr Arg Leu Ala
                405                 410                 415

Ile Ala Ala Ile Gly Lys Leu Met Phe Ala Gln Phe Ser Glu Leu Val
            420                 425                 430

Asn Asp Phe Tyr Asn Asn Gly Leu Pro Ser Asn Leu Thr Ala Ser Ser
        435                 440                 445

Asn Pro Ser Leu Asp Tyr Gly Phe Lys Gly Ala Glu Ile Ala Met Ala
```

-continued

```
    450                 455                 460

Ser Tyr Cys Ser Glu Leu Gln Tyr Leu Ala Asn Pro Val Thr Ser His
465                 470                 475                 480

Val Gln Ser Ala Glu Gln His Asn Gln Asp Val Asn Ser Leu Gly Leu
                485                 490                 495

Ile Ser Ser Arg Lys Thr Ser Glu Ala Val Asp Ile Leu Lys Leu Met
            500                 505                 510

Ser Thr Thr Phe Leu Val Gly Ile Cys Gln Ala Val Asp Leu Arg His
        515                 520                 525

Leu Glu Glu Asn Leu Arg Gln Thr Val Lys Asn Thr Val Ser Gln Val
    530                 535                 540

Ala Lys Lys Val Leu Thr Thr Gly Ile Asn Gly Glu Leu His Pro Ser
545                 550                 555                 560

Arg Phe Cys Glu Lys Asp Leu Leu Lys Val Val Asp Arg Glu Gln Val
                565                 570                 575

Phe Thr Tyr Val Asp Asp Pro Cys Ser Ala Thr Tyr Pro Leu Met Gln
            580                 585                 590

Arg Leu Arg Gln Val Ile Val Asp His Ala Leu Ser Asn Gly Glu Thr
        595                 600                 605

Glu Lys Asn Ala Val Thr Ser Ile Phe Gln Lys Ile Gly Ala Phe Glu
    610                 615                 620

Glu Glu Leu Lys Ala Val Leu Pro Lys Glu Val Glu Ala Ala Arg Ala
625                 630                 635                 640

Ala Tyr Gly Asn Gly Thr Ala Pro Ile Pro Asn Arg Ile Lys Glu Cys
                645                 650                 655

Arg Ser Tyr Pro Leu Tyr Arg Phe Val Arg Glu Glu Leu Gly Thr Lys
            660                 665                 670

Leu Leu Thr Gly Glu Lys Val Val Ser Pro Gly Glu Glu Phe Asp Lys
        675                 680                 685

Val Phe Thr Ala Met Cys Glu Gly Lys Leu Ile Asp Pro Leu Met Asp
    690                 695                 700

Cys Leu Lys Glu Trp Asn Gly Ala Pro Ile Pro Ile Cys
705                 710                 715
```

<210> SEQ ID NO 3
<211> LENGTH: 2112
<212> TYPE: DNA
<213> ORGANISM: Zea mays

<400> SEQUENCE: 3

```
atggcgggca acggcgccat cgtggagagc gacccgctga actggggcgc ggcggcggcg     60

gagctggccg ggagccacct ggacgaggtg aagcgcatgg tggcgcaggc ccggcagccc    120

gtggtcaaga tcgagggctc caccctccgc gtcggccagg tggccgccgt cgcctccgcc    180

aaggacgcgt ccggcgtcgc cgtcgagctc gacgaggagg cccgcccccg cgtcaaggcc    240

agcagcgagt ggatcctcga ctgcatcgcc cacggcggcg acatctacgg cgtcaccacc    300

ggcttcggcg gcacctccca ccgccgcacc aaggacgggc ccgcgctcca ggtcgagctg    360

ctcaggcatc tcaacgccgg aatcttcggc accggcagcg acgggcacac gctgccgtcg    420

gaggtcaccc gcgcggcgat gctggtgcgc atcaacaccc tcctccaggg ctactccggc    480

atccgcttcg agatcctcga ggccatcacg aagctgctca acaccggtgt cagcccctgc    540

ctgccgctcc ggggcaccat caccgcgtcg ggcgacctgg tcccgctctc ctacatcgcc    600

ggcctcatca cgggccgccc caacgcgcag gccgtcaccg tcgacggaag gaaggtggac    660
```

-continued

```
gccgccgagg cgttcaagat cgccggcatc gagggcggct tcttcaagct caaccccaag    720

gagggcctcg ccatcgtcaa cggcacgtcc gtgggctccg cgctcgcggc caccgtgatg    780

tacgacgcca acgtcctggc cgtcctgtcg gaggtcctgt ccgccgtctt ctgcgaggtc    840

atgaacggca agcccgagta cacggaccac ctgacccaca agctgaagca ccacccgggg    900

tccatcgagg ccgcggccat catggagcac atcctggatg gcagctcctt catgaagcag    960

gccaagaagg tgaacgagct ggacccgctg ctgaagccca agcaggacag gtacgcgctc   1020

cgcacgtcgc cgcagtggct gggcccccag atcgaggtca tccgcgccgc caccaagtcc   1080

atcgagcgcg aggtcaactc cgtgaacgac aacccggtca tcgacgtcca ccgcggcaag   1140

gcgctgcacg gcggcaactt ccagggcacc cccatcggcg tgtccatgga caacgcccgc   1200

ctcgccatcg ccaacatcgg caagctcatg ttcgcgcagt tctccgagct cgtcaacgag   1260

ttctacaaca acgggctcac ctccaacctg gccggcagcc gcaaccccag cctggactac   1320

ggcttcaagg gcaccgagat cgccatggcc tcctactgct ccgagctcca gtacctgggc   1380

aaccccatca ccaaccacgt gcagagcgcg gacgagcaca accaggacgt gaactccctg   1440

ggcctcgtct cggccaggaa gaccgccgag gcgatcgaca tcctgaagct catgtcgtcc   1500

acctacatcg tggcgctgtg ccaggccgtg gacctgcgcc acctcgagga gaacatcaag   1560

gcgtcggtga agaacaccgt gacccaggtg gccaagaagg tgctgaccat gaacccctcg   1620

ggcgagctct ccagcgcccg cttcagcgag aaggagctga tcagcgccat cgaccgcgag   1680

gccgtgttca cgtacgcgga ggacgcggcc agcgccagcc tgccgctgat gcagaagctg   1740

cgcgccgtgc tggtggacca cgccctcagc agcggcgagc gcggagcggg agccctccgt   1800

gttctccaag atcaccaggt tcgaggagga gctccgcgcg gtgctgcccc aggaggtgga   1860

ggccgcccgc gtggcgtcgc cgagggcacc gcccccgtgg cgaaccggat cgcggacagc   1920

cggtcgttcc cgctgtaccg cttcgtgcgc gaggagctcg gctgcgtgtt cctgaccggc   1980

gagaggctca agtcccccgg cgaggagtgc aacaaggtgt tcgtcggcat cagccagggc   2040

aagctcgtgg accccatgct cgagtgcctc aaggagtggg acggcaagcc gctgcccatc   2100

aacatcaagt aa                                                       2112
```

<210> SEQ ID NO 4
<211> LENGTH: 703
<212> TYPE: PRT
<213> ORGANISM: Zea mays

<400> SEQUENCE: 4

```
Met Ala Gly Asn Gly Ala Ile Val Glu Ser Asp Pro Leu Asn Trp Gly
1               5                   10                  15

Ala Ala Ala Ala Glu Leu Ala Gly Ser His Leu Asp Glu Val Lys Arg
            20                  25                  30

Met Val Ala Gln Ala Arg Gln Pro Val Val Lys Ile Glu Gly Ser Thr
        35                  40                  45

Leu Arg Val Gly Gln Val Ala Ala Val Ala Ser Ala Lys Asp Ala Ser
    50                  55                  60

Gly Val Ala Val Glu Leu Asp Glu Glu Ala Arg Pro Arg Val Lys Ala
65                  70                  75                  80

Ser Ser Glu Trp Ile Leu Asp Cys Ile Ala His Gly Gly Asp Ile Tyr
                85                  90                  95

Gly Val Thr Thr Gly Phe Gly Gly Thr Ser His Arg Arg Thr Lys Asp
            100                 105                 110
```

-continued

```
Gly Pro Ala Leu Gln Val Glu Leu Leu Arg His Leu Asn Ala Gly Ile
        115                 120                 125

Phe Gly Thr Gly Ser Asp Gly His Thr Leu Pro Ser Glu Val Thr Arg
    130                 135                 140

Ala Ala Met Leu Val Arg Ile Asn Thr Leu Leu Gln Gly Tyr Ser Gly
145                 150                 155                 160

Ile Arg Phe Glu Ile Leu Glu Ala Ile Thr Lys Leu Leu Asn Thr Gly
                165                 170                 175

Val Ser Pro Cys Leu Pro Leu Arg Gly Thr Ile Thr Ala Ser Gly Asp
            180                 185                 190

Leu Val Pro Leu Ser Tyr Ile Ala Gly Leu Ile Thr Gly Arg Pro Asn
        195                 200                 205

Ala Gln Ala Val Thr Val Asp Gly Arg Lys Val Asp Ala Ala Glu Ala
    210                 215                 220

Phe Lys Ile Ala Gly Ile Glu Gly Gly Phe Phe Lys Leu Asn Pro Lys
225                 230                 235                 240

Glu Gly Leu Ala Ile Val Asn Gly Thr Ser Val Gly Ser Ala Leu Ala
                245                 250                 255

Ala Thr Val Met Tyr Asp Ala Asn Val Leu Ala Val Leu Ser Glu Val
            260                 265                 270

Leu Ser Ala Val Phe Cys Glu Val Met Asn Gly Lys Pro Glu Tyr Thr
        275                 280                 285

Asp His Leu Thr His Lys Leu Lys His His Pro Gly Ser Ile Glu Ala
    290                 295                 300

Ala Ala Ile Met Glu His Ile Leu Asp Gly Ser Ser Phe Met Lys Gln
305                 310                 315                 320

Ala Lys Lys Val Asn Glu Leu Asp Pro Leu Leu Lys Pro Lys Gln Asp
                325                 330                 335

Arg Tyr Ala Leu Arg Thr Ser Pro Gln Trp Leu Gly Pro Gln Ile Glu
            340                 345                 350

Val Ile Arg Ala Ala Thr Lys Ser Ile Glu Arg Glu Val Asn Ser Val
        355                 360                 365

Asn Asp Asn Pro Val Ile Asp Val His Arg Gly Lys Ala Leu His Gly
    370                 375                 380

Gly Asn Phe Gln Gly Thr Pro Ile Gly Val Ser Met Asp Asn Ala Arg
385                 390                 395                 400

Leu Ala Ile Ala Asn Ile Gly Lys Leu Met Phe Ala Gln Phe Ser Glu
                405                 410                 415

Leu Val Asn Glu Phe Tyr Asn Asn Gly Leu Thr Ser Asn Leu Ala Gly
            420                 425                 430

Ser Arg Asn Pro Ser Leu Asp Tyr Gly Phe Lys Gly Thr Glu Ile Ala
        435                 440                 445

Met Ala Ser Tyr Cys Ser Glu Leu Gln Tyr Leu Gly Asn Pro Ile Thr
    450                 455                 460

Asn His Val Gln Ser Ala Asp Glu His Asn Gln Asp Val Asn Ser Leu
465                 470                 475                 480

Gly Leu Val Ser Ala Arg Lys Thr Ala Glu Ala Ile Asp Ile Leu Lys
                485                 490                 495

Leu Met Ser Ser Thr Tyr Ile Val Ala Leu Cys Gln Ala Val Asp Leu
            500                 505                 510

Arg His Leu Glu Glu Asn Ile Lys Ala Ser Val Lys Asn Thr Val Thr
        515                 520                 525
```

-continued

```
Gln Val Ala Lys Lys Val Leu Thr Met Asn Pro Ser Gly Glu Leu Ser
    530                 535                 540

Ser Ala Arg Phe Ser Glu Lys Glu Leu Ile Ser Ala Ile Asp Arg Glu
545                 550                 555                 560

Ala Val Phe Thr Tyr Ala Glu Asp Ala Ala Ser Ala Ser Leu Pro Leu
                565                 570                 575

Met Gln Lys Leu Arg Ala Val Leu Val Asp His Ala Leu Ser Ser Gly
            580                 585                 590

Glu Arg Gly Ala Gly Ala Leu Arg Val Leu Gln Asp His Gln Val Arg
        595                 600                 605

Gly Gly Ala Pro Arg Gly Ala Ala Pro Gly Gly Gly Gly Arg Pro Arg
    610                 615                 620

Gly Val Ala Glu Gly Thr Ala Pro Val Ala Asn Arg Ile Ala Asp Ser
625                 630                 635                 640

Arg Ser Phe Pro Leu Tyr Arg Phe Val Arg Glu Glu Leu Gly Cys Val
                645                 650                 655

Phe Leu Thr Gly Glu Arg Leu Lys Ser Pro Gly Glu Glu Cys Asn Lys
            660                 665                 670

Val Phe Val Gly Ile Ser Gln Gly Lys Leu Val Asp Pro Met Leu Glu
        675                 680                 685

Cys Leu Lys Glu Trp Asp Gly Lys Pro Leu Pro Ile Asn Ile Lys
    690                 695                 700


<210> SEQ ID NO 5
<211> LENGTH: 1521
<212> TYPE: DNA
<213> ORGANISM: Ammi majus

<400> SEQUENCE: 5

atgatggatt ttgttttgtt agaaaaagct cttcttggtt tgttcattgc aactatagta     60

gccatcacaa tctctaagct aaggggaaag aaacttaagt tgcctccagg cccaatccct    120

gtcccagtgt ttggtaattg gttacaagtt ggcgacgact taaaccagag gaatttggta    180

gagtatgcta aaaagttcgg cgacttattt ctacttagga tgggtcaaag aaacttggtc    240

gtggtttcat cccctgactt agcaaaagac gtactacata cccagggtgt cgagttcgga    300

agtagaacta gaaatgttgt gtttgatatt ttcacaggca aaggtcaaga tatggttttt    360

accgtataca gcgagcactg gaggaaaatg agaagaataa tgactgtccc attctttaca    420

aacaaagtgg ttcaacagta taggttcgga tgggaggacg aagccgctag agtagtcgag    480

gatgttaagg caaatcctga agccgctacc aacggtattg tgttgaggaa tagattacaa    540

cttttgatgt acaacaatat gtatagaata atgtttgaca ggagatttga atctgttgat    600

gatccattat tcctaaaact taaggcattg aatggcgaga gatcaaggtt agctcaatcc    660

tttgaataca acttcggtga cttcattcct atattgaggc cattcttgag aggatatctt    720

aagttgtgtc aggaaatcaa ggacaaaagg ttaaagctat tcaaggacta cttcgtcgac    780

gagagaaaaa agttggagag tatcaagagc gtaggtaata actccttaaa gtgcgccata    840

gatcatatta tcgaggcaca agaaaaaggc gagataaacg aggataacgt gttatacatc    900

gtcgagaata tcaacgtggc tgccattgaa actacacttt ggtctattga atggggtata    960

gcagaactag tgaataaccc tgaaatccag aaaaaattga gacacgaatt agacaccgta   1020

cttggagctg gtgttcaaat ttgtgaacca gatgttcaaa aattgcctta tctacaggcc   1080

gtgataaaag agactttaag gtacaggatg gcaattccat tgttagtccc acatatgaat   1140
```

-continued

```
cttcacgaag ccaaattggc cggctatgat atccctgcag agagcaaaat tttggtaaac   1200

gcttggtggt tagccaataa tccagcacat tggaacaaac ctgatgagtt tagaccagaa   1260

agatttttgg aggaagaatc caaggtcgag gctaatggaa acgactttaa gtacatccct   1320

ttcggtgttg gcagaagatc ttgcccaggt ataattcttg ctttaccaat ccttggaata   1380

gtaattggta ggttggttca aaacttcgag ttacttccac ctccaggcca aagcaaaata   1440

gatacagccg aaaaaggtgg acagttttca ttgcaaatcc taaagcattc cactattgtg   1500

tgtaaaccta gaagttctta a                                             1521
```

<210> SEQ ID NO 6
<211> LENGTH: 506
<212> TYPE: PRT
<213> ORGANISM: Ammi majus

<400> SEQUENCE: 6

```
Met Met Asp Phe Val Leu Leu Glu Lys Ala Leu Leu Gly Leu Phe Ile
1               5                   10                  15

Ala Thr Ile Val Ala Ile Thr Ile Ser Lys Leu Arg Gly Lys Lys Leu
            20                  25                  30

Lys Leu Pro Pro Gly Pro Ile Pro Val Pro Val Phe Gly Asn Trp Leu
        35                  40                  45

Gln Val Gly Asp Asp Leu Asn Gln Arg Asn Leu Val Glu Tyr Ala Lys
    50                  55                  60

Lys Phe Gly Asp Leu Phe Leu Leu Arg Met Gly Gln Arg Asn Leu Val
65                  70                  75                  80

Val Val Ser Ser Pro Asp Leu Ala Lys Asp Val Leu His Thr Gln Gly
                85                  90                  95

Val Glu Phe Gly Ser Arg Thr Arg Asn Val Val Phe Asp Ile Phe Thr
            100                 105                 110

Gly Lys Gly Gln Asp Met Val Phe Thr Val Tyr Ser Glu His Trp Arg
        115                 120                 125

Lys Met Arg Arg Ile Met Thr Val Pro Phe Phe Thr Asn Lys Val Val
    130                 135                 140

Gln Gln Tyr Arg Phe Gly Trp Glu Asp Glu Ala Ala Arg Val Val Glu
145                 150                 155                 160

Asp Val Lys Ala Asn Pro Glu Ala Ala Thr Asn Gly Ile Val Leu Arg
                165                 170                 175

Asn Arg Leu Gln Leu Leu Met Tyr Asn Asn Met Tyr Arg Ile Met Phe
            180                 185                 190

Asp Arg Arg Phe Glu Ser Val Asp Asp Pro Leu Phe Leu Lys Leu Lys
        195                 200                 205

Ala Leu Asn Gly Glu Arg Ser Arg Leu Ala Gln Ser Phe Glu Tyr Asn
    210                 215                 220

Phe Gly Asp Phe Ile Pro Ile Leu Arg Pro Phe Leu Arg Gly Tyr Leu
225                 230                 235                 240

Lys Leu Cys Gln Glu Ile Lys Asp Lys Arg Leu Lys Leu Phe Lys Asp
                245                 250                 255

Tyr Phe Val Asp Glu Arg Lys Lys Leu Glu Ser Ile Lys Ser Val Gly
            260                 265                 270

Asn Asn Ser Leu Lys Cys Ala Ile Asp His Ile Ile Glu Ala Gln Glu
        275                 280                 285

Lys Gly Glu Ile Asn Glu Asp Asn Val Leu Tyr Ile Val Glu Asn Ile
    290                 295                 300
```

-continued

```
Asn Val Ala Ala Ile Glu Thr Thr Leu Trp Ser Ile Glu Trp Gly Ile
305                 310                 315                 320

Ala Glu Leu Val Asn Asn Pro Glu Ile Gln Lys Lys Leu Arg His Glu
                325                 330                 335

Leu Asp Thr Val Leu Gly Ala Gly Val Gln Ile Cys Glu Pro Asp Val
            340                 345                 350

Gln Lys Leu Pro Tyr Leu Gln Ala Val Ile Lys Glu Thr Leu Arg Tyr
        355                 360                 365

Arg Met Ala Ile Pro Leu Leu Val Pro His Met Asn Leu His Glu Ala
    370                 375                 380

Lys Leu Ala Gly Tyr Asp Ile Pro Ala Glu Ser Lys Ile Leu Val Asn
385                 390                 395                 400

Ala Trp Trp Leu Ala Asn Asn Pro Ala His Trp Asn Lys Pro Asp Glu
                405                 410                 415

Phe Arg Pro Glu Arg Phe Leu Glu Glu Glu Ser Lys Val Glu Ala Asn
            420                 425                 430

Gly Asn Asp Phe Lys Tyr Ile Pro Phe Gly Val Gly Arg Arg Ser Cys
        435                 440                 445

Pro Gly Ile Ile Leu Ala Leu Pro Ile Leu Gly Ile Val Ile Gly Arg
    450                 455                 460

Leu Val Gln Asn Phe Glu Leu Leu Pro Pro Pro Gly Gln Ser Lys Ile
465                 470                 475                 480

Asp Thr Ala Glu Lys Gly Gly Gln Phe Ser Leu Gln Ile Leu Lys His
                485                 490                 495

Ser Thr Ile Val Cys Lys Pro Arg Ser Ser
            500                 505
```

<210> SEQ ID NO 7
<211> LENGTH: 1671
<212> TYPE: DNA
<213> ORGANISM: Arabidopsis thaliana

<400> SEQUENCE: 7

```
atgacgacac aagatgtgat agtcaatgat cagaatgatc agaaacagtg tagtaatgac      60

gtcattttcc gatcgagatt gcctgatata tacatcccta accacctccc actccacgac     120

tacatcttcg aaaatatctc agagttcgcc gctaagccat gcttgatcaa cggtcccacc     180

ggcgaagtat acacctacgc cgatgtccac gtaacatctc ggaaactcgc cgccggtctt     240

cataacctcg gcgtgaagca acacgacgtt gtaatgatcc tcctcccgaa ctctcctgaa     300

gtagtcctca ctttccttgc cgcctccttc atcggcgcaa tcaccacctc cgcgaacccg     360

ttcttcactc cggcggagat ttctaaacaa gccaaagcct ccgctgcgaa actcatcgtc     420

actcaatccc gttacgtcga taaaatcaag aacctccaaa acgacggcgt tttgatcgtc     480

accaccgact ccgacgccat ccccgaaaac tgcctccgtt tctccgagtt aactcagtcc     540

gaagaaccac gagtggactc aataccggag aagatttcgc cagaagacgt cgtggcgctt     600

cctttctcat ccggcacgac gggtctcccc aaaggagtga tgctaacaca caaaggtcta     660

gtcacgagcg tggcgcagca agtcgacggc gagaatccga atctttactt caacagagac     720

gacgtgatcc tctgtgtctt gcctatgttc catatatacg ctctcaactc catcatgctc     780

tgtagtctca gagttggtgc cacgatcttg ataatgccta agttcgaaat cactctcttg     840

ttagagcaga tacaaaggtg taaagtcacg gtggctatgg tcgtgccacc gatcgtttta     900

gctatcgcga agtcgccgga gacggagaag tatgatctga gctcggttag gatggttaag     960
```

-continued

```
tctggagcag ctcctcttgg taaggagctt gaagatgcta ttagtgctaa gtttcctaac   1020

gccaagctag gtcagggcta tgggatgaca gaagcaggtc cggtgctagc aatgtcgtta   1080

gggtttgcta aagagccgtt tccagtgaag tcaggagcat gtggtacggt ggtgaggaac   1140

gccgagatga agatacttga tccagacaca ggagattctt tgcctaggaa caaacccggc   1200

gaaatatgca tccgtggcaa ccaaatcatg aaaggctatc tcaatgaccc cttggccacg   1260

gcatcgacga tcgataaaga tggttggctt cacactggag acgtcggatt tatcgatgat   1320

gacgacgagc ttttcattgt ggatagattg aaagaactca tcaagtacaa aggatttcaa   1380

gtggctccag ctgagctaga gtctctcctc ataggtcatc cagaaatcaa tgatgttgct   1440

gtcgtcgcca tgaaggaaga agatgctggt gaggttcctg ttgcgtttgt ggtgagatcg   1500

aaagattcaa atatatccga agatgaaatc aagcaattcg tgtcaaaaca ggttgtgttt   1560

tataagagaa tcaacaaagt gttcttcact gactctattc ctaaagctcc atcagggaag   1620

atattgagga aggatctaag agcaagacta gcaaatggat taatgaacta g            1671
```

<210> SEQ ID NO 8
<211> LENGTH: 556
<212> TYPE: PRT
<213> ORGANISM: Arabidopsis thaliana

<400> SEQUENCE: 8

```
Met Thr Thr Gln Asp Val Ile Val Asn Asp Gln Asn Asp Gln Lys Gln
1               5                   10                  15

Cys Ser Asn Asp Val Ile Phe Arg Ser Arg Leu Pro Asp Ile Tyr Ile
            20                  25                  30

Pro Asn His Leu Pro Leu His Asp Tyr Ile Phe Glu Asn Ile Ser Glu
        35                  40                  45

Phe Ala Ala Lys Pro Cys Leu Ile Asn Gly Pro Thr Gly Glu Val Tyr
    50                  55                  60

Thr Tyr Ala Asp Val His Val Thr Ser Arg Lys Leu Ala Ala Gly Leu
65                  70                  75                  80

His Asn Leu Gly Val Lys Gln His Asp Val Val Met Ile Leu Leu Pro
                85                  90                  95

Asn Ser Pro Glu Val Val Leu Thr Phe Leu Ala Ala Ser Phe Ile Gly
            100                 105                 110

Ala Ile Thr Thr Ser Ala Asn Pro Phe Phe Thr Pro Ala Glu Ile Ser
        115                 120                 125

Lys Gln Ala Lys Ala Ser Ala Ala Lys Leu Ile Val Thr Gln Ser Arg
    130                 135                 140

Tyr Val Asp Lys Ile Lys Asn Leu Gln Asn Asp Gly Val Leu Ile Val
145                 150                 155                 160

Thr Thr Asp Ser Asp Ala Ile Pro Glu Asn Cys Leu Arg Phe Ser Glu
                165                 170                 175

Leu Thr Gln Ser Glu Glu Pro Arg Val Asp Ser Ile Pro Glu Lys Ile
            180                 185                 190

Ser Pro Glu Asp Val Val Ala Leu Pro Phe Ser Ser Gly Thr Thr Gly
        195                 200                 205

Leu Pro Lys Gly Val Met Leu Thr His Lys Gly Leu Val Thr Ser Val
    210                 215                 220

Ala Gln Gln Val Asp Gly Glu Asn Pro Asn Leu Tyr Phe Asn Arg Asp
225                 230                 235                 240

Asp Val Ile Leu Cys Val Leu Pro Met Phe His Ile Tyr Ala Leu Asn
                245                 250                 255
```

Ser Ile Met Leu Cys Ser Leu Arg Val Gly Ala Thr Ile Leu Ile Met
260 265 270

Pro Lys Phe Glu Ile Thr Leu Leu Leu Glu Gln Ile Gln Arg Cys Lys
275 280 285

Val Thr Val Ala Met Val Val Pro Pro Ile Val Leu Ala Ile Ala Lys
290 295 300

Ser Pro Glu Thr Glu Lys Tyr Asp Leu Ser Ser Val Arg Met Val Lys
305 310 315 320

Ser Gly Ala Ala Pro Leu Gly Lys Glu Leu Glu Asp Ala Ile Ser Ala
325 330 335

Lys Phe Pro Asn Ala Lys Leu Gly Gln Gly Tyr Gly Met Thr Glu Ala
340 345 350

Gly Pro Val Leu Ala Met Ser Leu Gly Phe Ala Lys Glu Pro Phe Pro
355 360 365

Val Lys Ser Gly Ala Cys Gly Thr Val Val Arg Asn Ala Glu Met Lys
370 375 380

Ile Leu Asp Pro Asp Thr Gly Asp Ser Leu Pro Arg Asn Lys Pro Gly
385 390 395 400

Glu Ile Cys Ile Arg Gly Asn Gln Ile Met Lys Gly Tyr Leu Asn Asp
405 410 415

Pro Leu Ala Thr Ala Ser Thr Ile Asp Lys Asp Gly Trp Leu His Thr
420 425 430

Gly Asp Val Gly Phe Ile Asp Asp Asp Asp Glu Leu Phe Ile Val Asp
435 440 445

Arg Leu Lys Glu Leu Ile Lys Tyr Lys Gly Phe Gln Val Ala Pro Ala
450 455 460

Glu Leu Glu Ser Leu Leu Ile Gly His Pro Glu Ile Asn Asp Val Ala
465 470 475 480

Val Val Ala Met Lys Glu Glu Asp Ala Gly Glu Val Pro Val Ala Phe
485 490 495

Val Val Arg Ser Lys Asp Ser Asn Ile Ser Glu Asp Glu Ile Lys Gln
500 505 510

Phe Val Ser Lys Gln Val Val Phe Tyr Lys Arg Ile Asn Lys Val Phe
515 520 525

Phe Thr Asp Ser Ile Pro Lys Ala Pro Ser Gly Lys Ile Leu Arg Lys
530 535 540

Asp Leu Arg Ala Arg Leu Ala Asn Gly Leu Met Asn
545 550 555

<210> SEQ ID NO 9
<211> LENGTH: 1173
<212> TYPE: DNA
<213> ORGANISM: Hypericum androsaemum

<400> SEQUENCE: 9
atggttactg ttgaagaagt tagaaaagct caaagggcag aaggtccagc cacagtgatg 60
gctattggaa ccgcagttcc tccaaattgt gtagatcagg ccacttatcc tgactactac 120
tttagaataa caaactctga gcataaggct gaattgaaag aaaagttcca aaggatgtgc 180
gacaaatcac agatcaagaa aagatacatg taccttaatg aggaagtcct aaaggaaaac 240
ccaaatatgt gtgcatacat ggccccttcc cttgacgcta gacaagatat tgtggttgta 300
gaggtcccaa aattgggcaa ggaagcagct gttaaagcca taaaggaatg ggtcaacct 360 aagagcaaaa tcacccacct tgtgttttgc actacaagcg gagttgacat gccaggcgca 420

```
gattatcagc taaccaaact tttgggttta aggccttctg taaaaagatt gatgatgtac    480

caacaaggtt gtttcgctgg aggcactgtc ttaagactag ccaaggatct tgcagagaac    540

aacaaaggtg ctagggtgtt ggttgtatgc tcagaaatta cagccgtcac ctttagagga    600

ccaactgaca ctcacttaga ttccctagtt ggtcaggcat tgtttggcga cggtgctgcc    660

gcaataatca ttggaagtga tcctattcca gaggtggaaa agcctctttt tgaacttgtt    720

agcgctgccc aaactatatt gccagattct gagggtgcaa tcgacggcca cttaagggaa    780

gtaggtctaa ccttccatct tttgaaagat gtccctggtt taatttcaaa gaacgtggaa    840

aaatccctaa cagaggcttt taaaccattg ggtataagtg actggaatag cttattctgg    900

atcgctcacc caggcggccc tgccatactt gaccaggttg aagcaaaatt gagcttaaag    960

ccagaaaaac taagagctac tagacatgta ttgtcagagt atggtaacat gtccagtgcc   1020

tgtgtccttt tcattttgga tgaaatgagg agaaaaagca aggaggacgg cctaaaaacc   1080

acaggtgagg gaatcgaatg ggtgttccta ttcggctttg gtccaggcct tactgtggag   1140

acagttgtac ttcattcagt cgcaattaat tag                                1173
```

<210> SEQ ID NO 10
<211> LENGTH: 390
<212> TYPE: PRT
<213> ORGANISM: Hypericum androsaemum

<400> SEQUENCE: 10

```
Met Val Thr Val Glu Glu Val Arg Lys Ala Gln Arg Ala Glu Gly Pro
1               5                   10                  15

Ala Thr Val Met Ala Ile Gly Thr Ala Val Pro Pro Asn Cys Val Asp
            20                  25                  30

Gln Ala Thr Tyr Pro Asp Tyr Tyr Phe Arg Ile Thr Asn Ser Glu His
        35                  40                  45

Lys Ala Glu Leu Lys Glu Lys Phe Gln Arg Met Cys Asp Lys Ser Gln
    50                  55                  60

Ile Lys Lys Arg Tyr Met Tyr Leu Asn Glu Glu Val Leu Lys Glu Asn
65                  70                  75                  80

Pro Asn Met Cys Ala Tyr Met Ala Pro Ser Leu Asp Ala Arg Gln Asp
                85                  90                  95

Ile Val Val Val Glu Val Pro Lys Leu Gly Lys Glu Ala Ala Val Lys
            100                 105                 110

Ala Ile Lys Glu Trp Gly Gln Pro Lys Ser Lys Ile Thr His Leu Val
        115                 120                 125

Phe Cys Thr Thr Ser Gly Val Asp Met Pro Gly Ala Asp Tyr Gln Leu
    130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Thr Asp Thr His Leu Asp Ser
        195                 200                 205

Leu Val Gly Gln Ala Leu Phe Gly Asp Gly Ala Ala Ala Ile Ile Ile
    210                 215                 220

Gly Ser Asp Pro Ile Pro Glu Val Glu Lys Pro Leu Phe Glu Leu Val
225                 230                 235                 240
```

-continued

Ser Ala Ala Gln Thr Ile Leu Pro Asp Ser Glu Gly Ala Ile Asp Gly
245 250 255

His Leu Arg Glu Val Gly Leu Thr Phe His Leu Leu Lys Asp Val Pro
260 265 270

Gly Leu Ile Ser Lys Asn Val Glu Lys Ser Leu Thr Glu Ala Phe Lys
275 280 285

Pro Leu Gly Ile Ser Asp Trp Asn Ser Leu Phe Trp Ile Ala His Pro
290 295 300

Gly Gly Pro Ala Ile Leu Asp Gln Val Glu Ala Lys Leu Ser Leu Lys
305 310 315 320

Pro Glu Lys Leu Arg Ala Thr Arg His Val Leu Ser Glu Tyr Gly Asn
325 330 335

Met Ser Ser Ala Cys Val Leu Phe Ile Leu Asp Glu Met Arg Arg Lys
340 345 350

Ser Lys Glu Asp Gly Leu Lys Thr Thr Gly Glu Gly Ile Glu Trp Gly
355 360 365

Val Leu Phe Gly Phe Gly Pro Gly Leu Thr Val Glu Thr Val Val Leu
370 375 380

His Ser Val Ala Ile Asn
385 390

<210> SEQ ID NO 11
<211> LENGTH: 669
<212> TYPE: DNA
<213> ORGANISM: Medicago sativa

<400> SEQUENCE: 11
atggctgctt ccattaccgc tattaccgtt gaaaatttgg aatacccagc tgttgttact 60
tctccagtta ctggtaagtc ttactttttg ggtggtgctg gtgaaagagg tttgactatt 120
gaaggtaact tcattaagtt caccgccatc ggtgtttact tggaagatat tgctgttgct 180
tctttggctg ctaaatggaa gggtaaatcc tccgaagaat tattggaaac cttggacttc 240
tacagagaca ttatttctgg tccattcgaa aagttgatca gaggttccaa gatcagagaa 300
ttgtctggtc cagaatactc cagaaaggtt atggaaaatt gcgttgccca tttgaagtct 360
gttggtactt atggtgatgc tgaagctgaa gctatgcaaa aatttgctga agcctttaag 420
ccagttaatt ttccaccagg tgcttccgtt ttttacagac aatctccaga tggtatcttg 480
ggtttgtctt tttcaccaga tacctccatc ccagaaaaag aagctgcttt gattgaaaac 540
aaggctgttt cttctgctgt cttggaaact atgattggtg aacatgctgt ttccccagat 600
ttgaaaagat gtttagctgc tagattgcct gccttgttga atgaaggtgc ttttaagatt 660
ggtaactaa 669

<210> SEQ ID NO 12
<211> LENGTH: 222
<212> TYPE: PRT
<213> ORGANISM: Medicago sativa

<400> SEQUENCE: 12

Met Ala Ala Ser Ile Thr Ala Ile Thr Val Glu Asn Leu Glu Tyr Pro
1 5 10 15

Ala Val Val Thr Ser Pro Val Thr Gly Lys Ser Tyr Phe Leu Gly Gly
20 25 30

Ala Gly Glu Arg Gly Leu Thr Ile Glu Gly Asn Phe Ile Lys Phe Thr
35 40 45

-continued

```
Ala Ile Gly Val Tyr Leu Glu Asp Ile Ala Val Ala Ser Leu Ala Ala
    50                  55                  60

Lys Trp Lys Gly Lys Ser Ser Glu Glu Leu Leu Glu Thr Leu Asp Phe
65                  70                  75                  80

Tyr Arg Asp Ile Ile Ser Gly Pro Phe Glu Lys Leu Ile Arg Gly Ser
                85                  90                  95

Lys Ile Arg Glu Leu Ser Gly Pro Glu Tyr Ser Arg Lys Val Met Glu
            100                 105                 110

Asn Cys Val Ala His Leu Lys Ser Val Gly Thr Tyr Gly Asp Ala Glu
        115                 120                 125

Ala Glu Ala Met Gln Lys Phe Ala Glu Ala Phe Lys Pro Val Asn Phe
    130                 135                 140

Pro Pro Gly Ala Ser Val Phe Tyr Arg Gln Ser Pro Asp Gly Ile Leu
145                 150                 155                 160

Gly Leu Ser Phe Ser Pro Asp Thr Ser Ile Pro Glu Lys Glu Ala Ala
                165                 170                 175

Leu Ile Glu Asn Lys Ala Val Ser Ser Ala Val Leu Glu Thr Met Ile
            180                 185                 190

Gly Glu His Ala Val Ser Pro Asp Leu Lys Arg Cys Leu Ala Ala Arg
        195                 200                 205

Leu Pro Ala Leu Leu Asn Glu Gly Ala Phe Lys Ile Gly Asn
    210                 215                 220
```

<210> SEQ ID NO 13
<211> LENGTH: 633
<212> TYPE: DNA
<213> ORGANISM: Petunia x hybrida

<400> SEQUENCE: 13

```
atgggtaaga acgaagttat ggttgacgaa attccattcc catctcaatt catgatgact      60

actaagccat tgccattgat gggtcacggt attactgaca ttgaaattca cttcttgcaa     120

attaagttca ctgctattgg tgtttacttg gacccagaaa ttgttactca cttgcaacaa     180

tggaagggta agtctggtgc tgaattgatt gaaaacgacg aattcttcga agctattgtt     240

aacgctccag ttgacaagtt cttgagagtt gttgttatta aggaaattaa gggttctcaa     300

tacggtgttc aattggaatc tgctgttaga gacagattgg ctgaagttga caagtacgaa     360

gaagaagaag aagaagcttt ggaaaagatt gttgaattct tccaatctaa gtacttcaag     420

aaggactctg ttgttactta ctctttccca gctacttctg gtaacgttaa gatttctttc     480

gctactgaag gtaaggaaga ctctgaaatt gaagttcaaa acgctaacgt tgctggtgaa     540

attaagaagt ggtacttggg tggttctaga ggtttgtctc caactactat ttcttctttg     600

gctaacactt tgtctgctga attgtctaag taa                                  633
```

<210> SEQ ID NO 14
<211> LENGTH: 210
<212> TYPE: PRT
<213> ORGANISM: Petunia x hybrida

<400> SEQUENCE: 14

```
Met Gly Lys Asn Glu Val Met Val Asp Glu Ile Pro Phe Pro Ser Gln
1               5                   10                  15

Phe Met Met Thr Thr Lys Pro Leu Pro Leu Met Gly His Gly Ile Thr
            20                  25                  30

Asp Ile Glu Ile His Phe Leu Gln Ile Lys Phe Thr Ala Ile Gly Val
```

```
        35                  40                  45

Tyr Leu Asp Pro Glu Ile Val Thr His Leu Gln Gln Trp Lys Gly Lys
    50                  55                  60

Ser Gly Ala Glu Leu Ile Glu Asn Asp Glu Phe Phe Glu Ala Ile Val
65                  70                  75                  80

Asn Ala Pro Val Asp Lys Phe Leu Arg Val Val Val Ile Lys Glu Ile
                85                  90                  95

Lys Gly Ser Gln Tyr Gly Val Gln Leu Glu Ser Ala Val Arg Asp Arg
            100                 105                 110

Leu Ala Glu Val Asp Lys Tyr Glu Glu Glu Glu Glu Glu Ala Leu Glu
        115                 120                 125

Lys Ile Val Glu Phe Phe Gln Ser Lys Tyr Phe Lys Lys Asp Ser Val
    130                 135                 140

Val Thr Tyr Ser Phe Pro Ala Thr Ser Gly Asn Val Lys Ile Ser Phe
145                 150                 155                 160

Ala Thr Glu Gly Lys Glu Asp Ser Glu Ile Glu Val Gln Asn Ala Asn
                165                 170                 175

Val Ala Gly Glu Ile Lys Lys Trp Tyr Leu Gly Gly Ser Arg Gly Leu
            180                 185                 190

Ser Pro Thr Thr Ile Ser Ser Leu Ala Asn Thr Leu Ser Ala Glu Leu
        195                 200                 205

Ser Lys
    210


<210> SEQ ID NO 15
<211> LENGTH: 630
<212> TYPE: DNA
<213> ORGANISM: Arabidopsis thaliana

<400> SEQUENCE: 15

atgggtactg aaatggttat ggttcacgaa gttccattcc caccacaaat tattacttct      60

aagccattgt ctttgttggg tcaaggtatt actgacattg aaattcactt cttgcaagtt     120

aagttcactg ctattggtgt ttacttggac ccatctgacg ttaagactca cttggacaac     180

tggaagggta agactggtaa ggaattggct ggtgacgacg acttcttcga cgctttggct     240

tctgctgaaa tggaaaaggt tattagagtt gttgttatta aggaaattaa gggtgctcaa     300

tacggtgttc aattggaaaa cactgttaga gacagattgg ctgaagaaga caagtacgaa     360

gaagaagaag aaactgaatt ggaaaaggtt gttggtttct tccaatctaa gtacttcaag     420

gctaactctg ttattactta ccacttctct gctaaggacg gtatttgtga aattggtttc     480

gaaactgaag gtaaggaaga agaaaagttg aaggttgaaa acgctaacgt tgttggtatg     540

atgcaaagat ggtacttgtc tggttctaga ggtgtttctc catctactat tgtttctatt     600

gctgactcta tttctgctgt tttgacttag                                      630


<210> SEQ ID NO 16
<211> LENGTH: 209
<212> TYPE: PRT
<213> ORGANISM: Arabidopsis thaliana

<400> SEQUENCE: 16

Met Gly Thr Glu Met Val Met Val His Glu Val Pro Phe Pro Pro Gln
1               5                   10                  15

Ile Ile Thr Ser Lys Pro Leu Ser Leu Leu Gly Gln Gly Ile Thr Asp
            20                  25                  30
```

-continued

```
Ile Glu Ile His Phe Leu Gln Val Lys Phe Thr Ala Ile Gly Val Tyr
        35                  40                  45

Leu Asp Pro Ser Asp Val Lys Thr His Leu Asp Asn Trp Lys Gly Lys
    50                  55                  60

Thr Gly Lys Glu Leu Ala Gly Asp Asp Asp Phe Phe Asp Ala Leu Ala
65                  70                  75                  80

Ser Ala Glu Met Glu Lys Val Ile Arg Val Val Val Ile Lys Glu Ile
                85                  90                  95

Lys Gly Ala Gln Tyr Gly Val Gln Leu Glu Asn Thr Val Arg Asp Arg
            100                 105                 110

Leu Ala Glu Glu Asp Lys Tyr Glu Glu Glu Glu Glu Thr Glu Leu Glu
        115                 120                 125

Lys Val Val Gly Phe Phe Gln Ser Lys Tyr Phe Lys Ala Asn Ser Val
    130                 135                 140

Ile Thr Tyr His Phe Ser Ala Lys Asp Gly Ile Cys Glu Ile Gly Phe
145                 150                 155                 160

Glu Thr Glu Gly Lys Glu Glu Glu Lys Leu Lys Val Glu Asn Ala Asn
                165                 170                 175

Val Val Gly Met Met Gln Arg Trp Tyr Leu Ser Gly Ser Arg Gly Val
            180                 185                 190

Ser Pro Ser Thr Ile Val Ser Ile Ala Asp Ser Ile Ser Ala Val Leu
        195                 200                 205

Thr
```

<210> SEQ ID NO 17
<211> LENGTH: 621
<212> TYPE: DNA
<213> ORGANISM: Ipomoea nil

<400> SEQUENCE: 17

```
atgggtactg aaatggttat ggttgacgaa attccattcc caccacaagt taacttggac      60

aacaagttgt tgtctttgat gggtcacggt attactgacg ttgaaattca cttcttgcaa     120

attaagtaca ctgctattgg tgtttacttg gacccagaaa ttgtttctca cttgcaaaag     180

tggaagggta agactccagt tgacttggct caagacgacg acttcttcga agctattatt     240

aacgctccag ttgacaaggt tttgagagtt gttgttatta aggaaattaa gggttctcaa     300

tacggtgttc aattggaaaa ctctgttaga gacttgttgg ctgaagttga caagtacgaa     360

gaagaagaag aagctgcttt ggaaaaggtt gttgacttct tccaatctaa gtacttcaag     420

aagtcttctg ttattacttt ctctttccca gctaacactg ctactgctaa gattgttttc     480

gctactgaag gtaaggaaga ctcttctatt gaagttgaaa acgctaacgt tggtggtatg     540

attaagaagt ggtacttggg tggttctaga gctgtttctc catctactat ttcttctttg     600

gctaacattt tgccagacta g                                                621
```

<210> SEQ ID NO 18
<211> LENGTH: 206
<212> TYPE: PRT
<213> ORGANISM: Ipomoea nil

<400> SEQUENCE: 18

```
Met Gly Thr Glu Met Val Met Val Asp Glu Ile Pro Phe Pro Pro Gln
1               5                   10                  15

Val Asn Leu Asp Asn Lys Leu Leu Ser Leu Met Gly His Gly Ile Thr
            20                  25                  30
```

Asp Val Glu Ile His Phe Leu Gln Ile Lys Tyr Thr Ala Ile Gly Val
35 40 45

Tyr Leu Asp Pro Glu Ile Val Ser His Leu Gln Lys Trp Lys Gly Lys
50 55 60

Thr Pro Val Asp Leu Ala Gln Asp Asp Asp Phe Phe Glu Ala Ile Ile
65 70 75 80

Asn Ala Pro Val Asp Lys Val Leu Arg Val Val Val Ile Lys Glu Ile
85 90 95

Lys Gly Ser Gln Tyr Gly Val Gln Leu Glu Asn Ser Val Arg Asp Leu
100 105 110

Leu Ala Glu Val Asp Lys Tyr Glu Glu Glu Glu Glu Ala Ala Leu Glu
115 120 125

Lys Val Val Asp Phe Phe Gln Ser Lys Tyr Phe Lys Lys Ser Ser Val
130 135 140

Ile Thr Phe Ser Phe Pro Ala Asn Thr Ala Thr Ala Lys Ile Val Phe
145 150 155 160

Ala Thr Glu Gly Lys Glu Asp Ser Ser Ile Glu Val Glu Asn Ala Asn
165 170 175

Val Gly Gly Met Ile Lys Lys Trp Tyr Leu Gly Gly Ser Arg Ala Val
180 185 190

Ser Pro Ser Thr Ile Ser Ser Leu Ala Asn Ile Leu Pro Asp
195 200 205

<210> SEQ ID NO 19
<211> LENGTH: 639
<212> TYPE: DNA
<213> ORGANISM: Antirrhinum majus

<400> SEQUENCE: 19
atgggttctg aagttgttga cgttgttatg gttgacgaag ttccattccc atctaagatt 60
actttcgcta agccattgtc tttgttgggt cacggtttga ctgacattga aattcacttc 120
ttgcaaatta agttcactgc tattggtgtt tacttggacc cagaaattgt tgctcacttg 180
ttgaagtgga agggtaagcc agctactgaa ttggctgaag acgacgactt gttcgacgct 240
attatttctg ctccagttga caagattgtt agagttgttg ttattaagga aattaagggt 300
tctcaatacg gtgttcaatt ggaatctgct gttagagaca gattggctga cgaagacaag 360
tacgaagacg aagaagaaga agctttggaa caaattattg acttcttgca atctaagtac 420
ttcaagaaga actctgtttt gacttactac ttcccagcta cttctgctac tgctgaaatt 480
attttcgcta ctgaaggtaa ggaagactct aagattgaag ttaagaacgc taacgttgtt 540
gacatgttga agaagtggta cttgggtggt actagaggtg tttctccaac tactattgct 600
tctttggcta ctggtttgtc tactgaattg tctaagtag 639

<210> SEQ ID NO 20
<211> LENGTH: 212
<212> TYPE: PRT
<213> ORGANISM: Antirrhinum majus

<400> SEQUENCE: 20

Met Gly Ser Glu Val Val Asp Val Val Met Val Asp Glu Val Pro Phe
1 5 10 15

Pro Ser Lys Ile Thr Phe Ala Lys Pro Leu Ser Leu Leu Gly His Gly
20 25 30

Leu Thr Asp Ile Glu Ile His Phe Leu Gln Ile Lys Phe Thr Ala Ile
35 40 45

Gly Val Tyr Leu Asp Pro Glu Ile Val Ala His Leu Leu Lys Trp Lys
    50                  55                  60

Gly Lys Pro Ala Thr Glu Leu Ala Glu Asp Asp Asp Leu Phe Asp Ala
65                  70                  75                  80

Ile Ile Ser Ala Pro Val Asp Lys Ile Val Arg Val Val Val Ile Lys
                85                  90                  95

Glu Ile Lys Gly Ser Gln Tyr Gly Val Gln Leu Glu Ser Ala Val Arg
            100                 105                 110

Asp Arg Leu Ala Asp Glu Asp Lys Tyr Glu Asp Glu Glu Glu Glu Ala
        115                 120                 125

Leu Glu Gln Ile Ile Asp Phe Leu Gln Ser Lys Tyr Phe Lys Lys Asn
    130                 135                 140

Ser Val Leu Thr Tyr Tyr Phe Pro Ala Thr Ser Ala Thr Ala Glu Ile
145                 150                 155                 160

Ile Phe Ala Thr Glu Gly Lys Glu Asp Ser Lys Ile Glu Val Lys Asn
                165                 170                 175

Ala Asn Val Val Asp Met Leu Lys Lys Trp Tyr Leu Gly Gly Thr Arg
            180                 185                 190

Gly Val Ser Pro Thr Thr Ile Ala Ser Leu Ala Thr Gly Leu Ser Thr
        195                 200                 205

Glu Leu Ser Lys
    210

<210> SEQ ID NO 21
<211> LENGTH: 630
<212> TYPE: DNA
<213> ORGANISM: Glycine max

<400> SEQUENCE: 21
atggctactg aagaagtttt ggttgacgaa attacttacc caactaagat tactactact 60
aagccattgt ctttgttggg tcacggtatt actgacatgg aaattcactt cattcacgtt 120
aagttctact ctattggtgt ttacttggaa ccagaagttg ttggtcactt ggaccaattc 180
aagggtaagt ctgctaagga attggaagac aacgaagaat tcttcaacgc tttgatttct 240
gctccagttg aaaagttcat tagattggtt gttattaagg aaattaaggg tgctcaatac 300
ggtgttcaaa ttgaaactgc tgttagagac agattggctg ctgaagacaa gtacgaagaa 360
gaagaagaag aagctttgga aaaggttatt gaattcttcc aatctaagta cttcaagaag 420
ttgtctgtta ttacttacca cttcccagct aactctgcta ctgctgaaat tgttgtttct 480
ttggaaggta aggaagactc taagtacgtt attgaaaacg ctaacgttgt tgaagctatt 540
aagaagtggt acttgggtgg ttcttctgct gtttcttctt ctactattca atctttggct 600
tctactttct ctcaagaatt gtctaagtag 630

<210> SEQ ID NO 22
<211> LENGTH: 209
<212> TYPE: PRT
<213> ORGANISM: Glycine max

<400> SEQUENCE: 22

Met Ala Thr Glu Glu Val Leu Val Asp Glu Ile Thr Tyr Pro Thr Lys
1               5                   10                  15

Ile Thr Thr Thr Lys Pro Leu Ser Leu Leu Gly His Gly Ile Thr Asp
            20                  25                  30

Met Glu Ile His Phe Ile His Val Lys Phe Tyr Ser Ile Gly Val Tyr

-continued

```
        35                  40                  45

Leu Glu Pro Glu Val Val Gly His Leu Asp Gln Phe Lys Gly Lys Ser
    50                  55                  60

Ala Lys Glu Leu Glu Asp Asn Glu Glu Phe Phe Asn Ala Leu Ile Ser
65                  70                  75                  80

Ala Pro Val Glu Lys Phe Ile Arg Leu Val Val Ile Lys Glu Ile Lys
                85                  90                  95

Gly Ala Gln Tyr Gly Val Gln Ile Glu Thr Ala Val Arg Asp Arg Leu
            100                 105                 110

Ala Ala Glu Asp Lys Tyr Glu Glu Glu Glu Glu Glu Ala Leu Glu Lys
        115                 120                 125

Val Ile Glu Phe Phe Gln Ser Lys Tyr Phe Lys Lys Leu Ser Val Ile
    130                 135                 140

Thr Tyr His Phe Pro Ala Asn Ser Ala Thr Ala Glu Ile Val Val Ser
145                 150                 155                 160

Leu Glu Gly Lys Glu Asp Ser Lys Tyr Val Ile Glu Asn Ala Asn Val
                165                 170                 175

Val Glu Ala Ile Lys Lys Trp Tyr Leu Gly Gly Ser Ser Ala Val Ser
            180                 185                 190

Ser Ser Thr Ile Gln Ser Leu Ala Ser Thr Phe Ser Gln Glu Leu Ser
        195                 200                 205

Lys
```

<210> SEQ ID NO 23
<211> LENGTH: 2076
<212> TYPE: DNA
<213> ORGANISM: Saccharomyces cerevisiae

<400> SEQUENCE: 23

```
atgccgtttg gaatagacaa caccgacttc actgtcctgg cggggctagt gcttgccgtg      60

ctactgtacg taaagagaaa ctccatcaag gaactgctga tgtccgatga cggagatatc     120

acagctgtca gctcgggcaa cagagacatt gctcaggtgg tgaccgaaaa caacaagaac     180

tacttggtgt tgtatgcgtc gcagactggg actgccgagg attacgccaa aaagttttcc     240

aaggagctgg tggccaagtt caacctaaac gtgatgtgcg cagatgttga gaactacgac     300

tttgagtcgc taaacgatgt gcccgtcata gtctcgattt ttatctctac atatggtgaa     360

ggagacttcc ccgacggggc ggtcaacttt gaagacttta tttgtaatgc ggaagcgggt     420

gcactatcga acctgaggta taatatgttt ggtctgggaa attctactta tgaattcttt     480

aatggtgccg ccaagaaggc cgagaagcat ctctccgctg cgggcgctat cagactaggc     540

aagctcggtg aagctgatga tggtgcagga actacagacg aagattacat ggcctggaag     600

gactccatcc tggaggtttt gaaagacgaa ctgcatttgg acgaacagga agccaagttc     660

acctctcaat tccagtacac tgtgttgaac gaaatcactg actccatgtc gcttggtgaa     720

ccctctgctc actatttgcc ctcgcatcag ttgaaccgca acgcagacgg catccaattg     780

ggtcccttcg atttgtctca accgtatatt gcacccatcg tgaaatctcg cgaactgttc     840

tcttccaatg accgtaattg catccactct gaatttgact tgtccggctc taacatcaag     900

tactccactg gtgaccatct tgctgtttgg ccttccaacc cattggaaaa ggtcgaacag     960

ttcttatcca tattcaacct ggaccctgaa accatttttg acttgaagcc cctggatccc    1020

accgtcaaag tgcccttccc aacgccaact actattggcg ctgctattaa acactatttg    1080

gaaattacag gacctgtctc cagacaattg ttttcatctt tgattcagtt cgcccccaac    1140
```

-continued gctgacgtca aggaaaaatt gactctgctt tcgaaagaca aggaccaatt cgccgtcgag 1200
ataacctcca aatatttcaa catcgcagat gctctgaaat atttgtctga tggcgccaaa 1260
tgggacaccg tacccatgca attcttggtc gaatcagttc cccaaatgac tcctcgttac 1320
tactctatct cttcctcttc tctgtctgaa aagcaaaccg tccatgtcac ctccattgtg 1380
gaaaactttc ctaacccaga attgcctgat gctcctccag ttgttggtgt tacgactaac 1440
ttgttaagaa acattcaatt ggctcaaaac aatgttaaca ttgccgaaac taacctacct 1500
gttcactacg atttaaatgg cccacgtaaa cttttcgcca attacaaatt gcccgtccac 1560
gttcgtcgtt ctaacttcag attgccttcc aacccttcca ccccagttat catgatcggt 1620
ccaggtaccg gtgttgcccc attccgtggg tttatcagag agcgtgtcgc gttcctcgaa 1680
tcacaaaaga agggcggtaa caacgtttcg ctaggtaagc atatactgtt ttatggatcc 1740
cgtaacactg atgatttctt gtaccaggac gaatggccag aatacgccaa aaaattggat 1800
ggttcgttcg aaatggtcgt ggcccattcc aggttgccaa acaccaaaaa agtttatgtt 1860
caagataaat taaaggatta cgaagaccaa gtatttgaaa tgattaacaa cggtgcattt 1920
atctacgtct gtggtgatgc aaagggtatg gccaagggtg tgtcaaccgc attggttggc 1980
atcttatccc gtggtaaatc cattaccact gatgaagcaa cagagctaat caagatgctc 2040
aagacttcag gtagatacca agaagatgtc tggtaa 2076

<210> SEQ ID NO 24
<211> LENGTH: 691
<212> TYPE: PRT
<213> ORGANISM: Saccharomyces cerevisiae

<400> SEQUENCE: 24

Met Pro Phe Gly Ile Asp Asn Thr Asp Phe Thr Val Leu Ala Gly Leu
1 5 10 15

Val Leu Ala Val Leu Leu Tyr Val Lys Arg Asn Ser Ile Lys Glu Leu
20 25 30

Leu Met Ser Asp Asp Gly Asp Ile Thr Ala Val Ser Ser Gly Asn Arg
35 40 45

Asp Ile Ala Gln Val Val Thr Glu Asn Asn Lys Asn Tyr Leu Val Leu
50 55 60

Tyr Ala Ser Gln Thr Gly Thr Ala Glu Asp Tyr Ala Lys Lys Phe Ser
65 70 75 80

Lys Glu Leu Val Ala Lys Phe Asn Leu Asn Val Met Cys Ala Asp Val
85 90 95

Glu Asn Tyr Asp Phe Glu Ser Leu Asn Asp Val Pro Val Ile Val Ser
100 105 110

Ile Phe Ile Ser Thr Tyr Gly Glu Gly Asp Phe Pro Asp Gly Ala Val
115 120 125

Asn Phe Glu Asp Phe Ile Cys Asn Ala Glu Ala Gly Ala Leu Ser Asn
130 135 140

Leu Arg Tyr Asn Met Phe Gly Leu Gly Asn Ser Thr Tyr Glu Phe Phe
145 150 155 160

Asn Gly Ala Ala Lys Lys Ala Glu Lys His Leu Ser Ala Ala Gly Ala
165 170 175

Ile Arg Leu Gly Lys Leu Gly Glu Ala Asp Asp Gly Ala Gly Thr Thr
180 185 190

Asp Glu Asp Tyr Met Ala Trp Lys Asp Ser Ile Leu Glu Val Leu Lys
195 200 205

-continued

```
Asp Glu Leu His Leu Asp Glu Gln Glu Ala Lys Phe Thr Ser Gln Phe
    210                 215                 220

Gln Tyr Thr Val Leu Asn Glu Ile Thr Asp Ser Met Ser Leu Gly Glu
225                 230                 235                 240

Pro Ser Ala His Tyr Leu Pro Ser His Gln Leu Asn Arg Asn Ala Asp
                245                 250                 255

Gly Ile Gln Leu Gly Pro Phe Asp Leu Ser Gln Pro Tyr Ile Ala Pro
            260                 265                 270

Ile Val Lys Ser Arg Glu Leu Phe Ser Ser Asn Asp Arg Asn Cys Ile
        275                 280                 285

His Ser Glu Phe Asp Leu Ser Gly Ser Asn Ile Lys Tyr Ser Thr Gly
    290                 295                 300

Asp His Leu Ala Val Trp Pro Ser Asn Pro Leu Glu Lys Val Glu Gln
305                 310                 315                 320

Phe Leu Ser Ile Phe Asn Leu Asp Pro Glu Thr Ile Phe Asp Leu Lys
                325                 330                 335

Pro Leu Asp Pro Thr Val Lys Val Pro Phe Pro Thr Pro Thr Thr Ile
            340                 345                 350

Gly Ala Ala Ile Lys His Tyr Leu Glu Ile Thr Gly Pro Val Ser Arg
        355                 360                 365

Gln Leu Phe Ser Ser Leu Ile Gln Phe Ala Pro Asn Ala Asp Val Lys
    370                 375                 380

Glu Lys Leu Thr Leu Leu Ser Lys Asp Lys Asp Gln Phe Ala Val Glu
385                 390                 395                 400

Ile Thr Ser Lys Tyr Phe Asn Ile Ala Asp Ala Leu Lys Tyr Leu Ser
                405                 410                 415

Asp Gly Ala Lys Trp Asp Thr Val Pro Met Gln Phe Leu Val Glu Ser
            420                 425                 430

Val Pro Gln Met Thr Pro Arg Tyr Tyr Ser Ile Ser Ser Ser Ser Leu
        435                 440                 445

Ser Glu Lys Gln Thr Val His Val Thr Ser Ile Val Glu Asn Phe Pro
    450                 455                 460

Asn Pro Glu Leu Pro Asp Ala Pro Pro Val Val Gly Val Thr Thr Asn
465                 470                 475                 480

Leu Leu Arg Asn Ile Gln Leu Ala Gln Asn Asn Val Asn Ile Ala Glu
                485                 490                 495

Thr Asn Leu Pro Val His Tyr Asp Leu Asn Gly Pro Arg Lys Leu Phe
            500                 505                 510

Ala Asn Tyr Lys Leu Pro Val His Val Arg Arg Ser Asn Phe Arg Leu
        515                 520                 525

Pro Ser Asn Pro Ser Thr Pro Val Ile Met Ile Gly Pro Gly Thr Gly
    530                 535                 540

Val Ala Pro Phe Arg Gly Phe Ile Arg Glu Arg Val Ala Phe Leu Glu
545                 550                 555                 560

Ser Gln Lys Lys Gly Gly Asn Asn Val Ser Leu Gly Lys His Ile Leu
                565                 570                 575

Phe Tyr Gly Ser Arg Asn Thr Asp Asp Phe Leu Tyr Gln Asp Glu Trp
            580                 585                 590

Pro Glu Tyr Ala Lys Lys Leu Asp Gly Ser Phe Glu Met Val Val Ala
        595                 600                 605

His Ser Arg Leu Pro Asn Thr Lys Lys Val Tyr Val Gln Asp Lys Leu
    610                 615                 620
```

-continued

```
Lys Asp Tyr Glu Asp Gln Val Phe Glu Met Ile Asn Asn Gly Ala Phe
625                 630                 635                 640

Ile Tyr Val Cys Gly Asp Ala Lys Gly Met Ala Lys Gly Val Ser Thr
                645                 650                 655

Ala Leu Val Gly Ile Leu Ser Arg Gly Lys Ser Ile Thr Thr Asp Glu
            660                 665                 670

Ala Thr Glu Leu Ile Lys Met Leu Lys Thr Ser Gly Arg Tyr Gln Glu
        675                 680                 685

Asp Val Trp
    690

<210> SEQ ID NO 25
<211> LENGTH: 2079
<212> TYPE: DNA
<213> ORGANISM: Arabidopsis thaliana

<400> SEQUENCE: 25

atgacttctg cactttatgc ctccgatctt ttcaaacaat tgaaaagtat catgggaacg      60

gattctttgt ccgatgatgt tgtattagtt attgctacaa cttctctggc actggttgct     120

ggtttcgttg tcttattgtg gaaaaagacc acggcagatc gttccggcga gctaaagcca     180

ctaatgatcc ctaagtctct gatggcgaaa gatgaggatg atgacttaga tctaggttct     240

ggaaaaacga gagtctctat cttcttcggc acacaaaccg gaacagccga aggattcgct     300

aaagcacttt cagaagagat caaagcaaga tacgaaaagg cggctgtaaa agtaatcgat     360

ttggatgatt acgctgccga tgatgaccaa tatgaggaaa agttgaaaaa ggaaacattg     420

gctttctttt gtgtagccac gtatggtgat ggtgaaccaa ccgataacgc cgcaagattc     480

tacaagtggt ttactgaaga gaacgaaaga gatatcaagt tgcagcaact tgcttacggc     540

gtttttgcct taggtaacag acaatacgag cactttaaca agataggtat tgtcttagat     600

gaagagttat gcaaaaaggg tgcgaagaga ttgattgaag tcggtttagg agatgatgat     660

caatctatcg aggatgactt taatgcatgg aaggaatctt tgtggtctga attagataag     720

ttacttaagg acgaagatga taaatccgtt gccactccat acacagccgt cattccagaa     780

tatagagtag ttactcatga tccaagattc acaacacaga aatcaatgga aagtaatgtg     840

gctaatggta atactaccat cgatattcat catccatgta gagtagacgt tgcagttcaa     900

aaggaattgc acactcatga atcagacaga tcttgcatac atcttgaatt tgatatatca     960

cgtactggta tcacttacga aacaggtgat cacgtgggtg tctacgctga aaaccatgtt    1020

gaaattgtag aggaagctgg aaagttgttg ggccatagtt tagatcttgt tttctcaatt    1080

catgccgata aagaggatgg ctcaccacta gaaagtgcag tgcctccacc atttccagga    1140

ccatgcaccc taggtaccgg tttagctcgt tacgcggatc tgttaaatcc tccacgtaaa    1200

tcagctctag tggccttggc tgcgtacgcc acagaacctt ctgaggcaga aaaactgaaa    1260

catctaactt caccagatgg taaggatgaa tactcacaat ggatagtagc tagtcaacgt    1320

tctttactag aagttatggc tgctttccca tccgctaaac ctcctttggg tgttttcttc    1380

gccgcaatag cgcctagact gcaaccaaga tactattcaa tttcatcctc acctagactg    1440

gcaccatcaa gagttcatgt cacatccgct ttagtgtacg gtccaactcc tactggtaga    1500

atccataagg gcgtttgttc aacatggatg aaaaacgcgg ttccagcaga gaagtctcac    1560

gaatgttctg gtgctccaat ctttatcaga gcctccaact tcaaactgcc ttccaatcct    1620

tctactccta ttgtcatggt cggtcctggt acaggtcttg ctccattcag aggtttctta    1680
```

```
caagagagaa tggccttaaa ggaggatggt gaagagttgg gatcttcttt gttgtttttc   1740

ggctgtagaa acagacaaat ggatttcatc tacgaagatg aactgaataa ctttgtagat   1800

caaggagtta tttcagagtt gataatggct ttttctagag aaggtgctca gaaggagtac   1860

gtccaacaca aaatgatgga aaaggccgca caagtttggg acttaatcaa agaggaaggc   1920

tatctatatg tctgtggtga tgcaaagggt atggcaagag atgttcacag aacacttcat   1980

actatagtcc aggaacagga aggcgttagt tcttctgaag cggaagcaat tgtgaaaaag   2040

ttacaaacag agggaagata cttgagagat gtgtggtaa                          2079
```

<210> SEQ ID NO 26
<211> LENGTH: 692
<212> TYPE: PRT
<213> ORGANISM: Arabidopsis thaliana

<400> SEQUENCE: 26

```
Met Thr Ser Ala Leu Tyr Ala Ser Asp Leu Phe Lys Gln Leu Lys Ser
1               5                   10                  15

Ile Met Gly Thr Asp Ser Leu Ser Asp Asp Val Val Leu Val Ile Ala
            20                  25                  30

Thr Thr Ser Leu Ala Leu Val Ala Gly Phe Val Val Leu Leu Trp Lys
        35                  40                  45

Lys Thr Thr Ala Asp Arg Ser Gly Glu Leu Lys Pro Leu Met Ile Pro
    50                  55                  60

Lys Ser Leu Met Ala Lys Asp Glu Asp Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
            100                 105                 110

Lys Ala Ala Val Lys Val Ile Asp Leu Asp Asp Tyr Ala Ala Asp Asp
        115                 120                 125

Asp Gln Tyr Glu Glu Lys Leu Lys Lys Glu Thr Leu Ala Phe Phe Cys
    130                 135                 140

Val Ala Thr Tyr Gly Asp Gly Glu Pro Thr Asp Asn Ala Ala Arg Phe
145                 150                 155                 160

Tyr Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Glu Leu Cys Lys Lys Gly Ala
        195                 200                 205

Lys Arg Leu Ile Glu Val Gly Leu Gly Asp Asp Asp Gln Ser Ile Glu
    210                 215                 220

Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
        275                 280                 285

Ile His His Pro Cys Arg Val Asp Val Ala Val Gln Lys Glu Leu His
    290                 295                 300
```

-continued

```
Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
            340                 345                 350

Ser Leu Asp Leu Val Phe Ser Ile His Ala Asp Lys Glu Asp Gly Ser
        355                 360                 365

Pro Leu Glu Ser Ala Val Pro Pro Pro Phe Pro Gly Pro Cys Thr Leu
    370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
                405                 410                 415

Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
        435                 440                 445

Phe Pro Ser Ala Lys Pro Pro Leu Gly Val Phe Phe Ala Ala Ile Ala
    450                 455                 460

Pro Arg Leu Gln Pro Arg Tyr Tyr Ser Ile Ser Ser Ser Pro Arg Leu
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
    530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
        595                 600                 605

Met Ala Phe Ser Arg Glu Gly Ala Gln Lys Glu Tyr Val Gln His Lys
    610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Glu Gln Glu Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
    690
```

```
<210> SEQ ID NO 27
<211> LENGTH: 1539
<212> TYPE: DNA
```

<213> ORGANISM: Petunia x hybrida

<400> SEQUENCE: 27

```
atggagattt taagtttaat tttgtataca gttatcttca gtttcttatt gcaatttatt     60
ttgagatctt tctttaggaa aagatatcca ttaccattac ctccaggtcc aaaaccatgg    120
ccaataatag gcaacttagt acacttggga cccaaaccac accagtctac cgccgctatg    180
gcccaaacat atggtccatt gatgtactta aagatgggct tcgtagacgt cgttgtcgct    240
gcatctgcaa gtgttgctgc acaattcttg aagactcacg atgctaactt ctcttctaga    300
cctccaaata gtggcgctga gcatatggcc tataattacc aagacttggt tttcgcccca    360
tacggcccta ggtggagaat gttaaggaaa atatgttctg tgcacttgtt ctctacaaaa    420
gcattggatg atttcagaca tgtcagacaa gacgaagtaa agactttaac cagagcatta    480
gcttcagcag gtcagaagcc cgtgaagtta ggccaattat taaacgtctg tactactaat    540
gctttagcca gagtaatgtt aggtaaaaga gtcttcgctg acggttcagg cgatgttgac    600
ccacaagccg cagaattcaa atctatggta gttgagatga tggtcgtcgc cggtgtattt    660
aacataggag atttcattcc tcaattaaat tggttggaca ttcaaggtgt ggccgctaaa    720
atgaagaagt tacatgctag attcgatgct ttcttgacag acatattgga agaacataaa    780
ggtaaaatct ttggtgaaat gaaggattta ttaagtacct taatctcctt gaagaatgat    840
gatgccgaca atgatggtgg aaaattgaca gatacagaga ttaaagcatt attattaaac    900
ttgtttgttg caggaactga tacttcatcc tcaactgttg aatgggcaat tgccgaattg    960
atcagaaatc caaagatttt ggctcaggct caacaagaga tcgacaaagt ggtaggtaga   1020
gacaggttgg tgggcgaatt agatttagca caattaacct acttggaagc aattgttaag   1080
gaaaccttta gattgcatcc ctccactcca ttatcattgc caagaatagc atcagaatca   1140
tgtgaaatca acggttactt tatcccaaaa ggatccactt tattattgaa tgtttgggct   1200
atagccaggg atcctaatgc ttgggccgat cctttagaat ttagacctga aagattcttg   1260
cctggtggtg aaaagcctaa ggtggatgta aggggaaatg attttgaggt gattcccttt   1320
ggagcaggta ggaggatttg cgctggaatg aatttgggta ttaggatggt tcagttaatg   1380
atcgcaacat tgatacatgc atttaactgg gatttggttt ccggtcagtt gcctgaaatg   1440
ttgaacatgg aagaggctta tggtttgaca ttgcagagag ctgatccttt ggttgttcat   1500
cccagaccca gattggaagc tcaggcttat atcggttga                           1539
```

<210> SEQ ID NO 28
<211> LENGTH: 512
<212> TYPE: PRT
<213> ORGANISM: Petunia x hybrida

<400> SEQUENCE: 28

```
Met Glu Ile Leu Ser Leu Ile Leu Tyr Thr Val Ile Phe Ser Phe Leu
1               5                   10                  15

Leu Gln Phe Ile Leu Arg Ser Phe Phe Arg Lys Arg Tyr Pro Leu Pro
            20                  25                  30

Leu Pro Pro Gly Pro Lys Pro Trp Pro Ile Ile Gly Asn Leu Val His
        35                  40                  45

Leu Gly Pro Lys Pro His Gln Ser Thr Ala Ala Met Ala Gln Thr Tyr
    50                  55                  60

Gly Pro Leu Met Tyr Leu Lys Met Gly Phe Val Asp Val Val Val Ala
65                  70                  75                  80
```

-continued

```
Ala Ser Ala Ser Val Ala Ala Gln Phe Leu Lys Thr His Asp Ala Asn
                85                  90                  95

Phe Ser Ser Arg Pro Pro Asn Ser Gly Ala Glu His Met Ala Tyr Asn
            100                 105                 110

Tyr Gln Asp Leu Val Phe Ala Pro Tyr Gly Pro Arg Trp Arg Met Leu
        115                 120                 125

Arg Lys Ile Cys Ser Val His Leu Phe Ser Thr Lys Ala Leu Asp Asp
    130                 135                 140

Phe Arg His Val Arg Gln Asp Glu Val Lys Thr Leu Thr Arg Ala Leu
145                 150                 155                 160

Ala Ser Ala Gly Gln Lys Pro Val Lys Leu Gly Gln Leu Leu Asn Val
                165                 170                 175

Cys Thr Thr Asn Ala Leu Ala Arg Val Met Leu Gly Lys Arg Val Phe
            180                 185                 190

Ala Asp Gly Ser Gly Asp Val Asp Pro Gln Ala Ala Glu Phe Lys Ser
        195                 200                 205

Met Val Val Glu Met Met Val Val Ala Gly Val Phe Asn Ile Gly Asp
    210                 215                 220

Phe Ile Pro Gln Leu Asn Trp Leu Asp Ile Gln Gly Val Ala Ala Lys
225                 230                 235                 240

Met Lys Lys Leu His Ala Arg Phe Asp Ala Phe Leu Thr Asp Ile Leu
                245                 250                 255

Glu Glu His Lys Gly Lys Ile Phe Gly Glu Met Lys Asp Leu Leu Ser
            260                 265                 270

Thr Leu Ile Ser Leu Lys Asn Asp Asp Ala Asp Asn Asp Gly Gly Lys
        275                 280                 285

Leu Thr Asp Thr Glu Ile Lys Ala Leu Leu Leu Asn Leu Phe Val Ala
    290                 295                 300

Gly Thr Asp Thr Ser Ser Ser Thr Val Glu Trp Ala Ile Ala Glu Leu
305                 310                 315                 320

Ile Arg Asn Pro Lys Ile Leu Ala Gln Ala Gln Gln Glu Ile Asp Lys
                325                 330                 335

Val Val Gly Arg Asp Arg Leu Val Gly Glu Leu Asp Leu Ala Gln Leu
            340                 345                 350

Thr Tyr Leu Glu Ala Ile Val Lys Glu Thr Phe Arg Leu His Pro Ser
        355                 360                 365

Thr Pro Leu Ser Leu Pro Arg Ile Ala Ser Glu Ser Cys Glu Ile Asn
    370                 375                 380

Gly Tyr Phe Ile Pro Lys Gly Ser Thr Leu Leu Leu Asn Val Trp Ala
385                 390                 395                 400

Ile Ala Arg Asp Pro Asn Ala Trp Ala Asp Pro Leu Glu Phe Arg Pro
                405                 410                 415

Glu Arg Phe Leu Pro Gly Gly Glu Lys Pro Lys Val Asp Val Arg Gly
            420                 425                 430

Asn Asp Phe Glu Val Ile Pro Phe Gly Ala Gly Arg Arg Ile Cys Ala
        435                 440                 445

Gly Met Asn Leu Gly Ile Arg Met Val Gln Leu Met Ile Ala Thr Leu
    450                 455                 460

Ile His Ala Phe Asn Trp Asp Leu Val Ser Gly Gln Leu Pro Glu Met
465                 470                 475                 480

Leu Asn Met Glu Glu Ala Tyr Gly Leu Thr Leu Gln Arg Ala Asp Pro
                485                 490                 495

Leu Val Val His Pro Arg Pro Arg Leu Glu Ala Gln Ala Tyr Ile Gly
```

500 505 510

<210> SEQ ID NO 29
<211> LENGTH: 1521
<212> TYPE: DNA
<213> ORGANISM: Petunia x hybrida

<400> SEQUENCE: 29

```
atgatgttgt tgaccgaatt gggtgctgct acttccattt ttttgattgc ccatatcatc     60

atctccacct tgatttctaa aaccaccggt agacatttgc caccaggtcc aagaggttgg    120

ccagttattg gtgctttgcc attattgggt gcaatgccac atgtttcttt ggctaaaatg    180

gctaagaaat acggtgccat catgtacttg aaagttggta cttgtggtat ggctgttgct    240

tctactccag atgctgctaa ggcttttttg aaaaccttgg acatcaactt ctctaacaga    300

ccaccaaatg ctggtgctac tcatttggct tataatgccc aagatatggt tttcgctcat    360

tatggtccaa gatggaagtt gttgagaaag ttgtctaact tgcatatgtt gggtggtaag    420

gctttggaaa attgggctaa tgttagagcc aatgaattgg gtcatatgtt gaagtccatg    480

tccgatatgt ctagagaagg tcaaagagtt gttgtcgctg aaatgttgac ttttgctatg    540

gctaacatga tcggtcaagt catgttgtct aagagagttt tcgttgataa gggtgtcgaa    600

gtcaacgaat tcaaggatat ggttgttgaa ttgatgacca ttgccggtta ctttaacatc    660

ggtgatttca ttccatgttt ggcttggatg gacttgcaag gtattgaaaa gagaatgaag    720

agattgcaca agaagttcga cgctttgttg actaagatgt tcgatgaaca taaggctacc    780

acctacgaaa gaaaaggtaa gccagatttc ttggatgtcg ttatggaaaa cggtgataac    840

tctgaaggtg aaagattgtc taccaccaat attaaggcct tgttgttgaa cttgttcacc    900

gctggtactg atacttcttc ttctgctatt gaatgggctt tggcagaaat gatgaagaac    960

ccagctattt tgaaaaaggc tcaagccgaa atggatcaag ttatcggtag aaacagaaga   1020

ttattggaat ccgacattcc aaacttgcca tacttgagag ctatctgcaa agaaactttt   1080

agaaagcacc catctacccc attgaacttg ccaagaattt ctaacgaacc atgcatcgtt   1140

gatggttact acatcccaaa aaacaccaga ttgtccgtta acatttgggc cattggtaga   1200

gatccacaag tttgggaaaa tccattggaa ttcaacccag aaagattctt gtctggtaga   1260

aactccaaga ttgacccaag aggtaatgac ttcgaattga ttccatttgg tgccggtaga   1320

agaatttgtg ctggtactag aatgggtatc gttatggtcg aatatatctt aggtactttg   1380

gtccactctt tcgattggaa attgccatcc gaagttatcg aattgaatat ggaagaagcc   1440

tttggtttgg ccttgcaaaa agctgttcca ttagaagcta tggttacccc aagattgcaa   1500

ttggatgttt acgttccata a                                             1521
```

<210> SEQ ID NO 30
<211> LENGTH: 506
<212> TYPE: PRT
<213> ORGANISM: Petunia x hybrida

<400> SEQUENCE: 30

```
Met Met Leu Leu Thr Glu Leu Gly Ala Ala Thr Ser Ile Phe Leu Ile
1               5                   10                  15

Ala His Ile Ile Ile Ser Thr Leu Ile Ser Lys Thr Thr Gly Arg His
            20                  25                  30

Leu Pro Pro Gly Pro Arg Gly Trp Pro Val Ile Gly Ala Leu Pro Leu
        35                  40                  45
```

-continued

```
Leu Gly Ala Met Pro His Val Ser Leu Ala Lys Met Ala Lys Lys Tyr
    50                  55                  60

Gly Ala Ile Met Tyr Leu Lys Val Gly Thr Cys Gly Met Ala Val Ala
65                  70                  75                  80

Ser Thr Pro Asp Ala Ala Lys Ala Phe Leu Lys Thr Leu Asp Ile Asn
                85                  90                  95

Phe Ser Asn Arg Pro Pro Asn Ala Gly Ala Thr His Leu Ala Tyr Asn
            100                 105                 110

Ala Gln Asp Met Val Phe Ala His Tyr Gly Pro Arg Trp Lys Leu Leu
        115                 120                 125

Arg Lys Leu Ser Asn Leu His Met Leu Gly Gly Lys Ala Leu Glu Asn
    130                 135                 140

Trp Ala Asn Val Arg Ala Asn Glu Leu Gly His Met Leu Lys Ser Met
145                 150                 155                 160

Ser Asp Met Ser Arg Glu Gly Gln Arg Val Val Val Ala Glu Met Leu
                165                 170                 175

Thr Phe Ala Met Ala Asn Met Ile Gly Gln Val Met Leu Ser Lys Arg
            180                 185                 190

Val Phe Val Asp Lys Gly Val Glu Val Asn Glu Phe Lys Asp Met Val
        195                 200                 205

Val Glu Leu Met Thr Ile Ala Gly Tyr Phe Asn Ile Gly Asp Phe Ile
    210                 215                 220

Pro Cys Leu Ala Trp Met Asp Leu Gln Gly Ile Glu Lys Arg Met Lys
225                 230                 235                 240

Arg Leu His Lys Lys Phe Asp Ala Leu Leu Thr Lys Met Phe Asp Glu
                245                 250                 255

His Lys Ala Thr Thr Tyr Glu Arg Lys Gly Lys Pro Asp Phe Leu Asp
            260                 265                 270

Val Val Met Glu Asn Gly Asp Asn Ser Glu Gly Glu Arg Leu Ser Thr
        275                 280                 285

Thr Asn Ile Lys Ala Leu Leu Leu Asn Leu Phe Thr Ala Gly Thr Asp
    290                 295                 300

Thr Ser Ser Ser Ala Ile Glu Trp Ala Leu Ala Glu Met Met Lys Asn
305                 310                 315                 320

Pro Ala Ile Leu Lys Lys Ala Gln Ala Glu Met Asp Gln Val Ile Gly
                325                 330                 335

Arg Asn Arg Arg Leu Leu Glu Ser Asp Ile Pro Asn Leu Pro Tyr Leu
            340                 345                 350

Arg Ala Ile Cys Lys Glu Thr Phe Arg Lys His Pro Ser Thr Pro Leu
        355                 360                 365

Asn Leu Pro Arg Ile Ser Asn Glu Pro Cys Ile Val Asp Gly Tyr Tyr
    370                 375                 380

Ile Pro Lys Asn Thr Arg Leu Ser Val Asn Ile Trp Ala Ile Gly Arg
385                 390                 395                 400

Asp Pro Gln Val Trp Glu Asn Pro Leu Glu Phe Asn Pro Glu Arg Phe
                405                 410                 415

Leu Ser Gly Arg Asn Ser Lys Ile Asp Pro Arg Gly Asn Asp Phe Glu
            420                 425                 430

Leu Ile Pro Phe Gly Ala Gly Arg Arg Ile Cys Ala Gly Thr Arg Met
        435                 440                 445

Gly Ile Val Met Val Glu Tyr Ile Leu Gly Thr Leu Val His Ser Phe
    450                 455                 460

Asp Trp Lys Leu Pro Ser Glu Val Ile Glu Leu Asn Met Glu Glu Ala
```

-continued 465 470 475 480

Phe Gly Leu Ala Leu Gln Lys Ala Val Pro Leu Glu Ala Met Val Thr
485 490 495

Pro Arg Leu Gln Leu Asp Val Tyr Val Pro
500 505

<210> SEQ ID NO 31
<211> LENGTH: 1098
<212> TYPE: DNA
<213> ORGANISM: Petroselinum crispum

<400> SEQUENCE: 31
atggctccaa ctactattac tgctttggct aaggaaaaga ctttgaactt ggacttcgtt 60
agagacgaag acgaaagacc aaaggttgct tacaaccaat tctctaacga aattccaatt 120
atttctttgg ctggtttgga cgacgactct gacggtagaa gaccagaaat ttgtagaaag 180
attgttaagg cttgtgaaga ctggggtatt ttccaagttg ttgaccacgg tattgactct 240
ggtttgattt ctgaaatgac tagattgtct agagaattct tcgctttgcc agctgaagaa 300
aagttggaat acgacactac tggtggtaag agaggtggtt tcactatttc tactgttttg 360
caaggtgacg acgctatgga ctggagagaa ttcgttactt acttctctta cccaattaac 420
gctagagact actctagatg gccaaagaag ccagaaggtt ggagatctac tactgaagtt 480
tactctgaaa agttgatggt tttgggtgct aagttgttgg aagttttgtc tgaagctatg 540
ggtttggaaa agggtgactt gactaaggct tgtgttgaca tggaacaaaa ggttttgatt 600
aactactacc caacttgtcc acaaccagac ttgactttgg gtgttagaag acacactgac 660
ccaggtacta ttactatttt gttgcaagac atggttggtg gtttgcaagc tactagagac 720
ggtggtaaga cttggattac tgttcaacca gttgaaggtg ctttcgttgt taacttgggt 780
gaccacggtc actacttgtc taacggtaga ttcagaaacg ctgaccacca agctgttgtt 840
aactctactt cttctagatt gtctattgct actttccaaa acccagctca aaacgctatt 900
gtttacccat tgaagattag agaaggtgaa aaggctattt tggacgaagc tattacttac 960
gctgaaatgt acaagaagtg tatgactaag cacattgaag ttgctactag aaagaagttg 1020
gctaaggaaa agagattgca agacgaaaag gctaagttgg aaatgaagtc taagtctgct 1080
gacgaaaact tggcttag 1098

<210> SEQ ID NO 32
<211> LENGTH: 365
<212> TYPE: PRT
<213> ORGANISM: Petroselinum crispum

<400> SEQUENCE: 32

Met Ala Pro Thr Thr Ile Thr Ala Leu Ala Lys Glu Lys Thr Leu Asn
1 5 10 15

Leu Asp Phe Val Arg Asp Glu Asp Glu Arg Pro Lys Val Ala Tyr Asn
20 25 30

Gln Phe Ser Asn Glu Ile Pro Ile Ile Ser Leu Ala Gly Leu Asp Asp
35 40 45

Asp Ser Asp Gly Arg Arg Pro Glu Ile Cys Arg Lys Ile Val Lys Ala
50 55 60

Cys Glu Asp Trp Gly Ile Phe Gln Val Val Asp His Gly Ile Asp Ser
65 70 75 80

Gly Leu Ile Ser Glu Met Thr Arg Leu Ser Arg Glu Phe Phe Ala Leu
85 90 95

```
Pro Ala Glu Glu Lys Leu Glu Tyr Asp Thr Thr Gly Gly Lys Arg Gly
            100                 105                 110

Gly Phe Thr Ile Ser Thr Val Leu Gln Gly Asp Asp Ala Met Asp Trp
        115                 120                 125

Arg Glu Phe Val Thr Tyr Phe Ser Tyr Pro Ile Asn Ala Arg Asp Tyr
    130                 135                 140

Ser Arg Trp Pro Lys Lys Pro Glu Gly Trp Arg Ser Thr Thr Glu Val
145                 150                 155                 160

Tyr Ser Glu Lys Leu Met Val Leu Gly Ala Lys Leu Leu Glu Val Leu
                165                 170                 175

Ser Glu Ala Met Gly Leu Glu Lys Gly Asp Leu Thr Lys Ala Cys Val
            180                 185                 190

Asp Met Glu Gln Lys Val Leu Ile Asn Tyr Tyr Pro Thr Cys Pro Gln
        195                 200                 205

Pro Asp Leu Thr Leu Gly Val Arg Arg His Thr Asp Pro Gly Thr Ile
    210                 215                 220

Thr Ile Leu Leu Gln Asp Met Val Gly Gly Leu Gln Ala Thr Arg Asp
225                 230                 235                 240

Gly Gly Lys Thr Trp Ile Thr Val Gln Pro Val Glu Gly Ala Phe Val
                245                 250                 255

Val Asn Leu Gly Asp His Gly His Tyr Leu Ser Asn Gly Arg Phe Arg
            260                 265                 270

Asn Ala Asp His Gln Ala Val Val Asn Ser Thr Ser Ser Arg Leu Ser
        275                 280                 285

Ile Ala Thr Phe Gln Asn Pro Ala Gln Asn Ala Ile Val Tyr Pro Leu
    290                 295                 300

Lys Ile Arg Glu Gly Glu Lys Ala Ile Leu Asp Glu Ala Ile Thr Tyr
305                 310                 315                 320

Ala Glu Met Tyr Lys Lys Cys Met Thr Lys His Ile Glu Val Ala Thr
                325                 330                 335

Arg Lys Lys Leu Ala Lys Glu Lys Arg Leu Gln Asp Glu Lys Ala Lys
            340                 345                 350

Leu Glu Met Lys Ser Lys Ser Ala Asp Glu Asn Leu Ala
        355                 360                 365
```

<210> SEQ ID NO 33
<211> LENGTH: 1521
<212> TYPE: DNA
<213> ORGANISM: Antirrhinum majus

<400> SEQUENCE: 33

```
atgtctactt tggtttactc tactttgttc attttgtcta ctttgttgtt gactttgttg      60

actagaacta gaagaaagac tagaccacca ggtccattgg ctttgccatt gattggtcac     120

ttgcacttgt tgggtccaaa gttgcaccac actttccacc aattctctca aagatacggt     180

ccattgattc aattgtactt gggttctgtt ccatgtgttg ttgcttctac tccagaattg     240

gctagagaat tcttgaagac tcacgaattg gacttctctt ctagaaagca ctctactgct     300

attgacattg ttacttacga ctcttctttc gctttcgctc catacggtcc atactggaag     360

ttcattaaga agttgtgtac ttacgaattg ttgggtgcta gaaacttgtc tcacttccaa     420

ccaattagag ctttggaagt taactctttc ttgagaattt tgtacgaaaa gactgaacaa     480

aagcaatctg ttaacgttac tgaagaattg gttaagttga cttctaacgt tatttctaac     540

atgatgttgg gtattagatg ttctggtact gaaggtgaag ctgaagttgc tagaactgtt     600
```

attagagaag ttactcaaat tttcggtgaa ttcgacgttt ctgaaattgt ttggttctgt 660
aagaacttgg acttgcaagg tattagaaag agatctgaag acattagaag aagatacgac 720
gctttgttgg aaaagattat ttctgacaga gaaagattga gattgagagg tggtggtggt 780
ggtggtggtg gtgaagttaa ggacttcttg gacatgttgt tggacgttat ggaatctgaa 840
aagtctgaag ttgaattcac tagagaacac ttgaaggctt tgattttgga cttcttcact 900
gctggtactg acactactgc tattactact gaatgggcta ttgctgaatt gatttctaac 960
ccaaacgttt tgaagaaggc tcaagaagaa atggacaagg ttattggttc tcaaagattg 1020
ttgcaagaat ctgacgctcc aaacttgcca tacttgaacg ctattattaa ggaaactttc 1080
agattgcacc caccaattcc aatgttgact agaaagtcta tttctgacgt tgttgttaac 1140
ggttacacta ttccagctaa gactttgttg ttcgttaact tgtggtctat gggtagaaac 1200
ccaaactact gggaaaaccc aatggaattc agaccagaaa gattcttgga aaagggtact 1260
ggttctattg acgttaaggg tcaacacttc gaattgttgc cattcggtac tggtagaaga 1320
ggttgtccag gtatgttgtt gggtatgcaa gaattgttct ctattattgg tgctatggtt 1380
caatgtttcg actggaagtt gccagacggt gttaagtctg ttgacatgac tgaaagacca 1440
ggtttgactg ctccaagagc taacgacttg gtttgtcaat tggttccaag aattgaccca 1500
gttgttgttt ctggtccata a 1521

<210> SEQ ID NO 34
<211> LENGTH: 506
<212> TYPE: PRT
<213> ORGANISM: Antirrhinum majus

<400> SEQUENCE: 34

Met Ser Thr Leu Val Tyr Ser Thr Leu Phe Ile Leu Ser Thr Leu Leu
1               5                   10                  15

Leu Thr Leu Leu Thr Arg Thr Arg Arg Lys Thr Arg Pro Pro Gly Pro
            20                  25                  30

Leu Ala Leu Pro Leu Ile Gly His Leu His Leu Leu Gly Pro Lys Leu
        35                  40                  45

His His Thr Phe His Gln Phe Ser Gln Arg Tyr Gly Pro Leu Ile Gln
    50                  55                  60

Leu Tyr Leu Gly Ser Val Pro Cys Val Val Ala Ser Thr Pro Glu Leu
65                  70                  75                  80

Ala Arg Glu Phe Leu Lys Thr His Glu Leu Asp Phe Ser Ser Arg Lys
                85                  90                  95

His Ser Thr Ala Ile Asp Ile Val Thr Tyr Asp Ser Ser Phe Ala Phe
            100                 105                 110

Ala Pro Tyr Gly Pro Tyr Trp Lys Phe Ile Lys Lys Leu Cys Thr Tyr
        115                 120                 125

Glu Leu Leu Gly Ala Arg Asn Leu Ser His Phe Gln Pro Ile Arg Ala
    130                 135                 140

Leu Glu Val Asn Ser Phe Leu Arg Ile Leu Tyr Glu Lys Thr Glu Gln
145                 150                 155                 160

Lys Gln Ser Val Asn Val Thr Glu Glu Leu Val Lys Leu Thr Ser Asn
                165                 170                 175

Val Ile Ser Asn Met Met Leu Gly Ile Arg Cys Ser Gly Thr Glu Gly
            180                 185                 190

Glu Ala Glu Val Ala Arg Thr Val Ile Arg Glu Val Thr Gln Ile Phe
        195                 200                 205

Gly Glu Phe Asp Val Ser Glu Ile Val Trp Phe Cys Lys Asn Leu Asp
    210                 215                 220

Leu Gln Gly Ile Arg Lys Arg Ser Glu Asp Ile Arg Arg Arg Tyr Asp
225                 230                 235                 240

Ala Leu Leu Glu Lys Ile Ile Ser Asp Arg Glu Arg Leu Arg Leu Arg
                245                 250                 255

Gly Gly Gly Gly Gly Gly Gly Gly Glu Val Lys Asp Phe Leu Asp Met
            260                 265                 270

Leu Leu Asp Val Met Glu Ser Glu Lys Ser Glu Val Glu Phe Thr Arg
        275                 280                 285

Glu His Leu Lys Ala Leu Ile Leu Asp Phe Phe Thr Ala Gly Thr Asp
    290                 295                 300

Thr Thr Ala Ile Thr Thr Glu Trp Ala Ile Ala Glu Leu Ile Ser Asn
305                 310                 315                 320

Pro Asn Val Leu Lys Lys Ala Gln Glu Glu Met Asp Lys Val Ile Gly
                325                 330                 335

Ser Gln Arg Leu Leu Gln Glu Ser Asp Ala Pro Asn Leu Pro Tyr Leu
            340                 345                 350

Asn Ala Ile Ile Lys Glu Thr Phe Arg Leu His Pro Pro Ile Pro Met
        355                 360                 365

Leu Thr Arg Lys Ser Ile Ser Asp Val Val Val Asn Gly Tyr Thr Ile
    370                 375                 380

Pro Ala Lys Thr Leu Leu Phe Val Asn Leu Trp Ser Met Gly Arg Asn
385                 390                 395                 400

Pro Asn Tyr Trp Glu Asn Pro Met Glu Phe Arg Pro Glu Arg Phe Leu
                405                 410                 415

Glu Lys Gly Thr Gly Ser Ile Asp Val Lys Gly Gln His Phe Glu Leu
            420                 425                 430

Leu Pro Phe Gly Thr Gly Arg Arg Gly Cys Pro Gly Met Leu Leu Gly
        435                 440                 445

Met Gln Glu Leu Phe Ser Ile Ile Gly Ala Met Val Gln Cys Phe Asp
    450                 455                 460

Trp Lys Leu Pro Asp Gly Val Lys Ser Val Asp Met Thr Glu Arg Pro
465                 470                 475                 480

Gly Leu Thr Ala Pro Arg Ala Asn Asp Leu Val Cys Gln Leu Val Pro
                485                 490                 495

Arg Ile Asp Pro Val Val Val Ser Gly Pro
            500                 505

<210> SEQ ID NO 35
<211> LENGTH: 1566
<212> TYPE: DNA
<213> ORGANISM: Glycine max

<400> SEQUENCE: 35
atgttgttgg aattggcttt gggtttgttc gttttggctt tgttcttgca cttgagacca     60
actccatctg ctaagtctaa ggctttgaga cacttgccaa acccaccatc tccaaagcca    120
agattgccat tcattggtca cttgcacttg ttgaaggaca agttgttgca ctacgctttg    180
attgacttgt ctaagaagca cggtccattg ttctctttgt ctttcggttc tatgccaact    240
gttgttgctt ctactccaga attgttcaag ttgttcttgc aaactcacga agctacttct    300
ttcaacacta gattccaaac ttctgctatt agaagattga cttacgacaa ctctgttgct    360
atggttccat tcggtccata ctggaagttc gttagaaagt tgattatgaa cgacttgttg    420
aacgctacta ctgttaacaa gttgagacca ttgagaactc aacaaattag aaagttcttg 480
agagttatgg ctcaatctgc tgaagctcaa aagccattgg acgttactga agaattgttg 540
aagtggacta actctactat ttctatgatg atgttgggtg aagctgaaga aattagagac 600
attgctagag aagttttgaa gattttcggt gaatactctt tgactgactt catttggcca 660
ttgaagtact tgaaggttgg taagtacgaa aagagaattg acgacatttt gaacaagttc 720
gacccagttg ttgaaagagt tattaagaag agaagagaaa ttgttagaag aagaaagaac 780
ggtgaagttg ttgaaggtga agcttctggt gttttcttgg acactttgtt ggaattcgct 840
gaagacgaaa ctatggaaat taagattact aaggaacaaa ttaagggttt ggttgttgac 900
ttcttctctg ctggtactga ctctactgct gttgctactg aatgggcttt ggctgaattg 960
attaacaacc caagagtttt gcaaaaggct agagaagaag tttactctgt tgttggtaag 1020
gacagattgg ttgacgaagt tgacactcaa aacttgccat acattagagc tattgttaag 1080
gaaactttca gaatgcaccc accattgcca gttgttaaga gaaagtgtac tgaagaatgt 1140
gaaattaacg gttacgttat tccagaaggt gctttggttt tgttcaacgt ttggcaagtt 1200
ggtagagacc caaagtactg ggacagacca tctgaattca gaccagaaag attcttggaa 1260
actggtgctg aaggtgaagc tggtccattg gacttgagag gtcaacactt ccaattgttg 1320
ccattcggtt ctggtagaag aatgtgtcca ggtgttaact tggctacttc tggtatggct 1380
actttgttgg cttctttgat tcaatgtttc gacttgcaag ttttgggtcc acaaggtcaa 1440
attttgaagg gtgacgacgc taaggtttct atggaagaaa gagctggttt gactgttcca 1500
agagctcact ctttggtttg tgttccattg gctagaattg gtgttgcttc taagttgttg 1560
tcttaa 1566

<210> SEQ ID NO 36
<211> LENGTH: 521
<212> TYPE: PRT
<213> ORGANISM: Glycine max

<400> SEQUENCE: 36

Met Leu Leu Glu Leu Ala Leu Gly Leu Phe Val Leu Ala Leu Phe Leu
1 5 10 15

His Leu Arg Pro Thr Pro Ser Ala Lys Ser Lys Ala Leu Arg His Leu
20 25 30

Pro Asn Pro Pro Ser Pro Lys Pro Arg Leu Pro Phe Ile Gly His Leu
35 40 45

His Leu Leu Lys Asp Lys Leu Leu His Tyr Ala Leu Ile Asp Leu Ser
50 55 60

Lys Lys His Gly Pro Leu Phe Ser Leu Ser Phe Gly Ser Met Pro Thr
65 70 75 80

Val Val Ala Ser Thr Pro Glu Leu Phe Lys Leu Phe Leu Gln Thr His
85 90 95

Glu Ala Thr Ser Phe Asn Thr Arg Phe Gln Thr Ser Ala Ile Arg Arg
100 105 110

Leu Thr Tyr Asp Asn Ser Val Ala Met Val Pro Phe Gly Pro Tyr Trp
115 120 125

Lys Phe Val Arg Lys Leu Ile Met Asn Asp Leu Leu Asn Ala Thr Thr
130 135 140

Val Asn Lys Leu Arg Pro Leu Arg Thr Gln Gln Ile Arg Lys Phe Leu
145 150 155 160

-continued

```
Arg Val Met Ala Gln Ser Ala Glu Ala Gln Lys Pro Leu Asp Val Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys Tyr Leu
    210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Ala Ser Gly Val Phe
            260                 265                 270

Leu Asp Thr Leu Leu Glu Phe Ala Glu Asp Glu Thr Met Glu Ile Lys
        275                 280                 285

Ile Thr Lys Glu Gln Ile Lys Gly Leu Val Val Asp Phe Phe Ser Ala
    290                 295                 300

Gly Thr Asp Ser Thr Ala Val Ala Thr Glu Trp Ala Leu Ala Glu Leu
305                 310                 315                 320

Ile Asn Asn Pro Arg Val Leu Gln Lys Ala Arg Glu Glu Val Tyr Ser
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Lys Cys Thr Glu Glu Cys Glu Ile Asn Gly
    370                 375                 380

Tyr Val Ile Pro Glu Gly Ala Leu Val Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

Arg Phe Leu Glu Thr Gly Ala Glu Gly Glu Ala Gly Pro Leu Asp Leu
            420                 425                 430

Arg Gly Gln His Phe Gln Leu Leu Pro Phe Gly Ser Gly Arg Arg Met
        435                 440                 445

Cys Pro Gly Val Asn Leu Ala Thr Ser Gly Met Ala Thr Leu Leu Ala
    450                 455                 460

Ser Leu Ile Gln Cys Phe Asp Leu Gln Val Leu Gly Pro Gln Gly Gln
465                 470                 475                 480

Ile Leu Lys Gly Asp Asp Ala Lys Val Ser Met Glu Glu Arg Ala Gly
                485                 490                 495

Leu Thr Val Pro Arg Ala His Ser Leu Val Cys Val Pro Leu Ala Arg
            500                 505                 510

Ile Gly Val Ala Ser Lys Leu Leu Ser
        515                 520
```

<210> SEQ ID NO 37
<211> LENGTH: 960
<212> TYPE: DNA
<213> ORGANISM: Glycine max

<400> SEQUENCE: 37
atggctaagg aaattgttaa ggaattgttg ccattgatta gagtttacaa ggacggttct     60

-continued

```
gttgaaagat tgttgtcttc tgaaaacgtt gctgcttctc cagaagaccc acaaactggt    120

gtttcttcta aggacattgt tattgctgac aacccatacg tttctgctag aattttcttg    180

ccaaagtctc accacactaa caacaagttg ccaattttct tgtacttcca cggtggtgct    240

ttctgtgttg aatctgcttt ctctttcttc gttcacagat acttgaacat tttggcttct    300

gaagctaaca ttattgctat ttctgttgac ttcagattgt tgccacacca cccaattcca    360

gctgcttacg aagacggttg gactactttg aagtggattg cttctcacgc taacaacact    420

aacactacta acccagaacc atggttgttg aaccacgctg acttcactaa ggtttacgtt    480

ggtggtgaaa cttctggtgc taacattgct cacaacttgt tgttgagagc tggtaacgaa    540

tctttgccag gtgacttgaa gattttgggt ggtttgttgt gttgtccatt cttctggggt    600

tctaagccaa ttggttctga agctgttgaa ggtcacgaac aatctttggc tatgaaggtt    660

tggaacttcg cttgtccaga cgctccaggt ggtattgaca acccatggat taacccatgt    720

gttccaggtg ctccatcttt ggctactttg gcttgttcta agttgttggt tactattact    780

ggtaaggacg aattcagaga cagagacatt ttgtaccacc acactgttga acaatctggt    840

tggcaaggtg aattgcaatt gttcgacgct ggtgacgaag aacacgcttt ccaattgttc    900

aagccagaaa ctcacttggc taaggctatg attaagagat tggcttcttt cttggtttaa    960
```

```
<210> SEQ ID NO 38
<211> LENGTH: 319
<212> TYPE: PRT
<213> ORGANISM: Glycine max

<400> SEQUENCE: 38

Met Ala Lys Glu Ile Val Lys Glu Leu Leu Pro Leu Ile Arg Val Tyr
1               5                   10                  15

Lys Asp Gly Ser Val Glu Arg Leu Leu Ser Ser Glu Asn Val Ala Ala
            20                  25                  30

Ser Pro Glu Asp Pro Gln Thr Gly Val Ser Ser Lys Asp Ile Val Ile
        35                  40                  45

Ala Asp Asn Pro Tyr Val Ser Ala Arg Ile Phe Leu Pro Lys Ser His
    50                  55                  60

His Thr Asn Asn Lys Leu Pro Ile Phe Leu Tyr Phe His Gly Gly Ala
65                  70                  75                  80

Phe Cys Val Glu Ser Ala Phe Ser Phe Phe Val His Arg Tyr Leu Asn
                85                  90                  95

Ile Leu Ala Ser Glu Ala Asn Ile Ile Ala Ile Ser Val Asp Phe Arg
            100                 105                 110

Leu Leu Pro His His Pro Ile Pro Ala Ala Tyr Glu Asp Gly Trp Thr
        115                 120                 125

Thr Leu Lys Trp Ile Ala Ser His Ala Asn Asn Thr Asn Thr Thr Asn
    130                 135                 140

Pro Glu Pro Trp Leu Leu Asn His Ala Asp Phe Thr Lys Val Tyr Val
145                 150                 155                 160

Gly Gly Glu Thr Ser Gly Ala Asn Ile Ala His Asn Leu Leu Leu Arg
                165                 170                 175

Ala Gly Asn Glu Ser Leu Pro Gly Asp Leu Lys Ile Leu Gly Gly Leu
            180                 185                 190

Leu Cys Cys Pro Phe Phe Trp Gly Ser Lys Pro Ile Gly Ser Glu Ala
        195                 200                 205

Val Glu Gly His Glu Gln Ser Leu Ala Met Lys Val Trp Asn Phe Ala
    210                 215                 220
```

```
Cys Pro Asp Ala Pro Gly Gly Ile Asp Asn Pro Trp Ile Asn Pro Cys
225                 230                 235                 240

Val Pro Gly Ala Pro Ser Leu Ala Thr Leu Ala Cys Ser Lys Leu Leu
                245                 250                 255

Val Thr Ile Thr Gly Lys Asp Glu Phe Arg Asp Arg Asp Ile Leu Tyr
            260                 265                 270

His His Thr Val Glu Gln Ser Gly Trp Gln Gly Glu Leu Gln Leu Phe
        275                 280                 285

Asp Ala Gly Asp Glu Glu His Ala Phe Gln Leu Phe Lys Pro Glu Thr
    290                 295                 300

His Leu Ala Lys Ala Met Ile Lys Arg Leu Ala Ser Phe Leu Val
305                 310                 315


<210> SEQ ID NO 39
<211> LENGTH: 1095
<212> TYPE: DNA
<213> ORGANISM: Malus domestica

<400> SEQUENCE: 39

atggctccag ccactacctt aacctctatt gcacatgaaa agacattaca gcagaagttc      60

gttagagatg aggatgaaag gcctaaggtt gcctataacg acttttctaa tgaaattcca     120

ataatctctt tggctggtat agacgaagta gaaggtagaa ggggagaaat atgtaagaag     180

attgttgcag cttgcgaaga ttggggcatt ttccagatcg tagaccatgg tgtagatgcc     240

gaattgatat cagaaatgac aggtttggct agagaattct tcgcattgcc ttcagaagag     300

aagttaaggt ttgatatgtc cggtggtaag aaaggtggtt ttatagtctc tagtcattta     360

cagggtgaag ccgttcaaga ttggagagaa atcgtaacat atttctcata cccaattaga     420

cacagagatt actccaggtg gcctgataag ccagaagcct ggagggaagt tactaagaaa     480

tactcagatg agttgatggg attagcttgt aaattgttgg gcgtgttgtc agaagccatg     540

ggattggata cagaggcctt gaccaaagca tgtgttgata tggaccaaaa ggtagttgtc     600

aacttctacc ctaaatgccc tcaaccagac ttgacattag gcttgaaaag acataccgac     660

cccggcacta tcactttatt attacaagac caagtcggtg gtttgcaggc tactagagac     720

gacggtaaaa cctggatcac tgttcaaccc gttgaaggag cattcgtcgt taatttgggc     780

gatcatggac acttattgtc caatggtaga tttaagaatg ctgatcacca agctgtggtc     840

aactctaata gtagtagatt atccattgct acatttcaga acccagcaca agaagcaatt     900

gtttatcctt tatctgtgag agaaggagag aagcctattt tagaggcacc aattacatat     960

actgagatgt ataagaagaa gatgtctaaa gatttggagt tagcaagatt gaagaaatta    1020

gctaaagagc aacaaagtca agatttagag aaggctaaag tggatactaa accagtggat    1080

gatatcttcg cttaa                                                     1095


<210> SEQ ID NO 40
<211> LENGTH: 364
<212> TYPE: PRT
<213> ORGANISM: Malus domestica

<400> SEQUENCE: 40

Met Ala Pro Ala Thr Thr Leu Thr Ser Ile Ala His Glu Lys Thr Leu
1               5                   10                  15

Gln Gln Lys Phe Val Arg Asp Glu Asp Glu Arg Pro Lys Val Ala Tyr
            20                  25                  30
```

-continued

```
Asn Asp Phe Ser Asn Glu Ile Pro Ile Ile Ser Leu Ala Gly Ile Asp
        35                  40                  45

Glu Val Glu Gly Arg Arg Gly Glu Ile Cys Lys Lys Ile Val Ala Ala
    50                  55                  60

Cys Glu Asp Trp Gly Ile Phe Gln Ile Val Asp His Gly Val Asp Ala
65                  70                  75                  80

Glu Leu Ile Ser Glu Met Thr Gly Leu Ala Arg Glu Phe Phe Ala Leu
                85                  90                  95

Pro Ser Glu Glu Lys Leu Arg Phe Asp Met Ser Gly Gly Lys Lys Gly
            100                 105                 110

Gly Phe Ile Val Ser Ser His Leu Gln Gly Glu Ala Val Gln Asp Trp
        115                 120                 125

Arg Glu Ile Val Thr Tyr Phe Ser Tyr Pro Ile Arg His Arg Asp Tyr
    130                 135                 140

Ser Arg Trp Pro Asp Lys Pro Glu Ala Trp Arg Glu Val Thr Lys Lys
145                 150                 155                 160

Tyr Ser Asp Glu Leu Met Gly Leu Ala Cys Lys Leu Leu Gly Val Leu
                165                 170                 175

Ser Glu Ala Met Gly Leu Asp Thr Glu Ala Leu Thr Lys Ala Cys Val
            180                 185                 190

Asp Met Asp Gln Lys Val Val Val Asn Phe Tyr Pro Lys Cys Pro Gln
        195                 200                 205

Pro Asp Leu Thr Leu Gly Leu Lys Arg His Thr Asp Pro Gly Thr Ile
    210                 215                 220

Thr Leu Leu Leu Gln Asp Gln Val Gly Gly Leu Gln Ala Thr Arg Asp
225                 230                 235                 240

Asp Gly Lys Thr Trp Ile Thr Val Gln Pro Val Glu Gly Ala Phe Val
                245                 250                 255

Val Asn Leu Gly Asp His Gly His Leu Leu Ser Asn Gly Arg Phe Lys
            260                 265                 270

Asn Ala Asp His Gln Ala Val Val Asn Ser Asn Ser Ser Arg Leu Ser
        275                 280                 285

Ile Ala Thr Phe Gln Asn Pro Ala Gln Glu Ala Ile Val Tyr Pro Leu
    290                 295                 300

Ser Val Arg Glu Gly Glu Lys Pro Ile Leu Glu Ala Pro Ile Thr Tyr
305                 310                 315                 320

Thr Glu Met Tyr Lys Lys Lys Met Ser Lys Asp Leu Glu Leu Ala Arg
                325                 330                 335

Leu Lys Lys Leu Ala Lys Glu Gln Gln Ser Gln Asp Leu Glu Lys Ala
            340                 345                 350

Lys Val Asp Thr Lys Pro Val Asp Asp Ile Phe Ala
        355                 360
```

<210> SEQ ID NO 41
<211> LENGTH: 1008
<212> TYPE: DNA
<213> ORGANISM: Citrus unshiu

<400> SEQUENCE: 41

```
atggaagttg aaagagttca agctattgct tctttgtctc actctaacgg tactattcca      60

gctgaattca ttagaccaga aaaggaacaa ccagcttcta ctacttacca cggtccagct     120

ccagaaattc caactattga cttggacgac ccagttcaag acagattggt tagatctatt     180

gctgaagctt ctagagaatg ggtattttc caagttacta accacggtat tccatctgac     240
```

-continued

```
ttgatttgta agttgcaagc tgttggtaag gaattcttcg aattgccaca agaagaaaag    300

gaagtttact ctagaccagc tgacgctaag gacgttcaag gttacggtac taagttgcaa    360

aaggaagttg aaggtaagaa gtcttgggtt gaccacttgt tccacagagt ttggccacca    420

tcttctatta actacagatt ctggccaaag aacccaccat cttacagagc tgttaacgaa    480

gaatacgcta agtacatgag agaagttgtt gacaagttgt tcacttactt gtctttgggt    540

ttgggtgttg aaggtggtgt tttgaaggaa gctgctggtg gtgacgacat tgaatacatg    600

ttgaagatta actactaccc accatgtcca agaccagact tggctttggg tgttgttgct    660

cacactgact tgtctgcttt gactgttttg gttccaaacg aagttccagg tttgcaagtt    720

ttcaaggacg acagatggat tgacgctaag tacattccaa acgctttggt tattcacatt    780

ggtgaccaaa ttgaaatttt gtctaacggt aagtacaagg ctgttttgca cagaactact    840

gttaacaagg acaagactag aatgtcttgg ccagttttct tggaaccacc agctgacact    900

gttgttggtc cattgccaca attggttgac gacgaaaacc caccaaagta caaggctaag    960

aagttcaagg actactctta ctgtaagttg aacaagttgc cacaataa                1008
```

```
<210> SEQ ID NO 42
<211> LENGTH: 335
<212> TYPE: PRT
<213> ORGANISM: Citrus unshiu

<400> SEQUENCE: 42

Met Glu Val Glu Arg Val Gln Ala Ile Ala Ser Leu Ser His Ser Asn
1               5                   10                  15

Gly Thr Ile Pro Ala Glu Phe Ile Arg Pro Glu Lys Glu Gln Pro Ala
            20                  25                  30

Ser Thr Thr Tyr His Gly Pro Ala Pro Glu Ile Pro Thr Ile Asp Leu
        35                  40                  45

Asp Asp Pro Val Gln Asp Arg Leu Val Arg Ser Ile Ala Glu Ala Ser
    50                  55                  60

Arg Glu Trp Gly Ile Phe Gln Val Thr Asn His Gly Ile Pro Ser Asp
65                  70                  75                  80

Leu Ile Cys Lys Leu Gln Ala Val Gly Lys Glu Phe Phe Glu Leu Pro
                85                  90                  95

Gln Glu Glu Lys Glu Val Tyr Ser Arg Pro Ala Asp Ala Lys Asp Val
            100                 105                 110

Gln Gly Tyr Gly Thr Lys Leu Gln Lys Glu Val Glu Gly Lys Lys Ser
        115                 120                 125

Trp Val Asp His Leu Phe His Arg Val Trp Pro Pro Ser Ser Ile Asn
    130                 135                 140

Tyr Arg Phe Trp Pro Lys Asn Pro Pro Ser Tyr Arg Ala Val Asn Glu
145                 150                 155                 160

Glu Tyr Ala Lys Tyr Met Arg Glu Val Val Asp Lys Leu Phe Thr Tyr
                165                 170                 175

Leu Ser Leu Gly Leu Gly Val Glu Gly Gly Val Leu Lys Glu Ala Ala
            180                 185                 190

Gly Gly Asp Asp Ile Glu Tyr Met Leu Lys Ile Asn Tyr Tyr Pro Pro
        195                 200                 205

Cys Pro Arg Pro Asp Leu Ala Leu Gly Val Val Ala His Thr Asp Leu
    210                 215                 220

Ser Ala Leu Thr Val Leu Val Pro Asn Glu Val Pro Gly Leu Gln Val
225                 230                 235                 240
```

```
Phe Lys Asp Asp Arg Trp Ile Asp Ala Lys Tyr Ile Pro Asn Ala Leu
                245                 250                 255

Val Ile His Ile Gly Asp Gln Ile Glu Ile Leu Ser Asn Gly Lys Tyr
            260                 265                 270

Lys Ala Val Leu His Arg Thr Thr Val Asn Lys Asp Lys Thr Arg Met
        275                 280                 285

Ser Trp Pro Val Phe Leu Glu Pro Pro Ala Asp Thr Val Val Gly Pro
    290                 295                 300

Leu Pro Gln Leu Val Asp Asp Glu Asn Pro Pro Lys Tyr Lys Ala Lys
305                 310                 315                 320

Lys Phe Lys Asp Tyr Ser Tyr Cys Lys Leu Asn Lys Leu Pro Gln
                325                 330                 335
```

<210> SEQ ID NO 43
<211> LENGTH: 1044
<212> TYPE: DNA
<213> ORGANISM: Anthurium andraeanum

<400> SEQUENCE: 43

```
atgatgcaca aaggtacagt ttgtgttact ggtgctgccg gcttcgtagg tagttggtta      60

atcatgaggt tattagaaca aggttactcc gttaaggcta cagtgagaga tccttctaac     120

atgaagaaag ttaagcattt gttggattta cccggagcag caaataggtt gactttgtgg     180

aaggcagatt tagttgatga aggttccttt gatgaaccta ttcaaggttg cacaggtgta     240

ttccatgtcg caactccaat ggatttcgag tctaaagatc ctgagagtga gatgattaaa     300

cctacaatcg agggcatgtt aaacgttttg aggtcatgtg caagagcatc cagtactgtc     360

agaagggtag ttttcacttc ctctgccggt actgttagta tccatgaagg cagaagacac     420

ttatacgatg aaaccagttg gtcagacgtc gatttctgca gggccaagaa gatgacaggt     480

tggatgtatt tcgtctctaa aaccttagca gaaaaggccg cctgggattt cgcagaaaag     540

aataacattg acttcatttc tattataccc actttagtca atggtccctt tgttatgcca     600

actatgccac catcaatgtt gtcagctttg gctttaatta ccagaaatga acctcattac     660

tcaattttga accctgtgca atttgtacat ttggatgatt tatgcaatgc tcatattttc     720

ttgtttgaat gtccagatgc taagggtaga tacatctgtt cttcacacga tgtaacaatc     780

gccggtttag ctcaaatatt gagacaaaga tatccagagt ttgacgtgcc aacagaattt     840

ggagaaatgg aggtgtttga cattatatca tattcttcta agaagttaac tgacttggga     900

tttgaattta aatattcttt agaggacatg tttgacggcg ctatacagtc ttgtagagaa     960

aagggcttgt tgcctccagc tacaaaagaa ccatcctatg ctaccgaaca attgatagct    1020

accggacagg acaatggaca ctaa                                           1044
```

<210> SEQ ID NO 44
<211> LENGTH: 347
<212> TYPE: PRT
<213> ORGANISM: Anthurium andraeanum

<400> SEQUENCE: 44

```
Met Met His Lys Gly Thr Val Cys Val Thr Gly Ala Ala Gly Phe Val
1               5                   10                  15

Gly Ser Trp Leu Ile Met Arg Leu Leu Glu Gln Gly Tyr Ser Val Lys
            20                  25                  30

Ala Thr Val Arg Asp Pro Ser Asn Met Lys Lys Val Lys His Leu Leu
        35                  40                  45
```

-continued

```
Asp Leu Pro Gly Ala Ala Asn Arg Leu Thr Leu Trp Lys Ala Asp Leu
    50                  55                  60

Val Asp Glu Gly Ser Phe Asp Glu Pro Ile Gln Gly Cys Thr Gly Val
65                  70                  75                  80

Phe His Val Ala Thr Pro Met Asp Phe Glu Ser Lys Asp Pro Glu Ser
                85                  90                  95

Glu Met Ile Lys Pro Thr Ile Glu Gly Met Leu Asn Val Leu Arg Ser
            100                 105                 110

Cys Ala Arg Ala Ser Ser Thr Val Arg Arg Val Val Phe Thr Ser Ser
        115                 120                 125

Ala Gly Thr Val Ser Ile His Glu Gly Arg Arg His Leu Tyr Asp Glu
    130                 135                 140

Thr Ser Trp Ser Asp Val Asp Phe Cys Arg Ala Lys Lys Met Thr Gly
145                 150                 155                 160

Trp Met Tyr Phe Val Ser Lys Thr Leu Ala Glu Lys Ala Ala Trp Asp
                165                 170                 175

Phe Ala Glu Lys Asn Asn Ile Asp Phe Ile Ser Ile Ile Pro Thr Leu
            180                 185                 190

Val Asn Gly Pro Phe Val Met Pro Thr Met Pro Pro Ser Met Leu Ser
        195                 200                 205

Ala Leu Ala Leu Ile Thr Arg Asn Glu Pro His Tyr Ser Ile Leu Asn
    210                 215                 220

Pro Val Gln Phe Val His Leu Asp Asp Leu Cys Asn Ala His Ile Phe
225                 230                 235                 240

Leu Phe Glu Cys Pro Asp Ala Lys Gly Arg Tyr Ile Cys Ser Ser His
                245                 250                 255

Asp Val Thr Ile Ala Gly Leu Ala Gln Ile Leu Arg Gln Arg Tyr Pro
            260                 265                 270

Glu Phe Asp Val Pro Thr Glu Phe Gly Glu Met Glu Val Phe Asp Ile
        275                 280                 285

Ile Ser Tyr Ser Ser Lys Lys Leu Thr Asp Leu Gly Phe Glu Phe Lys
    290                 295                 300

Tyr Ser Leu Glu Asp Met Phe Asp Gly Ala Ile Gln Ser Cys Arg Glu
305                 310                 315                 320

Lys Gly Leu Leu Pro Pro Ala Thr Lys Glu Pro Ser Tyr Ala Thr Glu
                325                 330                 335

Gln Leu Ile Ala Thr Gly Gln Asp Asn Gly His
            340                 345
```

<210> SEQ ID NO 45
<211> LENGTH: 1041
<212> TYPE: DNA
<213> ORGANISM: Populus trichocarpa

<400> SEQUENCE: 45

```
atgggtactg aagctgaaac cgtttgtgtt actggtgctt ctggttttat tggttcctgg      60

ttgatcatga gattattgga aaaaggttac gctgttagag ccactgttag agatccagat     120

aatatgaaga aggtcaccca cttgttggaa ttgccaaagg cttctactca tttgactttg     180

tggaaagccg atttgtctgt tgaaggttct tacgatgaag ctattcaagg ttgtactggt     240

gttttccatg ttgctactcc aatggatttc gaatctaagg atccagaaaa cgaagttatc     300

aagccaacca ttaacggtgt tttggatatt atgagagctt gcgctaactc taagaccgtt     360

agaaagatcg ttttcacttc ttctgctggt actgttgatg tcgaagaaaa aagaaagcca     420
```

-continued

```
gtctacgatg aatcttgctg gtctgatttg gatttcgtcc aatctattaa gatgaccggt    480

tggatgtact tcgtttctaa aactttggct gaacaagctg cttggaagtt cgctaaagaa    540

aacaacttgg acttcatctc cattatccca actttggttg ttggtccatt catcatgcaa    600

tctatgccac catctttgtt gactgccttg tctttgatta ctggtaacga agctcattac    660

ggtatcttga aacaaggtca ttacgttcac ttggatgact tgtgtatgtc ccatatcttc    720

ttgtacgaaa acccaaaagc tgaaggtaga tatatctgca actctgatga tgccaacatt    780

catgatttgg ctaagttgtt gagagaaaag tacccagaat acaacgttcc agctaagttc    840

aaggatatcg acgaaaattt ggcttgcgtt gctttctcat ctaagaagtt gacagatttg    900

ggtttcgaat tcaagtactc cttggaagat atgtttgctg gtgcagttga aacctgtaga    960

gaaaagggtt tgattccatt gtcccacaga aaacaagtcg tcgaagaatg caaagaaaat   1020

gaagttgttc cagcttctta a                                             1041


<210> SEQ ID NO 46
<211> LENGTH: 346
<212> TYPE: PRT
<213> ORGANISM: Populus trichocarpa

<400> SEQUENCE: 46

Met Gly Thr Glu Ala Glu Thr Val Cys Val Thr Gly Ala Ser Gly Phe
1               5                   10                  15

Ile Gly Ser Trp Leu Ile Met Arg Leu Leu Glu Lys Gly Tyr Ala Val
            20                  25                  30

Arg Ala Thr Val Arg Asp Pro Asp Asn Met Lys Lys Val Thr His Leu
        35                  40                  45

Leu Glu Leu Pro Lys Ala Ser Thr His Leu Thr Leu Trp Lys Ala Asp
    50                  55                  60

Leu Ser Val Glu Gly Ser Tyr Asp Glu Ala Ile Gln Gly Cys Thr Gly
65                  70                  75                  80

Val Phe His Val Ala Thr Pro Met Asp Phe Glu Ser Lys Asp Pro Glu
                85                  90                  95

Asn Glu Val Ile Lys Pro Thr Ile Asn Gly Val Leu Asp Ile Met Arg
            100                 105                 110

Ala Cys Ala Asn Ser Lys Thr Val Arg Lys Ile Val Phe Thr Ser Ser
        115                 120                 125

Ala Gly Thr Val Asp Val Glu Glu Lys Arg Lys Pro Val Tyr Asp Glu
    130                 135                 140

Ser Cys Trp Ser Asp Leu Asp Phe Val Gln Ser Ile Lys Met Thr Gly
145                 150                 155                 160

Trp Met Tyr Phe Val Ser Lys Thr Leu Ala Glu Gln Ala Ala Trp Lys
                165                 170                 175

Phe Ala Lys Glu Asn Asn Leu Asp Phe Ile Ser Ile Ile Pro Thr Leu
            180                 185                 190

Val Val Gly Pro Phe Ile Met Gln Ser Met Pro Pro Ser Leu Leu Thr
        195                 200                 205

Ala Leu Ser Leu Ile Thr Gly Asn Glu Ala His Tyr Gly Ile Leu Lys
    210                 215                 220

Gln Gly His Tyr Val His Leu Asp Asp Leu Cys Met Ser His Ile Phe
225                 230                 235                 240

Leu Tyr Glu Asn Pro Lys Ala Glu Gly Arg Tyr Ile Cys Asn Ser Asp
                245                 250                 255

Asp Ala Asn Ile His Asp Leu Ala Lys Leu Leu Arg Glu Lys Tyr Pro
```

```
            260                 265                 270

Glu Tyr Asn Val Pro Ala Lys Phe Lys Asp Ile Asp Glu Asn Leu Ala
        275                 280                 285

Cys Val Ala Phe Ser Ser Lys Lys Leu Thr Asp Leu Gly Phe Glu Phe
    290                 295                 300

Lys Tyr Ser Leu Glu Asp Met Phe Ala Gly Ala Val Glu Thr Cys Arg
305                 310                 315                 320

Glu Lys Gly Leu Ile Pro Leu Ser His Arg Lys Gln Val Val Glu Glu
                325                 330                 335

Cys Lys Glu Asn Glu Val Val Pro Ala Ser
            340                 345
```

<210> SEQ ID NO 47
<211> LENGTH: 1086
<212> TYPE: DNA
<213> ORGANISM: Iris x hollandica

<400> SEQUENCE: 47

```
atgatgtccc cagttgttgt tactggtgct tctggttatg ttggttcttg gttggttatg     60

aagttgttga gagatggtta tgctgttaga gctactgtta gagatccaac taatgtcgaa    120

aagaccaagc ctttgttgga tttgccaggt gctgatgctt tgttgactat ttggaaagct    180

gatttgggtc aagatggttc ttttgataag gctgttgctg gttgtactgc tgtttttcat    240

gttgctactc caatggactt cgaatctaag gatccagaaa acgaagttat caagccaacc    300

attaacggtg tcttgtccat tatgagatcc tgtaaaaaag ccggtactgt taagagagtt    360

gttttcactt cttctgctgg tactgtcgat gtcaaagaac atcaacaaac cgaatacgac    420

gaatcctctt ggtctgatgt tgatttctgt agaagagtta agatgaccgg ttggatgtac    480

ttcgtttcta aaactttggc tgaaagagct gcttgggaat ttgctagaga aaacggtatt    540

gacttcatct ccattatccc aactttggtt gttggtccat tcattactac tactatgcca    600

ccatctatgg ttaccgcttt gtcttttatg actggtaacg aagctcatta ccacattatt    660

aagcacgccc aattggttca cttggatgat ttgtgtgctg ctcatatcta cttgttgaat    720

agacctgaag ctaacggtag atatatctgc tcatctcatg aagccaccat tcatgatttg    780

gctagaatgg ttagagaaag acatccatgg tgtggttcta ttccagaaaa gttcgatggt    840

atcgaaaagg atgttagaac cgttcacttc tcatccaaga gattattgga tttgggtttc    900

gaattcaagt acaccgtcga agaaatgttc gacgaagcta ttagatcctg cgttgaaaag    960

aagttgattc cattgccaga aaatggtaac gttgatgctg ctgctggtgc taaagatatg   1020

gttcatggtg ctgaagaaca tgctagaatt gctatggaat tggaacctaa gaagaaggtt   1080

aagtaa                                                              1086
```

<210> SEQ ID NO 48
<211> LENGTH: 361
<212> TYPE: PRT
<213> ORGANISM: Iris x hollandica

<400> SEQUENCE: 48

```
Met Met Ser Pro Val Val Val Thr Gly Ala Ser Gly Tyr Val Gly Ser
1               5                   10                  15

Trp Leu Val Met Lys Leu Leu Arg Asp Gly Tyr Ala Val Arg Ala Thr
            20                  25                  30

Val Arg Asp Pro Thr Asn Val Glu Lys Thr Lys Pro Leu Leu Asp Leu
        35                  40                  45
```

-continued

```
Pro Gly Ala Asp Ala Leu Leu Thr Ile Trp Lys Ala Asp Leu Gly Gln
    50                  55                  60

Asp Gly Ser Phe Asp Lys Ala Val Ala Gly Cys Thr Ala Val Phe His
65                  70                  75                  80

Val Ala Thr Pro Met Asp Phe Glu Ser Lys Asp Pro Glu Asn Glu Val
                85                  90                  95

Ile Lys Pro Thr Ile Asn Gly Val Leu Ser Ile Met Arg Ser Cys Lys
            100                 105                 110

Lys Ala Gly Thr Val Lys Arg Val Val Phe Thr Ser Ser Ala Gly Thr
        115                 120                 125

Val Asp Val Lys Glu His Gln Gln Thr Glu Tyr Asp Glu Ser Ser Trp
    130                 135                 140

Ser Asp Val Asp Phe Cys Arg Arg Val Lys Met Thr Gly Trp Met Tyr
145                 150                 155                 160

Phe Val Ser Lys Thr Leu Ala Glu Arg Ala Ala Trp Glu Phe Ala Arg
                165                 170                 175

Glu Asn Gly Ile Asp Phe Ile Ser Ile Ile Pro Thr Leu Val Val Gly
            180                 185                 190

Pro Phe Ile Thr Thr Thr Met Pro Pro Ser Met Val Thr Ala Leu Ser
        195                 200                 205

Phe Met Thr Gly Asn Glu Ala His Tyr His Ile Ile Lys His Ala Gln
    210                 215                 220

Leu Val His Leu Asp Asp Leu Cys Ala Ala His Ile Tyr Leu Leu Asn
225                 230                 235                 240

Arg Pro Glu Ala Asn Gly Arg Tyr Ile Cys Ser Ser His Glu Ala Thr
                245                 250                 255

Ile His Asp Leu Ala Arg Met Val Arg Glu Arg His Pro Trp Cys Gly
            260                 265                 270

Ser Ile Pro Glu Lys Phe Asp Gly Ile Glu Lys Asp Val Arg Thr Val
        275                 280                 285

His Phe Ser Ser Lys Arg Leu Leu Asp Leu Gly Phe Glu Phe Lys Tyr
    290                 295                 300

Thr Val Glu Glu Met Phe Asp Glu Ala Ile Arg Ser Cys Val Glu Lys
305                 310                 315                 320

Lys Leu Ile Pro Leu Pro Glu Asn Gly Asn Val Asp Ala Ala Ala Gly
                325                 330                 335

Ala Lys Asp Met Val His Gly Ala Glu Glu His Ala Arg Ile Ala Met
            340                 345                 350

Glu Leu Glu Pro Lys Lys Lys Val Lys
        355                 360
```

<210> SEQ ID NO 49
<211> LENGTH: 1041
<212> TYPE: DNA
<213> ORGANISM: Vitis vinifera

<400> SEQUENCE: 49

```
atgactgttt ctccagttcc atctccaaag ggtagagttt tgattgctgg tgctactggt     60

ttcattggtc aattcgttgc tgctgcttct ttggacgctc acagaccaac ttacattttg    120

gctagaccag gtccaagatc tccatctaag gctaacattt tcaaggcttt ggaagacaag    180

ggtgctatta ttgtttacgg tttgattaac gaacaagaag ctatggaaaa gattttgaag    240

gaacacgaaa ttgacattgt tgtttctact gttggtggtg aatctatttt ggaccaaatt    300
```

```
gctttggtta aggctatgaa ggctgttggt actattaaga gattcttgcc atctgaattc    360

ggtcacgacg ttaacagagc tgacccagtt gaaccaggtt tgaacatgta cagagaaaag    420

agaagagtta gacaattggt tgaagaatct ggtattccat tcacttacat ttgttgtaac    480

tctattgctt cttggccata ctacaacaac attcacccat ctgaagtttt gccaccaact    540

gacttcttcc aaatttacgg tgacggtaac gttaaggctt acttcgttgc tggtactgac    600

attggtaagt tcactatgaa gactgttgac gacgttagaa ctttgaacaa gtctgttcac    660

ttcagaccat cttgtaactg tttgaacatt aacgaattgg cttctgtttg ggaaaagaag    720

attggtagaa ctttgccaag agttactgtt actgaagacg acttgttggc tgctgctggt    780

gaaaacatta ttccacaatc tgttgttgct gctttcactc acgacatttt cattaagggt    840

tgtcaagtta acttctctat tgacggtcca gaagacgttg aagttactac tttgtaccca    900

gaagactctt tcagaactgt tgaagaatgt ttcggtgaat acattgttaa gattgaagaa    960

aagcaaccaa ctgctgactc tgctattgct aacactggtc cagttgttgg tatgagacaa   1020

gttactgcta cttgtgctta a                                             1041
```

<210> SEQ ID NO 50
<211> LENGTH: 346
<212> TYPE: PRT
<213> ORGANISM: Vitis vinifera

<400> SEQUENCE: 50

```
Met Thr Val Ser Pro Val Pro Ser Pro Lys Gly Arg Val Leu Ile Ala
1               5                   10                  15

Gly Ala Thr Gly Phe Ile Gly Gln Phe Val Ala Ala Ala Ser Leu Asp
            20                  25                  30

Ala His Arg Pro Thr Tyr Ile Leu Ala Arg Pro Gly Pro Arg Ser Pro
        35                  40                  45

Ser Lys Ala Asn Ile Phe Lys Ala Leu Glu Asp Lys Gly Ala Ile Ile
    50                  55                  60

Val Tyr Gly Leu Ile Asn Glu Gln Glu Ala Met Glu Lys Ile Leu Lys
65                  70                  75                  80

Glu His Glu Ile Asp Ile Val Val Ser Thr Val Gly Gly Glu Ser Ile
                85                  90                  95

Leu Asp Gln Ile Ala Leu Val Lys Ala Met Lys Ala Val Gly Thr Ile
            100                 105                 110

Lys Arg Phe Leu Pro Ser Glu Phe Gly His Asp Val Asn Arg Ala Asp
        115                 120                 125

Pro Val Glu Pro Gly Leu Asn Met Tyr Arg Glu Lys Arg Arg Val Arg
    130                 135                 140

Gln Leu Val Glu Glu Ser Gly Ile Pro Phe Thr Tyr Ile Cys Cys Asn
145                 150                 155                 160

Ser Ile Ala Ser Trp Pro Tyr Tyr Asn Asn Ile His Pro Ser Glu Val
                165                 170                 175

Leu Pro Pro Thr Asp Phe Phe Gln Ile Tyr Gly Asp Gly Asn Val Lys
            180                 185                 190

Ala Tyr Phe Val Ala Gly Thr Asp Ile Gly Lys Phe Thr Met Lys Thr
        195                 200                 205

Val Asp Asp Val Arg Thr Leu Asn Lys Ser Val His Phe Arg Pro Ser
    210                 215                 220

Cys Asn Cys Leu Asn Ile Asn Glu Leu Ala Ser Val Trp Glu Lys Lys
225                 230                 235                 240
```

-continued

Ile Gly Arg Thr Leu Pro Arg Val Thr Val Thr Glu Asp Asp Leu Leu
245 250 255

Ala Ala Ala Gly Glu Asn Ile Ile Pro Gln Ser Val Val Ala Ala Phe
260 265 270

Thr His Asp Ile Phe Ile Lys Gly Cys Gln Val Asn Phe Ser Ile Asp
275 280 285

Gly Pro Glu Asp Val Glu Val Thr Thr Leu Tyr Pro Glu Asp Ser Phe
290 295 300

Arg Thr Val Glu Glu Cys Phe Gly Glu Tyr Ile Val Lys Ile Glu Glu
305 310 315 320

Lys Gln Pro Thr Ala Asp Ser Ala Ile Ala Asn Thr Gly Pro Val Val
325 330 335

Gly Met Arg Gln Val Thr Ala Thr Cys Ala
340 345

<210> SEQ ID NO 51
<211> LENGTH: 1017
<212> TYPE: DNA
<213> ORGANISM: Lotus corniculatus

<400> SEQUENCE: 51
atggcttcta ttaagccaat ttacgaaaag aagaaggctt gtgttattgg tggtactggt 60
ttcgttgctt ctttgttgat taagcaattg ttggaaaagg gttacgctgt taacactact 120
gttagagacc cagacaacca caagaagatt tctcacttgt tggttttgca atctttgggt 180
gaattgaaca ttttcggtgg tgaattgact gttgaaaacg acttcgacac tccaattgaa 240
ggttctgaat tggttttcca attggctact ccagttaact tcgcttctga agacccagaa 300
aacgacatga ttaagccagc tattaagggt gttttgaacg ttttgaagtc ttgtgctaga 360
gctaaggtta agagagttat tttgacttct tctgctgctt ctgttactat tggtgaattg 420
aagggtactg acttggttat ggacgaatct aactggactg acgttgaatt cttgtctaac 480
gctaagccac caacttgggg ttacccagct tctaagactt tggctgaaaa ggctgcttgg 540
aagttcgctg aagaaaacca cattgacttg attactgtta ttccatcttt gattactggt 600
ccatctttga ctccagacat tccatcttct gttggtttgg ctacttcttt gattactggt 660
aacgacttct tgattaacgc tatgaagggt atgcaattgt tgtctggttc tatttctatt 720
actcacgttg aagacgtttg tagagctcac attttcgttg ctgaaaagca atctgcttct 780
ggtagataca tttgttgtgc tcacaacact tctgttccag aattggctaa gttcttgaac 840
aagagatacc cacaatacaa ggtttctact gaattcaacg acttcccagc taaggctaag 900
ttgattattt ctccagaaaa gttgattaag gaaggtttct ctttcaagta cggtgttgaa 960
gaaattttcg accaaacttt ggaatacttg aagactaagg gtgctttgaa gaactaa 1017

<210> SEQ ID NO 52
<211> LENGTH: 338
<212> TYPE: PRT
<213> ORGANISM: Lotus corniculatus

<400> SEQUENCE: 52

Met Ala Ser Ile Lys Pro Ile Tyr Glu Lys Lys Lys Ala Cys Val Ile
1 5 10 15

Gly Gly Thr Gly Phe Val Ala Ser Leu Leu Ile Lys Gln Leu Leu Glu
20 25 30

Lys Gly Tyr Ala Val Asn Thr Thr Val Arg Asp Pro Asp Asn His Lys
35 40 45

```
Lys Ile Ser His Leu Leu Val Leu Gln Ser Leu Gly Glu Leu Asn Ile
    50                  55                  60

Phe Gly Gly Glu Leu Thr Val Glu Asn Asp Phe Asp Thr Pro Ile Glu
65                  70                  75                  80

Gly Ser Glu Leu Val Phe Gln Leu Ala Thr Pro Val Asn Phe Ala Ser
                85                  90                  95

Glu Asp Pro Glu Asn Asp Met Ile Lys Pro Ala Ile Lys Gly Val Leu
            100                 105                 110

Asn Val Leu Lys Ser Cys Ala Arg Ala Lys Val Lys Arg Val Ile Leu
        115                 120                 125

Thr Ser Ser Ala Ala Ser Val Thr Ile Gly Glu Leu Lys Gly Thr Asp
    130                 135                 140

Leu Val Met Asp Glu Ser Asn Trp Thr Asp Val Glu Phe Leu Ser Asn
145                 150                 155                 160

Ala Lys Pro Pro Thr Trp Gly Tyr Pro Ala Ser Lys Thr Leu Ala Glu
                165                 170                 175

Lys Ala Ala Trp Lys Phe Ala Glu Glu Asn His Ile Asp Leu Ile Thr
            180                 185                 190

Val Ile Pro Ser Leu Ile Thr Gly Pro Ser Leu Thr Pro Asp Ile Pro
        195                 200                 205

Ser Ser Val Gly Leu Ala Thr Ser Leu Ile Thr Gly Asn Asp Phe Leu
    210                 215                 220

Ile Asn Ala Met Lys Gly Met Gln Leu Leu Ser Gly Ser Ile Ser Ile
225                 230                 235                 240

Thr His Val Glu Asp Val Cys Arg Ala His Ile Phe Val Ala Glu Lys
                245                 250                 255

Gln Ser Ala Ser Gly Arg Tyr Ile Cys Cys Ala His Asn Thr Ser Val
            260                 265                 270

Pro Glu Leu Ala Lys Phe Leu Asn Lys Arg Tyr Pro Gln Tyr Lys Val
        275                 280                 285

Ser Thr Glu Phe Asn Asp Phe Pro Ala Lys Ala Lys Leu Ile Ile Ser
    290                 295                 300

Pro Glu Lys Leu Ile Lys Glu Gly Phe Ser Phe Lys Tyr Gly Val Glu
305                 310                 315                 320

Glu Ile Phe Asp Gln Thr Leu Glu Tyr Leu Lys Thr Lys Gly Ala Leu
                325                 330                 335

Lys Asn
```

<210> SEQ ID NO 53
<211> LENGTH: 1293
<212> TYPE: DNA
<213> ORGANISM: Petunia x hybrida

<400> SEQUENCE: 53

```
atggttaacg ccgttgttac taccccatct agagttgaat ctttggctaa gtctggtatt      60

caagccatcc caaaagaata cgttagacca caagaagaat tgaacggtat cggtaacatt     120

ttcgaagaag aaaagaaaga cgaaggtcca caagttccaa ccatcgattt gaaagaaatc     180

gactccgaag acaaagaaat cagagaaaag tgccaccaat tgaaaaaggc tgctatggaa     240

tggggtgtta tgcatttggt taatcacggt atctccgacg aattgatcaa cagagttaag     300

gttgctggtg aaaccttttt cgatcaacca gtcgaagaaa aagaaaagta cgctaacgat     360

caagccaacg gtaatgttca aggttacggt tctaaattgg ctaactctgc ttgtggtcaa     420
```

-continued

```
ttggaatggg aagattactt tttccattgc gctttcccag aagataagag agatttgtct    480

atctggccaa agaacccaac tgattatact ccagctactt ctgaatacgc caagcaaatt    540

agagctttgg ctactaagat tttgaccgtc ttgtctattg gtttgggttt ggaagaaggt    600

agattggaaa aagaagttgg tggtatggaa gatttgttgt tgcaaatgaa gatcaactac    660

tacccaaagt gtccacaacc agaattggct ttgggtgttg aagctcatac tgatgtttct    720

gctttgacct tcatcttgca taatatggtc ccaggtttac aattattcta cgaaggtcaa    780

tgggttaccg ctaagtgtgt tccaaattcc attatcatgc atatcggtga caccatcgaa    840

atcttgtcta acggtaaata caagtccatc ttgcacagag gtgttgtcaa caaagaaaag    900

gttagattct cctgggctat ttctgtgaa ccacctaaag aaaagatcat cttgaagcca    960

ttgccagaaa ctgttactga agctgaacca ccaagatttc caccaagaac ttttgctcaa   1020

catatggccc ataagttgtt cagaaaggat gataaggatg ctgccgttga acataaggtt   1080

ttcaacgaag atgaattgga tactgctgct gaacacaaag tcttgaagaa ggataatcaa   1140

gacgctgttg ctgaaaacaa ggacatcaaa gaagatgaac aatgtggtcc agcagaacac   1200

aaagatatca aagaagatgg tcaaggtgct gctgcagaaa acaaggtttt caaagaaaac   1260

aatcaagatg tcgccgccga agaatctaag taa                                1293
```

<210> SEQ ID NO 54
<211> LENGTH: 430
<212> TYPE: PRT
<213> ORGANISM: Petunia x hybrida

<400> SEQUENCE: 54

```
Met Val Asn Ala Val Val Thr Thr Pro Ser Arg Val Glu Ser Leu Ala
1               5                   10                  15

Lys Ser Gly Ile Gln Ala Ile Pro Lys Glu Tyr Val Arg Pro Gln Glu
            20                  25                  30

Glu Leu Asn Gly Ile Gly Asn Ile Phe Glu Glu Glu Lys Lys Asp Glu
        35                  40                  45

Gly Pro Gln Val Pro Thr Ile Asp Leu Lys Glu Ile Asp Ser Glu Asp
    50                  55                  60

Lys Glu Ile Arg Glu Lys Cys His Gln Leu Lys Lys Ala Ala Met Glu
65                  70                  75                  80

Trp Gly Val Met His Leu Val Asn His Gly Ile Ser Asp Glu Leu Ile
                85                  90                  95

Asn Arg Val Lys Val Ala Gly Glu Thr Phe Phe Asp Gln Pro Val Glu
            100                 105                 110

Glu Lys Glu Lys Tyr Ala Asn Asp Gln Ala Asn Gly Asn Val Gln Gly
        115                 120                 125

Tyr Gly Ser Lys Leu Ala Asn Ser Ala Cys Gly Gln Leu Glu Trp Glu
    130                 135                 140

Asp Tyr Phe Phe His Cys Ala Phe Pro Glu Asp Lys Arg Asp Leu Ser
145                 150                 155                 160

Ile Trp Pro Lys Asn Pro Thr Asp Tyr Thr Pro Ala Thr Ser Glu Tyr
                165                 170                 175

Ala Lys Gln Ile Arg Ala Leu Ala Thr Lys Ile Leu Thr Val Leu Ser
            180                 185                 190

Ile Gly Leu Gly Leu Glu Glu Gly Arg Leu Glu Lys Glu Val Gly Gly
        195                 200                 205

Met Glu Asp Leu Leu Leu Gln Met Lys Ile Asn Tyr Tyr Pro Lys Cys
    210                 215                 220
```

```
Pro Gln Pro Glu Leu Ala Leu Gly Val Glu Ala His Thr Asp Val Ser
225                 230                 235                 240

Ala Leu Thr Phe Ile Leu His Asn Met Val Pro Gly Leu Gln Leu Phe
                245                 250                 255

Tyr Glu Gly Gln Trp Val Thr Ala Lys Cys Val Pro Asn Ser Ile Ile
            260                 265                 270

Met His Ile Gly Asp Thr Ile Glu Ile Leu Ser Asn Gly Lys Tyr Lys
        275                 280                 285

Ser Ile Leu His Arg Gly Val Val Asn Lys Glu Lys Val Arg Phe Ser
    290                 295                 300

Trp Ala Ile Phe Cys Glu Pro Pro Lys Glu Lys Ile Ile Leu Lys Pro
305                 310                 315                 320

Leu Pro Glu Thr Val Thr Glu Ala Glu Pro Pro Arg Phe Pro Pro Arg
                325                 330                 335

Thr Phe Ala Gln His Met Ala His Lys Leu Phe Arg Lys Asp Asp Lys
            340                 345                 350

Asp Ala Ala Val Glu His Lys Val Phe Asn Glu Asp Glu Leu Asp Thr
        355                 360                 365

Ala Ala Glu His Lys Val Leu Lys Lys Asp Asn Gln Asp Ala Val Ala
    370                 375                 380

Glu Asn Lys Asp Ile Lys Glu Asp Glu Gln Cys Gly Pro Ala Glu His
385                 390                 395                 400

Lys Asp Ile Lys Glu Asp Gly Gln Gly Ala Ala Ala Glu Asn Lys Val
                405                 410                 415

Phe Lys Glu Asn Asn Gln Asp Val Ala Ala Glu Glu Ser Lys
            420                 425                 430
```

<210> SEQ ID NO 55
<211> LENGTH: 699
<212> TYPE: DNA
<213> ORGANISM: Petunia x hybrida

<400> SEQUENCE: 55

```
atggttgtta aggtccacgg ttctgctatg gctgcttgtc cacaaagagt tatggtttgc     60

ttgattgaat tgggtgtgga cttcgaattg atccacgttg atttggattc cttggaacaa    120

aagaagccag agtttttggt cttgcaacca tttggtcaag ttccagttat tgaagatggt    180

gactttaggt tgttcgaatc cagagctatt attaggtact acgctgctaa gtacgaagtc    240

aaaggttcta aattgactgg tactaccttg gaagaaaagg ctttggttga tcaatggttg    300

gaagtcgaat ctaacaacta caacgatctg gtttacaaca tggtcttgca gttgttggtt    360

tttccaaaga tgggtcaaac ttccgatttg accttggtta caaaatgcgc taacaagttg    420

gaaaacgtgt tcgacatcta cgaacagaga ttgtctaagt ctaaatactt ggctggtgag    480

ttcttctctt tggctgattt gtctcatttg ccatccttga gattcttgat gaatgaaggt    540

ggtttctccc acttggttac taagagaaag tgtttacacg aatggtactt ggacatctcc    600

tcaagagatt cttggaaaaa ggttctggac ctgatgatga agaagatttc cgaaattgaa    660

gccgtttcca ttccagctaa agaagaagct aaggtctga                           699
```

<210> SEQ ID NO 56
<211> LENGTH: 232
<212> TYPE: PRT
<213> ORGANISM: Petunia x hybrida

<400> SEQUENCE: 56

-continued

Met Val Val Lys Val His Gly Ser Ala Met Ala Ala Cys Pro Gln Arg
1 5 10 15

Val Met Val Cys Leu Ile Glu Leu Gly Val Asp Phe Glu Leu Ile His
20 25 30

Val Asp Leu Asp Ser Leu Glu Gln Lys Lys Pro Glu Phe Leu Val Leu
35 40 45

Gln Pro Phe Gly Gln Val Pro Val Ile Glu Asp Gly Asp Phe Arg Leu
50 55 60

Phe Glu Ser Arg Ala Ile Ile Arg Tyr Tyr Ala Ala Lys Tyr Glu Val
65 70 75 80

Lys Gly Ser Lys Leu Thr Gly Thr Thr Leu Glu Glu Lys Ala Leu Val
85 90 95

Asp Gln Trp Leu Glu Val Glu Ser Asn Asn Tyr Asn Asp Leu Val Tyr
100 105 110

Asn Met Val Leu Gln Leu Leu Val Phe Pro Lys Met Gly Gln Thr Ser
115 120 125

Asp Leu Thr Leu Val Thr Lys Cys Ala Asn Lys Leu Glu Asn Val Phe
130 135 140

Asp Ile Tyr Glu Gln Arg Leu Ser Lys Ser Lys Tyr Leu Ala Gly Glu
145 150 155 160

Phe Phe Ser Leu Ala Asp Leu Ser His Leu Pro Ser Leu Arg Phe Leu
165 170 175

Met Asn Glu Gly Gly Phe Ser His Leu Val Thr Lys Arg Lys Cys Leu
180 185 190

His Glu Trp Tyr Leu Asp Ile Ser Ser Arg Asp Ser Trp Lys Lys Val
195 200 205

Leu Asp Leu Met Met Lys Lys Ile Ser Glu Ile Glu Ala Val Ser Ile
210 215 220

Pro Ala Lys Glu Glu Ala Lys Val
225 230

<210> SEQ ID NO 57
<211> LENGTH: 1380
<212> TYPE: DNA
<213> ORGANISM: Dianthus caryophyllus

<400> SEQUENCE: 57
atgtccgcca actccaacta catgaacaag tctagattgc atgttgccgt ttttccattt 60
ccatttggta ctcatgctac ccctttgttc aacattactc aaaagttggc ttccttcatg 120
ccagatgttg ttttctcctt cttcaacatc ccacaatcca acgctaagat ttcctctgat 180
tttaagaacg acaccatcaa catgtacgat gtttgggatg gtgttccaga aggttacgtt 240
tttaaaggta agccacaaga agatatcgaa ttattcatgt tggctgctcc accaactttg 300
actgaagcct tggctaaagc tgaagttgaa actggtacaa aggtttcctg tattttgggt 360
gatgctttct tgtggttctt ggaagaattg gctcaacaaa aacaagttcc atggattacc 420
acctacatgt ccgaagaaca ttctttgttg gctcatatct gcaccgattt gattagacaa 480
accattggta ttcacgaaaa ggccgaagaa agaaaggatg aagaattaga tttcatccca 540
ggtttgtcca agatcagagt tcaagatttg cctgaaggta tcgttatggg taacttggat 600
tcttacttcg ccagaatgtt gcatcaaatg ggtagagctt tgccaagagc atctgctgta 660
tgtatttcta gttgccaaga attggatcca gttgctacca atgaattgaa cagaaagttg 720
aacaagttga ttaacgttgg tccattgtcc ttgattaccc aatcaaattc tttgccatcc 780

-continued ggtacaaaca aatctttggg ttggttggat aagcaagaat ccgaaaattc tgttgcctac 840
gtttcttttg gttcagttgc tagaccagat gctactgaaa ttactgcttt ggctcaagcc 900
ttagaagcta gtcaagttaa gttcatctgg tccatcagag ataacttgaa ggttcatttg 960
ccaggtggtt tcattgaaaa cactaaggat aagggtatgg ttgtttcttg ggttccacaa 1020
actgctgttt tagctcataa ggctgttggt gttttcatta cccatttcgg tcataactcc 1080
attatggaat ccattgcttc tgaagttcca atgattggta gaccattcat cggtgaacaa 1140
aaattgaacg gtagaatcgt tgaagccaag tggtgtattg gtttggttgt tgaaggtggt 1200
gtttttacta aggatggtgt cttgagatcc ttgaacaaga ttttgggttc tacccaaggt 1260
gaagaaatga gaagaaacat cagagacttg agattgatgg ttgataaggc tttgtctcca 1320
gatggttctt gtaacaccaa cttgaaacac ttggttgata tgatcgtcac ctccaactaa 1380

<210> SEQ ID NO 58
<211> LENGTH: 459
<212> TYPE: PRT
<213> ORGANISM: Dianthus caryophyllus

<400> SEQUENCE: 58

Met Ser Ala Asn Ser Asn Tyr Met Asn Lys Ser Arg Leu His Val Ala
1               5                   10                  15

Val Phe Pro Phe Pro Phe Gly Thr His Ala Thr Pro Leu Phe Asn Ile
            20                  25                  30

Thr Gln Lys Leu Ala Ser Phe Met Pro Asp Val Val Phe Ser Phe Phe
        35                  40                  45

Asn Ile Pro Gln Ser Asn Ala Lys Ile Ser Ser Asp Phe Lys Asn Asp
    50                  55                  60

Thr Ile Asn Met Tyr Asp Val Trp Asp Gly Val Pro Glu Gly Tyr Val
65                  70                  75                  80

Phe Lys Gly Lys Pro Gln Glu Asp Ile Glu Leu Phe Met Leu Ala Ala
                85                  90                  95

Pro Pro Thr Leu Thr Glu Ala Leu Ala Lys Ala Glu Val Glu Thr Gly
            100                 105                 110

Thr Lys Val Ser Cys Ile Leu Gly Asp Ala Phe Leu Trp Phe Leu Glu
        115                 120                 125

Glu Leu Ala Gln Gln Lys Gln Val Pro Trp Ile Thr Thr Tyr Met Ser
    130                 135                 140

Glu Glu His Ser Leu Leu Ala His Ile Cys Thr Asp Leu Ile Arg Gln
145                 150                 155                 160

Thr Ile Gly Ile His Glu Lys Ala Glu Glu Arg Lys Asp Glu Glu Leu
                165                 170                 175

Asp Phe Ile Pro Gly Leu Ser Lys Ile Arg Val Gln Asp Leu Pro Glu
            180                 185                 190

Gly Ile Val Met Gly Asn Leu Asp Ser Tyr Phe Ala Arg Met Leu His
        195                 200                 205

Gln Met Gly Arg Ala Leu Pro Arg Ala Ser Ala Val Cys Ile Ser Ser
    210                 215                 220

Cys Gln Glu Leu Asp Pro Val Ala Thr Asn Glu Leu Asn Arg Lys Leu
225                 230                 235                 240

Asn Lys Leu Ile Asn Val Gly Pro Leu Ser Leu Ile Thr Gln Ser Asn
                245                 250                 255

Ser Leu Pro Ser Gly Thr Asn Lys Ser Leu Gly Trp Leu Asp Lys Gln
            260                 265                 270

```
Glu Ser Glu Asn Ser Val Ala Tyr Val Ser Phe Gly Ser Val Ala Arg
        275                 280                 285

Pro Asp Ala Thr Glu Ile Thr Ala Leu Ala Gln Ala Leu Glu Ala Ser
    290                 295                 300

Gln Val Lys Phe Ile Trp Ser Ile Arg Asp Asn Leu Lys Val His Leu
305                 310                 315                 320

Pro Gly Gly Phe Ile Glu Asn Thr Lys Asp Lys Gly Met Val Val Ser
                325                 330                 335

Trp Val Pro Gln Thr Ala Val Leu Ala His Lys Ala Val Gly Val Phe
            340                 345                 350

Ile Thr His Phe Gly His Asn Ser Ile Met Glu Ser Ile Ala Ser Glu
        355                 360                 365

Val Pro Met Ile Gly Arg Pro Phe Ile Gly Glu Gln Lys Leu Asn Gly
    370                 375                 380

Arg Ile Val Glu Ala Lys Trp Cys Ile Gly Leu Val Val Glu Gly Gly
385                 390                 395                 400

Val Phe Thr Lys Asp Gly Val Leu Arg Ser Leu Asn Lys Ile Leu Gly
                405                 410                 415

Ser Thr Gln Gly Glu Glu Met Arg Arg Asn Ile Arg Asp Leu Arg Leu
            420                 425                 430

Met Val Asp Lys Ala Leu Ser Pro Asp Gly Ser Cys Asn Thr Asn Leu
        435                 440                 445

Lys His Leu Val Asp Met Ile Val Thr Ser Asn
    450                 455


<210> SEQ ID NO 59
<211> LENGTH: 1392
<212> TYPE: DNA
<213> ORGANISM: Fragaria x ananassa

<400> SEQUENCE: 59

atggcctcta atcaagctgg tggtcatgtt gctgttttgg cttttccatt ttctactcat     60

gctgcccctt tgttgaatat tgtctgtaga ttggctgctg ctgctccatc tactttgttt    120

tcttttttca acaccaaaca atccaactcc tccattttgg cttcagatac ttctgttttg    180

agatacacca acgtttgcgt ttgtgaagtt gctgatggtg ttccagaagg ttacgttttt    240

gttggtaaac cacaagaaga tatcgaatta ttcatgaagg ctgccccaga taacttcaga    300

aaatgtttgg aagctagtgt tgccgaatct ggtagagaag tttcttgttt ggttaccgat    360

gctttttttt ggttcggtgc tcatatggct gatgatatgg gtggtgttcc ttgggttcct    420

ttttggactg ctggtccagc ttctttgtct gctcatgttc atactgattt gatcagaaac    480

actacctctg gtgattgcca tgacgaaaaa gaaaccatta ctgttattgc cggtatgtcc    540

aaagttagac cacaagattt gccagaaggt atcattttcg gtaacttgga atccttgttc    600

tccagaatgt tgcatcaaat gggtttgatg ttgccattag ctactgccgt ttttatcaac    660

tccttcgaag aattggatcc agttatcacc aacgacttga agtctaagtt caagagattt    720

ttgaacgtcg gtccattgga tttgttggaa cctactgctt ctgctgctac tactacacca    780

caaactgctg aagctgttgc tggtgatggt tgtttgtctt ggttggataa gcaaaaagct    840

gcctctgttg tttacgtttc tttcggttct gttactagac catctcctga agaattgatg    900

gctttggctg aagccttgga agcctctaga gttccatttt tgtggtcttt gagagacaac    960

ttgaagaacc cacaattgga cgaatttttg tccaagggta aattgaacgg tatggttgtt   1020
```

-continued

```
ccatgggctc cacaaccaca agttttggct catggttctg ttggtgcttt tgttactcat   1080

tgtggttgga actctgtttt ggaatctgtt gccggtggtg taccattgat atgtagacca   1140

tttttcggtg accaaaagtt gaacgctaga atggttgaag atgtctggaa gattggtttg   1200

agattggaag gtggtgtttt caccaagaat ggtatgttga agtccttgga catgttgttg   1260

tctcaagata agggtactaa gatgaagaac aagatccaca ccttgaagca attggctcaa   1320

caagctgttg aacctaaagg ttcttctacc agaaacttcg aatctttgtt agaaatggct   1380

accaccaact aa                                                       1392


<210> SEQ ID NO 60
<211> LENGTH: 463
<212> TYPE: PRT
<213> ORGANISM: Fragaria x ananassa

<400> SEQUENCE: 60

Met Ala Ser Asn Gln Ala Gly Gly His Val Ala Val Leu Ala Phe Pro
1               5                   10                  15

Phe Ser Thr His Ala Ala Pro Leu Leu Asn Ile Val Cys Arg Leu Ala
            20                  25                  30

Ala Ala Ala Pro Ser Thr Leu Phe Ser Phe Phe Asn Thr Lys Gln Ser
        35                  40                  45

Asn Ser Ser Ile Leu Ala Ser Asp Thr Ser Val Leu Arg Tyr Thr Asn
    50                  55                  60

Val Cys Val Cys Glu Val Ala Asp Gly Val Pro Glu Gly Tyr Val Phe
65                  70                  75                  80

Val Gly Lys Pro Gln Glu Asp Ile Glu Leu Phe Met Lys Ala Ala Pro
                85                  90                  95

Asp Asn Phe Arg Lys Cys Leu Glu Ala Ser Val Ala Glu Ser Gly Arg
            100                 105                 110

Glu Val Ser Cys Leu Val Thr Asp Ala Phe Phe Trp Phe Gly Ala His
        115                 120                 125

Met Ala Asp Asp Met Gly Gly Val Pro Trp Val Pro Phe Trp Thr Ala
    130                 135                 140

Gly Pro Ala Ser Leu Ser Ala His Val His Thr Asp Leu Ile Arg Asn
145                 150                 155                 160

Thr Thr Ser Gly Asp Cys His Asp Glu Lys Glu Thr Ile Thr Val Ile
                165                 170                 175

Ala Gly Met Ser Lys Val Arg Pro Gln Asp Leu Pro Glu Gly Ile Ile
            180                 185                 190

Phe Gly Asn Leu Glu Ser Leu Phe Ser Arg Met Leu His Gln Met Gly
        195                 200                 205

Leu Met Leu Pro Leu Ala Thr Ala Val Phe Ile Asn Ser Phe Glu Glu
    210                 215                 220

Leu Asp Pro Val Ile Thr Asn Asp Leu Lys Ser Lys Phe Lys Arg Phe
225                 230                 235                 240

Leu Asn Val Gly Pro Leu Asp Leu Leu Glu Pro Thr Ala Ser Ala Ala
                245                 250                 255

Thr Thr Thr Pro Gln Thr Ala Glu Ala Val Ala Gly Asp Gly Cys Leu
            260                 265                 270

Ser Trp Leu Asp Lys Gln Lys Ala Ala Ser Val Val Tyr Val Ser Phe
        275                 280                 285

Gly Ser Val Thr Arg Pro Ser Pro Glu Glu Leu Met Ala Leu Ala Glu
    290                 295                 300
```

-continued

```
Ala Leu Glu Ala Ser Arg Val Pro Phe Leu Trp Ser Leu Arg Asp Asn
305                 310                 315                 320

Leu Lys Asn Pro Gln Leu Asp Glu Phe Leu Ser Lys Gly Lys Leu Asn
                325                 330                 335

Gly Met Val Val Pro Trp Ala Pro Gln Pro Gln Val Leu Ala His Gly
            340                 345                 350

Ser Val Gly Ala Phe Val Thr His Cys Gly Trp Asn Ser Val Leu Glu
        355                 360                 365

Ser Val Ala Gly Gly Val Pro Leu Ile Cys Arg Pro Phe Phe Gly Asp
    370                 375                 380

Gln Lys Leu Asn Ala Arg Met Val Glu Asp Val Trp Lys Ile Gly Leu
385                 390                 395                 400

Arg Leu Glu Gly Gly Val Phe Thr Lys Asn Gly Met Leu Lys Ser Leu
                405                 410                 415

Asp Met Leu Leu Ser Gln Asp Lys Gly Thr Lys Met Lys Asn Lys Ile
            420                 425                 430

His Thr Leu Lys Gln Leu Ala Gln Gln Ala Val Glu Pro Lys Gly Ser
        435                 440                 445

Ser Thr Arg Asn Phe Glu Ser Leu Leu Glu Met Ala Thr Thr Asn
    450                 455                 460


<210> SEQ ID NO 61
<211> LENGTH: 1098
<212> TYPE: DNA
<213> ORGANISM: Medicago sativa

<400> SEQUENCE: 61

atgggttcaa caggtgaaac tcaaataaca ccaacccaca tatcagatga agaagcaaac      60

ctcttcgcca tgcaactagc aagtgcttca gttcttccca tgattttgaa atcagctctt     120

gaacttgatc tcttagaaat cattgctaaa gctggacctg gtgctcaaat ttcacctatt     180

gaaattgctt ctcagctacc aacaactaac cctgatgcac cagttatgtt ggaccgaatg     240

ttgcgtctct tggcttgtta cataatcctc acatgttcag ttcgtactca acaagatgga     300

aaggttcaga gactttatgg tttggctact gttgctaagt atttggttaa gaatgaagat     360

ggtgtatcca tttctgctct taatctcatg aatcaggata aagtgctcat ggaaagctgg     420

taccacctaa aagatgcagt ccttgatggg ggcattccat tcaacaaggc ttatggaatg     480

acagcctttg aataccatgg aacagatcca aggtttaaca aggttttcaa caaggggatg     540

tctgatcact ctaccatcac aatgaagaaa attcttgaga cctacacagg ttttgaaggc     600

cttaaatctc ttgttgatgt aggtggtggt actggagctg taattaacac gattgtctca     660

aaatatccca ctataaaggg tataaatttt gatttacccc atgtcattga agatgctcca     720

tcttatccag gagttgagca tgttggtgga gacatgtttg tcagtattcc aaaggctgat     780

gctgttttta tgaagtggat ttgtcatgac tggagtgatg agcactgctt gaaatttttg     840

aagaactgct atgaggcact gccagacaat ggaaaagtga ttgtggcaga atgcatactt     900

ccagtggctc cagattcaag cctggccaca aaaggtgtgg ttcacattga tgtgatcatg     960

ttggctcata atcctggtgg gaaagagaga acacaaaaag agtttgagga tcttgccaaa    1020

ggtgctggat tccaaggttt caaagtccat tgtaatgctt tcaacacata catcatggag    1080

tttcttaaga aggtttaa                                                  1098


<210> SEQ ID NO 62
<211> LENGTH: 365
```

<212> TYPE: PRT
<213> ORGANISM: Medicago sativa

<400> SEQUENCE: 62

Met Gly Ser Thr Gly Glu Thr Gln Ile Thr Pro Thr His Ile Ser Asp
1 5 10 15

Glu Glu Ala Asn Leu Phe Ala Met Gln Leu Ala Ser Ala Ser Val Leu
20 25 30

Pro Met Ile Leu Lys Ser Ala Leu Glu Leu Asp Leu Leu Glu Ile Ile
35 40 45

Ala Lys Ala Gly Pro Gly Ala Gln Ile Ser Pro Ile Glu Ile Ala Ser
50 55 60

Gln Leu Pro Thr Thr Asn Pro Asp Ala Pro Val Met Leu Asp Arg Met
65 70 75 80

Leu Arg Leu Leu Ala Cys Tyr Ile Ile Leu Thr Cys Ser Val Arg Thr
85 90 95

Gln Gln Asp Gly Lys Val Gln Arg Leu Tyr Gly Leu Ala Thr Val Ala
100 105 110

Lys Tyr Leu Val Lys Asn Glu Asp Gly Val Ser Ile Ser Ala Leu Asn
115 120 125

Leu Met Asn Gln Asp Lys Val Leu Met Glu Ser Trp Tyr His Leu Lys
130 135 140

Asp Ala Val Leu Asp Gly Gly Ile Pro Phe Asn Lys Ala Tyr Gly Met
145 150 155 160

Thr Ala Phe Glu Tyr His Gly Thr Asp Pro Arg Phe Asn Lys Val Phe
165 170 175

Asn Lys Gly Met Ser Asp His Ser Thr Ile Thr Met Lys Lys Ile Leu
180 185 190

Glu Thr Tyr Thr Gly Phe Glu Gly Leu Lys Ser Leu Val Asp Val Gly
195 200 205

Gly Gly Thr Gly Ala Val Ile Asn Thr Ile Val Ser Lys Tyr Pro Thr
210 215 220

Ile Lys Gly Ile Asn Phe Asp Leu Pro His Val Ile Glu Asp Ala Pro
225 230 235 240

Ser Tyr Pro Gly Val Glu His Val Gly Gly Asp Met Phe Val Ser Ile
245 250 255

Pro Lys Ala Asp Ala Val Phe Met Lys Trp Ile Cys His Asp Trp Ser
260 265 270

Asp Glu His Cys Leu Lys Phe Leu Lys Asn Cys Tyr Glu Ala Leu Pro
275 280 285

Asp Asn Gly Lys Val Ile Val Ala Glu Cys Ile Leu Pro Val Ala Pro
290 295 300

Asp Ser Ser Leu Ala Thr Lys Gly Val Val His Ile Asp Val Ile Met
305 310 315 320

Leu Ala His Asn Pro Gly Gly Lys Glu Arg Thr Gln Lys Glu Phe Glu
325 330 335

Asp Leu Ala Lys Gly Ala Gly Phe Gln Gly Phe Lys Val His Cys Asn
340 345 350

Ala Phe Asn Thr Tyr Ile Met Glu Phe Leu Lys Lys Val
355 360 365

<210> SEQ ID NO 63
<211> LENGTH: 699
<212> TYPE: DNA
<213> ORGANISM: Arabidopsis thaliana

<400> SEQUENCE: 63
atggctaagg atgaagccaa gggattgctg aaaagtgaag agctctataa atatatactg 60
gagactagtg tgtacccacg cgagccagag gttctcaggg agcttaggaa cattactcat 120
aaccaccctc aagctggtat ggctactgca ccagacgctg gccagttgat ggggatgctg 180
ctgaatctgg taaatgcaag aaagactatc gaggttgggg ttttcactgg atactctctt 240
ctcctcactg ctcttacgct accagaagat ggcaaggtta tcgccattga catgaataga 300
gactcgtatg aaataggatt gccggttata aagaaagctg gtgttgaaca caaaattgat 360
ttcaaagagt ctgaagctct tccagccctc gacgagcttt taaacaataa agtgaatgag 420
ggtggattcg acttcgcatt tgtggatgca gacaagctga attattggaa ctatcatgag 480
aggcttatta gattgatcaa ggttggtggg atcatagtgt atgataacac tctctgggga 540
ggatcagttg ctgaaccgga ctcgtccacg cccgagtgga ggatagaagt caagaaagca 600
accctcgagc tgaacaagaa actctcggct gatcagcgtg tgcagatctc gcaagctgcg 660
cttggcgatg gtatcactat ttgcaggagg ttatattga 699

<210> SEQ ID NO 64
<211> LENGTH: 232
<212> TYPE: PRT
<213> ORGANISM: Arabidopsis thaliana

<400> SEQUENCE: 64

Met Ala Lys Asp Glu Ala Lys Gly Leu Leu Lys Ser Glu Glu Leu Tyr
1 5 10 15

Lys Tyr Ile Leu Glu Thr Ser Val Tyr Pro Arg Glu Pro Glu Val Leu
20 25 30

Arg Glu Leu Arg Asn Ile Thr His Asn His Pro Gln Ala Gly Met Ala
35 40 45

Thr Ala Pro Asp Ala Gly Gln Leu Met Gly Met Leu Leu Asn Leu Val
50 55 60

Asn Ala Arg Lys Thr Ile Glu Val Gly Val Phe Thr Gly Tyr Ser Leu
65 70 75 80

Leu Leu Thr Ala Leu Thr Leu Pro Glu Asp Gly Lys Val Ile Ala Ile
85 90 95

Asp Met Asn Arg Asp Ser Tyr Glu Ile Gly Leu Pro Val Ile Lys Lys
100 105 110

Ala Gly Val Glu His Lys Ile Asp Phe Lys Glu Ser Glu Ala Leu Pro
115 120 125

Ala Leu Asp Glu Leu Leu Asn Asn Lys Val Asn Glu Gly Gly Phe Asp
130 135 140

Phe Ala Phe Val Asp Ala Asp Lys Leu Asn Tyr Trp Asn Tyr His Glu
145 150 155 160

Arg Leu Ile Arg Leu Ile Lys Val Gly Gly Ile Ile Val Tyr Asp Asn
165 170 175

Thr Leu Trp Gly Gly Ser Val Ala Glu Pro Asp Ser Ser Thr Pro Glu
180 185 190

Trp Arg Ile Glu Val Lys Lys Ala Thr Leu Glu Leu Asn Lys Lys Leu
195 200 205

Ser Ala Asp Gln Arg Val Gln Ile Ser Gln Ala Ala Leu Gly Asp Gly
210 215 220

Ile Thr Ile Cys Arg Arg Leu Tyr
225 230

<210> SEQ ID NO 65
<211> LENGTH: 1527
<212> TYPE: DNA
<213> ORGANISM: Arabidopsis thaliana

<400> SEQUENCE: 65
atgtcgtggt ttctaatagc ggtggcgaca atcgccgccg tcgtatccta caagctaatc 60
caacggctaa gatacaagtt cccaccaggc ccaagcccca agccgatcgt cggtaacctc 120
tacgacataa aaccggtccg gttcagatgt tactacgagt gggctcaatc ttatggacca 180
atcatatcgg tctggatcgg ttcaattcta aacgtggtcg tatctagcgc cgagctagca 240
aaagaagttc tgaaagaaca cgaccagaaa ctcgccgacc ggcaccggaa cagatcgacg 300
gaagcattta gccgcaacgg tcaggatctt atatgggccg attatgggcc tcattacgtg 360
aaggtgagaa aagtttgcac gcttgagctc ttcacaccga aacgactcga gtctctcaga 420
cctatccgtg aagatgaagt caccgccatg gttgaatccg tcttcagaga ctgtaacctt 480
cctgaaaaca gagcaaaagg tttacaactg aggaagtact taggagcggt tgcgttcaac 540
aacataacgc ggctagcctt tgggaagcgt tttatgaacg ctgaaggtgt tgtggacgag 600
caagggcttg agttcaaggc catagtatcc aacggtctga agctaggtgc ttcactgtca 660
atagctgaac acatcccgtg gctcaggtgg atgtttccgg ctgatgagaa ggcgtttgct 720
gagcacgggg ctcgtcgtga ccgcctcact cgagctatca tggaggagca tactttggcc 780
cgtcaaaagt ctagtggagc gaaacagcat ttcgttgatg cgttgctaac gttgaaggat 840
cagtatgatc ttagtgagga tactatcatt ggtcttctat gggatatgat cacggcaggg 900
atggacacga cagcgataac agcggaatgg gcgatggcgg aaatgatcaa gaatccaaga 960
gtgcaacaaa aagtgcaaga agagttcgac agagtggttg gacttgaccg gatcttaacc 1020
gaggcagatt tctcccgctt accttacttg caatgcgtgg tgaaagagtc attcaggctg 1080
catcctccaa cgcctctaat gctacctcac cgaagcaacg cagatgtcaa gatcggaggc 1140
tatgatattc ccaaaggatc aaacgttcat gtgaatgtgt gggctgtggc tagagacccg 1200
gctgtatgga aaaatccatt tgagtttaga ccagagagat tcttggaaga agatgttgac 1260
atgaagggtc atgattttag gctgcttccg tttggagctg gaagacgggt ttgtcccggt 1320
gcacaacttg gtatcaattt ggtaacttcg atgatgagtc atttgcttca ccattttgtt 1380
tggacacctc ctcaagggac taaaccggag gagattgaca tgtctgaaaa ccctggactc 1440
gttacttaca tgcgtacccc tgtgcaagcg gttgcaacgc ctcggttgcc ttcggatctg 1500
tacaaacgcg tgccttacga tatgtaa 1527

<210> SEQ ID NO 66
<211> LENGTH: 508
<212> TYPE: PRT
<213> ORGANISM: Arabidopsis thaliana

<400> SEQUENCE: 66

Met Ser Trp Phe Leu Ile Ala Val Ala Thr Ile Ala Ala Val Val Ser
1 5 10 15

Tyr Lys Leu Ile Gln Arg Leu Arg Tyr Lys Phe Pro Pro Gly Pro Ser
20 25 30

Pro Lys Pro Ile Val Gly Asn Leu Tyr Asp Ile Lys Pro Val Arg Phe
35 40 45

Arg Cys Tyr Tyr Glu Trp Ala Gln Ser Tyr Gly Pro Ile Ile Ser Val

-continued

```
    50                  55                  60

Trp Ile Gly Ser Ile Leu Asn Val Val Val Ser Ser Ala Glu Leu Ala
65                  70                  75                  80

Lys Glu Val Leu Lys Glu His Asp Gln Lys Leu Ala Asp Arg His Arg
                85                  90                  95

Asn Arg Ser Thr Glu Ala Phe Ser Arg Asn Gly Gln Asp Leu Ile Trp
            100                 105                 110

Ala Asp Tyr Gly Pro His Tyr Val Lys Val Arg Lys Val Cys Thr Leu
        115                 120                 125

Glu Leu Phe Thr Pro Lys Arg Leu Glu Ser Leu Arg Pro Ile Arg Glu
    130                 135                 140

Asp Glu Val Thr Ala Met Val Glu Ser Val Phe Arg Asp Cys Asn Leu
145                 150                 155                 160

Pro Glu Asn Arg Ala Lys Gly Leu Gln Leu Arg Lys Tyr Leu Gly Ala
                165                 170                 175

Val Ala Phe Asn Asn Ile Thr Arg Leu Ala Phe Gly Lys Arg Phe Met
            180                 185                 190

Asn Ala Glu Gly Val Val Asp Glu Gln Gly Leu Glu Phe Lys Ala Ile
        195                 200                 205

Val Ser Asn Gly Leu Lys Leu Gly Ala Ser Leu Ser Ile Ala Glu His
    210                 215                 220

Ile Pro Trp Leu Arg Trp Met Phe Pro Ala Asp Glu Lys Ala Phe Ala
225                 230                 235                 240

Glu His Gly Ala Arg Arg Asp Arg Leu Thr Arg Ala Ile Met Glu Glu
                245                 250                 255

His Thr Leu Ala Arg Gln Lys Ser Ser Gly Ala Lys Gln His Phe Val
            260                 265                 270

Asp Ala Leu Leu Thr Leu Lys Asp Gln Tyr Asp Leu Ser Glu Asp Thr
        275                 280                 285

Ile Ile Gly Leu Leu Trp Asp Met Ile Thr Ala Gly Met Asp Thr Thr
    290                 295                 300

Ala Ile Thr Ala Glu Trp Ala Met Ala Glu Met Ile Lys Asn Pro Arg
305                 310                 315                 320

Val Gln Gln Lys Val Gln Glu Glu Phe Asp Arg Val Val Gly Leu Asp
                325                 330                 335

Arg Ile Leu Thr Glu Ala Asp Phe Ser Arg Leu Pro Tyr Leu Gln Cys
            340                 345                 350

Val Val Lys Glu Ser Phe Arg Leu His Pro Pro Thr Pro Leu Met Leu
        355                 360                 365

Pro His Arg Ser Asn Ala Asp Val Lys Ile Gly Gly Tyr Asp Ile Pro
    370                 375                 380

Lys Gly Ser Asn Val His Val Asn Val Trp Ala Val Ala Arg Asp Pro
385                 390                 395                 400

Ala Val Trp Lys Asn Pro Phe Glu Phe Arg Pro Glu Arg Phe Leu Glu
                405                 410                 415

Glu Asp Val Asp Met Lys Gly His Asp Phe Arg Leu Leu Pro Phe Gly
            420                 425                 430

Ala Gly Arg Arg Val Cys Pro Gly Ala Gln Leu Gly Ile Asn Leu Val
        435                 440                 445

Thr Ser Met Met Ser His Leu Leu His His Phe Val Trp Thr Pro Pro
    450                 455                 460

Gln Gly Thr Lys Pro Glu Glu Ile Asp Met Ser Glu Asn Pro Gly Leu
465                 470                 475                 480
```

-continued

```
Val Thr Tyr Met Arg Thr Pro Val Gln Ala Val Ala Thr Pro Arg Leu
                485                 490                 495

Pro Ser Asp Leu Tyr Lys Arg Val Pro Tyr Asp Met
            500                 505


<210> SEQ ID NO 67
<211> LENGTH: 1302
<212> TYPE: DNA
<213> ORGANISM: Arabidopsis thaliana

<400> SEQUENCE: 67

atgaaaatta acatcagaga ttccaccatg gtccggcctg ccaccgagac accaatcact      60

aatctttgga actccaacgt cgaccttgtc atccccagat tccatacccc tagtgtctac     120

ttctacagac ccaccggcgc ttccaatttc tttgaccctc aggtcatgaa ggaagctctt     180

tccaaagccc ttgtcccttt ttaccctatg gctggtcgct tgaagagaga cgatgatggt     240

cgtattgaga tcgattgtaa cggtgctggt gttctcttcg ttgtggctga tactccttct     300

gttatcgatg attttggtga ttttgctcct acccttaatc tccgtcagct tattcccgaa     360

gttgatcact ccgctggcat tcactctttc ccgcttctcg ttttgcaggt gactttcttt     420

aaatgtgggg gagcttcact tggggttggg atgcaacatc acgcggcaga tggtttctct     480

ggtcttcatt ttatcaacac atggtctgat atggctcgtg gtcttgacct aaccattcca     540

cctttcattg atcgaacact cctccgagct agggacccgc cacagcctgc ttttcatcat     600

gttgaatatc agcctgcacc aagtatgaag atacctcttg atccgtctaa atcaggacct     660

gagaatacca ctgtctctat attcaaatta acacgagacc agcttgttgc tcttaaggcg     720

aaatccaagg aggatgggaa cactgtcagc tacagctcat acgagatgtt ggcagggcat     780

gtgtggagat cagtgggaaa ggcgcgaggg cttccaaacg accaagagac gaaactgtac     840

attgcaactg atggaaggtc tagactacgt ccgcagctgc ctcctggtta ctttgggaat     900

gtgatattca ctgcaacacc attggctgtt gcaggggatt tgttatctaa gccaacatgg     960

tatgctgcag gacagattca tgatttcttg gttcgtatgg atgataacta tctgaggtca    1020

gctcttgact acctggagat gcagcctgat ctgtcagccc ttgtccgcgg tgcacatacc    1080

tacaagtgcc caaatttggg aatcacaagc tgggttagat tacctattta tgatgcagac    1140

tttggttggg gtcgtcctat ctttatggga cctggtggaa ttccatacga gggtttgtct    1200

tttgtgctac caagtcctac taatgatggc agcttatccg ttgccattgc cctccaatct    1260

gaacacatga aactgtttga gaagtttttg tttgagatat ga                       1302


<210> SEQ ID NO 68
<211> LENGTH: 433
<212> TYPE: PRT
<213> ORGANISM: Arabidopsis thaliana

<400> SEQUENCE: 68

Met Lys Ile Asn Ile Arg Asp Ser Thr Met Val Arg Pro Ala Thr Glu
1               5                   10                  15

Thr Pro Ile Thr Asn Leu Trp Asn Ser Asn Val Asp Leu Val Ile Pro
            20                  25                  30

Arg Phe His Thr Pro Ser Val Tyr Phe Tyr Arg Pro Thr Gly Ala Ser
        35                  40                  45

Asn Phe Phe Asp Pro Gln Val Met Lys Glu Ala Leu Ser Lys Ala Leu
    50                  55                  60
```

-continued

```
Val Pro Phe Tyr Pro Met Ala Gly Arg Leu Lys Arg Asp Asp Asp Gly
65                  70                  75                  80

Arg Ile Glu Ile Asp Cys Asn Gly Ala Gly Val Leu Phe Val Val Ala
                85                  90                  95

Asp Thr Pro Ser Val Ile Asp Asp Phe Gly Asp Phe Ala Pro Thr Leu
            100                 105                 110

Asn Leu Arg Gln Leu Ile Pro Glu Val Asp His Ser Ala Gly Ile His
        115                 120                 125

Ser Phe Pro Leu Leu Val Leu Gln Val Thr Phe Phe Lys Cys Gly Gly
    130                 135                 140

Ala Ser Leu Gly Val Gly Met Gln His His Ala Ala Asp Gly Phe Ser
145                 150                 155                 160

Gly Leu His Phe Ile Asn Thr Trp Ser Asp Met Ala Arg Gly Leu Asp
                165                 170                 175

Leu Thr Ile Pro Pro Phe Ile Asp Arg Thr Leu Leu Arg Ala Arg Asp
            180                 185                 190

Pro Pro Gln Pro Ala Phe His His Val Glu Tyr Gln Pro Ala Pro Ser
        195                 200                 205

Met Lys Ile Pro Leu Asp Pro Ser Lys Ser Gly Pro Glu Asn Thr Thr
    210                 215                 220

Val Ser Ile Phe Lys Leu Thr Arg Asp Gln Leu Val Ala Leu Lys Ala
225                 230                 235                 240

Lys Ser Lys Glu Asp Gly Asn Thr Val Ser Tyr Ser Ser Tyr Glu Met
                245                 250                 255

Leu Ala Gly His Val Trp Arg Ser Val Gly Lys Ala Arg Gly Leu Pro
            260                 265                 270

Asn Asp Gln Glu Thr Lys Leu Tyr Ile Ala Thr Asp Gly Arg Ser Arg
        275                 280                 285

Leu Arg Pro Gln Leu Pro Pro Gly Tyr Phe Gly Asn Val Ile Phe Thr
    290                 295                 300

Ala Thr Pro Leu Ala Val Ala Gly Asp Leu Leu Ser Lys Pro Thr Trp
305                 310                 315                 320

Tyr Ala Ala Gly Gln Ile His Asp Phe Leu Val Arg Met Asp Asp Asn
                325                 330                 335

Tyr Leu Arg Ser Ala Leu Asp Tyr Leu Glu Met Gln Pro Asp Leu Ser
            340                 345                 350

Ala Leu Val Arg Gly Ala His Thr Tyr Lys Cys Pro Asn Leu Gly Ile
        355                 360                 365

Thr Ser Trp Val Arg Leu Pro Ile Tyr Asp Ala Asp Phe Gly Trp Gly
    370                 375                 380

Arg Pro Ile Phe Met Gly Pro Gly Gly Ile Pro Tyr Glu Gly Leu Ser
385                 390                 395                 400

Phe Val Leu Pro Ser Pro Thr Asn Asp Gly Ser Leu Ser Val Ala Ile
                405                 410                 415

Ala Leu Gln Ser Glu His Met Lys Leu Phe Glu Lys Phe Leu Phe Glu
            420                 425                 430

Ile
```

<210> SEQ ID NO 69
<211> LENGTH: 1518
<212> TYPE: DNA
<213> ORGANISM: Delphinium grandiflorum

<400> SEQUENCE: 69

-continued

```
atgtgcccct cttttctagt gactcttctt cttctccagc ttagtagtct agtggtggta     60
ctagttgttt gggcagaaca attgcccgaa tttaatgtca gaagagatga tttcccatct    120
aactttgtgt tcggcgctgg tacttcagct cttcaggttg aaggggccat tgcagaagat    180
ggaaaaacac ctaatatctg ggacgtcgac agtcatatgg ggcatatgcc ggacaagagc    240
accacagata tagcttgcga ttcataccac agatataagg aagatgtgaa gataatgagt    300
gatataggac tcgaagctta tcgattttcc attgcatgga ccagaattct tccatatggg    360
agaggattca tcaatccaaa aggggtcgag tattataaca atctcatcga cacactgttg    420
gaacatggaa ttcaaccaca tgctacaata taccatatag atcaccctca gatacttgaa    480
gatgaatacg gaggatggtt aagcccgaga atgatcgagg acttcaccac ctacgcagat    540
gtatgtttta gagagtttgg cgacagggtt tcgcactgga caaccatcaa cgaacctaac    600
ataataagct tgggggctta cgacagtggt cagattccac cccatcgatg tacgcccccca   660
ggtgcctaca actgtacagc tggtaactca tccgtcgaac cttacaaagc aatgcaccat    720
ttcttgctag cccatgcgtc tgctgtgcaa atctacagga caaaatacca ggctaagcag    780
aaaggtttga tagggctcaa tgtgtacggt ttctggtgtg cacctcagac aaactcgagg    840
gcagatattg aagcaaccaa aagagccaca gctttctaca ctggctgggc tgctgatccc    900
ctcgttttcg gggactatcc aataatcatg aaagagaatg ttggctccag acttccatcg    960
tttaccaaga acgagtccga gcttgtaaaa gggtcatttg actttattgg gctgaaccat   1020
tatttcgtat tttacataca agatgaccct gaagagatta caacaccaat tagcctgaga   1080
aatttcgata gtgacatgcg tgtcaaagct tcagttaagc caggggactc tggtgatcca   1140
tctggtttaa agaacctgct tcgatatttc aaggacaact atggaaatcc tcctgtctat   1200
gttcatgaga atggatttgg gtcgccgcaa aatgagacac ttgatgacga catgggcagg   1260
atccggtaca taagcggcta cataggaagc atgcttgaag caatcaagaa tggatcagac   1320
acaagaggat attttgtgtg gtcgttcatg gacgcttttg agattctaag tggataccaa   1380
acccggtatg ggattgttca cgtcgacttt gatgataaga gtttgaagag acagctcaag   1440
ccatcagccc agtggtattc caacttcatc aagaagaaga acacaacaga ggatgagata   1500
tcgtactctt cacagtag                                                 1518
```

<210> SEQ ID NO 70
<211> LENGTH: 505
<212> TYPE: PRT
<213> ORGANISM: Delphinium grandiflorum

<400> SEQUENCE: 70

```
Met Cys Pro Ser Phe Leu Val Thr Leu Leu Leu Leu Gln Leu Ser Ser
1               5                   10                  15

Leu Val Val Val Leu Val Val Trp Ala Glu Gln Leu Pro Glu Phe Asn
            20                  25                  30

Val Arg Arg Asp Asp Phe Pro Ser Asn Phe Val Phe Gly Ala Gly Thr
        35                  40                  45

Ser Ala Leu Gln Val Glu Gly Ala Ile Ala Glu Asp Gly Lys Thr Pro
    50                  55                  60

Asn Ile Trp Asp Val Asp Ser His Met Gly His Met Pro Asp Lys Ser
65                  70                  75                  80

Thr Thr Asp Ile Ala Cys Asp Ser Tyr His Arg Tyr Lys Glu Asp Val
                85                  90                  95

Lys Ile Met Ser Asp Ile Gly Leu Glu Ala Tyr Arg Phe Ser Ile Ala
```

```
            100                 105                 110

Trp Thr Arg Ile Leu Pro Tyr Gly Arg Gly Phe Ile Asn Pro Lys Gly
        115                 120                 125

Val Glu Tyr Tyr Asn Asn Leu Ile Asp Thr Leu Leu Glu His Gly Ile
    130                 135                 140

Gln Pro His Ala Thr Ile Tyr His Ile Asp His Pro Gln Ile Leu Glu
145                 150                 155                 160

Asp Glu Tyr Gly Gly Trp Leu Ser Pro Arg Met Ile Glu Asp Phe Thr
                165                 170                 175

Thr Tyr Ala Asp Val Cys Phe Arg Glu Phe Gly Asp Arg Val Ser His
            180                 185                 190

Trp Thr Thr Ile Asn Glu Pro Asn Ile Ile Ser Leu Gly Ala Tyr Asp
        195                 200                 205

Ser Gly Gln Ile Pro Pro His Arg Cys Thr Pro Pro Gly Ala Tyr Asn
    210                 215                 220

Cys Thr Ala Gly Asn Ser Ser Val Glu Pro Tyr Lys Ala Met His His
225                 230                 235                 240

Phe Leu Leu Ala His Ala Ser Ala Val Gln Ile Tyr Arg Thr Lys Tyr
                245                 250                 255

Gln Ala Lys Gln Lys Gly Leu Ile Gly Leu Asn Val Tyr Gly Phe Trp
            260                 265                 270

Cys Ala Pro Gln Thr Asn Ser Arg Ala Asp Ile Glu Ala Thr Lys Arg
        275                 280                 285

Ala Thr Ala Phe Tyr Thr Gly Trp Ala Ala Asp Pro Leu Val Phe Gly
    290                 295                 300

Asp Tyr Pro Ile Ile Met Lys Glu Asn Val Gly Ser Arg Leu Pro Ser
305                 310                 315                 320

Phe Thr Lys Asn Glu Ser Glu Leu Val Lys Gly Ser Phe Asp Phe Ile
                325                 330                 335

Gly Leu Asn His Tyr Phe Val Phe Tyr Ile Gln Asp Asp Pro Glu Glu
            340                 345                 350

Ile Thr Thr Pro Ile Ser Leu Arg Asn Phe Asp Ser Asp Met Arg Val
        355                 360                 365

Lys Ala Ser Val Lys Pro Gly Asp Ser Gly Asp Pro Ser Gly Leu Lys
    370                 375                 380

Asn Leu Leu Arg Tyr Phe Lys Asp Asn Tyr Gly Asn Pro Pro Val Tyr
385                 390                 395                 400

Val His Glu Asn Gly Phe Gly Ser Pro Gln Asn Glu Thr Leu Asp Asp
                405                 410                 415

Asp Met Gly Arg Ile Arg Tyr Ile Ser Gly Tyr Ile Gly Ser Met Leu
            420                 425                 430

Glu Ala Ile Lys Asn Gly Ser Asp Thr Arg Gly Tyr Phe Val Trp Ser
        435                 440                 445

Phe Met Asp Ala Phe Glu Ile Leu Ser Gly Tyr Gln Thr Arg Tyr Gly
    450                 455                 460

Ile Val His Val Asp Phe Asp Asp Lys Ser Leu Lys Arg Gln Leu Lys
465                 470                 475                 480

Pro Ser Ala Gln Trp Tyr Ser Asn Phe Ile Lys Lys Lys Asn Thr Thr
                485                 490                 495

Glu Asp Glu Ile Ser Tyr Ser Ser Gln
            500                 505
```

<210> SEQ ID NO 71

<211> LENGTH: 1182
<212> TYPE: DNA
<213> ORGANISM: Pinus densiflora

<400> SEQUENCE: 71

```
atgggtggtg ttgacttcga aggtttcaga aagttgcaaa gagctgacgg tttcgcttct     60

attttggcta ttggtactgc taacccacca aacgctgttg accaatctac ttacccagac    120

tactacttca gaattactgg taacgaacac aacactgaat tgaaggacaa gttcaagaga    180

atttgtgaaa gatctgctat taagcaaaga tacatgtact tgactgaaga aattttgaag    240

aagaacccag acgtttgtgc tttcgttgaa gttccatctt tggacgctag acaagctatg    300

ttggctatgg aagttccaag attggctaag gaagctgctg aaaaggctat tcacgaatgg    360

ggtcaatcta agtctggtat tactcacttg attttctgtt ctactactac tccagacttg    420

ccaggtgctg acttcgaagt tgctaagttg ttgggtttgc acccatctgt taagagagtt    480

ggtgttttcc aacacggttg tttcgctggt ggtactgttt tgagattggc taaggacttg    540

gctgaaaaca acagaggtgc tagagttttg gttatttgtt ctgaaactac tgctgttact    600

ttcagaggtc catctgaaac tcacttggac tctttggttg gtcaagcttt gttcggtgac    660

ggtgcttctg ctttgattgt tggtgctgac ccaattccac aagttgaaaa ggcttgtttc    720

gaaattgtta gaacttctca aactgttgtt ccaaactctg acggtgctat tggtggtaag    780

gttagagaag ttggtttgac tttccaattg aagggtgctg ttccagactt gatttctgct    840

aacattgaaa actgtttggt tgaagctttc tctcaattca agatttgtga ctggaacaag    900

ttgttctggg ttgttcaccc aggtggtaga gctattttgg acagagttga agctaagttg    960

aacttggacc caactaagtt gattccaact agacacgtta tgtctgaata cggtaacatg   1020

tcttctgctt gtgttcactt cattttggac gaaactagaa aggcttcttt gagaaacggt   1080

tgttctacta ctggtgaagg tttggaaatg ggtgttttgt tcggtttcgg tccaggtttg   1140

actattgaaa ctgttgtttt gaagtctgtt ccattgcaat ag                       1182
```

<210> SEQ ID NO 72
<211> LENGTH: 393
<212> TYPE: PRT
<213> ORGANISM: Pinus densiflora

<400> SEQUENCE: 72

```
Met Gly Gly Val Asp Phe Glu Gly Phe Arg Lys Leu Gln Arg Ala Asp
1               5                   10                  15

Gly Phe Ala Ser Ile Leu Ala Ile Gly Thr Ala Asn Pro Pro Asn Ala
            20                  25                  30

Val Asp Gln Ser Thr Tyr Pro Asp Tyr Tyr Phe Arg Ile Thr Gly Asn
        35                  40                  45

Glu His Asn Thr Glu Leu Lys Asp Lys Phe Lys Arg Ile Cys Glu Arg
    50                  55                  60

Ser Ala Ile Lys Gln Arg Tyr Met Tyr Leu Thr Glu Glu Ile Leu Lys
65                  70                  75                  80

Lys Asn Pro Asp Val Cys Ala Phe Val Glu Val Pro Ser Leu Asp Ala
                85                  90                  95

Arg Gln Ala Met Leu Ala Met Glu Val Pro Arg Leu Ala Lys Glu Ala
            100                 105                 110

Ala Glu Lys Ala Ile His Glu Trp Gly Gln Ser Lys Ser Gly Ile Thr
        115                 120                 125

His Leu Ile Phe Cys Ser Thr Thr Thr Pro Asp Leu Pro Gly Ala Asp
```

-continued

```
130                 135                 140

Phe Glu Val Ala Lys Leu Leu Gly Leu His Pro Ser Val Lys Arg Val
145                 150                 155                 160

Gly Val Phe Gln His Gly Cys Phe Ala Gly Gly Thr Val Leu Arg Leu
                165                 170                 175

Ala Lys Asp Leu Ala Glu Asn Asn Arg Gly Ala Arg Val Leu Val Ile
            180                 185                 190

Cys Ser Glu Thr Thr Ala Val Thr Phe Arg Gly Pro Ser Glu Thr His
        195                 200                 205

Leu Asp Ser Leu Val Gly Gln Ala Leu Phe Gly Asp Gly Ala Ser Ala
    210                 215                 220

Leu Ile Val Gly Ala Asp Pro Ile Pro Gln Val Glu Lys Ala Cys Phe
225                 230                 235                 240

Glu Ile Val Arg Thr Ser Gln Thr Val Val Pro Asn Ser Asp Gly Ala
                245                 250                 255

Ile Gly Gly Lys Val Arg Glu Val Gly Leu Thr Phe Gln Leu Lys Gly
            260                 265                 270

Ala Val Pro Asp Leu Ile Ser Ala Asn Ile Glu Asn Cys Leu Val Glu
        275                 280                 285

Ala Phe Ser Gln Phe Lys Ile Cys Asp Trp Asn Lys Leu Phe Trp Val
    290                 295                 300

Val His Pro Gly Gly Arg Ala Ile Leu Asp Arg Val Glu Ala Lys Leu
305                 310                 315                 320

Asn Leu Asp Pro Thr Lys Leu Ile Pro Thr Arg His Val Met Ser Glu
                325                 330                 335

Tyr Gly Asn Met Ser Ser Ala Cys Val His Phe Ile Leu Asp Glu Thr
            340                 345                 350

Arg Lys Ala Ser Leu Arg Asn Gly Cys Ser Thr Thr Gly Glu Gly Leu
        355                 360                 365

Glu Met Gly Val Leu Phe Gly Phe Gly Pro Gly Leu Thr Ile Glu Thr
    370                 375                 380

Val Val Leu Lys Ser Val Pro Leu Gln
385                 390
```

<210> SEQ ID NO 73
<211> LENGTH: 1179
<212> TYPE: DNA
<213> ORGANISM: Vitis vinifera

<400> SEQUENCE: 73

```
atggcttctg ttgaagaaat tagaaacgct caaagagcta agggtccagc tactattttg     60

gctattggta ctgctactcc agaccactgt gtttaccaat ctgactacgc tgactactac    120

ttcagagtta ctaagtctga acacatgact gctttgaaga agaagttcaa cagaatttgt    180

gacaagtcta tgattaagaa gagatacatt cacttgactg aagaaatgtt ggaagaacac    240

ccaaacattg gtgcttacat ggctccatct ttgaacatta gacaagaaat tattactgct    300

gaagttccaa agttgggtaa ggaagctgct ttgaaggctt tgaaggaatg gggtcaacca    360

aagtctaaga ttactcactt ggttttctgt actacttctg gtgttgaaat gccaggtgct    420

gactacaagt tggctaactt gttgggtttg gaaccatctg ttagaagagt tatgttggac    480

caacaaggtt gttacgctgg tggtactgtt ttgagaactg ctaaggactt ggctgaaaac    540

aacgctggtg ctagagtttt ggttgtttgt tctgaatcta ctgttgttac tttcagaggt    600

ccatctgaag acgctttgga ctctttggtt ggtcaagctt tgttcggtga cggttctgct    660
```

```
gctgttattg ttggttctga cccagacatt tctattgaaa gaccattgtt ccaattggtt    720

tctgctgctc aaactttcat tccaaactct gctggtgcta ttgctggtaa cttgagagaa    780

gttggtttga ctttccactt gtggccaaac gttccaactt tgatttctga aaacattgaa    840

aagtgtttga ctcaagcttt cgacccattg ggtatttctg actggaactc tttgttctgg    900

attgctcacc caggtggtcc agctattttg gacgctgttg aagctaagtt gaacttggac    960

aagaagaagt tggaagctac tagacacgtt ttgtctgaat acggtaacat gtcttctgct   1020

tgtgttttgt tcattttgga cgaaatgaga aagaagtctt tgaagggtga aagagctact   1080

actggtgaag gtttggactg gggtgttttg ttcggtttcg gtccaggttt gactattgaa   1140

actgttgttt tgcactctat tccaatggtt actaactaa                          1179
```

<210> SEQ ID NO 74
<211> LENGTH: 392
<212> TYPE: PRT
<213> ORGANISM: Vitis vinifera

<400> SEQUENCE: 74

```
Met Ala Ser Val Glu Glu Ile Arg Asn Ala Gln Arg Ala Lys Gly Pro
1               5                   10                  15

Ala Thr Ile Leu Ala Ile Gly Thr Ala Thr Pro Asp His Cys Val Tyr
            20                  25                  30

Gln Ser Asp Tyr Ala Asp Tyr Tyr Phe Arg Val Thr Lys Ser Glu His
        35                  40                  45

Met Thr Ala Leu Lys Lys Lys Phe Asn Arg Ile Cys Asp Lys Ser Met
    50                  55                  60

Ile Lys Lys Arg Tyr Ile His Leu Thr Glu Glu Met Leu Glu Glu His
65                  70                  75                  80

Pro Asn Ile Gly Ala Tyr Met Ala Pro Ser Leu Asn Ile Arg Gln Glu
                85                  90                  95

Ile Ile Thr Ala Glu Val Pro Lys Leu Gly Lys Glu Ala Ala Leu Lys
            100                 105                 110

Ala Leu Lys Glu Trp Gly Gln Pro Lys Ser Lys Ile Thr His Leu Val
        115                 120                 125

Phe Cys Thr Thr Ser Gly Val Glu Met Pro Gly Ala Asp Tyr Lys Leu
    130                 135                 140

Ala Asn Leu Leu Gly Leu Glu Pro Ser Val Arg Arg Val Met Leu Asp
145                 150                 155                 160

Gln Gln Gly Cys Tyr Ala Gly Gly Thr Val Leu Arg Thr Ala Lys Asp
                165                 170                 175

Leu Ala Glu Asn Asn Ala Gly Ala Arg Val Leu Val Val Cys Ser Glu
            180                 185                 190

Ser Thr Val Val Thr Phe Arg Gly Pro Ser Glu Asp Ala Leu Asp Ser
        195                 200                 205

Leu Val Gly Gln Ala Leu Phe Gly Asp Gly Ser Ala Ala Val Ile Val
    210                 215                 220

Gly Ser Asp Pro Asp Ile Ser Ile Glu Arg Pro Leu Phe Gln Leu Val
225                 230                 235                 240

Ser Ala Ala Gln Thr Phe Ile Pro Asn Ser Ala Gly Ala Ile Ala Gly
                245                 250                 255

Asn Leu Arg Glu Val Gly Leu Thr Phe His Leu Trp Pro Asn Val Pro
            260                 265                 270

Thr Leu Ile Ser Glu Asn Ile Glu Lys Cys Leu Thr Gln Ala Phe Asp
```

275 280 285

Pro Leu Gly Ile Ser Asp Trp Asn Ser Leu Phe Trp Ile Ala His Pro
290 295 300

Gly Gly Pro Ala Ile Leu Asp Ala Val Glu Ala Lys Leu Asn Leu Asp
305 310 315 320

Lys Lys Lys Leu Glu Ala Thr Arg His Val Leu Ser Glu Tyr Gly Asn
325 330 335

Met Ser Ser Ala Cys Val Leu Phe Ile Leu Asp Glu Met Arg Lys Lys
340 345 350

Ser Leu Lys Gly Glu Arg Ala Thr Thr Gly Glu Gly Leu Asp Trp Gly
355 360 365

Val Leu Phe Gly Phe Gly Pro Gly Leu Thr Ile Glu Thr Val Val Leu
370 375 380

His Ser Ile Pro Met Val Thr Asn
385 390

<210> SEQ ID NO 75
<211> LENGTH: 1125
<212> TYPE: DNA
<213> ORGANISM: Sorghum bicolor

<400> SEQUENCE: 75
atggtactca tcagcgagga cagtagggag ttgctccaag cccacgtcga gctatggaac 60
cagacctaca gctttatgaa gtcggtggcg ctcgccgttg ctttagacct ccgcatcgct 120
gatgccatcc accgctgcgg tggcgccgcc accctctccc agatactcgg agagattggt 180
gtccgcccat gtaagcttcc cgccctccac cgcctaatgc gtgttctgac cgtctcagga 240
accttcacca tcgtccagcc atcagcggca accatgtcat tggtgtcgga cgggaatgag 300
cttgtctata agctgacaac agcgtcccgc ctcctcgtca gcagcgaaag ctcggcgacg 360
gcgagcttgt ctcctatgct gaaccacgtg cttagcccct tccgtgactc gcccctcagc 420
atggggctca ctgcgtggtt ccggcacgat gaagatgaac aggcgcctgg cccatgcccg 480
ttcaccctga tgtacggcac aaccttgtgg gaggtgtgca gtcgtgacga cgcaatcaac 540
gcgttgttca acaacgccat ggccgcagac agcaacttcc tgatgcagat tgtgttgagg 600
gagttcggca aggtcttcca cgggatagac tcgctggtcg acgtcggcgg tggggttggg 660
ggagccacca tggccattgc cacggcgttc ccgtctttga agtgtaccgt actagacctc 720
cctcacgttg tcgccaaggc tccgtccagt tctattggca acgtgcagtt tgttgggggt 780
gacatgtttg agagcattcc accagcgaat gttgtcttcc tcaagtggat tttgcatgac 840
tggagcaatg acgagtgtat caagatatta aagaactgca agcaagctat cccttctaga 900
gatgcaggag gaaagataat aatcattgat gttgtggttg ggtctgagtc atcagacacc 960
aagcttctgg agacacaagt aatgtatgat ctccatctca tgaaaattgg tggggttgaa 1020
cgagatgagc aagagtggaa gaaaatattc ctcgaagctg gatttaagga ctacaatatt 1080
ataccagttt taggcctccg atcgatcatt gagctatatc catga 1125

<210> SEQ ID NO 76
<211> LENGTH: 374
<212> TYPE: PRT
<213> ORGANISM: Sorghum bicolor

<400> SEQUENCE: 76

Met Val Leu Ile Ser Glu Asp Ser Arg Glu Leu Leu Gln Ala His Val
1 5 10 15

```
Glu Leu Trp Asn Gln Thr Tyr Ser Phe Met Lys Ser Val Ala Leu Ala
            20                  25                  30

Val Ala Leu Asp Leu Arg Ile Ala Asp Ala Ile His Arg Cys Gly Gly
        35                  40                  45

Ala Ala Thr Leu Ser Gln Ile Leu Gly Glu Ile Gly Val Arg Pro Cys
    50                  55                  60

Lys Leu Pro Ala Leu His Arg Leu Met Arg Val Leu Thr Val Ser Gly
65                  70                  75                  80

Thr Phe Thr Ile Val Gln Pro Ser Ala Ala Thr Met Ser Leu Val Ser
                85                  90                  95

Asp Gly Asn Glu Leu Val Tyr Lys Leu Thr Thr Ala Ser Arg Leu Leu
            100                 105                 110

Val Ser Ser Glu Ser Ser Ala Thr Ala Ser Leu Ser Pro Met Leu Asn
        115                 120                 125

His Val Leu Ser Pro Phe Arg Asp Ser Pro Leu Ser Met Gly Leu Thr
    130                 135                 140

Ala Trp Phe Arg His Asp Glu Asp Glu Gln Ala Pro Gly Pro Cys Pro
145                 150                 155                 160

Phe Thr Leu Met Tyr Gly Thr Thr Leu Trp Glu Val Cys Ser Arg Asp
                165                 170                 175

Asp Ala Ile Asn Ala Leu Phe Asn Asn Ala Met Ala Ala Asp Ser Asn
            180                 185                 190

Phe Leu Met Gln Ile Val Leu Arg Glu Phe Gly Lys Val Phe His Gly
        195                 200                 205

Ile Asp Ser Leu Val Asp Val Gly Gly Gly Val Gly Gly Ala Thr Met
    210                 215                 220

Ala Ile Ala Thr Ala Phe Pro Ser Leu Lys Cys Thr Val Leu Asp Leu
225                 230                 235                 240

Pro His Val Val Ala Lys Ala Pro Ser Ser Ser Ile Gly Asn Val Gln
                245                 250                 255

Phe Val Gly Gly Asp Met Phe Glu Ser Ile Pro Pro Ala Asn Val Val
            260                 265                 270

Phe Leu Lys Trp Ile Leu His Asp Trp Ser Asn Asp Glu Cys Ile Lys
        275                 280                 285

Ile Leu Lys Asn Cys Lys Gln Ala Ile Pro Ser Arg Asp Ala Gly Gly
    290                 295                 300

Lys Ile Ile Ile Ile Asp Val Val Val Gly Ser Glu Ser Ser Asp Thr
305                 310                 315                 320

Lys Leu Leu Glu Thr Gln Val Met Tyr Asp Leu His Leu Met Lys Ile
                325                 330                 335

Gly Gly Val Glu Arg Asp Glu Gln Glu Trp Lys Lys Ile Phe Leu Glu
            340                 345                 350

Ala Gly Phe Lys Asp Tyr Asn Ile Ile Pro Val Leu Gly Leu Arg Ser
        355                 360                 365

Ile Ile Glu Leu Tyr Pro
    370


<210> SEQ ID NO 77
<211> LENGTH: 1383
<212> TYPE: DNA
<213> ORGANISM: Dahlia variabilis

<400> SEQUENCE: 77

atggacaaca tcccaaactt gaccatcttg gaacactcta gaatttctcc accaccatct      60
```

```
actattggtc atagatcatt gccattgact ttcttcgata ttgcctggtt gttgtttcca    120

ccagttcatc acttgtactt ctaccatttt ccatactcca agtcccattt caccgaaact    180

gttatcccaa atttgaagca ctccttgtcc attaccttgc aacattactt tccattcgtc    240

ggtaagttga tcgtttaccc aaatccacat gattctacca gaaagccaga aatcagacat    300

gttgaaggtg attctgttgc tttgactttc gctgaaacta ccttggattt caacgatttg    360

tctgctaacc atccaagaaa gtgcgaaaat ttctatccat tggttccacc attgggtaac    420

gctgtaaaag aatctgatta cgttaccttg ccagttttct ctgttcaagt tacttacttc    480

ccaaactccg gtatttctat tggtttgacc aaccatcact ctttgtctga tgctaacact    540

agattcggtt ttttgaaggc ttgggcttct gtttgtgaaa ctggtgaaga tcaaccattc    600

ttgaaaaatg gttccccacc agttttcgat agagttgttg ttaacccaca attatacgaa    660

aacagattga atcaaaccag attgggtact ttctaccaag ctccttcttt ggttggttct    720

tcatctgata gagttagagc tactttcgtt ttggccagaa ctcatatttc cggtttgaag    780

aagcaagtct tgactcaatt gccaatgttg gaatacactt cttctttcac tgttacctgc    840

ggttacattt ggtcttgtat cgttaagtcc ttggtcaaca tgggtgaaaa aaagggtgaa    900

gatgaattgg aacaattcat cgtttctgtc ggttgcagat caagattaga tccaccatta    960

ccagaaaact acttcggtaa ctgttctgct ccatgtattg tcactattaa gaacggtgtc   1020

ttgaagggtg aaaacggttt tgttatggct gctaagttga ttggtgaagg tatctctaag   1080

atggttaaca agaagggtgg tattttggaa tacgctgata gatggtacga tggttttaag   1140

attccagcta gaaagatggg tatttctggt actccaaagt tgaacttcta cgatattgat   1200

ttcggttggg gtaaggctat gaagtacgaa gttgtttcta ttgactactc cgcctctgtt   1260

tctttgtcag cttgtaaaga atccgcccaa gatttgaaa ttggtgtttg tttcccatcc    1320

atgcaaatgg aagcctttgg taaaatcttt aacgacggtt tggaatccgc tattgcttct   1380

taa                                                                 1383
```

```
<210> SEQ ID NO 78
<211> LENGTH: 460
<212> TYPE: PRT
<213> ORGANISM: Dahlia variabilis

<400> SEQUENCE: 78

Met Asp Asn Ile Pro Asn Leu Thr Ile Leu Glu His Ser Arg Ile Ser
1               5                   10                  15

Pro Pro Pro Ser Thr Ile Gly His Arg Ser Leu Pro Leu Thr Phe Phe
            20                  25                  30

Asp Ile Ala Trp Leu Leu Phe Pro Pro Val His His Leu Tyr Phe Tyr
        35                  40                  45

His Phe Pro Tyr Ser Lys Ser His Phe Thr Glu Thr Val Ile Pro Asn
    50                  55                  60

Leu Lys His Ser Leu Ser Ile Thr Leu Gln His Tyr Phe Pro Phe Val
65                  70                  75                  80

Gly Lys Leu Ile Val Tyr Pro Asn Pro His Asp Ser Thr Arg Lys Pro
                85                  90                  95

Glu Ile Arg His Val Glu Gly Asp Ser Val Ala Leu Thr Phe Ala Glu
            100                 105                 110

Thr Thr Leu Asp Phe Asn Asp Leu Ser Ala Asn His Pro Arg Lys Cys
        115                 120                 125
```

-continued

```
Glu Asn Phe Tyr Pro Leu Val Pro Pro Leu Gly Asn Ala Val Lys Glu
    130                 135                 140

Ser Asp Tyr Val Thr Leu Pro Val Phe Ser Val Gln Val Thr Tyr Phe
145                 150                 155                 160

Pro Asn Ser Gly Ile Ser Ile Gly Leu Thr Asn His His Ser Leu Ser
                165                 170                 175

Asp Ala Asn Thr Arg Phe Gly Phe Leu Lys Ala Trp Ala Ser Val Cys
            180                 185                 190

Glu Thr Gly Glu Asp Gln Pro Phe Leu Lys Asn Gly Ser Pro Pro Val
        195                 200                 205

Phe Asp Arg Val Val Val Asn Pro Gln Leu Tyr Glu Asn Arg Leu Asn
    210                 215                 220

Gln Thr Arg Leu Gly Thr Phe Tyr Gln Ala Pro Ser Leu Val Gly Ser
225                 230                 235                 240

Ser Ser Asp Arg Val Arg Ala Thr Phe Val Leu Ala Arg Thr His Ile
                245                 250                 255

Ser Gly Leu Lys Lys Gln Val Leu Thr Gln Leu Pro Met Leu Glu Tyr
            260                 265                 270

Thr Ser Ser Phe Thr Val Thr Cys Gly Tyr Ile Trp Ser Cys Ile Val
        275                 280                 285

Lys Ser Leu Val Asn Met Gly Glu Lys Lys Gly Glu Asp Glu Leu Glu
    290                 295                 300

Gln Phe Ile Val Ser Val Gly Cys Arg Ser Arg Leu Asp Pro Pro Leu
305                 310                 315                 320

Pro Glu Asn Tyr Phe Gly Asn Cys Ser Ala Pro Cys Ile Val Thr Ile
                325                 330                 335

Lys Asn Gly Val Leu Lys Gly Glu Asn Gly Phe Val Met Ala Ala Lys
            340                 345                 350

Leu Ile Gly Glu Gly Ile Ser Lys Met Val Asn Lys Lys Gly Gly Ile
        355                 360                 365

Leu Glu Tyr Ala Asp Arg Trp Tyr Asp Gly Phe Lys Ile Pro Ala Arg
    370                 375                 380

Lys Met Gly Ile Ser Gly Thr Pro Lys Leu Asn Phe Tyr Asp Ile Asp
385                 390                 395                 400

Phe Gly Trp Gly Lys Ala Met Lys Tyr Glu Val Val Ser Ile Asp Tyr
                405                 410                 415

Ser Ala Ser Val Ser Leu Ser Ala Cys Lys Glu Ser Ala Gln Asp Phe
            420                 425                 430

Glu Ile Gly Val Cys Phe Pro Ser Met Gln Met Glu Ala Phe Gly Lys
        435                 440                 445

Ile Phe Asn Asp Gly Leu Glu Ser Ala Ile Ala Ser
    450                 455                 460
```

<210> SEQ ID NO 79
<211> LENGTH: 1407
<212> TYPE: DNA
<213> ORGANISM: Arabidopsis thaliana

<400> SEQUENCE: 79

```
atggttgctc acttgcaacc accaaagatt attgaaactt gtcacatttc tccaccaaag     60

ggtactgttc catctactac tttgccattg actttcttcg acgctccatg gttgtctttg    120

ccattggctg actctttgtt cttcttctct taccaaaact ctactgaatc tttcttgcaa    180

gacttcgttc caaacttgaa gcactctttg tctattactt tgcaacactt cttcccatac    240
```

-continued

```
gctggtaagt tgattattcc accaagacca gacccaccat acttgcacta caacgacggt    300
caagactctt tggttttcac tgttgctgaa tctactgaaa ctgacttcga ccaattgaag    360
tctgactctc caaaggacat ttctgttttg cacggtgttt tgccaaagtt gccaccacca    420
cacgtttctc cagaaggtat tcaaatgaga ccaattatgg ctatgcaagt tactattttc    480
ccaggtgctg gtatttgtat tggtaactct gctactcacg ttgttgctga cggtgttact    540
ttctctcact tcatgaagta ctggatgtct ttgactaagt cttctggtaa ggacccagct    600
actgttttgt tgccatcttt gccaattcac tcttgtagaa acatgattaa ggacccaggt    660
gaagttggtg ctggtcactt ggaaagattc tggtctcaaa actctgctaa gcactcttct    720
cacgttactc cagaaaacat ggttagagct actttcactt tgtctagaaa gcaaattgac    780
aacttgaagt cttgggttac tgaacaatct gaaaaccaat ctccagtttc tactttcgtt    840
gttactttgg ctttcatttg ggtttctttg attaagactt tggttcaaga ctctgaaact    900
aaggctaacg aagaagacaa ggacgaagtt ttccacttga tgattaacgt tgactgtaga    960
aacagattga agtacactca accaattcca caaacttact tcggtaactg tatggctcca   1020
ggtattgttt ctgttaagaa gcacgacttg ttgggtgaaa agtgtgtttt ggctgcttct   1080
gacgctatta ctgctagaat taaggacatg ttgtcttctg acttgttgaa gactgctcca   1140
agatggggtc aaggtgttag aaagtgggtt atgtctcact acccaacttc tattgctggt   1200
gctccaaagt tgggtttgta cgacatggac ttcggtttgg gtaagccatg taagatggaa   1260
attgttcaca ttgaaactgg tggttctatt gctttctctg aatctagaga cggttctaac   1320
ggtgttgaaa ttggtattgc tttggaaaag aagaagatgg acgttttcga ctctattttg   1380
caacaaggta ttaagaagtt cgctact                                       1407

<210> SEQ ID NO 80
<211> LENGTH: 469
<212> TYPE: PRT
<213> ORGANISM: Arabidopsis thaliana

<400> SEQUENCE: 80

Met Val Ala His Leu Gln Pro Pro Lys Ile Ile Glu Thr Cys His Ile
1               5                   10                  15

Ser Pro Pro Lys Gly Thr Val Pro Ser Thr Thr Leu Pro Leu Thr Phe
            20                  25                  30

Phe Asp Ala Pro Trp Leu Ser Leu Pro Leu Ala Asp Ser Leu Phe Phe
        35                  40                  45

Phe Ser Tyr Gln Asn Ser Thr Glu Ser Phe Leu Gln Asp Phe Val Pro
    50                  55                  60

Asn Leu Lys His Ser Leu Ser Ile Thr Leu Gln His Phe Phe Pro Tyr
65                  70                  75                  80

Ala Gly Lys Leu Ile Ile Pro Pro Arg Pro Asp Pro Pro Tyr Leu His
                85                  90                  95

Tyr Asn Asp Gly Gln Asp Ser Leu Val Phe Thr Val Ala Glu Ser Thr
            100                 105                 110

Glu Thr Asp Phe Asp Gln Leu Lys Ser Asp Ser Pro Lys Asp Ile Ser
        115                 120                 125

Val Leu His Gly Val Leu Pro Lys Leu Pro Pro Pro His Val Ser Pro
    130                 135                 140

Glu Gly Ile Gln Met Arg Pro Ile Met Ala Met Gln Val Thr Ile Phe
145                 150                 155                 160

Pro Gly Ala Gly Ile Cys Ile Gly Asn Ser Ala Thr His Val Val Ala
```

165 170 175

Asp Gly Val Thr Phe Ser His Phe Met Lys Tyr Trp Met Ser Leu Thr
180 185 190

Lys Ser Ser Gly Lys Asp Pro Ala Thr Val Leu Leu Pro Ser Leu Pro
195 200 205

Ile His Ser Cys Arg Asn Met Ile Lys Asp Pro Gly Glu Val Gly Ala
210 215 220

Gly His Leu Glu Arg Phe Trp Ser Gln Asn Ser Ala Lys His Ser Ser
225 230 235 240

His Val Thr Pro Glu Asn Met Val Arg Ala Thr Phe Thr Leu Ser Arg
245 250 255

Lys Gln Ile Asp Asn Leu Lys Ser Trp Val Thr Glu Gln Ser Glu Asn
260 265 270

Gln Ser Pro Val Ser Thr Phe Val Val Thr Leu Ala Phe Ile Trp Val
275 280 285

Ser Leu Ile Lys Thr Leu Val Gln Asp Ser Glu Thr Lys Ala Asn Glu
290 295 300

Glu Asp Lys Asp Glu Val Phe His Leu Met Ile Asn Val Asp Cys Arg
305 310 315 320

Asn Arg Leu Lys Tyr Thr Gln Pro Ile Pro Gln Thr Tyr Phe Gly Asn
325 330 335

Cys Met Ala Pro Gly Ile Val Ser Val Lys Lys His Asp Leu Leu Gly
340 345 350

Glu Lys Cys Val Leu Ala Ala Ser Asp Ala Ile Thr Ala Arg Ile Lys
355 360 365

Asp Met Leu Ser Ser Asp Leu Leu Lys Thr Ala Pro Arg Trp Gly Gln
370 375 380

Gly Val Arg Lys Trp Val Met Ser His Tyr Pro Thr Ser Ile Ala Gly
385 390 395 400

Ala Pro Lys Leu Gly Leu Tyr Asp Met Asp Phe Gly Leu Gly Lys Pro
405 410 415

Cys Lys Met Glu Ile Val His Ile Glu Thr Gly Gly Ser Ile Ala Phe
420 425 430

Ser Glu Ser Arg Asp Gly Ser Asn Gly Val Glu Ile Gly Ile Ala Leu
435 440 445

Glu Lys Lys Lys Met Asp Val Phe Asp Ser Ile Leu Gln Gln Gly Ile
450 455 460

Lys Lys Phe Ala Thr
465

<210> SEQ ID NO 81
<211> LENGTH: 1395
<212> TYPE: DNA
<213> ORGANISM: Vitis amurensis

<400> SEQUENCE: 81
atggctaacc cacacccaca tttcttgatt attacttttc cagcccaagg tcatattaac 60
ccagctttgg aattggccaa aagattgatt ggtgttggtg ctgatgttac tttcgctact 120
actattcatg ccaagtccag attggttaag aacccaactg ttgatggttt gagattctct 180
actttctccg atggtcaaga agaaggtgtt aagagaggtc caaacgaatt gccagttttt 240
caaagattgg cctccgaaaa cttgtccgaa ttgattatgg cttctgctaa tgaaggtaga 300
ccaatctctt gtttgatcta ctccattttg attccaggtg ctgctgaatt ggctagatca 360

```
ttcaatattc catctgcttt cttgtggatt caaccagcta ctgttttgga catctattac    420

tactacttca acggtttcgg tgacttgatc agatccaaat cttctgatcc atccttctcc    480

attgaattac caggtttgcc atctttgtcc agacaagatt tgccatcctt tttcgttggt    540

tccgaccaaa atcaagaaaa ccatgctttg gctgcctttc aaaagcactt ggaaattttg    600

gaacaagaag aaaacccaaa ggtcttggtt aacactttcg atgctttaga accagaagcc    660

ttgagagctg ttgaaaagtt gaaattgact gctgttggtc cattggttcc atctggtttt    720

tctgatggta aagatgcttc tgatacacca tctggtggtg atttgtctga tggttctaga    780

gattatatgg aatggttgaa gtccaagcca gaatctactg ttgtttacgt ttccttcggt    840

tccatcagta tgttctctat gcaacaaatg gaagaaatcg ccagaggttt gttggaatct    900

ggtagaccat ttttgtgggt tatcagagct aaagaaaacg gtgaagaaaa caaagaagaa    960

gataagttgt cctgccaaga agaattggaa aagcaaggta tgttgatcca atggtgctct   1020

caaatggaag ttttgtctca tccatctttg ggttgtttcg ttactcattg tggttggaac   1080

tcctctattg aatctttagc ttctggtgtt ccaatgattg catttccaca atgggctgat   1140

caaggtacta ataccaagtt gattaaggac gtttggaaaa ccggtgttag attgatggtt   1200

aacgaagaag aaattgtcac ctccgacgaa ttgagaagat gcttggaatt agttatgggt   1260

gatggtgaaa agggtcaaga aatgagaaag aatgctaaga agtggaagat tttggctaaa   1320

gaagccttaa aagaaggtgg ttcctctcac aagaatttga agaacttcgt tgacgaagtc   1380

atccaaggtt actga                                                    1395
```

<210> SEQ ID NO 82
<211> LENGTH: 464
<212> TYPE: PRT
<213> ORGANISM: Vitis amurensis

<400> SEQUENCE: 82

```
Met Ala Asn Pro His Pro His Phe Leu Ile Ile Thr Phe Pro Ala Gln
1               5                   10                  15

Gly His Ile Asn Pro Ala Leu Glu Leu Ala Lys Arg Leu Ile Gly Val
            20                  25                  30

Gly Ala Asp Val Thr Phe Ala Thr Thr Ile His Ala Lys Ser Arg Leu
        35                  40                  45

Val Lys Asn Pro Thr Val Asp Gly Leu Arg Phe Ser Thr Phe Ser Asp
    50                  55                  60

Gly Gln Glu Glu Gly Val Lys Arg Gly Pro Asn Glu Leu Pro Val Phe
65                  70                  75                  80

Gln Arg Leu Ala Ser Glu Asn Leu Ser Glu Leu Ile Met Ala Ser Ala
                85                  90                  95

Asn Glu Gly Arg Pro Ile Ser Cys Leu Ile Tyr Ser Ile Leu Ile Pro
            100                 105                 110

Gly Ala Ala Glu Leu Ala Arg Ser Phe Asn Ile Pro Ser Ala Phe Leu
        115                 120                 125

Trp Ile Gln Pro Ala Thr Val Leu Asp Ile Tyr Tyr Tyr Tyr Phe Asn
    130                 135                 140

Gly Phe Gly Asp Leu Ile Arg Ser Lys Ser Ser Asp Pro Ser Phe Ser
145                 150                 155                 160

Ile Glu Leu Pro Gly Leu Pro Ser Leu Ser Arg Gln Asp Leu Pro Ser
                165                 170                 175

Phe Phe Val Gly Ser Asp Gln Asn Gln Glu Asn His Ala Leu Ala Ala
            180                 185                 190
```

```
Phe Gln Lys His Leu Glu Ile Leu Glu Gln Glu Glu Asn Pro Lys Val
        195                 200                 205

Leu Val Asn Thr Phe Asp Ala Leu Glu Pro Glu Ala Leu Arg Ala Val
    210                 215                 220

Glu Lys Leu Lys Leu Thr Ala Val Gly Pro Leu Val Pro Ser Gly Phe
225                 230                 235                 240

Ser Asp Gly Lys Asp Ala Ser Asp Thr Pro Ser Gly Gly Asp Leu Ser
                245                 250                 255

Asp Gly Ser Arg Asp Tyr Met Glu Trp Leu Lys Ser Lys Pro Glu Ser
            260                 265                 270

Thr Val Val Tyr Val Ser Phe Gly Ser Ile Ser Met Phe Ser Met Gln
        275                 280                 285

Gln Met Glu Glu Ile Ala Arg Gly Leu Leu Glu Ser Gly Arg Pro Phe
    290                 295                 300

Leu Trp Val Ile Arg Ala Lys Glu Asn Gly Glu Glu Asn Lys Glu Glu
305                 310                 315                 320

Asp Lys Leu Ser Cys Gln Glu Glu Leu Glu Lys Gln Gly Met Leu Ile
                325                 330                 335

Gln Trp Cys Ser Gln Met Glu Val Leu Ser His Pro Ser Leu Gly Cys
            340                 345                 350

Phe Val Thr His Cys Gly Trp Asn Ser Ser Ile Glu Ser Leu Ala Ser
        355                 360                 365

Gly Val Pro Met Ile Ala Phe Pro Gln Trp Ala Asp Gln Gly Thr Asn
    370                 375                 380

Thr Lys Leu Ile Lys Asp Val Trp Lys Thr Gly Val Arg Leu Met Val
385                 390                 395                 400

Asn Glu Glu Glu Ile Val Thr Ser Asp Glu Leu Arg Arg Cys Leu Glu
                405                 410                 415

Leu Val Met Gly Asp Gly Glu Lys Gly Gln Glu Met Arg Lys Asn Ala
            420                 425                 430

Lys Lys Trp Lys Ile Leu Ala Lys Glu Ala Leu Lys Glu Gly Gly Ser
        435                 440                 445

Ser His Lys Asn Leu Lys Asn Phe Val Asp Glu Val Ile Gln Gly Tyr
    450                 455                 460
```

<210> SEQ ID NO 83
<211> LENGTH: 1398
<212> TYPE: DNA
<213> ORGANISM: Nierembergia sp. NB17

<400> SEQUENCE: 83

```
atggaaaacg aaaaggtctt gcacgttgtc atgtttccat tctttgcttt cggtcatatt      60

tccccatttg ctcaattggc taacaagttg tcatctcacg gtgttaaggt ttctttcttt     120

actgcttctg gtaacgcctc tagattgaga tcaatgttga attctgctcc aaccaccacc     180

catattgata tagttccatt gactttgcca cacgttgaag gtttgccacc aggttctgaa     240

tctactgctg aattgactcc agttaccgct gaattattga aggttgcttt ggatttgatg     300

caaccacaaa tcaagacctt gttgtctcat ttgaagccac acttcgtttt gttcgatttt     360

gctcaagaat ggttgccaaa gatggctgat gaattgggta ttaagaccgt tttctactcc     420

gttttcgttg ctttgtctac tgcttttttg acttgtccag ctagagttac tgaacctaaa     480

aagtacccaa ccttggaaga tatgaagaaa ccaccattgg gtttcccaca tacttctatt     540

acatctgtta agaccttcga agcccaagac ttcttgtaca ttttcaagtc ctttaacaac     600
```

-continued

```
agaccaaccg tttacgatag agtcttgtct ggtttgaaag gttgctctgc tattttggct    660

aagacctgtt ctcaaatgga aggtccttat atcgaatacg tcaagtccca attcaagaag    720

ccagttttgt tggttggtcc agttgttcca gatccaccat ctggtaaatt ggaagaaaaa    780

tgggatgctt ggttgaacaa gtttgaagct ggtactgtta tctactgcag tttcggttct    840

gaaaccttct tgaaggatga tcaaatcaaa gaattggcct tgggtttgga acaaactggt    900

ttgccttttt tcttggtctt gaatttccca gctaacgttg atgcttcagc cgaattgaat    960

agaggtttgc ctgaaggttt tagagaaaga gtcaaagaaa agggtgttat ccattctggt   1020

tgggttcaac aacaacatat tttggcacat acctctgttg gttgttacgt ttgtcatgct   1080

ggtttctcat ctgttattga agccttcatg aacgattgcc aagttgttat gttgccacaa   1140

aagggtgacc aattattgaa cgctaaattg gtttccggtg atatgaaggc tggtgttgaa   1200

gttaatagaa gagatgaaga tggttacttc tccaaggatg atattgaaga agccgttgaa   1260

aaggtcatgg tcgaaaaagt catcagagaa aatcaaaaga agtggaaaga atttttgttg   1320

aacaaagaca cccactccaa gttcgttgaa gatttggttc atgatatgat ggctatggct   1380

aagttgtcta ctacctga                                                 1398


<210> SEQ ID NO 84
<211> LENGTH: 465
<212> TYPE: PRT
<213> ORGANISM: Nierembergia sp. NB17

<400> SEQUENCE: 84

Met Glu Asn Glu Lys Val Leu His Val Val Met Phe Pro Phe Phe Ala
1               5                   10                  15

Phe Gly His Ile Ser Pro Phe Ala Gln Leu Ala Asn Lys Leu Ser Ser
            20                  25                  30

His Gly Val Lys Val Ser Phe Phe Thr Ala Ser Gly Asn Ala Ser Arg
        35                  40                  45

Leu Arg Ser Met Leu Asn Ser Ala Pro Thr Thr Thr His Ile Asp Ile
    50                  55                  60

Val Pro Leu Thr Leu Pro His Val Glu Gly Leu Pro Pro Gly Ser Glu
65                  70                  75                  80

Ser Thr Ala Glu Leu Thr Pro Val Thr Ala Glu Leu Leu Lys Val Ala
                85                  90                  95

Leu Asp Leu Met Gln Pro Gln Ile Lys Thr Leu Leu Ser His Leu Lys
            100                 105                 110

Pro His Phe Val Leu Phe Asp Phe Ala Gln Glu Trp Leu Pro Lys Met
        115                 120                 125

Ala Asp Glu Leu Gly Ile Lys Thr Val Phe Tyr Ser Val Phe Val Ala
    130                 135                 140

Leu Ser Thr Ala Phe Leu Thr Cys Pro Ala Arg Val Thr Glu Pro Lys
145                 150                 155                 160

Lys Tyr Pro Thr Leu Glu Asp Met Lys Lys Pro Pro Leu Gly Phe Pro
                165                 170                 175

His Thr Ser Ile Thr Ser Val Lys Thr Phe Glu Ala Gln Asp Phe Leu
            180                 185                 190

Tyr Ile Phe Lys Ser Phe Asn Asn Arg Pro Thr Val Tyr Asp Arg Val
        195                 200                 205

Leu Ser Gly Leu Lys Gly Cys Ser Ala Ile Leu Ala Lys Thr Cys Ser
    210                 215                 220
```

-continued

```
Gln Met Glu Gly Pro Tyr Ile Glu Tyr Val Lys Ser Gln Phe Lys Lys
225                 230                 235                 240

Pro Val Leu Leu Val Gly Pro Val Val Pro Asp Pro Pro Ser Gly Lys
                245                 250                 255

Leu Glu Glu Lys Trp Asp Ala Trp Leu Asn Lys Phe Glu Ala Gly Thr
            260                 265                 270

Val Ile Tyr Cys Ser Phe Gly Ser Glu Thr Phe Leu Lys Asp Asp Gln
        275                 280                 285

Ile Lys Glu Leu Ala Leu Gly Leu Glu Gln Thr Gly Leu Pro Phe Phe
    290                 295                 300

Leu Val Leu Asn Phe Pro Ala Asn Val Asp Ala Ser Ala Glu Leu Asn
305                 310                 315                 320

Arg Gly Leu Pro Glu Gly Phe Arg Glu Arg Val Lys Glu Lys Gly Val
                325                 330                 335

Ile His Ser Gly Trp Val Gln Gln Gln His Ile Leu Ala His Thr Ser
            340                 345                 350

Val Gly Cys Tyr Val Cys His Ala Gly Phe Ser Ser Val Ile Glu Ala
        355                 360                 365

Phe Met Asn Asp Cys Gln Val Val Met Leu Pro Gln Lys Gly Asp Gln
    370                 375                 380

Leu Leu Asn Ala Lys Leu Val Ser Gly Asp Met Lys Ala Gly Val Glu
385                 390                 395                 400

Val Asn Arg Arg Asp Glu Asp Gly Tyr Phe Ser Lys Asp Asp Ile Glu
                405                 410                 415

Glu Ala Val Glu Lys Val Met Val Glu Lys Val Ile Arg Glu Asn Gln
            420                 425                 430

Lys Lys Trp Lys Glu Phe Leu Leu Asn Lys Asp Thr His Ser Lys Phe
        435                 440                 445

Val Glu Asp Leu Val His Asp Met Met Ala Met Ala Lys Leu Ser Thr
    450                 455                 460

Thr
465
```

<210> SEQ ID NO 85
<211> LENGTH: 1344
<212> TYPE: DNA
<213> ORGANISM: Clitoria ternatea

<400> SEQUENCE: 85

```
atggaaaaca acaagcacgt cgtcattttc ccatttccat ttggttctca tttgccacct     60

ttgttgaact tggttttcaa attggctcat gctgctccaa atacctcttt ctcttttatt    120

ggtactcata cctccaacgc tttcttgttc acaaaaagac atgttccaga caacatcaga    180

gttttcacca tttctgatgg tatcccagaa ggttacgttc caggtaacaa tccaattgtc    240

aagttggact tcttcttgtc tactggtcca gataatttgt gcaagggtat tgaattggct    300

gttgccgaaa caaagcaatc tgttacctgt attattgccg atgctttcgt tacctcttct    360

ttgttggttg ctcaaacttt gaatgttcca tggatcgttt tctggccaaa tgtttcatgt    420

tccttgtcct tgtacttctc catcgatttg attagagata agtgcaccaa cgatgctaag    480

aacgcttctt tggatttttt gccaggtttg tccaagttga gagttgaaga tgttccaaga    540

ccacaagcta tagttttgga tggtaaagaa accttgttcg ccagaacttt gaactctttg    600

ggtactgttt tgccacaagc aaaagctgtt gttgttaact tcttcgctga attggatcca    660

ccattattcg ttaaggacat gagatccaag ttgcaatcct tgttgttcgt tgatccattg    720
```

```
ccatgtccac aattgttgtt gccagaaact gattctaacg gttgtatgtc ttggttggac    780

tccaaatctt ctagatcagt tgcttacgtt tgcttcggta ctgctgtttc tttgccacca    840

caagaagttg ttgaagttgc tgaagccttg gaagaatctg gttttccttt tttgttggcc    900

ttgtccgaat ctttgattgg tgttttacca aagggtttgg tcgaaagaac tatgactaga    960

ggtaaagttg tttcttgggc tccacaatct ttggttttgt ctcatggttc tgttggtgtc   1020

tttgttactc attgtggtgc taactctgtt accgaatcta tttctaatgg tgtccctatg   1080

atctgcagac catttttttgg tgatcaaggt attgctgcca gagttattca agatatttgg   1140

gaaatcggtg tcatcttgga aggtagaatt ttcactaaga acggtttcgt caagaacttg   1200

aacttgatct tggtccaaga agaaggtaaa aagatcagag ataacgcctt gaaggttaag   1260

caaatcgttc aagatgctgc tggtccacat ggtcaagctg ctgaagattt taacactttg   1320

gttgaaatga tctcctcttc ttaa                                          1344
```

<210> SEQ ID NO 86
<211> LENGTH: 447
<212> TYPE: PRT
<213> ORGANISM: Clitoria ternatea

<400> SEQUENCE: 86

```
Met Glu Asn Asn Lys His Val Val Ile Phe Pro Phe Pro Phe Gly Ser
1               5                   10                  15

His Leu Pro Pro Leu Leu Asn Leu Val Phe Lys Leu Ala His Ala Ala
            20                  25                  30

Pro Asn Thr Ser Phe Ser Phe Ile Gly Thr His Thr Ser Asn Ala Phe
        35                  40                  45

Leu Phe Thr Lys Arg His Val Pro Asp Asn Ile Arg Val Phe Thr Ile
    50                  55                  60

Ser Asp Gly Ile Pro Glu Gly Tyr Val Pro Gly Asn Asn Pro Ile Val
65                  70                  75                  80

Lys Leu Asp Phe Phe Leu Ser Thr Gly Pro Asp Asn Leu Cys Lys Gly
                85                  90                  95

Ile Glu Leu Ala Val Ala Glu Thr Lys Gln Ser Val Thr Cys Ile Ile
            100                 105                 110

Ala Asp Ala Phe Val Thr Ser Ser Leu Leu Val Ala Gln Thr Leu Asn
        115                 120                 125

Val Pro Trp Ile Val Phe Trp Pro Asn Val Ser Cys Ser Leu Ser Leu
    130                 135                 140

Tyr Phe Ser Ile Asp Leu Ile Arg Asp Lys Cys Thr Asn Asp Ala Lys
145                 150                 155                 160

Asn Ala Ser Leu Asp Phe Leu Pro Gly Leu Ser Lys Leu Arg Val Glu
                165                 170                 175

Asp Val Pro Arg Pro Gln Ala Ile Val Leu Asp Gly Lys Glu Thr Leu
            180                 185                 190

Phe Ala Arg Thr Leu Asn Ser Leu Gly Thr Val Leu Pro Gln Ala Lys
        195                 200                 205

Ala Val Val Val Asn Phe Phe Ala Glu Leu Asp Pro Pro Leu Phe Val
    210                 215                 220

Lys Asp Met Arg Ser Lys Leu Gln Ser Leu Leu Phe Val Asp Pro Leu
225                 230                 235                 240

Pro Cys Pro Gln Leu Leu Leu Pro Glu Thr Asp Ser Asn Gly Cys Met
                245                 250                 255
```

-continued

```
Ser Trp Leu Asp Ser Lys Ser Ser Arg Ser Val Ala Tyr Val Cys Phe
            260                 265                 270

Gly Thr Ala Val Ser Leu Pro Pro Gln Glu Val Val Glu Val Ala Glu
        275                 280                 285

Ala Leu Glu Glu Ser Gly Phe Pro Phe Leu Leu Ala Leu Ser Glu Ser
    290                 295                 300

Leu Ile Gly Val Leu Pro Lys Gly Leu Val Glu Arg Thr Met Thr Arg
305                 310                 315                 320

Gly Lys Val Val Ser Trp Ala Pro Gln Ser Leu Val Leu Ser His Gly
                325                 330                 335

Ser Val Gly Val Phe Val Thr His Cys Gly Ala Asn Ser Val Thr Glu
            340                 345                 350

Ser Ile Ser Asn Gly Val Pro Met Ile Cys Arg Pro Phe Phe Gly Asp
        355                 360                 365

Gln Gly Ile Ala Ala Arg Val Ile Gln Asp Ile Trp Glu Ile Gly Val
    370                 375                 380

Ile Leu Glu Gly Arg Ile Phe Thr Lys Asn Gly Phe Val Lys Asn Leu
385                 390                 395                 400

Asn Leu Ile Leu Val Gln Glu Glu Gly Lys Lys Ile Arg Asp Asn Ala
                405                 410                 415

Leu Lys Val Lys Gln Ile Val Gln Asp Ala Ala Gly Pro His Gly Gln
            420                 425                 430

Ala Ala Glu Asp Phe Asn Thr Leu Val Glu Met Ile Ser Ser Ser
        435                 440                 445
```

<210> SEQ ID NO 87
<211> LENGTH: 1449
<212> TYPE: DNA
<213> ORGANISM: Gentiana triflora

<400> SEQUENCE: 87

```
atggaccaat tgcacgtttt cttcttccca ttcttggcta acggtcacat tttgccaact     60

attgacatgg ctaagttgtt ctcttctaga ggtgttaagg ctactttgat tactactcac    120

aacaactctg ctattttctt gaaggctatt aacagatcta agattttggg tttcgacatt    180

tctgttttga ctattaagtt cccatctgct gaattcggtt tgccagaagg ttacgaaact    240

gctgaccaag ctagatctat tgacatgatg gacgaattct tcagagcttg tattttgttg    300

caagaaccat tggaagaatt gttgaaggaa cacagaccac aagctttggt tgctgacttg    360

ttcttctact gggctaacga cgctgctgct aagttcggta ttccaagatt gttgttccac    420

ggttcttctt ctttcgctat gattgctgct gaatctgtta gaagaaacaa gccatacaag    480

aacttgtctt ctgactctga cccattcgtt gttccagaca ttccagacaa gattattttg    540

actaagtctc aagttccaac tccagacgaa actgaagaaa acaacactca cattactgaa    600

atgtggaaga acatttctga atctgaaaac gactgttacg gtgttattgt taactctttc    660

tacgaattgg aaccagacta cgttgactac tgtaagaacg ttttgggtag aagagcttgg    720

cacattggtc cattgtcttt gtgtaacaac gaaggtgaag acgttgctga aagaggtaag    780

aagtctgaca ttgacgctca cgaatgtttg aactggttgg actctaagaa cccagactct    840

gttgtttacg tttgtttcgg ttctatggct aacttcaacg ctgctcaatt gcacgaattg    900

gctatgggtt tggaagaatc tggtcaagaa ttcatttggg ttgttagaac ttgtgttgac    960

gaagaagacg aatctaagtg gttcccagac ggtttcgaaa agagagttca agaaaacaac   1020

aagggtttga ttattaaggg ttgggctcca caagttttga ttttggaaca cgaagctgtt   1080
```

ggtgctttcg tttctcactg tggttggaac tctactttgg aaggtatttg tggtggtgtt 1140
gctatggtta cttggccatt gttcgctgaa caattctaca acgaaaagtt gatgactgac 1200
attttgagaa ctggtgtttc tgttggttct ttgcaatggt ctagagttac tacttctgct 1260
gttgttgtta agagagaatc tatttctaag gctgttagaa gattgatggc tgaagaagaa 1320
ggtgttgaca ttagaaacag agctaaggct ttgaaggaaa aggctaagaa ggctgttgaa 1380
ggtggtggtt cttcttactc tgacttgtct gctttgttgg ttgaattgtc ttcttaccca 1440
cacaactag 1449

<210> SEQ ID NO 88
<211> LENGTH: 482
<212> TYPE: PRT
<213> ORGANISM: Gentiana triflora

<400> SEQUENCE: 88

Met Asp Gln Leu His Val Phe Phe Phe Pro Phe Leu Ala Asn Gly His
1 5 10 15

Ile Leu Pro Thr Ile Asp Met Ala Lys Leu Phe Ser Ser Arg Gly Val
20 25 30

Lys Ala Thr Leu Ile Thr Thr His Asn Asn Ser Ala Ile Phe Leu Lys
35 40 45

Ala Ile Asn Arg Ser Lys Ile Leu Gly Phe Asp Ile Ser Val Leu Thr
50 55 60

Ile Lys Phe Pro Ser Ala Glu Phe Gly Leu Pro Glu Gly Tyr Glu Thr
65 70 75 80

Ala Asp Gln Ala Arg Ser Ile Asp Met Met Asp Glu Phe Phe Arg Ala
85 90 95

Cys Ile Leu Leu Gln Glu Pro Leu Glu Glu Leu Leu Lys Glu His Arg
100 105 110

Pro Gln Ala Leu Val Ala Asp Leu Phe Phe Tyr Trp Ala Asn Asp Ala
115 120 125

Ala Ala Lys Phe Gly Ile Pro Arg Leu Leu Phe His Gly Ser Ser Ser
130 135 140

Phe Ala Met Ile Ala Ala Glu Ser Val Arg Arg Asn Lys Pro Tyr Lys
145 150 155 160

Asn Leu Ser Ser Asp Ser Asp Pro Phe Val Val Pro Asp Ile Pro Asp
165 170 175

Lys Ile Ile Leu Thr Lys Ser Gln Val Pro Thr Pro Asp Glu Thr Glu
180 185 190

Glu Asn Asn Thr His Ile Thr Glu Met Trp Lys Asn Ile Ser Glu Ser
195 200 205

Glu Asn Asp Cys Tyr Gly Val Ile Val Asn Ser Phe Tyr Glu Leu Glu
210 215 220

Pro Asp Tyr Val Asp Tyr Cys Lys Asn Val Leu Gly Arg Arg Ala Trp
225 230 235 240

His Ile Gly Pro Leu Ser Leu Cys Asn Asn Glu Gly Glu Asp Val Ala
245 250 255

Glu Arg Gly Lys Lys Ser Asp Ile Asp Ala His Glu Cys Leu Asn Trp
260 265 270

Leu Asp Ser Lys Asn Pro Asp Ser Val Val Tyr Val Cys Phe Gly Ser
275 280 285

Met Ala Asn Phe Asn Ala Ala Gln Leu His Glu Leu Ala Met Gly Leu
290 295 300

-continued

```
Glu Glu Ser Gly Gln Glu Phe Ile Trp Val Val Arg Thr Cys Val Asp
305                 310                 315                 320

Glu Glu Asp Glu Ser Lys Trp Phe Pro Asp Gly Phe Glu Lys Arg Val
                325                 330                 335

Gln Glu Asn Asn Lys Gly Leu Ile Ile Lys Gly Trp Ala Pro Gln Val
            340                 345                 350

Leu Ile Leu Glu His Glu Ala Val Gly Ala Phe Val Ser His Cys Gly
        355                 360                 365

Trp Asn Ser Thr Leu Glu Gly Ile Cys Gly Gly Val Ala Met Val Thr
    370                 375                 380

Trp Pro Leu Phe Ala Glu Gln Phe Tyr Asn Glu Lys Leu Met Thr Asp
385                 390                 395                 400

Ile Leu Arg Thr Gly Val Ser Val Gly Ser Leu Gln Trp Ser Arg Val
                405                 410                 415

Thr Thr Ser Ala Val Val Val Lys Arg Glu Ser Ile Ser Lys Ala Val
            420                 425                 430

Arg Arg Leu Met Ala Glu Glu Glu Gly Val Asp Ile Arg Asn Arg Ala
        435                 440                 445

Lys Ala Leu Lys Glu Lys Ala Lys Lys Ala Val Glu Gly Gly Gly Ser
    450                 455                 460

Ser Tyr Ser Asp Leu Ser Ala Leu Leu Val Glu Leu Ser Ser Tyr Pro
465                 470                 475                 480

His Asn


<210> SEQ ID NO 89
<211> LENGTH: 1410
<212> TYPE: DNA
<213> ORGANISM: Gentiana triflora

<400> SEQUENCE: 89

atggaacaaa ttcaaatggt taaggttttg gaaaagtgtc aagttactcc accatctgac     60

actactgacg ttgaattgtc tttgccagtt actttcttcg acattccatg gttgcacttg    120

aacaagatgc aatctttgtt gttctacgac ttcccatacc caagaactca cttcttggac    180

actgttattc caaacttgaa ggcttctttg tctttgactt tgaagcacta cgttccattg    240

tctggtaact tgttgatgcc aattaagtct ggtgaaatgc caaagttcca atactctaga    300

gacgaaggtg actctattac tttgattgtt gctgaatctg accaagactt cgactacttg    360

aagggtcacc aattggttga ctctaacgac ttgcacggtt tgttctacgt tatgccaaga    420

gttattagaa ctatgcaaga ctacaaggtt attccattgg ttgctgttca agttactgtt    480

ttcccaaaca gaggtattgc tgttgctttg actgctcacc actctattgc tgacgctaag    540

tctttcgtta tgttcattaa cgcttgggct tacattaaca agttcggtaa ggacgctgac    600

ttgttgtctg ctaacttgtt gccatctttc gacagatcta ttattaagga cttgtacggt    660

ttggaagaaa ctttctggaa cgaaatgcaa gacgttttgg aaatgttctc tagattcggt    720

tctaagccac caagattcaa caaggttaga gctacttacg ttttgtcttt ggctgaaatt    780

caaaagttga agaacaaggt tttgaacttg agaggttctg aaccaactat tagagttact    840

actttcacta tgacttgtgg ttacgtttgg acttgtatgg ttaagtctaa ggacgacgtt    900

gtttctgaag aatcttctaa cgacgaaaac gaattggaat acttctcttt cactgctgac    960

tgtagaggtt tgttgactcc accatgtcca ccaaactact tcggtaactg tttggcttct   1020

tgtgttgcta aggctactca caaggaattg gttggtgaca agggtttgtt ggttgctgtt   1080
```

gctgctattg gtgaagctat tgaaaagaga ttgcacaacg aaaagggtgt tttggctgac 1140
gctaagactt ggttgtctga atctaacggt attccatcta agagattctt gggtattact 1200
ggttctccaa agttcgactc ttacggtgtt gacttcggtt ggggtaagcc agctaagttc 1260
gacattactt ctgttgacta cgctgaattg atttacgtta ttcaatctag agacttcgaa 1320
aagggtgttg aaattggtgt ttctttgcca aagattcaca tggacgcttt cgctaagatt 1380
ttcgaagaag gtttctgttc tttgtcttag 1410

<210> SEQ ID NO 90
<211> LENGTH: 469
<212> TYPE: PRT
<213> ORGANISM: Gentiana triflora

<400> SEQUENCE: 90

Met Glu Gln Ile Gln Met Val Lys Val Leu Glu Lys Cys Gln Val Thr
1               5                   10                  15

Pro Pro Ser Asp Thr Thr Asp Val Glu Leu Ser Leu Pro Val Thr Phe
            20                  25                  30

Phe Asp Ile Pro Trp Leu His Leu Asn Lys Met Gln Ser Leu Leu Phe
        35                  40                  45

Tyr Asp Phe Pro Tyr Pro Arg Thr His Phe Leu Asp Thr Val Ile Pro
    50                  55                  60

Asn Leu Lys Ala Ser Leu Ser Leu Thr Leu Lys His Tyr Val Pro Leu
65                  70                  75                  80

Ser Gly Asn Leu Leu Met Pro Ile Lys Ser Gly Glu Met Pro Lys Phe
                85                  90                  95

Gln Tyr Ser Arg Asp Glu Gly Asp Ser Ile Thr Leu Ile Val Ala Glu
            100                 105                 110

Ser Asp Gln Asp Phe Asp Tyr Leu Lys Gly His Gln Leu Val Asp Ser
        115                 120                 125

Asn Asp Leu His Gly Leu Phe Tyr Val Met Pro Arg Val Ile Arg Thr
    130                 135                 140

Met Gln Asp Tyr Lys Val Ile Pro Leu Val Ala Val Gln Val Thr Val
145                 150                 155                 160

Phe Pro Asn Arg Gly Ile Ala Val Ala Leu Thr Ala His His Ser Ile
                165                 170                 175

Ala Asp Ala Lys Ser Phe Val Met Phe Ile Asn Ala Trp Ala Tyr Ile
            180                 185                 190

Asn Lys Phe Gly Lys Asp Ala Asp Leu Leu Ser Ala Asn Leu Leu Pro
        195                 200                 205

Ser Phe Asp Arg Ser Ile Ile Lys Asp Leu Tyr Gly Leu Glu Glu Thr
    210                 215                 220

Phe Trp Asn Glu Met Gln Asp Val Leu Glu Met Phe Ser Arg Phe Gly
225                 230                 235                 240

Ser Lys Pro Pro Arg Phe Asn Lys Val Arg Ala Thr Tyr Val Leu Ser
                245                 250                 255

Leu Ala Glu Ile Gln Lys Leu Lys Asn Lys Val Leu Asn Leu Arg Gly
            260                 265                 270

Ser Glu Pro Thr Ile Arg Val Thr Thr Phe Thr Met Thr Cys Gly Tyr
        275                 280                 285

Val Trp Thr Cys Met Val Lys Ser Lys Asp Asp Val Val Ser Glu Glu
    290                 295                 300

Ser Ser Asn Asp Glu Asn Glu Leu Glu Tyr Phe Ser Phe Thr Ala Asp

```
305                 310                 315                 320

Cys Arg Gly Leu Leu Thr Pro Pro Cys Pro Pro Asn Tyr Phe Gly Asn
                325                 330                 335

Cys Leu Ala Ser Cys Val Ala Lys Ala Thr His Lys Glu Leu Val Gly
            340                 345                 350

Asp Lys Gly Leu Leu Val Ala Val Ala Ala Ile Gly Glu Ala Ile Glu
        355                 360                 365

Lys Arg Leu His Asn Glu Lys Gly Val Leu Ala Asp Ala Lys Thr Trp
    370                 375                 380

Leu Ser Glu Ser Asn Gly Ile Pro Ser Lys Arg Phe Leu Gly Ile Thr
385                 390                 395                 400

Gly Ser Pro Lys Phe Asp Ser Tyr Gly Val Asp Phe Gly Trp Gly Lys
                405                 410                 415

Pro Ala Lys Phe Asp Ile Thr Ser Val Asp Tyr Ala Glu Leu Ile Tyr
            420                 425                 430

Val Ile Gln Ser Arg Asp Phe Glu Lys Gly Val Glu Ile Gly Val Ser
        435                 440                 445

Leu Pro Lys Ile His Met Asp Ala Phe Ala Lys Ile Phe Glu Glu Gly
    450                 455                 460

Phe Cys Ser Leu Ser
465
```

<210> SEQ ID NO 91
<211> LENGTH: 933
<212> TYPE: DNA
<213> ORGANISM: Saccharomyces cerevisiae

<400> SEQUENCE: 91

```
atgcctatca ccataaaaag ccgctctaaa gggttaaggg acactgaaat tgacttatcc     60

aaaaagccta ctttagatga tgttttgaaa aaaatctctg ctaataacca caatatcagc    120

aagtacagga taagattaac ctacaaaaag gaatctaaac aagttccggt tatttcagaa    180

tcgttttttc aagaagaggc tgatgactca atggaattct tcatcaaaga tttgggtccc    240

caaatttcat ggagattagt cttcttttgt gagtatttgg gtccagtctt ggttcactcc    300

ctttttttatt atctatctac cattcccaca gttgttgata gatggcacag tgctagctcc    360

gactataatc catttttaaa cagggttgca tattttttaa ttttaggaca ttatggaaag    420

agattatttg aaaccttatt tgttcaccaa ttctctttag ctactatgcc aattttcaac    480

ctgttcaaaa attgtttcca ttactgggtt ctaagcggtc tcatttcatt cggttacttt    540

ggctacggct tccccctttgg gaatgctaag ttattcaaat actattcata tttgaaattg    600

gatgacttga gtacattaat tggtcttttc gtgctttcag aactatggaa cttttattgc    660

cacattaaat tgcgcctatg gggtgactat caaaagaagc atggtaacgc taagatccgt    720

gtcccattga atcaaggtat tttcaatctt tttgttgctc ccaactatac ttttgaagtt    780

tggtcttgga tttggtttac ttttgtgttc aagttcaatt tatttgccgt tttatttttg    840

actgtttcaa cagctcaaat gtacgcatgg gctcaaaaga aaaacaaaaa gtatcatacc    900

agaagagcat tcttgattcc atttgtattt tga                                 933
```

<210> SEQ ID NO 92
<211> LENGTH: 310
<212> TYPE: PRT
<213> ORGANISM: Saccharomyces cerevisiae

<400> SEQUENCE: 92

```
Met Pro Ile Thr Ile Lys Ser Arg Ser Lys Gly Leu Arg Asp Thr Glu
1               5                   10                  15

Ile Asp Leu Ser Lys Lys Pro Thr Leu Asp Asp Val Leu Lys Lys Ile
            20                  25                  30

Ser Ala Asn Asn His Asn Ile Ser Lys Tyr Arg Ile Arg Leu Thr Tyr
        35                  40                  45

Lys Lys Glu Ser Lys Gln Val Pro Val Ile Ser Glu Ser Phe Phe Gln
    50                  55                  60

Glu Glu Ala Asp Asp Ser Met Glu Phe Phe Ile Lys Asp Leu Gly Pro
65                  70                  75                  80

Gln Ile Ser Trp Arg Leu Val Phe Phe Cys Glu Tyr Leu Gly Pro Val
                85                  90                  95

Leu Val His Ser Leu Phe Tyr Tyr Leu Ser Thr Ile Pro Thr Val Val
            100                 105                 110

Asp Arg Trp His Ser Ala Ser Ser Asp Tyr Asn Pro Phe Leu Asn Arg
        115                 120                 125

Val Ala Tyr Phe Leu Ile Leu Gly His Tyr Gly Lys Arg Leu Phe Glu
    130                 135                 140

Thr Leu Phe Val His Gln Phe Ser Leu Ala Thr Met Pro Ile Phe Asn
145                 150                 155                 160

Leu Phe Lys Asn Cys Phe His Tyr Trp Val Leu Ser Gly Leu Ile Ser
                165                 170                 175

Phe Gly Tyr Phe Gly Tyr Gly Phe Pro Phe Gly Asn Ala Lys Leu Phe
            180                 185                 190

Lys Tyr Tyr Ser Tyr Leu Lys Leu Asp Asp Leu Ser Thr Leu Ile Gly
        195                 200                 205

Leu Phe Val Leu Ser Glu Leu Trp Asn Phe Tyr Cys His Ile Lys Leu
    210                 215                 220

Arg Leu Trp Gly Asp Tyr Gln Lys Lys His Gly Asn Ala Lys Ile Arg
225                 230                 235                 240

Val Pro Leu Asn Gln Gly Ile Phe Asn Leu Phe Val Ala Pro Asn Tyr
                245                 250                 255

Thr Phe Glu Val Trp Ser Trp Ile Trp Phe Thr Phe Val Phe Lys Phe
            260                 265                 270

Asn Leu Phe Ala Val Leu Phe Leu Thr Val Ser Thr Ala Gln Met Tyr
        275                 280                 285

Ala Trp Ala Gln Lys Lys Asn Lys Lys Tyr His Thr Arg Arg Ala Phe
    290                 295                 300

Leu Ile Pro Phe Val Phe
305                 310
```

<210> SEQ ID NO 93
<211> LENGTH: 1452
<212> TYPE: DNA
<213> ORGANISM: Pyrus communis

<400> SEQUENCE: 93

```
atgggtgacg ttattgtttt gtacgcttct ccaggtatgg gtcacattgt tgctatggtt      60

gaattgggta agttcattgt tcacagatac ggtccacaca agttctctat tactattttg     120

tacacttgtg gttctattgt tgacactgct tctattccag tttacattag aagaatttct     180

cactctcacc cattcatttc tttcagacaa ttcccaagag ttactaacaa cattactaga     240

aacatttctg ttccagctat tactttcgac ttcattagac aaaacgaccc acacgttaga     300
```

-continued

```
tctgctttgc aagaaatttc taagtctgct actgttagag ctttcattat tgacttgttc    360

tgtacttctg ctttgccaat tggtaaggaa ttcaacattc caacttacta cttccacact    420

tctggtgctg ctgttttggc tgctttcttg tacttgccaa agattgacga acaaactaag    480

actactgaat ctttcaagga cttgagagac actgttttcg aattcccagg ttggaagtct    540

ccattgaagg ctactcacat ggttcaattg gttttggaca gaaacgaccc agcttactct    600

gacatgattt acttctgttc tcacttgcca aagtctaacg gtattattgt taacactttc    660

gaagaattgg aaccaccatc tgttttgcaa gctattgctg gtggtttgtg tgttccagac    720

ggtccaactc caccagttta ctacgttggt ccattgattg aagaagaaaa ggaattgtct    780

aaggacgctg acgctgctga aaaggaagac tgtttgtctt ggttggacaa gcaaccatct    840

agatctgttt tgttcttgtg tttcggttct atgggttctt tcccagctgc tcaattgaag    900

gaaattgcta acggtttgga agcttctggt caaagattct tgtgggttgt taagaagcca    960

ccagttgaag aaaagtctaa gcaagttcac ggtgttgacg acttcgactt gaagggtgtt   1020

ttgccagaag gtttcttgga aagaactgct gacagaggta tggttgttaa gtcttgggct   1080

ccacaagttg ttgttttgaa gaaggaatct gttggtggtt tcgttactca ctgtggttgg   1140

aactctgttt tggaagctgt tgttgctggt gttccaatga ttgcttggcc attgtacgct   1200

gaacaacaca tgaacagaaa cgttttggtt actgacatgg aaattgctat tggtgttgaa   1260

caaagagacg aagaaggtgg tttcgtttct ggtgaagaag ttgaaagaag agttagagaa   1320

ttgatggaat ctgaaggtgg tagagctttg agagaaagat gtaagaagtt gggtgaaatg   1380

gcttctgctg ctttgggtga aactggttct tctactagaa acttggttaa cttcgtttct   1440

tctattactt aa                                                        1452


<210> SEQ ID NO 94
<211> LENGTH: 483
<212> TYPE: PRT
<213> ORGANISM: Pyrus communis

<400> SEQUENCE: 94

Met Gly Asp Val Ile Val Leu Tyr Ala Ser Pro Gly Met Gly His Ile
1               5                   10                  15

Val Ala Met Val Glu Leu Gly Lys Phe Ile Val His Arg Tyr Gly Pro
            20                  25                  30

His Lys Phe Ser Ile Thr Ile Leu Tyr Thr Cys Gly Ser Ile Val Asp
        35                  40                  45

Thr Ala Ser Ile Pro Val Tyr Ile Arg Arg Ile Ser His Ser His Pro
    50                  55                  60

Phe Ile Ser Phe Arg Gln Phe Pro Arg Val Thr Asn Asn Ile Thr Arg
65                  70                  75                  80

Asn Ile Ser Val Pro Ala Ile Thr Phe Asp Phe Ile Arg Gln Asn Asp
                85                  90                  95

Pro His Val Arg Ser Ala Leu Gln Glu Ile Ser Lys Ser Ala Thr Val
            100                 105                 110

Arg Ala Phe Ile Ile Asp Leu Phe Cys Thr Ser Ala Leu Pro Ile Gly
        115                 120                 125

Lys Glu Phe Asn Ile Pro Thr Tyr Tyr Phe His Thr Ser Gly Ala Ala
    130                 135                 140

Val Leu Ala Ala Phe Leu Tyr Leu Pro Lys Ile Asp Glu Gln Thr Lys
145                 150                 155                 160

Thr Thr Glu Ser Phe Lys Asp Leu Arg Asp Thr Val Phe Glu Phe Pro
```

-continued

```
                165                 170                 175

Gly Trp Lys Ser Pro Leu Lys Ala Thr His Met Val Gln Leu Val Leu
            180                 185                 190

Asp Arg Asn Asp Pro Ala Tyr Ser Asp Met Ile Tyr Phe Cys Ser His
        195                 200                 205

Leu Pro Lys Ser Asn Gly Ile Ile Val Asn Thr Phe Glu Glu Leu Glu
    210                 215                 220

Pro Pro Ser Val Leu Gln Ala Ile Ala Gly Gly Leu Cys Val Pro Asp
225                 230                 235                 240

Gly Pro Thr Pro Pro Val Tyr Tyr Val Gly Pro Leu Ile Glu Glu Glu
                245                 250                 255

Lys Glu Leu Ser Lys Asp Ala Asp Ala Ala Glu Lys Glu Asp Cys Leu
            260                 265                 270

Ser Trp Leu Asp Lys Gln Pro Ser Arg Ser Val Leu Phe Leu Cys Phe
        275                 280                 285

Gly Ser Met Gly Ser Phe Pro Ala Ala Gln Leu Lys Glu Ile Ala Asn
    290                 295                 300

Gly Leu Glu Ala Ser Gly Gln Arg Phe Leu Trp Val Val Lys Lys Pro
305                 310                 315                 320

Pro Val Glu Glu Lys Ser Lys Gln Val His Gly Val Asp Asp Phe Asp
                325                 330                 335

Leu Lys Gly Val Leu Pro Glu Gly Phe Leu Glu Arg Thr Ala Asp Arg
            340                 345                 350

Gly Met Val Val Lys Ser Trp Ala Pro Gln Val Val Val Leu Lys Lys
        355                 360                 365

Glu Ser Val Gly Gly Phe Val Thr His Cys Gly Trp Asn Ser Val Leu
    370                 375                 380

Glu Ala Val Val Ala Gly Val Pro Met Ile Ala Trp Pro Leu Tyr Ala
385                 390                 395                 400

Glu Gln His Met Asn Arg Asn Val Leu Val Thr Asp Met Glu Ile Ala
                405                 410                 415

Ile Gly Val Glu Gln Arg Asp Glu Glu Gly Gly Phe Val Ser Gly Glu
            420                 425                 430

Glu Val Glu Arg Arg Val Arg Glu Leu Met Glu Ser Glu Gly Gly Arg
        435                 440                 445

Ala Leu Arg Glu Arg Cys Lys Lys Leu Gly Glu Met Ala Ser Ala Ala
    450                 455                 460

Leu Gly Glu Thr Gly Ser Ser Thr Arg Asn Leu Val Asn Phe Val Ser
465                 470                 475                 480

Ser Ile Thr
```

<210> SEQ ID NO 95
<211> LENGTH: 1416
<212> TYPE: DNA
<213> ORGANISM: Oryza sativa

<400> SEQUENCE: 95

```
atgccgagct ctggcgacgc ggcgggcagg cggccgcatg tggtgctcat cccgagcgcc      60

ggcatgggcc acctcgtccc cttcggccgc ctcgccgtgg cgctgtcctc cggccacggc     120

tgcgacgtct ccctcgtcac ggtgctcccc accgtgtcca ccgcggagtc gaagcacctc     180

gacgcgctgt tcgacgcgtt cccggcggtg cggcggctcg acttcgagct cgcgccgttc     240

gacgcgtccg agttccccgg cgccgacccg ttcttcctcc ggttcgaggc catgcggcgg     300
```

```
tcggcgccgc tcctcggccc gctcctcacc ggcgccggcg cgtcggcgct cgccacggac    360

atcgcgctga catccgtcgt catacccgtg gcgaaggagc agggcctccc gtgccacatc    420

ctcttcaccg cctccgccgc gatgctctcc ctctgcgcct acttccccac atacctcgac    480

gccaacgctg gcggcggcgg cggcgtcggc gacgtcgaca tccccggcgt gtaccgcatc    540

cccaaggcct ccatcccgca ggcgctgcac gaccccaacc acctcttcac ccgccagttc    600

gtcgccaacg gccggagcct cacgagcgcc gccggcatcc tcgtcaacac gttcgacgcc    660

ttggagccgg aggccgtcgc ggccctgcag cagggcaagg tcgcctccgg cttcccgccg    720

gtgttcgccg tggggccact tctcccggcg agcaaccagg cgaaagatcc gcaggcgaac    780

tacatggagt ggctcgacgc gcagccggcg cggtcggtgg tgtacgtgag cttcggcagc    840

cggaaggcca tctcaaggga gcagctcagg gagctcgccg ccgggctgga gggcagcggc    900

caccggttcc tgtgggtggt gaagagcacc gtcgtggaca gggacgacgc cgccgagctc    960

ggcgagctgc tcgacgaggg gttcttggag cgggtggaga agcgaggcct cgtcaccaag   1020

gcatgggtgg atcaggaaga ggtcctgaag cacgagtccg tggcgctgtt cgtgagccac   1080

tgcggctgga actcggtgac ggaggcggcg gcgagcggcg tcccggtgct ggcgctgccg   1140

aggttcggcg accagcgggt gaactccggc gtggtggcgc gcgccgggct cggcgtgtgg   1200

gcggacacct ggagctggga gggggaggcc ggggtgatcg gcgcggagga gatatcggag   1260

aaggtgaagg cggcgatggc ggacgaggcg ttgcggatga aggcggcgag cctcgccgag   1320

gccgccgcga aggccgtcgc cggcggtgga tcgagccacc gttgtctggc cgagttcgcg   1380

cggctgtgcc aagggggaac atgtcgcact aattga                             1416
```

<210> SEQ ID NO 96
<211> LENGTH: 471
<212> TYPE: PRT
<213> ORGANISM: Oryza sativa

<400> SEQUENCE: 96

```
Met Pro Ser Ser Gly Asp Ala Ala Gly Arg Arg Pro His Val Val Leu
1               5                   10                  15

Ile Pro Ser Ala Gly Met Gly His Leu Val Pro Phe Gly Arg Leu Ala
            20                  25                  30

Val Ala Leu Ser Ser Gly His Gly Cys Asp Val Ser Leu Val Thr Val
        35                  40                  45

Leu Pro Thr Val Ser Thr Ala Glu Ser Lys His Leu Asp Ala Leu Phe
    50                  55                  60

Asp Ala Phe Pro Ala Val Arg Arg Leu Asp Phe Glu Leu Ala Pro Phe
65                  70                  75                  80

Asp Ala Ser Glu Phe Pro Gly Ala Asp Pro Phe Phe Leu Arg Phe Glu
                85                  90                  95

Ala Met Arg Arg Ser Ala Pro Leu Leu Gly Pro Leu Leu Thr Gly Ala
            100                 105                 110

Gly Ala Ser Ala Leu Ala Thr Asp Ile Ala Leu Thr Ser Val Val Ile
        115                 120                 125

Pro Val Ala Lys Glu Gln Gly Leu Pro Cys His Ile Leu Phe Thr Ala
    130                 135                 140

Ser Ala Ala Met Leu Ser Leu Cys Ala Tyr Phe Pro Thr Tyr Leu Asp
145                 150                 155                 160

Ala Asn Ala Gly Gly Gly Gly Gly Val Gly Asp Val Asp Ile Pro Gly
                165                 170                 175
```

-continued

```
Val Tyr Arg Ile Pro Lys Ala Ser Ile Pro Gln Ala Leu His Asp Pro
            180                 185                 190

Asn His Leu Phe Thr Arg Gln Phe Val Ala Asn Gly Arg Ser Leu Thr
        195                 200                 205

Ser Ala Ala Gly Ile Leu Val Asn Thr Phe Asp Ala Leu Glu Pro Glu
    210                 215                 220

Ala Val Ala Ala Leu Gln Gln Gly Lys Val Ala Ser Gly Phe Pro Pro
225                 230                 235                 240

Val Phe Ala Val Gly Pro Leu Leu Pro Ala Ser Asn Gln Ala Lys Asp
                245                 250                 255

Pro Gln Ala Asn Tyr Met Glu Trp Leu Asp Ala Gln Pro Ala Arg Ser
            260                 265                 270

Val Val Tyr Val Ser Phe Gly Ser Arg Lys Ala Ile Ser Arg Glu Gln
        275                 280                 285

Leu Arg Glu Leu Ala Ala Gly Leu Glu Gly Ser Gly His Arg Phe Leu
    290                 295                 300

Trp Val Val Lys Ser Thr Val Val Asp Arg Asp Asp Ala Ala Glu Leu
305                 310                 315                 320

Gly Glu Leu Leu Asp Glu Gly Phe Leu Glu Arg Val Glu Lys Arg Gly
                325                 330                 335

Leu Val Thr Lys Ala Trp Val Asp Gln Glu Glu Val Leu Lys His Glu
            340                 345                 350

Ser Val Ala Leu Phe Val Ser His Cys Gly Trp Asn Ser Val Thr Glu
        355                 360                 365

Ala Ala Ala Ser Gly Val Pro Val Leu Ala Leu Pro Arg Phe Gly Asp
    370                 375                 380

Gln Arg Val Asn Ser Gly Val Val Ala Arg Ala Gly Leu Gly Val Trp
385                 390                 395                 400

Ala Asp Thr Trp Ser Trp Glu Gly Glu Ala Gly Val Ile Gly Ala Glu
                405                 410                 415

Glu Ile Ser Glu Lys Val Lys Ala Ala Met Ala Asp Glu Ala Leu Arg
            420                 425                 430

Met Lys Ala Ala Ser Leu Ala Glu Ala Ala Ala Lys Ala Val Ala Gly
        435                 440                 445

Gly Gly Ser Ser His Arg Cys Leu Ala Glu Phe Ala Arg Leu Cys Gln
    450                 455                 460

Gly Gly Thr Cys Arg Thr Asn
465                 470
```

<210> SEQ ID NO 97
<211> LENGTH: 708
<212> TYPE: DNA
<213> ORGANISM: Vitis vinifera

<400> SEQUENCE: 97

```
atgtcttctt cttctcacag aggtattttg aagactgaag ctttgactaa gtacttgttg      60

gaaacttctg cttacccaag agaacacgaa caattgaagg gtttgagaga agctactgtt     120

gaaaagtaca agtactggtc tttgatgaac gttccagttg acgaaggttt gttcatttct     180

atgttgttga agattatgaa cgctaagaag actattgaat tgggtgtttt cactggttac     240

tctttgttgg ctactgcttt ggctttgcca caagacggta agattattgc tgttgaccca     300

gacaaggaag cttaccaaac tggtgttcca ttcattaaga aggctggtgt tgaacacaag     360

attaacttca ttcaatctga cgctatgact gttttgaacg acttgattgc tgacggtaag     420
```

-continued gaagaaggta ctttggactt cgctatggtt gacgctgaca aggaaaacta cttgaactac 480
cacgaattgt tgttgaagtt ggttagagtt ggtggtatta ttgcttacga caacactttg 540
tggttcggtt ctgttgctag atctgaagaa gaagaaatga tggacttcga aagagctggt 600
agagttcact tgatgaagtt gaacaagttc ttggcttctg acccaagagt tgaattgtct 660
cacttgtcta ttggtgacgg tgttgctttg tgtagaagat tgtactag 708

<210> SEQ ID NO 98
<211> LENGTH: 235
<212> TYPE: PRT
<213> ORGANISM: Vitis vinifera

<400> SEQUENCE: 98

Met Ser Ser Ser Ser His Arg Gly Ile Leu Lys Thr Glu Ala Leu Thr
1 5 10 15

Lys Tyr Leu Leu Glu Thr Ser Ala Tyr Pro Arg Glu His Glu Gln Leu
20 25 30

Lys Gly Leu Arg Glu Ala Thr Val Glu Lys Tyr Lys Tyr Trp Ser Leu
35 40 45

Met Asn Val Pro Val Asp Glu Gly Leu Phe Ile Ser Met Leu Leu Lys
50 55 60

Ile Met Asn Ala Lys Lys Thr Ile Glu Leu Gly Val Phe Thr Gly Tyr
65 70 75 80

Ser Leu Leu Ala Thr Ala Leu Ala Leu Pro Gln Asp Gly Lys Ile Ile
85 90 95

Ala Val Asp Pro Asp Lys Glu Ala Tyr Gln Thr Gly Val Pro Phe Ile
100 105 110

Lys Lys Ala Gly Val Glu His Lys Ile Asn Phe Ile Gln Ser Asp Ala
115 120 125

Met Thr Val Leu Asn Asp Leu Ile Ala Asp Gly Lys Glu Glu Gly Thr
130 135 140

Leu Asp Phe Ala Met Val Asp Ala Asp Lys Glu Asn Tyr Leu Asn Tyr
145 150 155 160

His Glu Leu Leu Leu Lys Leu Val Arg Val Gly Gly Ile Ile Ala Tyr
165 170 175

Asp Asn Thr Leu Trp Phe Gly Ser Val Ala Arg Ser Glu Glu Glu Glu
180 185 190

Met Met Asp Phe Glu Arg Ala Gly Arg Val His Leu Met Lys Leu Asn
195 200 205

Lys Phe Leu Ala Ser Asp Pro Arg Val Glu Leu Ser His Leu Ser Ile
210 215 220

Gly Asp Gly Val Ala Leu Cys Arg Arg Leu Tyr
225 230 235

<210> SEQ ID NO 99
<211> LENGTH: 2004
<212> TYPE: DNA
<213> ORGANISM: Arabidopsis thaliana

<400> SEQUENCE: 99
atggatgata ctacgtataa gccaaagaac attctcatta ctggagctgc tggatttatt 60
gcttctcatg ttgccaacag attaatccgt aactatcctg attacaagat cgttgttctt 120
gacaagctag attactgttc agatctgaag aatcttgatc cttctttttc ttcaccaaat 180
ttcaagtttg tcaaaggaga tatcgcgagt gatgatctcg ttaactacct tctcatcact 240

-continued

```
gaaaacattg atacgataat gcattttgct gctcaaactc atgttgataa ctcttttggt    300
aatagctttg agtttaccaa gaacaatatt tatggtactc atgttctttt ggaagcctgt    360
aaagttacag gacagatcag gaggtttatc catgtgagta ccgatgaagt ctatggagaa    420
accgatgagg atgctgctgt aggaaaccat gaagcctctc agctgttacc gacgaatcct    480
tactctgcaa ctaaggctgg tgctgagatg cttgtgatgg cttatggtag atcatatgga    540
ttgcctgtta ttacgactcg cgggaacaat gtttatgggc ctaaccagtt tcctgaaaaa    600
atgattccta agttcatctt gttggctatg agtgggaagc cgcttcccat ccatggagat    660
ggatctaatg tccggagtta cttgtactgc gaagacgttg ctgaggcttt tgaggttgtt    720
cttcacaaag gagaaatcgg tcatgtctac aatgtcggca caaaaagaga aaggagagtg    780
atcgatgtgg ctagagacat ctgcaaactt ttcgggaaag accctgagtc aagcattcag    840
tttgtggaga accggccctt taatgatcaa aggtacttcc ttgatgatca gaagctgaag    900
aaattggggt ggcaagagcg aacaaattgg gaagatggat tgaagaagac aatggactgg    960
tacactcaga atcctgagtg gtggggtgat gtttctggag ctttgcttcc tcatccgaga   1020
atgcttatga tgcccggtgg aagactttct gatggatcta gtgagaagaa agacgtttca   1080
agcaacacgg tccagacatt tacggttgta acacctaaga atggtgattc tggtgacaag   1140
gcttcgttga agtttttgat ctatggtaag actggttggc ttggtggtct tctagggaaa   1200
ctatgtgaga agcaagggat tacatatgag tatgggaaag gacgtctgga ggatagagct   1260
tctcttgtgg cggatattcg tagcatcaaa cctactcatg tgtttaatgc tgctggttta   1320
actggcagac ccaacgttga ctggtgtgaa tctcacaaac cagagaccat tcgtgtaaat   1380
gtcgcaggta ctttgactct agctgatgtt tgcagagaga atgatctctt gatgatgaac   1440
ttcgccaccg gttgcatctt tgagtatgac gctacacatc ctgagggttc gggtataggt   1500
ttcaaggaag aagacaagcc aaatttcttt ggttctttct actcgaaaac caaagccatg   1560
gttgaggagc tcttgagaga atttgacaat gtatgtacct tgagagtccg gatgccaatc   1620
tcctcagacc taaacaaccc gagaaacttc atcacgaaga tctcgcgcta caacaaagtg   1680
gtggacatcc cgaacagcat gaccgtacta gacgagcttc tcccaatctc tatcgagatg   1740
gcgaagagaa acctaagagg catatggaat ttcaccaacc caggggtggt gagccacaac   1800
gagatattgg agatgtacaa gaattacatc gagccaggtt ttaaatggtc caacttcaca   1860
gtggaagaac aagcaaaggt cattgttgct gctcgaagca acaacgaaat ggatggatct   1920
aaactaagca aggagttccc agagatgctc tccatcaaag agtcactgct caaatacgtc   1980
tttgaaccaa acaagagaac ctaa                                           2004
```

<210> SEQ ID NO 100
<211> LENGTH: 667
<212> TYPE: PRT
<213> ORGANISM: Arabidopsis thaliana

<400> SEQUENCE: 100

```
Met Asp Asp Thr Thr Tyr Lys Pro Lys Asn Ile Leu Ile Thr Gly Ala
1               5                   10                  15

Ala Gly Phe Ile Ala Ser His Val Ala Asn Arg Leu Ile Arg Asn Tyr
            20                  25                  30

Pro Asp Tyr Lys Ile Val Val Leu Asp Lys Leu Asp Tyr Cys Ser Asp
        35                  40                  45

Leu Lys Asn Leu Asp Pro Ser Phe Ser Ser Pro Asn Phe Lys Phe Val
    50                  55                  60
```

-continued

```
Lys Gly Asp Ile Ala Ser Asp Asp Leu Val Asn Tyr Leu Leu Ile Thr
65                  70                  75                  80

Glu Asn Ile Asp Thr Ile Met His Phe Ala Ala Gln Thr His Val Asp
                85                  90                  95

Asn Ser Phe Gly Asn Ser Phe Glu Phe Thr Lys Asn Asn Ile Tyr Gly
            100                 105                 110

Thr His Val Leu Leu Glu Ala Cys Lys Val Thr Gly Gln Ile Arg Arg
        115                 120                 125

Phe Ile His Val Ser Thr Asp Glu Val Tyr Gly Glu Thr Asp Glu Asp
    130                 135                 140

Ala Ala Val Gly Asn His Glu Ala Ser Gln Leu Leu Pro Thr Asn Pro
145                 150                 155                 160

Tyr Ser Ala Thr Lys Ala Gly Ala Glu Met Leu Val Met Ala Tyr Gly
                165                 170                 175

Arg Ser Tyr Gly Leu Pro Val Ile Thr Thr Arg Gly Asn Asn Val Tyr
            180                 185                 190

Gly Pro Asn Gln Phe Pro Glu Lys Met Ile Pro Lys Phe Ile Leu Leu
        195                 200                 205

Ala Met Ser Gly Lys Pro Leu Pro Ile His Gly Asp Gly Ser Asn Val
    210                 215                 220

Arg Ser Tyr Leu Tyr Cys Glu Asp Val Ala Glu Ala Phe Glu Val Val
225                 230                 235                 240

Leu His Lys Gly Glu Ile Gly His Val Tyr Asn Val Gly Thr Lys Arg
                245                 250                 255

Glu Arg Arg Val Ile Asp Val Ala Arg Asp Ile Cys Lys Leu Phe Gly
            260                 265                 270

Lys Asp Pro Glu Ser Ser Ile Gln Phe Val Glu Asn Arg Pro Phe Asn
        275                 280                 285

Asp Gln Arg Tyr Phe Leu Asp Asp Gln Lys Leu Lys Lys Leu Gly Trp
    290                 295                 300

Gln Glu Arg Thr Asn Trp Glu Asp Gly Leu Lys Lys Thr Met Asp Trp
305                 310                 315                 320

Tyr Thr Gln Asn Pro Glu Trp Trp Gly Asp Val Ser Gly Ala Leu Leu
                325                 330                 335

Pro His Pro Arg Met Leu Met Met Pro Gly Gly Arg Leu Ser Asp Gly
            340                 345                 350

Ser Ser Glu Lys Lys Asp Val Ser Ser Asn Thr Val Gln Thr Phe Thr
        355                 360                 365

Val Val Thr Pro Lys Asn Gly Asp Ser Gly Asp Lys Ala Ser Leu Lys
    370                 375                 380

Phe Leu Ile Tyr Gly Lys Thr Gly Trp Leu Gly Gly Leu Leu Gly Lys
385                 390                 395                 400

Leu Cys Glu Lys Gln Gly Ile Thr Tyr Glu Tyr Gly Lys Gly Arg Leu
                405                 410                 415

Glu Asp Arg Ala Ser Leu Val Ala Asp Ile Arg Ser Ile Lys Pro Thr
            420                 425                 430

His Val Phe Asn Ala Ala Gly Leu Thr Gly Arg Pro Asn Val Asp Trp
        435                 440                 445

Cys Glu Ser His Lys Pro Glu Thr Ile Arg Val Asn Val Ala Gly Thr
    450                 455                 460

Leu Thr Leu Ala Asp Val Cys Arg Glu Asn Asp Leu Leu Met Met Asn
465                 470                 475                 480
```

-continued

```
Phe Ala Thr Gly Cys Ile Phe Glu Tyr Asp Ala Thr His Pro Glu Gly
                485                 490                 495

Ser Gly Ile Gly Phe Lys Glu Glu Asp Lys Pro Asn Phe Phe Gly Ser
            500                 505                 510

Phe Tyr Ser Lys Thr Lys Ala Met Val Glu Glu Leu Leu Arg Glu Phe
        515                 520                 525

Asp Asn Val Cys Thr Leu Arg Val Arg Met Pro Ile Ser Ser Asp Leu
    530                 535                 540

Asn Asn Pro Arg Asn Phe Ile Thr Lys Ile Ser Arg Tyr Asn Lys Val
545                 550                 555                 560

Val Asp Ile Pro Asn Ser Met Thr Val Leu Asp Glu Leu Leu Pro Ile
                565                 570                 575

Ser Ile Glu Met Ala Lys Arg Asn Leu Arg Gly Ile Trp Asn Phe Thr
            580                 585                 590

Asn Pro Gly Val Val Ser His Asn Glu Ile Leu Glu Met Tyr Lys Asn
        595                 600                 605

Tyr Ile Glu Pro Gly Phe Lys Trp Ser Asn Phe Thr Val Glu Glu Gln
    610                 615                 620

Ala Lys Val Ile Val Ala Ala Arg Ser Asn Asn Glu Met Asp Gly Ser
625                 630                 635                 640

Lys Leu Ser Lys Glu Phe Pro Glu Met Leu Ser Ile Lys Glu Ser Leu
                645                 650                 655

Leu Lys Tyr Val Phe Glu Pro Asn Lys Arg Thr
            660                 665
```

<210> SEQ ID NO 101
<211> LENGTH: 827
<212> TYPE: DNA
<213> ORGANISM: Saccharomyces cerevisiae

<400> SEQUENCE: 101

```
gatcttccaa ctggcaccgc tggcttgaac aacaatacca gccttccaac ttctgtaaat     60

aacggcggta cgccagtgcc accagtaccg ttacctttcg gtatacctcc tttccccatg    120

tttccaatgc ccttcatgcc tccaacggct actatcacaa atcctcatca agctgacgca    180

agccctaaga aatgaataac aatactgaca gtactaaata attgcctact tggcttcaca    240

tacgttgcat acgtcgatat agataataat gataatgaca gcaggattat cgtaatacgt    300

aatagttgaa aatctcaaaa atgtgtgggt cattacgtaa ataatgatag gaatgggatt    360

cttctatttt tcctttttcc attctagcag ccgtcgggaa aacgtggcat cctctctttc    420

gggctcaatt ggagtcacgc tgccgtgagc atcctctctt tccatatcta acaactgagc    480

acgtaaccaa tggaaaagca tgagcttagc gttgctccaa aaaagtattg gatggttaat    540

accatttgtc tgttctcttc tgactttgac tcctcaaaaa aaaaaaatct acaatcaaca    600

gatcgcttca attacgccct cacaaaaact tttttccttc ttcttcgccc acgttaaatt    660

ttatccctca tgttgtctaa cggatttctg cacttgattt attataaaaa agacaaagac    720

ataatacttc tctatcaatt tcagttattg ttcttccttg cgttattctt ctgttcttct    780

ttttcttttg tcatatataa ccataaccaa gtaatacata ttcaaaa                  827
```

<210> SEQ ID NO 102
<211> LENGTH: 686
<212> TYPE: DNA
<213> ORGANISM: Saccharomyces cerevisiae

<400> SEQUENCE: 102
gatctcagtt cgagtttatc attatcaata ctgccatttc aaagaatacg taaataatta 60
atagtagtga ttttcctaac tttatttagt caaaaaatta gccttttaat tctgctgtaa 120
cccgtacatg cccaaaatag ggggcgggtt acacagaata tataacatcg taggtgtctg 180
ggtgaacagt ttattcctgg catccactaa atataatgga gcccgctttt taagctggca 240
tccagaaaaa aaaagaatcc cagcaccaaa atattgtttt cttcaccaac catcagttca 300
taggtccatt ctcttagcgc aactacagag aacaggggca caaacaggca aaaaacggac 360
acaacctcaa tggagtgatg caacctgcct ggagtaaatg atgacacaag gcaattgacc 420
cacgcatgta tctatctcat tttcttacac cttctattac cttctgctct ctctgatttg 480
gaaaaagctg aaaaaaaagg ttgaaaccag ttccctgaaa ttattcccct acttgactaa 540
taagtatata aagacggtag gtattgattg taattctgta aatctatttc ttaaacttct 600
taaattctac ttttatagtt agtctttttt ttagttttaa aacaccaaga acttagtttc 660
gaataaacac acataaacaa acaaaa 686

<210> SEQ ID NO 103
<211> LENGTH: 756
<212> TYPE: DNA
<213> ORGANISM: Saccharomyces cerevisiae

<400> SEQUENCE: 103
gatctacgca cagatattat aacatctgca taataggcat ttgcaagaat tactcgtgag 60
taaggaaaga gtgaggaact atcgcatacc tgcatttaaa gatgccgatt tgggcgcgaa 120
tcctttattt tggcttcacc ctcatactat tatcagggcc agaaaaagga agtgtttccc 180
tccttcttga attgatgtta ccctcataaa gcacgtggcc tcttatcgag aaagaaatta 240
ccgtcgctcg tgatttgttt gcaaaaagaa caaaactgaa aaaacccaga cacgctcgac 300
ttcctgtctt cctattgatt gcagcttcca atttcgtcac acaacaaggt cctagcgacg 360
gctcacaggt tttgtaacaa gcaatcgaag gttctggaat ggcgggaaag ggtttagtac 420
cacatgctat gatgcccact gtgatctcca gagcaaagtt cgttcgatcg tactgttact 480
ctctctcttt caaacagaat tgtccgaatc gtgtgacaac aacagcctgt tctcacacac 540
tcttttcttc taaccaaggg ggtggtttag tttagtagaa cctcgtgaaa cttacattta 600
catatatata aacttgcata aattggtcaa tgcaagaaat acatatttgg tcttttctaa 660
ttcgtagttt ttcaagttct tagatgcttt ctttttctct tttttacaga tcatcaagga 720
agtaattatc tactttttac aacaaatata aaacaa 756

<210> SEQ ID NO 104
<211> LENGTH: 805
<212> TYPE: DNA
<213> ORGANISM: Saccharomyces cerevisiae

<400> SEQUENCE: 104
gatctatgcg actgggtgag catatgttcc gctgatgtga tgtgcaagat aaacaagcaa 60
ggcagaaact aacttcttct tcatgtaata aacacacccc gcgtttattt acctatctct 120
aaacttcaac accttatatc ataactaata tttcttgaga taagcacact gcacccatac 180
cttccttaaa aacgtagctt ccagtttttg gtggttccgg cttccttccc gattccgccc 240
gctaaacgca tatttttgtt gcctggtggc atttgcaaaa tgcataacct atgcatttaa 300
aagattatgt atgctcttct gacttttcgt gtgatgaggc tcgtggaaaa aatgaataat 360

-continued

```
ttatgaattt gagaacaatt ttgtgttgtt acggtatttt actatggaat aatcaatcaa    420

ttgaggattt tatgcaaata tcgtttgaat atttttccga ccctttgagt acttttcttc    480

ataattgcat aatattgtcc gctgcccctt tttctgttag acggtgtctt gatctacttg    540

ctatcgttca acaccacctt attttctaac tatttttttt ttagctcatt tgaatcagct    600

tatggtgatg gcacattttt gcataaacct agctgtcctc gttgaacata ggaaaaaaaa    660

atatataaac aaggctcttt cactctcctt gcaatcagat ttgggtttgt tccctttatt    720

ttcatatttc ttgtcatatt cctttctcaa ttattatttt ctactcataa cctcacgcaa    780

aataacacag tcaaatctat caaaa                                          805
```

<210> SEQ ID NO 105
<211> LENGTH: 1003
<212> TYPE: DNA
<213> ORGANISM: Saccharomyces cerevisiae

<400> SEQUENCE: 105

```
gatctaatgc tactattttg gagatcaatc tcagtacaaa acaatattaa aaagaggtga     60

attattttc cccccttatt tttttttgt tagaattgat ccaaatgtaa ataaacaatc    120

acaaggaaaa aaaaaaaaaa aaaaaatagc cgccatgacc ccggatcgtc ggttgtgata    180

cggtcagggt agcgccctgg tcaaacttca gaactaaaaa aataataagg aagaaaaaaa    240

tagctaattt ttccggcaga aagattttcg ctacccgaaa gtttttccgg caagctaaat    300

ggaaaaagga aagattattg aaagagaaag aaagaaaaaa aaaaaatgta cacccagaca    360

tcgggcttcc acaatttcgg ctctattgtt ttccatctct cgcaacggcg ggattcctct    420

atggcgtgtg atgtctgtat ctgttactta atccagaaac tggcacttga cccaactctg    480

ccacgtgggt cgttttgcca tcgacagatt gggagatttt catagtagaa ttcagcatga    540

tagctacgta aatgtgttcc gcaccgtcac aaagtgtttt ctactgttct ttcttctttc    600

gttcattcag ttgagttgag tgagtgcttt gttcaatgga tcttagctaa atgcatattt    660

tttctcttgg taaatgaatg cttgtgatgt cttccaagtg atttcctttc cttcccatat    720

gatgctaggt acctttagtg tcttcctaaa aaaaaaaaaa ggctcgccat caaaacgata    780

ttcgttggct tttttttctg aattataaat actctttggt aacttttcat ttccaagaac    840

ctcttttttc cagttatatc atggtcccct ttcaaagtta ttctctactc tttttcatat    900

tcattctttt tcatcctttg gtttttttatt cttaacttgt ttattattct ctcttgtttc    960

tatttacaag acaccaatca aaacaaataa aacatcatca caa                     1003
```

<210> SEQ ID NO 106
<211> LENGTH: 417
<212> TYPE: DNA
<213> ORGANISM: Saccharomyces cerevisiae

<400> SEQUENCE: 106

```
gatcttagct tcaaaatgtt tctactcctt ttttactctt ccagattttc tcggactccg     60

cgcatcgccg taccacttca aaacacccaa gcacagcata ctaaatttcc cctctttctt    120

cctctagggt gtcgttaatt acccgtacta aaggtttgga aaagaaaaaa gagaccgcct    180

cgtttctttt tcttcgtcga aaaaggcaat aaaaattttt atcacgtttc tttttcttga    240

aaattttttt ttttgatttt tttctctttc gatgacctcc cattgatatt taagttaata    300

aacggtcttc aatttctcaa gtttcagttt catttttctt gttctattac aacttttttt    360

acttcttgct cattagaaag aaagcatagc aatctaatct aagttttaat tacaaaa      417
```

<210> SEQ ID NO 107
<211> LENGTH: 565
<212> TYPE: DNA
<213> ORGANISM: Saccharomyces cerevisiae

<400> SEQUENCE: 107
gatctgggcc gtatacttac atatagtaga tgtcaagcgt aggcgcttcc cctgccggct 60
gtgagggcgc cataaccaag gtatctatag accgccaatc agcaaactac ctccgtacat 120
tcatgttgca cccacacatt tatacaccca gaccgcgaca aattacccat aaggttgttt 180
gtgacggcgt cgtacaagag aacgtgggaa ctttttaggc tcaccaaaaa agaaagaaaa 240
aatacgagtt gctgacagaa gcctcaagaa aaaaaaaatt cttcttcgac tatgctggag 300
gcagagatga tcgagccggt agttaactat atatagctaa attggttcca tcaccttctt 360
ttctggtgtc gctccttcta gtgctatttc tggcttttcc tatttttttt tttccatttt 420
tctttctctc tttctaatat ataaattctc ttgcattttc tatttttctc tctatctatt 480
ctacttgttt attcccttca aggttttttt ttaaggagta cttgttttta gaatatacgg 540
tcaacgaact ataattaact aaaca 565

<210> SEQ ID NO 108
<211> LENGTH: 538
<212> TYPE: DNA
<213> ORGANISM: Saccharomyces cerevisiae

<400> SEQUENCE: 108
gatctagtta taataatcct acgttagtgt gagcgggatt taaactgtga ggaccttaat 60
acattcagac acttctgcgg tatcacccta cttattccct tcgagattat atctaggaac 120
ccatcaggtt ggtggaagat tacccgttct aagacttttc agcttcctct attgatgtta 180
cacctggaca cccctttttct ggcatccagt ttttaatctt cagtggcatg tgagattctc 240
cgaaattaat taaagcaatc acacaattct ctcggatacc acctcggttg aaactgacag 300
gtggtttgtt acacatgcta atgcaaagga gcctatatac ctttggctcg gctgctgtaa 360
cagggaatat aaagggcagc ataatttagg agtttagtga acttgcaaca tttactattt 420
tcccttctta cgtaaatatt tttcttttta attctaaatc aatcttttttc aattttttgt 480 ttgtattctt ttcttgctta aatctataac tacaaaaaac acatacataa actaaaaa 538

<210> SEQ ID NO 109
<211> LENGTH: 1269
<212> TYPE: DNA
<213> ORGANISM: Artificial Sequence
<220> FEATURE:
<223> OTHER INFORMATION: Synthetic

<400> SEQUENCE: 109
ggcgcgccag ttacttgctc tatgcgtttg cgcatcctct ttttactttt tttttttcag 60
taaagcctaa gcataaatcg ttttatacgt acgacacgtt caacttttct tggttagtag 120
tggcaatctc tgcaatacat acagggagtc atggtctatc atcttgtcca atcaaagaag 180
catcggttca gatcgagcaa actgtaggga gaaaggaaag tagaaatgca gagtgtgcta 240
tatgtccaat ctcggttttg tagtttggat gtcattagag atctaccacc caaccggctg 300
ctttcatgtg gaacagaaaa gaaatcgggg cgcttcctct tctgtattcc tttaattaac 360
gtttttattc agccatctaa ccatcatacc cccatacggt aacaaaacct cttctaagaa 420
aagaagtctc tgctcctccg ccatcttatt tttattcgct gcgcgcgttt attgtcgcat 480
cgctagccag caaaaagttg gttgcctttt tttacctaaa aaagacacat ctaactgatt 540
agttttccgt tttaggatat tgacgccaag cgtgcgtctg attcccgggt catcgtccac 600
ctccggagaa caggccacca tcacgcatct gtgtctgaat ttcatcacga ggcgcgcctt 660
ttcccgtctt tcagtgcctt gttcagttct tcctgacggg cggtatattt ctccagctta 720
ctagtttacg tggattgagc cagcaataca gatcattatt aaactgtttt gtacatgatg 780
ttagtatata atcgtaaagc ttttctaata tgtatacctt atacatggaa ctccacagaa 840
cttgcaaaca taccaaaaat cctttattct tgttcactca ttttacatca aaaaataata 900
tttcagttat taaggaaaat aaaaaaatag attagagaag cattttgaag aaatagtata 960
ttcttttatt gaacctaaga gcgtgatatt tttactcgaa ataaaatacg aaaaatctat 1020
acactcatct ttccgactac tattggctcc tgctcaaaaa aagagggaaa aaaagctcca 1080
aaattctatc ttttcctatc gctcctgtcc tatccttatt acgttcatta ctattttaat 1140
actatccatt cttttatttt cagtctaaaa aaaacatttc tcataacggg aaaagcaaaa 1200
aaatgtcaag cttatacatc aaaacaccac tgcatgcatt atctgctggt ccggattctc 1260
aggcgcgcc 1269

<210> SEQ ID NO 110
<211> LENGTH: 1288
<212> TYPE: DNA
<213> ORGANISM: Artificial Sequence
<220> FEATURE:
<223> OTHER INFORMATION: Synthetic

<400> SEQUENCE: 110
ggcgcgccga ggattttcga tggagcagga tgaggagaaa tagtaccaca tgtatatatc 60
cattacaaaa aggtttatat acaattacaa tagacccttg ttggggtttc tgaaaaaaga 120
agtagtcgat gccatcggca ataatacgga attacgagaa acacaatccc gatccttttt 180
tgggtaatta cttcaccgat tctaccgatt tatcatgcca aaaaaaattc accgtgggtt 240
ctagaagtgc cctttgagga ttgtagccac tctaacccac acggcctcct tactagctga 300
ctaaggtgac aaaaccgcaa ggactggaaa gtcgccactc atctgaaaat tctcaagttt 360
ttcactactg agtttatgct ttcgaatttt tttgttcggt aatagcacgg cggttcgatt 420
caattccgcc gctccgagcg atgctccgca aaactcagta ataagctttc tgatggttca 480 ccccttttt agcacgcggg gtgtaactca acagaaaaat gtgccataga acaagactag 540
gcaaaagcca aggagcgttt gccatgaact tccacaaccg ggtcatcgtc cacctccgga 600
gaacaggcca ccatcacgca tctgtgtctg aatttcatca cgaggcgcgc cttttcccgt 660
ctttcagtgc cttgttcagt tcttcctgac gggcggtata tttctccagc ttactagcac 720
acgactagcg ctttcagata ttaaaaagtt tagatgtagg ttttagcggt aacagttata 780
taaatcgtgt ttcttctctt gatgaaacaa aaaaatgcta gaaaaacttt gtcgtttctt 840
acttttggtg cgctttgcag ttttcgtggc tagacttaga atcatttctc ctcagatttc 900
ttgattaaag tttggtgcga agccctactc taacattggt gttcttcttt tcattcacgc 960
aagttaagtc caggaaggtg agcaaatgct catccttctg ttcatgcgtg acggctgaat 1020
tatccttatc tggcgtaccc gtgcagccgt ttccgtgcct cggttcctcc gagatatcct 1080
tagggaccgc cagggaccat gattgcgtca actgttgtca ccgctccaga ggatcctctg 1140
taaccttttc aaccataaaa atagaaaggg cacagggttg ggtatttgga attttttttt 1200
tgggtttttt cgtattactt attacttacc ttcttttcta tataattttg tttttccctg 1260
gtagagcgga atcttcccac ggcgcgcc 1288

<210> SEQ ID NO 111
<211> LENGTH: 1710
<212> TYPE: DNA
<213> ORGANISM: Artificial Sequence
<220> FEATURE:
<223> OTHER INFORMATION: Synthetic

<400> SEQUENCE: 111
ggcgcgcctc atcgtccacc tccggagaac aggccaccat cacgcatctg tgtctgaatt 60
tcatcacgac gcgccgctgc aggtcgacaa cccttaatat aacttcgtat aatgtatgct 120
atacgaagtt attaggtcta gagatcccaa tacaacagat cacgtgatct tttgtaagat 180
gaagttgaag tgagtgttgc accgtgccaa tgcaggtggc tattagatta aatatgtgat 240
ttgttctatt aagtttcctg tataattaat ggggagcgct gattctcttt tggtacgctt 300
cccatccagc atttctgtat ctttcacctt caaccttagg atctctaccc ttggcgaaaa 360
gtcctctgcc aacaatgatg atatctgatc caccacttac aacttcgtcg acggttctgt 420
actgctgacc caatgcatcg cctttgtcgt ctaaacctac acctggggtc atgattagcc 480
aatcaaaccc ttcttctctt cctcccatat cgttctgagc aatgaaccca ataacgaaat 540
ctttatcact ctttgcaata tcaacggtac ccttagtata ttcaccgtgt gctagagaac 600
ccttggaaga caattcagca agcatcaata atccccttgg ttctttggtg acctcttgcg 660
caccttgttt caagccagca acaataccag caccagtaac cccgtgggcg ttggtgatat 720
cagaccattc tgcgatacgg taaacgcccg atgtatattg taatttgact gtgttaccga 780
tatcggcgaa ttttctgtcc tcaaatatca agaacttgta tttctctgcc aatgctttca 840
atggaacgac agtaccctca taactgaaat catccaagat atcaacgtgt gttttcaaaa 900
ggcaaatgta tggacccaac gtttcaacaa gtttcaatag ctcatcagtc gaacgaacgt 960
caagagaagc acacaaattg gtcttctttt catccattaa acgtaaaagt ttcgatgcaa 1020
ccggacttgc atgagtctca gctctactgg tatatgattt tgtggacatg gtgcaactaa 1080
ttgacgggag tgtattgacg ctggcgtact ggctttcaca aaatggccca atcacaacca 1140
catcttagat agttgaaatg actttagata acatcaattg agatgagctt aatcatgtca 1200
aagctaaaag tgtcaccatg aacgacaatt cttaagcaaa tcacgtgata tagatccacg 1260
aataaccacc atttgatgct cgaggcaagt aatgtgtgta aaaaaatgcg ttaccaccat 1320
ccaatgcaga ccgatcttct acccagaatc acatatattt atgtaccgag tacctttttt 1380
ctatcttcca attgcttctc ccatatgatt gtctccgtaa gctcgaaatt tctaagttgg 1440
attttaatct tcacgcagga tgacagttcg atgagcttct gaggagtgtt tagaacataa 1500
tcagtttatc catggtctat ctcttcttgt cgctttttct cctcgataga acctaaataa 1560
aacgagctct cgagaaccct taatataact tcgtataatg tatgctatac gaagttatta 1620
ggtgatatca gatccggcgc gtggcaccct tgcgggccat gtcatacacc gccttcagag 1680
cagccggacc tatctgcccg ttggcgcgcc 1710

<210> SEQ ID NO 112
<211> LENGTH: 4427
<212> TYPE: DNA
<213> ORGANISM: Artificial Sequence
<220> FEATURE:

-continued

<223> OTHER INFORMATION: Synthetic

<400> SEQUENCE: 112
ggcgcgcctt tcccgtcttt cagtgccttg ttcagttctt cctgacgggc ggtatatttc 60
tccagcttgg cctatgcggc cctgtcagac caagtttacg agctcgcttg gactcctgtt 120
gatagatcca gtaatgacct cagaactcca tctggatttg ttcagaacgc tcggttgccg 180
ccgggcgttt tttattggtg agaatccaag cactagggac agtaagacgg gtaagcctgt 240
tgatgatacc gctgccttac tgggtgcatt agccagtctg aatgacctgt cacgggataa 300
tccgaagtgg tcagactgga aatcagaggg gcaggaactg ctgaacagca aaaagtcaga 360
tagcaccaca tagcagaccc gccataaaac gccctgagaa gcccgtgacg ggcttttctt 420
gtattatggg tagtttcctt gcatgaatcc ataaaaggcg cctgtagtgc catttacccc 480
cattcactgc cagagccgtg agcgcagcga actgaatgtc acgaaaaaga cagcgactca 540
ggtgcctgat ggtcggagac aaaaggaata ttcagcgatt tgcccgagct tgcgagggtg 600
ctacttaagc ctttagggtt ttaaggtctg ttttgtagag gagcaaacag cgtttgcgac 660
atccttttgt aatactgcgg aactgactaa agtagtgagt tatacacagg gctgggatct 720
attcttttta tcttttttta ttctttcttt attctataaa ttataaccac ttgaatataa 780
acaaaaaaaa cacacaaagg tctagcggaa tttacagagg gtctagcaga atttacaagt 840
tttccagcaa aggtctagca gaatttacag atacccacaa ctcaaaggaa aaggacatgt 900
aattatcatt gactagccca tctcaattgg tatagtgatt aaaatcacct agaccaattg 960
agatgtatgt ctgaattagt tgttttcaaa gcaaatgaac tagcgattag tcgctatgac 1020
ttaacggagc atgaaaccaa gctaatttta tgctgtgtgg cactactcaa ccccacgatt 1080
gaaaacccta caaggaaaga acggacggta tcgttcactt ataaccaata cgctcagatg 1140
atgaacatca gtagggaaaa tgcttatggt gtattagcta aagcaaccag agagctgatg 1200
acgagaactg tggaaatcag gaatcctttg gttaaaggct ttgagatttt ccagtggaca 1260
aactatgcca agttctcaag cgaaaaatta gaattagttt ttagtgaaga gatattgcct 1320
tatcttttcc agttaaaaaa attcataaaa tataatctgg aacatgttaa gtcttttgaa 1380
aacaaatact ctatgaggat ttatgagtgg ttattaaaag aactaacaca aaagaaaact 1440
cacaaggcaa atatagagat tagccttgat gaatttaagt tcatgttaat gcttgaaaat 1500
aactaccatg agtttaaaag gcttaaccaa tgggttttga aaccaataag taaagattta 1560
aacacttaca gcaatatgaa attggtggtt gataagcgag gccgcccgac tgatacgttg 1620
attttccaag ttgaactaga tagacaaatg gatctcgtaa ccgaacttga gaacaaccag 1680
ataaaaatga atggtgacaa aataccaaca accattacat cagattccta cctacataac 1740
ggactaagaa aaacactaca cgatgcttta actgcaaaaa ttcagctcac cagttttgag 1800
gcaaaatttt tgagtgacat gcaaagtaag tatgatctca atggttcgtt ctcatggctc 1860
acgcaaaaac aacgaaccac actagagaac atactggcta aatacggaag gatctgaggt 1920
tcttatggct cttgtatcta tcagtgaagc atcaagacta acaaacaaaa gtagaacaac 1980
tgttcaccgt tacatatcaa agggaaaact gtccatatgc acagatgaaa acggtgtaaa 2040
aaagatagat acatcagagc ttttacgagt ttttggtgca ttcaaagctg ttcaccatga 2100
acagatcgac aatgtaacgc ggccgctcga ctacgtcgta aggccgtttc tgacagagta 2160
aaattcttga gggaactttc accattatgg gaaatggttc aagaaggtat tgacttaaac 2220
tccatcaaat ggtcaggtca ttgagtgttt tttatttgtt gtattttttt ttttttagag 2280
aaaatcctcc aatatataaa ttaggaatca tagtttcatg attttctgtt acacctaact 2340
ttttgtgtgg tgccctcctc cttgtcaata ttaatgttaa agtgcaattc tttttcctta 2400
tcacgttgag ccattagtat caatttgctt acctgtattc ctttacatcc tcctttttct 2460
ccttcttgat aaatgtatgt agattgcgta tatagtttcg tctaccctat gaacatattc 2520
cattttgtaa tttcgtgtcg tttctattat gaatttcatt tataaagttt atgtacaaat 2580
atcataaaaa aagagaatct ttttaagcaa ggattttctt aacttcttcg gcgacagcat 2640
cactgacttc ggtggtactg ttggaaccac ctaaatcacc agttctgata cctgcatcca 2700
aaaccttttt aactgcatct tcaatggcct taccttcttc aggcaagttc aatgacaatt 2760
tcaacatcat tgcagcagac aagatagtgg cgatagggtt gaccttattc tttggcaaat 2820
ctggagcaga accgtggcat ggttcgtaca aaccaaatgc ggtgttcttg tctggcaaag 2880
aggccaagga cgcagatggc aacaaaccca aggaacctgg gataacggag gcttcatcgg 2940
agatgatatc accaaacatg ttgctggtga ttataatacc atttaggtgg gttgggttct 3000
taactaggat catggcggca gaatcaatca attgatgttg aaccttcaat gtagggaatt 3060
cgttcttgat ggtttcctcc acagtttttc tccataatct tgaagaggcc aaaacattag 3120
ctttatccaa ggaccaaata ggcaatggtg gctcatgttg tagggccatg aaagcggcca 3180
ttcttgtgat tctttgcact tctggaacgg tgtattgttc actatcccaa gcgacaccat 3240
caccatcgtc ttcctttctc ttaccaaagt aaatacctcc cactaattct ctgacaacaa 3300
cgaagtcagt acctttagca aattgtggct tgattggaga taagtctaaa agagagtcgg 3360
atgcaaagtt acatggtctt aagttggcgt acaattgaag ttctttacgg atttttagta 3420
aaccttgttc aggtctaaca ctaccggtac cccatttagg accacccaca gcacctaaca 3480
aaacggcatc agccttcttg gaggcttcca gcgcctcatc tggaagtgga acacctgtag 3540
catcgatagc agcaccacca attaaatgat tttcgaaatc gaacttgaca ttggaacgaa 3600
catcagaaat agctttaaga accttaatgg cttcggctgt gatttcttga ccaacgtggt 3660
cacctggcaa aacgacgatc ttcttagggg cagacattag aatggtatat ccttgaaata 3720
tatatatata tattgctgaa atgtaaaagg taagaaaagt tagaaagtaa gacgattgct 3780
aaccacctat tggaaaaaac aataggtcct taaataatat tgtcaacttc aagtattgtg 3840
atgcaagcat ttagtcatga acgcttctct attctatatg aaaagccggt tccggcgctc 3900
tcacctttcc tttttctccc aatttttcag ttgaaaaagg tatatgcgtc aggcgacctc 3960
tgaaattaac aaaaaatttc cagtcatcga atttgattct gtgcgatagc gcccctgtgt 4020
gttctcgtta tgttgaggaa aaaaataatg gttgctaaga gattcgaact cttgcatctt 4080
acgatacctg agtattccca cagttaactg cggtcaagat atttcttgaa tcaggcgcct 4140
tagaccgctc ggccaaacaa ccaattactt gttgagaaat agagtataat tatcctataa 4200
atataacgtt tttgaacaca catgaacaag gaagtacagg acaattgatt ttgaagagaa 4260
tgtggatttt gatgtaattg ttgggattcc atttttaata aggcaataat attaggtatg 4320
tagatatact agaagttctc ctcgagcggc cgcacgcgtt catcgtccac ctccggagaa 4380
caggccacca tcacgcatct gtgtctgaat ttcatcacgg gcgcgcc 4427

<210> SEQ ID NO 113
<211> LENGTH: 3967
<212> TYPE: DNA
<213> ORGANISM: Artificial Sequence
<220> FEATURE:

<223> OTHER INFORMATION: Synthetic

<400> SEQUENCE: 113
ggcgcgcctt tcccgtcttt cagtgccttg ttcagttctt cctgacgggc ggtatatttc 60
tccagcttgg cctatgcggc cctgtcagac caagtttacg agctcgcttg gactcctgtt 120
gatagatcca gtaatgacct cagaactcca tctggatttg ttcagaacgc tcggttgccg 180
ccgggcgttt tttattggtg agaatccaag cactagggac agtaagacgg gtaagcctgt 240
tgatgatacc gctgccttac tgggtgcatt agccagtctg aatgacctgt cacgggataa 300
tccgaagtgg tcagactgga aatcagaggg gcaggaactg ctgaacagca aaaagtcaga 360
tagcaccaca tagcagaccc gccataaaac gccctgagaa gcccgtgacg ggcttttctt 420
gtattatggg tagtttcctt gcatgaatcc ataaaaggcg cctgtagtgc catttacccc 480
cattcactgc cagagccgtg agcgcagcga actgaatgtc acgaaaaaga cagcgactca 540
ggtgcctgat ggtcggagac aaaaggaata ttcagcgatt tgcccgagct tgcgagggtg 600
ctacttaagc ctttagggtt ttaaggtctg ttttgtagag gagcaaacag cgtttgcgac 660
atccttttgt aatactgcgg aactgactaa agtagtgagt tatacacagg gctgggatct 720
attcttttta tcttttttta ttctttcttt attctataaa ttataaccac ttgaatataa 780
acaaaaaaaa cacacaaagg tctagcggaa tttacagagg gtctagcaga atttacaagt 840
tttccagcaa aggtctagca gaatttacag atacccacaa ctcaaaggaa aaggacatgt 900
aattatcatt gactagccca tctcaattgg tatagtgatt aaaatcacct agaccaattg 960
agatgtatgt ctgaattagt tgttttcaaa gcaaatgaac tagcgattag tcgctatgac 1020
ttaacggagc atgaaaccaa gctaatttta tgctgtgtgg cactactcaa ccccacgatt 1080
gaaaacccta caaggaaaga acggacggta tcgttcactt ataaccaata cgctcagatg 1140
atgaacatca gtagggaaaa tgcttatggt gtattagcta aagcaaccag agagctgatg 1200
acgagaactg tggaaatcag gaatcctttg gttaaaggct ttgagatttt ccagtggaca 1260
aactatgcca agttctcaag cgaaaaatta gaattagttt ttagtgaaga gatattgcct 1320
tatcttttcc agttaaaaaa attcataaaa tataatctgg aacatgttaa gtcttttgaa 1380
aacaaatact ctatgaggat ttatgagtgg ttattaaaag aactaacaca aaagaaaact 1440
cacaaggcaa atatagagat tagccttgat gaatttaagt tcatgttaat gcttgaaaat 1500
aactaccatg agtttaaaag gcttaaccaa tgggttttga aaccaataag taaagattta 1560
aacacttaca gcaatatgaa attggtggtt gataagcgag gccgcccgac tgatacgttg 1620
attttccaag ttgaactaga tagacaaatg gatctcgtaa ccgaacttga gaacaaccag 1680
ataaaaatga atggtgacaa aataccaaca accattacat cagattccta cctacataac 1740
ggactaagaa aaacactaca cgatgcttta actgcaaaaa ttcagctcac cagttttgag 1800
gcaaaatttt tgagtgacat gcaaagtaag tatgatctca atggttcgtt ctcatggctc 1860
acgcaaaaac aacgaaccac actagagaac atactggcta aatacggaag gatctgaggt 1920
tcttatggct cttgtatcta tcagtgaagc atcaagacta acaaacaaaa gtagaacaac 1980
tgttcaccgt tacatatcaa agggaaaact gtccatatgc acagatgaaa acggtgtaaa 2040
aaagatagat acatcagagc ttttacgagt ttttggtgca ttcaaagctg ttcaccatga 2100
acagatcgac aatgtaacgc ggccgcctgc acggtcctgt tccctagcat gtacgtgagc 2160
gtatttcctt ttaaaccacg acgctttgtc ttcattcaac gtttcccatt gttttttttct 2220
actattgctt tgctgtggga aaaacttatc gaaagatgac gactttttct taattctcgt 2280
tttaagagct tggtgagcgc taggagtcac tgccaggtat cgtttgaaca cggcattagt 2340
cagggaagtc ataacacagt cctttcccgc aattttcttt ttctattact cttggcctcc 2400
tctagtacac tctatatttt tttatgcctc ggtaatgatt ttcatttttt tttttccacc 2460
tagcggatga ctcttttttt ttcttagcga ttggcattat cacataatga attatacatt 2520
atataaagta atgtgatttc ttcgaagaat atactaaaaa atgagcaggc aagataaacg 2580
aaggcaaaga tgacagagca gaaagcccta gtaaagcgta ttacaaatga aaccaagatt 2640
cagattgcga tctctttaaa gggtggtccc ctagcgatag agcactcgat cttcccagaa 2700
aaagaggcag aagcagtagc agaacaggcc acacaatcgc aagtgattaa cgtccacaca 2760
ggtatagggt ttctggacca tatgatacat gctctggcca agcattccgg ctggtcgcta 2820
atcgttgagt gcattggtga cttacacata gacgaccatc acaccactga agactgcggg 2880
attgctctcg gtcaagcttt taaagaggcc ctaggggccg tgcgtggagt aaaaaggttt 2940
ggatcaggat ttgcgccttt ggatgaggca ctttccagag cggtggtaga tctttcgaac 3000
aggccgtacg cagttgtcga acttggtttg caaagggaga aagtaggaga tctctcttgc 3060
gagatgatcc cgcattttct tgaaagcttt gcagaggcta gcagaattac cctccacgtt 3120
gattgtctgc gaggcaagaa tgatcatcac cgtagtgaga gtgcgttcaa ggctcttgcg 3180
gttgccataa gagaagccac ctcgcccaat ggtaccaacg atgttccctc caccaaaggt 3240
gttcttatgt agtgacaccg attatttaaa gctgcagcat acgatatata tacatgtgta 3300
tatatgtata cctatgaatg tcagtaagta tgtatacgaa cagtatgata ctgaagatga 3360
caaggtaatg catcattcta tacgtgtcat tctgaacgag gcgcgctttc cttttttctt 3420
tttgcttttt cttttttttt ctcttgaact cgatcgagaa aaaaaatata aaagagatgg 3480
aggaacggga aaaagttagt tgtggtgata ggtggcaagt ggtattccgt aagaacaaca 3540
agaaaagcat ttcatattat ggctgaactg agcgaacaag tgcaaaattt aagcatcaac 3600
gacaacaacg agaatggtta tgttcctcct cacttaagag gaaaaccaag aagtgccaga 3660
aataacagta gcaactacaa taacaacaac ggcggctaca acggtggccg tggcggtggc 3720
agcttcttta gcaacaaccg tcgtggtggt tacggcaacg gtggtttctt cggtggaaac 3780
aacggtggca gcagatctaa cggccgttct ggtggtagat ggatcgatgg caaacatgtc 3840
ccagctccaa gaaacgaaaa ggccgagatc gccatatttg gtgtggcggc cgcacgcgtt 3900
catcgtccac ctccggagaa caggccacca tcacgcatct gtgtctgaat ttcatcacgg 3960
gcgcgcc 3967

<210> SEQ ID NO 114
<211> LENGTH: 1871
<212> TYPE: DNA
<213> ORGANISM: Artificial Sequence
<220> FEATURE:
<223> OTHER INFORMATION: Synthetic

<400> SEQUENCE: 114
ggcgcgcctc atcgtccacc tccggagaac aggccaccat cacgcatctg tgtctgaatt 60
tcatcacgac gcgccttaag ggcaccaata actgccttaa aaaaattacg ccccgccctg 120
ccactcatcg cagtactgtt gtaattcatt aagcattctg ccgacatgga agccatcaca 180
gacggcatga tgaacctgaa tcgccagcgg catcagcacc ttgtcgcctt gcgtataata 240
tttgcccatg gtgaaaacgg gggcgaagaa gttgtccata ttggccacgt ttaaatcaaa 300

```
actggtgaaa ctcacccagg gattggctga gacgaaaaac atattctcaa taaacccttt    360
agggaaatag gccaggtttt caccgtaaca cgccacatct tgcgaatata tgtgtagaaa    420
ctgccggaaa tcgtcgtggt attcactcca gagcgatgaa aacgtttcag tttgctcatg    480
gaaaacggtg taacaagggt gaacactatc ccatatcacc agctcaccgt ctttcattgc    540
catacggaat tccggatgag cattcatcag gcgggcaaga atgtgaataa aggccggata    600
aaacttgtgc ttatttttct ttacggtctt taaaaaggcc gtaatatcca gctgaacggt    660
ctggttatag gtacattgag caactgactg aaatgcctca aaatgttctt tacgatgcca    720
ttgggatata tcaacggtgg tatatccagt gatttttttc tccattttag cttccttagc    780
tcctgaaaat ctcgataact caaaaaatac gcccggtagt gatcttattt cattatggtg    840
aaagttggaa cctcttacgt gccgatcaac gtctcatttt cgccaaaagt tggcccaggg    900
cttcccggta tcaacaggga caccaggatt tatttattct gcgaagtgat cttccgtcac    960
aggtattgga ccaccctgtg ggtttataag cgcgctgctg gcgtgtaagg cggtgacggc   1020
gaaggaaggg tccttttcat cacgtgctat aaaaataatt ataatttaaa ttttttaata   1080
taaatatata aattaaaaat agaaagtaaa aaaagaaatt aaagaaaaaa tagtttttgt   1140
tttccgaaga tgtaaaagac tctagggggga tcgccaacaa atactacctt ttatcttgct   1200
cttcctgctc tcaggtatta atgccgaatt gtttcatctt gtctgtgtag aagaccacac   1260
acgaaaatcc tgtgatttta cattttactt atcgttaatc gaatgtatat ctatttaatc   1320
tgcttttctt gtctaataaa tatatatgta aagtacgctt tttgttgaaa ttttttaaac   1380
ctttgtttat ttttttttct tcattccgta actcttctac cttctttatt tactttctaa   1440
aatccaaata caaaacataa aaataaataa acacagagta aattcccaaa ttattccatc   1500
attaaaagat acgaggcgcg tgtaagttac aggcaagcga tccgtcctaa gaaaccatta   1560
ttatcatgac attaacctat aaaaataggc gtatcacgag gccctttcgt ctcgcgcgtt   1620
tcggtgatga cggtgaaaac ctctgacaca tgcagctccc ggagacggtc acagcttgtc   1680
tgtaagcgga tgccgggagc agacaagccc gtcagggcgc gtcagcgggt gttggcgggt   1740
gtcggggctg gcttaactat gcggcatcag agcagattgt actgagagtg caccacggcg   1800
cgtggcaccc ttgcgggcca tgtcatacac cgccttcaga gcagccggac ctatctgccc   1860
gttggcgcgc c                                                        1871
```

<210> SEQ ID NO 115
<211> LENGTH: 748
<212> TYPE: DNA
<213> ORGANISM: Artificial Sequence
<220> FEATURE:
<223> OTHER INFORMATION: Synthetic

<400> SEQUENCE: 115

```
ggcgcgcccc ggctgtctgc catgctgccc ggtgtaccga cataaccgcc ggtggcatag     60
ccgcgcatac gcgtctccag cgtgttttat ctctgcgagc ataatgcctg cgtcatccgc    120
cagcaggagc tggactttac tgatgcccgt tatatctgcg aaaagaccgg gatctggacc    180
cgtgatggca ttctctggtt ttcgtcatcc ggtgaagaga ttgagccacc tgacagtgtg    240
acctttcaca tctggacagc gtacagcccg ttcaccacct gggtgcagat tgtcaaagac    300
tggatgaaaa cgaaaggggga tacgggaaaa cgtaaaacct tcgtaaacac cacgctcggt    360
gagacgtggg aggcgaaaat tggcgaacgt ccggatgctg aagtgatggc agagcggaaa    420
gagcattatt cagcgcccgt tcctgaccgt gtggcttacc tgaccgccgg tatcgactcc    480
```

cagctggacc gctacgaaat gcgcgtatgg ggatgggggc cgggtgagga aagctggctg 540
attgaccggc agattattat gggccgccac gacgatgaac agacgctgct gcgtgtggat 600
gaggccatca ataaaaccta tacccgccgg aatggtgcag aaatgtcgat atcccgtatc 660
tgctgggata ctggacgcgt tttcccgtct ttcagtgcct tgttcagttc ttcctgacgg 720
gcggtatatt tctccagctt ggcgcgcc 748

<210> SEQ ID NO 116
<211> LENGTH: 748
<212> TYPE: DNA
<213> ORGANISM: Artificial Sequence
<220> FEATURE:
<223> OTHER INFORMATION: Synthetic

<400> SEQUENCE: 116
ggcgcgccca gccggtaaag attccccacg ccaatccggc tggttgcctc cttcgtgaag 60
acaaactcac gcgtccagta tcccagcaga tacgggatat cgacatttct gcaccattcc 120
ggcgggtata ggttttattg atggcctcat ccacacgcag cagcgtctgt tcatcgtcgt 180
ggcggcccat aataatctgc cggtcaatca gccagctttc ctcacccggc ccccatcccc 240
atacgcgcat ttcgtagcgg tccagctggg agtcgatacc ggcggtcagg taagccacac 300
ggtcaggaac gggcgctgaa taatgctctt tccgctctgc catcacttca gcatccggac 360
gttcgccaat tttcgcctcc cacgtctcac cgagcgtggt gtttacgaag gttttacgtt 420
ttcccgtatc ccctttcgtt ttcatccagt ctttgacaat ctgcacccag gtggtgaacg 480
ggctgtacgc tgtccagatg tgaaaggtca cactgtcagg tggctcaatc tcttcaccgg 540
atgacgaaaa ccagagaatg ccatcacggg tccagatccc ggtcttttcg cagatataac 600
gggcatcagt aaagtccagc tcctgctggc ggatgacgca ggcattatgc tcgcagagat 660
aaaacacgct ggagacgcgt tttcccgtct ttcagtgcct tgttcagttc ttcctgacgg 720
gcggtatatt tctccagctt ggcgcgcc 748

<210> SEQ ID NO 117
<211> LENGTH: 748
<212> TYPE: DNA
<213> ORGANISM: Artificial Sequence
<220> FEATURE:
<223> OTHER INFORMATION: Synthetic

<400> SEQUENCE: 117
ggcgcgccac cacggtgaac aatccccgct ggctcatatt tgccgccggt tcccgtaaat 60
cctccggtac gcgtccagta tcccagcaga tacgggatat cgacatttct gcaccattcc 120
ggcgggtata ggttttattg atggcctcat ccacacgcag cagcgtctgt tcatcgtcgt 180
ggcggcccat aataatctgc cggtcaatca gccagctttc ctcacccggc ccccatcccc 240
atacgcgcat ttcgtagcgg tccagctggg agtcgatacc ggcggtcagg taagccacac 300
ggtcaggaac gggcgctgaa taatgctctt tccgctctgc catcacttca gcatccggac 360
gttcgccaat tttcgcctcc cacgtctcac cgagcgtggt gtttacgaag gttttacgtt 420
ttcccgtatc ccctttcgtt ttcatccagt ctttgacaat ctgcacccag gtggtgaacg 480
ggctgtacgc tgtccagatg tgaaaggtca cactgtcagg tggctcaatc tcttcaccgg 540
atgacgaaaa ccagagaatg ccatcacggg tccagatccc ggtcttttcg cagatataac 600
gggcatcagt aaagtccagc tcctgctggc ggatgacgca ggcattatgc tcgcagagat 660
aaaacacgct ggagacgcgt tttcccgtct ttcagtgcct tgttcagttc ttcctgacgg 720
gcggtatatt tctccagctt ggcgcgcc 748

<210> SEQ ID NO 118
<211> LENGTH: 748
<212> TYPE: DNA
<213> ORGANISM: Artificial Sequence
<220> FEATURE:
<223> OTHER INFORMATION: Synthetic

<400> SEQUENCE: 118
ggcgcgccaa gctggagaaa tataccgccc gtcaggaaga actgaacaag gcactgaaag 60
acgggaaaac gcgtccagta tcccagcaga tacgggatat cgacatttct gcaccattcc 120
ggcgggtata ggttttattg atggcctcat ccacacgcag cagcgtctgt tcatcgtcgt 180
ggcggcccat aataatctgc cggtcaatca gccagctttc ctcacccggc ccccatcccc 240
atacgcgcat ttcgtagcgg tccagctggg agtcgatacc ggcggtcagg taagccacac 300
ggtcaggaac gggcgctgaa taatgctctt tccgctctgc catcacttca gcatccggac 360
gttcgccaat tttcgcctcc cacgtctcac cgagcgtggt gtttacgaag gttttacgtt 420
ttcccgtatc ccctttcgtt ttcatccagt ctttgacaat ctgcacccag gtggtgaacg 480
ggctgtacgc tgtccagatg tgaaaggtca cactgtcagg tggctcaatc tcttcaccgg 540
atgacgaaaa ccagagaatg ccatcacggg tccagatccc ggtcttttcg cagatataac 600
gggcatcagt aaagtccagc tcctgctggc ggatgacgca ggcattatgc tcgcagagat 660
aaaacacgct ggagacgcgt ggcgcatccg cgtcaggcgg tacagccatt caggccgctg 720
cggcgaaatt ccattttgca ggcgcgcc 748

<210> SEQ ID NO 119
<211> LENGTH: 748
<212> TYPE: DNA
<213> ORGANISM: Artificial Sequence
<220> FEATURE:
<223> OTHER INFORMATION: Synthetic

<400> SEQUENCE: 119
ggcgcgccgc caccaacagc cccgccaatg gcgctgccga tactcccgac aatccccacc 60
attgcctgac gcgtccagta tcccagcaga tacgggatat cgacatttct gcaccattcc 120
ggcgggtata ggttttattg atggcctcat ccacacgcag cagcgtctgt tcatcgtcgt 180
ggcggcccat aataatctgc cggtcaatca gccagctttc ctcacccggc ccccatcccc 240
atacgcgcat ttcgtagcgg tccagctggg agtcgatacc ggcggtcagg taagccacac 300
ggtcaggaac gggcgctgaa taatgctctt tccgctctgc catcacttca gcatccggac 360
gttcgccaat tttcgcctcc cacgtctcac cgagcgtggt gtttacgaag gttttacgtt 420
ttcccgtatc ccctttcgtt ttcatccagt ctttgacaat ctgcacccag gtggtgaacg 480
ggctgtacgc tgtccagatg tgaaaggtca cactgtcagg tggctcaatc tcttcaccgg 540
atgacgaaaa ccagagaatg ccatcacggg tccagatccc ggtcttttcg cagatataac 600
gggcatcagt aaagtccagc tcctgctggc ggatgacgca ggcattatgc tcgcagagat 660
aaaacacgct ggagacgcgt tttcccgtct ttcagtgcct tgttcagttc ttcctgacgg 720
gcggtatatt tctccagctt ggcgcgcc 748

<210> SEQ ID NO 120
<211> LENGTH: 1822

<212> TYPE: DNA
<213> ORGANISM: Artificial Sequence
<220> FEATURE:
<223> OTHER INFORMATION: Synthetic

<400> SEQUENCE: 120
cgcgccggca cccttgcggg ccatgtcata caccgccttc agagcagccg gacctatctg 60
cccgttacgc gccagcttgc aaattaaagc cttcgagcgt cccaaaacct tctcaagcaa 120
ggttttcagt ataatgttac atgcgtacac gcgtctgtac agaaaaaaaa gaaaaatttg 180
aaatataaat aacgttctta atactaacat aactataaaa aaataaatag ggacctagac 240
ttcaggttgt ctaactcctt ccttttcggt tagagcggat gtgggggggag ggcgtgaatg 300 taagcgtgac ataactaatt acatgatatc gacaaaggaa aagggggacg gatctccgag 360
gcctcggacc cgtcgggccg ccgtcggacg tgccgcggat ccccgggtcg agcctgaacg 420
gcctcgaggc ctgaacggcc tcgacgaatt cattatttgt agagctcatc catgccatgt 480
gtaatcccag cagcagttac aaactcaaga aggaccatgt ggtcacgctt ttcgttggga 540
tctttcgaaa gggcagattg tgtcgacagg taatggttgt ctggtaaaag gacagggcca 600
tcgccaattg gagtattttg ttgataatgg tctgctagtt gaacggatcc atcttcaatg 660
ttgtggcgaa ttttgaagtt agctttgatt ccattctttt gtttgtctgc cgtgatgtat 720
acattgtgtg agttatagtt gtactcgagt ttgtgtccga gaatgtttcc atcttcttta 780
aaatcaatac cttttaactc gatacgatta acaagggtat caccttcaaa cttgacttca 840
gcacgcgtct tgtagttccc gtcatctttg aaagatatag tgcgttcctg tacataacct 900
tcgggcatgg cactcttgaa aaagtcatgc cgtttcatat gatccggata acgggaaaag 960
cattgaacac cataagagaa agtagtgaca agtgttggcc atggaacagg tagttttcca 1020
gtagtgcaaa taaatttaag ggtaagctgg ccctgcaggc caagcttttt gtttgtttat 1080
gtgtgtttat tcgaaactaa gttcttggtg ttttaaaact aaaaaaaaga ctaactataa 1140
aagtagaatt taagaagttt aagaaataga tttacagaat tacaatcaat acctaccgtc 1200
tttatatact tattagtcaa gtaggggaat aatttcaggg aactggtttc aacctttttt 1260
ttcagctttt tccaaatcag agagagcaga aggtaataga aggtgtaaga aaatgagata 1320
gatacatgcg tgggtcaatt gccttgtgtc atcatttact ccaggcaggt tgcatcactc 1380
cattgaggtt gtgtccgttt tttgcctgtt tgtgcccctg ttctctgtag ttgcgctaag 1440
agaatggacc tatgaactga tggttggtga agaaaacaat attttggtgc tgggattctt 1500 ttttttctg gatgccagct taaaaagcgg gctccattat atttagtgga tgccaggaat 1560
aaactgttca cccagacacc tacgatgtta tatattctgt gtaacccgcc ccctattttg 1620
ggcatgtacg ggttacagca gaattaaaag gctaattttt tgactaaata aagttaggaa 1680
aatcactact attaattatt tacgtattct ttgaaatggc agtattgata atgataaact 1740
cgaactgggc gcgtcgtgcc gtcgttgtta atcaccacat ggttattctg ctcaaacgtc 1800
ccggacgcct gcgaggcgcg cc 1822

<210> SEQ ID NO 121
<211> LENGTH: 1879
<212> TYPE: DNA
<213> ORGANISM: Artificial Sequence
<220> FEATURE:
<223> OTHER INFORMATION: Synthetic

<400> SEQUENCE: 121

```
ggcgcgccat gcgcggctat gccaccggcg gttatgtcgg tacaccgggc agcatggcag      60

acagccggac gcgccacgca cagatattat aacatctgca taataggcat ttgcaagaat     120

tactcgtgag taaggaaaga gtgaggaact atcgcatacc tgcatttaaa gatgccgatt     180

tgggcgcgaa tcctttattt tggcttcacc ctcatactat tatcagggcc agaaaaagga     240

agtgtttccc tccttcttga attgatgtta ccctcataaa gcacgtggcc tcttatcgag     300

aaagaaatta ccgtcgctcg tgatttgttt gcaaaaagaa caaaactgaa aaaacccaga     360

cacgctcgac ttcctgtctt cctattgatt gcagcttcca atttcgtcac acaacaaggt     420

cctagcgacg gctcacaggt tttgtaacaa gcaatcgaag gttctggaat ggcgggaaag     480

ggtttagtac cacatgctat gatgcccact gtgatctcca gagcaaagtt cgttcgatcg     540

tactgttact ctctctcttt caaacagaat tgtccgaatc gtgtgacaac aacagcctgt     600

tctcacacac tcttttcttc taaccaaggg ggtggtttag tttagtagaa cctcgtgaaa     660

cttacattta catatatata aacttgcata aattggtcaa tgcaagaaat acatatttgg     720

tcttttctaa ttcgtagttt ttcaagttct tagatgcttt ctttttctct tttttacaga     780

tcatcaagga agtaattatc tactttttac aacaaatata aaacaaagct tggcctgcag     840

ggccagctta cccttaaatt tatttgcact actggaaaac tacctgttcc atggccaaca     900

cttgtcacta ctttctctta tggtgttcaa tgcttttccc gttatccgga tcatatgaaa     960

cggcatgact ttttcaagag tgccatgccc gaaggttatg tacaggaacg cactatatct    1020

ttcaaagatg acgggaacta caagacgcgt gctgaagtca agtttgaagg tgataccctt    1080

gttaatcgta tcgagttaaa aggtattgat tttaaagaag atggaaacat tctcggacac    1140

aaactcgagt acaactataa ctcacacaat gtatacatca cggcagacaa acaaaagaat    1200

ggaatcaaag ctaacttcaa aattcgccac aacattgaag atggatccgt tcaactagca    1260

gaccattatc aacaaaatac tccaattggc gatggccctg tccttttacc agacaaccat    1320

tacctgtcga cacaatctgc cctttcgaaa gatcccaacg aaaagcgtga ccacatggtc    1380

cttcttgagt ttgtaactgc tgctgggatt acacatggca tggatgagct ctacaaataa    1440

tgaattcgtc gaggccgttc aggcctcgag gccgttcagg ctcgacccgg ggatccgcgg    1500

atctcttatg tctttacgat ttatagtttt cattatcaag tatgcctata ttagtatata    1560

gcatctttag atgacagtgt tcgaagtttc acgaataaaa gataatattc tactttttgc    1620

tcccaccgcg tttgctagca cgagtgaaca ccatccctcg cctgtgagtt gtacccattc    1680

ctctaaactg tagacatggt agcttcagca gtgttcgtta tgtacggcat cctccaacaa    1740

acagtcggtt atagtttgtc ctgctcctct gaatcgtctc cctcgatatt tctcattttc    1800

cttcggcgcg ttcgcaggcg tccgggacgt ttgagcagaa taaccatgtg gtgattaaca    1860

acgacggcac gggcgcgcc                                                 1879
```

<210> SEQ ID NO 122
<211> LENGTH: 1587
<212> TYPE: DNA
<213> ORGANISM: Artificial Sequence
<220> FEATURE:
<223> OTHER INFORMATION: Synthetic

<400> SEQUENCE: 122

```
ggcgcgcccc ggctgtctgc catgctgccc ggtgtaccga cataaccgcc ggtggcatag      60

ccgcgcatac gcgccatttc cttccatctt gtgattcatg ctatccatct tttttgagta     120

tccaattaac gaagacgtta ccagctgatt gaaggttctc aaagtgactg tactccatgt     180
```

```
tttcttatca tccatgtagt tatttttcaa actgcaaatt caagaaaaag ccacgcgtgt    240

gcaccttttt tttccccttc cagtgcatta tgcaatagac agcacgagtc tttgaaaaag    300

taacttataa aactgtatca atttttaaac ctaaatagat tcataaacta ttcgttaata    360

taaagtgttc taaactatga tgaaaaaata agcagaaaag actaataatt cttagttaaa    420

agcactccgc ggatccccgg gtcgagcctg aacggcctcg aggcctgaac ggcctcgacg    480

aattcattat ttgtagagct catccatgcc atgtgtaatc ccagcagcag ttacaaactc    540

aagaaggacc atgtggtcac gcttttcgtt gggatctttc gaaagggcag attgtgtcga    600

caggtaatgg ttgtctggta aaaggacagg gccatcgcca attggagtat tttgttgata    660

atggtctgct agttgaacgg atccatcttc aatgttgtgg cgaattttga agttagcttt    720

gattccattc ttttgtttgt ctgccgtgat gtatacattg tgtgagttat agttgtactc    780

gagtttgtgt ccgagaatgt ttccatcttc tttaaaatca ataccttttta actcgatacg    840

attaacaagg gtatcacctt caaacttgac ttcagcacgc gtcttgtagt tcccgtcatc    900

tttgaaagat atagtgcgtt cctgtacata accttcgggc atggcactct tgaaaaagtc    960

atgccgtttc atatgatccg gataacggga aaagcattga acaccataag agaaagtagt   1020

gacaagtgtt ggccatggaa caggtagttt tccagtagtg caaataaatt taagggtaag   1080

ctggccctgc aggccaagct tttgtaatt aaaacttaga ttagattgct atgctttctt   1140

tctaatgagc aagaagtaaa aaaagttgta atagaacaag aaaaatgaaa ctgaaacttg   1200

agaaattgaa gaccgtttat taacttaaat atcaatggga ggtcatcgaa agagaaaaaa   1260

atcaaaaaaa aaaatttca agaaaaagaa acgtgataaa aatttttatt gcctttttcg   1320

acgaagaaaa agaaacgagg cggtctcttt tttcttttcc aaacctttag tacgggtaat   1380

taacgacacc ctagaggaag aaagagggga aatttagtat gctgtgcttg ggtgttttga   1440

agtggtacgg cgatgcgcgg agtccgagaa aatctggaag agtaaaaaag gagtagaaac   1500

attttgaagc taggcgcgtc agccggtaaa gattccccac gccaatccgg ctggttgcct   1560

ccttcgtgaa gacaaactcg gcgcgcc                                        1587
```

<210> SEQ ID NO 123
<211> LENGTH: 1928
<212> TYPE: DNA
<213> ORGANISM: Artificial Sequence
<220> FEATURE:
<223> OTHER INFORMATION: Synthetic

<400> SEQUENCE: 123

```
ggcgcgccca gccggtaaag attccccacg ccaatccggc tggttgcctc cttcgtgaag     60

acaaactcac gcgcctccaa aatgagctat caaaaacgat agatcgatta ggatgacttt    120

gaaatgactc cgcagtggac tggccgttaa tttcaagcgt gagtaaaata gtgcatgaca    180

aaagatgagc taggcttttg taaaaatatc ttacgttgta aaattttaga aatcattatt    240

tccttcatat cattttgtca ttgaccttca gaagaaaaga gccgaccaat aatataaata    300

aataaataaa aataatattc cattatttct aaacagattc aatactcatt aaaaaactat    360

atcaattaat ttgaattaac cgcggatccc cgggtcgagc ctgaacggcc tcgaggcctg    420

aacggcctcg acgaattcat tatttgtaga gctcatccat gccatgtgta atcccagcag    480

cagttacaaa ctcaagaagg accatgtggt cacgcttttc gttgggatct ttcgaaaggg    540

cagattgtgt cgacaggtaa tggttgtctg gtaaaaggac agggccatcg ccaattggag    600
```

tattttgttg ataatggtct gctagttgaa cggatccatc ttcaatgttg tggcgaattt 660
tgaagttagc tttgattcca ttcttttgtt tgtctgccgt gatgtataca ttgtgtgagt 720
tatagttgta ctcgagtttg tgtccgagaa tgtttccatc ttctttaaaa tcaatacctt 780
ttaactcgat acgattaaca agggtatcac cttcaaactt gacttcagca cgcgtcttgt 840
agttcccgtc atctttgaaa gatatagtgc gttcctgtac ataaccttcg ggcatggcac 900
tcttgaaaaa gtcatgccgt ttcatatgat ccggataacg ggaaaagcat tgaacaccat 960
aagagaaagt agtgacaagt gttggccatg gaacaggtag ttttccagta gtgcaaataa 1020
atttaagggt aagctggccc tgcaggccaa gctttttgat agatttgact gtgttatttt 1080
gcgtgaggtt atgagtagaa aataataatt gagaaaggaa tatgacaaga aatatgaaaa 1140
taaagggaac aaacccaaat ctgattgcaa ggagagtgaa agagccttgt ttatatattt 1200
tttttcccta tgttcaacga ggacagctag gtttatgcaa aaatgtgcca tcaccataag 1260
ctgattcaaa tgagctaaaa aaaaaatagt tagaaaataa ggtggtgttg aacgatagca 1320
agtagatcaa gacaccgtct aacagaaaaa ggggcagcgg acaatattat gcaattatga 1380
agaaaagtac tcaaagggtc ggaaaaatat tcaaacgata tttgcataaa atcctcaatt 1440
gattgattat tccatagtaa aataccgtaa caacacaaaa ttgttctcaa attcataaat 1500
tattcatttt ttccacgagc ctcatcacac gaaaagtcag aagagcatac ataatctttt 1560
aaatgcatag gttatgcatt ttgcaaatgc caccaggcaa caaaaaatatg cgtttagcgg 1620 gcggaatcgg gaaggaagcc ggaaccacca aaaactggaa gctacgtttt taaggaaggt 1680
atgggtgcag tgtgcttatc tcaagaaata ttagttatga tataaggtgt tgaagtttag 1740
agataggtaa ataaacgcgg ggtgtgttta ttacatgaag aagaagttag tttctgcctt 1800
gcttgtttat cttgcacatc acatcagcgg aacatatgct cacccagtcg catggcgcgt 1860
accacggtga acaatccccg ctggctcata tttgccgccg gttcccgtaa atcctccggt 1920
ggcgcgcc 1928

<210> SEQ ID NO 124
<211> LENGTH: 1736
<212> TYPE: DNA
<213> ORGANISM: Artificial Sequence
<220> FEATURE:
<223> OTHER INFORMATION: Synthetic

<400> SEQUENCE: 124
ggcgcgccac cacggtgaac aatccccgct ggctcatatt tgccgccggt tcccgtaaat 60
cctccggtac gcgccgggcc gtatacttac atatagtaga tgtcaagcgt aggcgcttcc 120
cctgccggct gtgagggcgc cataaccaag gtatctatag accgccaatc agcaaactac 180
ctccgtacat tcatgttgca cccacacatt tatacaccca gaccgcgaca aattacccat 240
aaggttgttt gtgacggcgt cgtacaagag aacgtgggaa ctttttaggc tcaccaaaaa 300
agaaagaaaa aatacgagtt gctgacagaa gcctcaagaa aaaaaaaatt cttcttcgac 360
tatgctggag gcagagatga tcgagccggt agttaactat atatagctaa attggttcca 420
tcaccttctt ttctggtgtc gctccttcta gtgctatttc tggcttttcc tatttttttt 480
tttccatttt tctttctctc tttctaatat ataaattctc ttgcattttc tatttttctc 540
tctatctatt ctacttgttt attcccttca aggttttttt ttaaggagta cttgttttta 600
gaatatacgg tcaacgaact ataattaact aaacaagctt ggcctgcagg gccagcttac 660
ccttaaattt atttgcacta ctggaaaact acctgttcca tggccaacac ttgtcactac 720
tttctcttat ggtgttcaat gcttttcccg ttatccggat catatgaaac ggcatgactt 780
tttcaagagt gccatgcccg aaggttatgt acaggaacgc actatatctt tcaaagatga 840
cgggaactac aagacgcgtg ctgaagtcaa gtttgaaggt gataccccttg ttaatcgtat 900 cgagttaaaa ggtattgatt ttaaagaaga tggaaacatt ctcggacaca aactcgagta 960
caactataac tcacacaatg tatacatcac ggcagacaaa caaaagaatg gaatcaaagc 1020
taacttcaaa attcgccaca acattgaaga tggatccgtt caactagcag accattatca 1080
acaaaatact ccaattggcg atggccctgt ccttttacca gacaaccatt acctgtcgac 1140
acaatctgcc ctttcgaaag atcccaacga aaagcgtgac cacatggtcc ttcttgagtt 1200
tgtaactgct gctgggatta cacatggcat ggatgagctc tacaaataat gaattcgtcg 1260
aggccgttca ggcctcgagg ccgttcaggc tcgacccggg gatccgcgga caaatcgctc 1320
ttaaatatat acctaaagaa cattaaagct atattataag caaagatacg taaattttgc 1380
ttatattatt atacacatat catatttcta tatttttaag atttggttat ataatgtacg 1440
taatgcaaag gaaataaatt ttatacatta ttgaacagcg tccaagtaac tacattatgt 1500
gcactaatag tttagcgtcg tgaagacttt attgtgtcgc gaaaagtaaa aattttaaaa 1560
attagagcac cttgaacttg cgaaaaaggt tctcatcaac tgtttaaaag gaggatatca 1620
ggtcctattt ctgacaaaca atatacaaat ttagtttcaa aggcgcgttg caaaatggaa 1680
tttcgccgca gcggcctgaa tggctgtacc gcctgacgcg gatgcgccgg cgcgcc 1736

<210> SEQ ID NO 125
<211> LENGTH: 2175
<212> TYPE: DNA
<213> ORGANISM: Artificial Sequence
<220> FEATURE:
<223> OTHER INFORMATION: Synthetic

<400> SEQUENCE: 125
ggcgcgccca ggcaatggtg gggattgtcg ggagtatcgg cagcgccatt ggcggggctg 60
ttggtggcac gcgccaatgc tactattttg gagatcaatc tcagtacaaa acaatattaa 120
aaagaggtga attatttttc ccccttattt ttttttttgt tagaattgat ccaaatgtaa 180
ataaacaatc acaaggaaaa aaaaaaaaaa aaaaaaatag ccgccatgac cccggatcgt 240
cggttgtgat acggtcaggg tagcgccctg gtcaaacttc agaactaaaa aaataataag 300
gaagaaaaaa atagctaatt tttccggcag aaagattttc gctacccgaa agtttttccg 360
gcaagctaaa tggaaaaagg aaagattatt gaaagagaaa gaaagaaaaa aaaaaaatgt 420
acacccagac atcgggcttc cacaatttcg gctctattgt tttccatctc tcgcaacggc 480
gggattcctc tatggcgtgt gatgtctgta tctgttactt aatccagaaa ctggcacttg 540
acccaactct gccacgtggg tcgttttgcc atcgacagat tgggagattt tcatagtaga 600
attcagcatg atagctacgt aaatgtgttc cgcaccgtca caaagtgttt tctactgttc 660
tttcttcttt cgttcattca gttgagttga gtgagtgctt tgttcaatgg atcttagcta 720
aaatgcatat tttttctctt ggtaaatgaa tgcttgtgat gtcttccaag tgatttcctt 780
tccttcccat atgatgctag gtacctttag tgtcttccta aaaaaaaaaa aaggctcgcc 840
atcaaaacga tattcgttgg cttttttttc tgaattataa atactctttg gtaacttttc 900
atttccaaga acctcttttt tccagttata tcatggtccc ctttcaaagt tattctctac 960
tctttttcat attcattctt tttcatcctt tggtttttta ttcttaactt gtttattatt 1020

-continued

```
ctctcttgtt tctatttaca agacaccaat caaaacaaat aaaacatcat cacaaagctt   1080

ggcctgcagg gccagcttac ccttaaattt atttgcacta ctggaaaact acctgttcca   1140

tggccaacac ttgtcactac tttctcttat ggtgttcaat gcttttcccg ttatccggat   1200

catatgaaac ggcatgactt tttcaagagt gccatgcccg aaggttatgt acaggaacgc   1260

actatatctt tcaaagatga cgggaactac aagacgcgtg ctgaagtcaa gtttgaaggt   1320

gataccettg ttaatcgtat cgagttaaaa ggtattgatt ttaaagaaga tggaaacatt   1380

ctcggacaca aactcgagta caactataac tcacacaatg tatacatcac ggcagacaaa   1440

caaaagaatg gaatcaaagc taacttcaaa attcgccaca acattgaaga tggatccgtt   1500

caactagcag accattatca acaaaatact ccaattggcg atggccctgt ccttttacca   1560

gacaaccatt acctgtcgac acaatctgcc ctttcgaaag atcccaacga aaagcgtgac   1620

cacatggtcc ttcttgagtt tgtaactgct gctgggatta cacatggcat ggatgagctc   1680

tacaaataat gaattcgtcg aggccgttca ggcctcgagg ccgttcaggc tcgacccggg   1740

gatccgcggc cgcaggccta aattgatcta gagctttgga cttcttcgcc agaggtttgg   1800

tcaagtctcc aatcaaggtt gtcggcttgt ctaccttgcc agaaatttac gaaaagatgg   1860

aaaagggtca aatcgttggt agatacgttg ttgacacttc taaataagcg aatttcttat   1920

gatttatgat ttttattatt aaataagtta taaaaaaaat aagtgtatac aaattttaaa   1980

gtgactctta ggttttaaaa cgaaaattct tattcttgag taactctttc ctgtaggtca   2040

ggttgctttc tcaggtatag catgaggtcg ctcttattga ccacacctct accggcatgc   2100

ggcgcgtggc gcatccgcgt caggcggtac agccattcag gccgctgcgg cgaaattcca   2160

ttttgcaggc gcgcc                                                   2175
```

RECOMBINANT HOST CELLS WITH IMPROVED PRODUCTION OF TETRAKETIDE DERIVATIVES

CROSS-REFERENCE TO RELATED APPLICATIONS

This is a national phase application of International Application No. PCT/EP2020/050150, filed 6 Jan. 2020, which claims the benefit of European Patent Application Ser. No. 19/150,443.0, filed 6 Jan. 2019, and European Patent Application No. 19167702.0 filed 5 Apr. 2019, and European Patent Application No. 19182812.8 filed 27 Jun. 2019, the disclosures of which are incorporated, in their entireties, by this reference.

FIELD OF THE INVENTION

The present invention relates to recombinant host cells producing tetraketide derivatives; to recombinant polynucleotides comprising a sequence encoding pathway enzymes and polypeptides, operably linked to promotor nucleotide sequences facilitating expression of the pathway enzymes. Further, the invention relates to cell cultures comprising the host cell of the invention, to methods of producing the tetraketide derivatives; to fermentation liquids resulting from such methods, to compositions comprising the fermentation liquid and to the use of such compositions.

BACKGROUND OF THE INVENTION

Tetraketide derivatives comprise a large and versatile group of compounds including chalcones, dihydrochalcones, stilbenes and dihydrostilbenes and further derivatives thereof.

Dihydrochalcones include subgroups of useful compounds such as phlorizin, nothofagin, and aspalatin, with reported human health benefits and other uses (Ibdah, 2018, J. Agric. Food Chem., 66 (10): 2273-2280; Eichenberger, 2017, Met. Eng. 39: 80-89)

Stilbenes include subgroups of compounds such as pinosylvin, resveratrol, piceatannol and pterostilbene with reported benefits in human health (Tsai, 2017, J. Food and Drug Analysis 25 (1): 134-147).

Dihydrostilbenes and their acids, dihydrostilbene carboxylates, include subgroups of useful compounds such as the amorfrutins, which has recently attracted attention due to their potential benefits in human health, including reported activities in the areas of diabetes and cancer (Weidner, 2012, Proc. Natl. Acad. Sci USA. 109 (19):7257-62; Weidner, 2016, J. Nat. Prod. 79(1):2-12).

Chalcone derivatives encompasses a significant group of compounds, such as flavonoids. Flavonoids derives in natural biological systems from various CoA activated phenylpropanoid precursors, most commonly cinnamoyl-CoA and p-coumaroyl-CoA, extended in successive rounds with multiple molecules of malonyl-CoA, to form the basic tetraketide backbone, which is then cyclized into the basic chalcone structure. The final ring closure is then isomerized to form the central flavanone structure, from which most other flavonoids, including anthocyanins, are derived. Anthocyanins is a flavonoid derivative derived from naringenin, which are found naturally in flowers, where they provide bright red and purple colors. Anthocyanins are also found in vegetables and fruits, mostly in the outer parts, such as stem and peel. Anthocyanins are useful as dyes or coloring agents, and furthermore, anthocyanins have caught attention for their human health promoting properties. Other useful flavonoids are epicatechins, which are used as dietary supplements.

Some efforts have been done in developing heterologous production of tetraketide derivatives using unicellular hosts, particularly *Escherichia coli* and *Saccharomyces cerevisiae.*

Regarding the chalcone derivatives various flavanones, flavones, and flavonols have been produced in *E. coli* from phenyl propanoid precursors (see e.g. Yan Y et al., Appl Environ Microbiol. 2005, 71(9):5610-3; Jiang H et al., Appl Environ Microbiol. 2005, 71(6):2962-9; and Leonard E et al., Appl Environ Microbiol. 2007, 73(12):3877-86). Production of other flavonoids have been demonstrated by exogenously feeding suitable precursors, for example isoflavonoids made by feeding liquiritigenin; flavan-3-ols and flavan-4-ols made from feeding flavanones; and anthocyanins made from feeding flavanones or (+)-catechin. In yeast some flavanones, flavones, and flavonols have been made from phenyl propanoids, while few reports have been made on producing flavonoids from sugar e.g. naringenin (Koopman et al. 2012, Microb Cell Fact. 11:155) or various flavanones and flavonols (Naesby et al. 2009, Microb Cell Fact. 8:45). WO2017/050853 discloses assembly of a pathway designed for production of anthocyanin in yeast.

One challenge in designing heterologous pathways and producing tetraketide derivatives in host cells is to achieve industrially and commercially relevant yields. One heterologous biosynthetic pathway for the central flavanone naringenin expressed in yeast lead to massive accumulation of p-coumaric acid and/or its degradation product phloretic acid (Lehka et al. FEMS Yeast Res. 2017, 17(1)). An effort to increase CHS activity, in order to balance the pathway, did not prevent the accumulation of phloretic acid, the degradation product of p-coumaric acid. (Koopman et al., Microb Cell Fact 2012, 11:155).

Morita et al. The Plant Journal, 2014, 78: 294-304 discloses that mutations in a chalcone isomerase-like protein (CHIL), a non-enzymatic type IV chalcone isomerase, seem to have effect on the production of flavonoids in plants, and suggests that in plants the wild type (wt) CHIL is involved in CHS activity though an unknown mechanism. Another study (Jiang et al., J. Exp. Bot. 2015, 66, 22:7165-7179), shows that expression of *Arabidopsis thaliana* CHIL seemingly affects the levels of flavonols and proanthocyanidins, but not that of anthocyanins. A further study (Fujino et al., Plant Biotechnol 2014, 31:105-114) showed that in snapdragon, CHIL was abundantly expressed irrespective of flower color, a trait closely linked to the production of anthocyanins. A recent study in hops (Ban et al., PNAS, 2018, 115(22): E5223-E5232) shows involvement of two CHILs in a biosynthetic pathway towards the prenylated chalcone xanthohumol. One CHIL (CHIL2), seemed to affect chalcone synthase and prenyl transferase through protein-protein interactions, whereas the other CHIL (CHIL1), was suggested to stabilize the ring-open conformation of the chalcone precursor. Based on these contradictory studies, no clear role can be assigned to CHILs in plants. CHIL is not known in unicellular microbial hosts and functions and effects in heterologous biosynthetic pathways in such hosts have not yet been explored.

Another obstacle challenging unicellular heterologous production of tetraketide derivatives such as anthocyanins (ACN) and epicatechins (EPC) is that several enzymes in the pathways are promiscuous in regards of both substrate and catalyzed reaction, which leads to poor efficiency for specific desired products.

Anthocyanin synthase (ANS), which is an enzyme known from pathways producing anthocyanins, has been shown to produce more flavonol than anthocyanidin in vitro (Turnbull et al., Chem. Commun., 2000, 2473-74; Turnbull et al., Bioorg. Med. Chem. Lett., 2003, 13: 3853-57; Turnbull et al., J. Biol. Chem. 2004, 279: 1206-16; Welford et al., Chem. Commun., 2001, 1828-29). In PhD thesis work of Michael Eisenberger: *Biosynthesis of plant polyketides in yeast*; Technical University, Darmstadt, Germany; published Apr. 3, 2019, production of anthocyanin in yeast employing a pathway including glutathione-S-transferase was tested.

In view of this art there is a need to modify and to improve pathways for industrial production of tetraketide derivatives in heterologous unicellular host cells, in order to increase the yield of such products to commercially sustainable levels.

SUMMARY OF THE INVENTION

The present inventors contemplate that the accumulation of p-coumaric acid and/or its degradation product phloretic acid reported by Lehka et al. FEMS Yeast Res. 2017, 17(1)), together with the failure to prevent the phloretic acid accumulation reported by Koopman et al., Microb Cell Fact 2012, 11:155, indicates a slow rate of conversion of the precursors phenylpropanoyl-CoA and malonyl-CoA into tetraketides, a process that is reported to rely on the activity of polyketide synthases (PKS) such as chalcone synthase (CHS) or stilbene synthase (STS). In search of solutions to improve the effectiveness of tetraketide derivative production by fermentation of simple carbon sources, e.g. sugars, and using biosynthetic pathways expressed in microbial hosts, the inventors have found that production is affected by non-structural genes such as CHIL's and surprisingly, it has been found that the co-expression of CHILs has a dramatically positive effect on production of tetraketide derivatives such as flavonoids in strains co-expressing PKS's in the biosynthetic pathway. The effect is evident as an improved activity is observed at the early committed steps of CHS and STS, leading to formation of tetraketide derivatives such as flavonoids, dihydrochalcones and stilbenes. It is contemplated that via the increase in upstream efficiency at PKS level increased production can be achieved of basically any downstream tetraketide derivative.

The present inventors have also found substrate and product promiscuity of pathway enzymes to impede the efficient heterologous production of end products. This is particularly noticeable for the anthocyanidin synthase (ANS), an enzyme belonging to the group of 2-oxoglutarate dependent dioxygenases (2ODDs). ANS has very high similarity to flavonol synthase (FLS), and in yeast and bacteria ANS has been found to catalyze many of the same reactions normally associated with FLS and flavonol synthesis. The inventors have found that expression of biosynthetic pathways directed to anthocyanin (ACN) production, can result in high amounts of undesired flavonols (both aglycones and their 3-O-glycosides) instead of the desired ACNs. Similarly, pathways directed towards epicatechins (EPC) is contemplated to result in flavonol accumulation at the expense of EPC's. Without being bound to the theory, the accumulation of flavonols is contemplated to be associated with an unwanted substrate/product promiscuity of ANS and the present inventors have observed that expressing the full length, structural ACN pathway in yeast can result in accumulation of up to a hundred fold more flavonols than ACNs—and that unwanted flavonol production was a general feature of all ANS enzymes observed. The present invention employing CHIL to further increase downstream metabolite levels in e.g. flavonoid pathways such as the pathway to ACN or EPC, is contemplated to further amplify the undesired formation of flavonols. In search of ways to improve biosynthetic pathways for producing ACN's and/or EPC's co-expression of a glutathione-S-transferase (GST) can direct ANS product specificity towards anthocyanidin and in particular in combination with the increased levels of precursor metabolites caused by employing the CHIL and PKS of the present invention, dramatically shift the preference of ANS towards anthocyanidins. The co-expression of GST, together with structural genes such as ANS, solves the inherent problem of unwanted flavonol side-product formation by the ANS enzyme. Hence, when ANS, GST, and an anthocyanin glycosyl transferase (such as A3GT) is co-expressed, this results predominantly in ACN production, and when ANS, GST, and an anthocyanidin reductase (ANR) is co-expressed the production is predominantly of EPCs.

Accordingly, the present invention provides in a first aspect a recombinant microbial host cell producing a tetraketide or derivatives thereof from one or more substrates selected from cinnamoyl-CoA, p-Coumaroyl-CoA, Caffeoyl-CoA, Feruloyl-CoA, malonyl-CoA, sinapoyl-CoA, and dihydro derivatives thereof, comprising an operative biosynthetic metabolic pathway for the tetraketide or derivatives thereof comprising a chalcone isomerase-like (CHIL) polypeptide heterologous to the host cell and a Type 3 polyketide synthase (PKS).

In a further aspect the invention provides a recombinant polynucleotide construct comprising a nucleotide encoding the chalcone isomerase-like (CHIL) polypeptide and/or the Type 3 polyketide synthase (PKS) of the invention, operably linked to a promotor which is heterologous to the CHIL and/or type 3 PKS encoding polynucleotide.

In a further aspect the invention provides an expression vector comprising the polynucleotide construct of the invention.

In a further aspect the invention provides a cell culture, comprising host cells of the invention and a growth medium.

In a further aspect the invention provides a method for producing a tetraketide derivative comprising a) culturing the cell culture of the invention at conditions allowing the host cell to convert the one or more substrates into the tetraketide derivative; and
b) optionally recovering and/or isolating the tetraketide derivative.

In a further aspect the invention provides a fermentation liquid comprising the cell culture of the invention and its contents of tetraketide or derivative thereof.

In a further aspect the invention provides a composition comprising the fermentation liquid of the invention and one or more agents, additives and/or excipients.

In a further aspect the invention provides a use of the composition of the invention, wherein the tetraketide derivative is an anthocyanin as a dye, colorant or non-therapeutic bioactive compound.

In a further aspect the invention provides a method of preparing a pharmaceutical preparation comprising subjecting the composition of the invention to one or more steps transforming the composition and its contents of tetraketide or derivative thereof into a therapeutically relevant mixture comprising one or more pharmaceutical grade additives and/or adjuvants.

In a further aspect the invention provides a pharmaceutical preparation obtainable from the pharmaceutical preparation method of the invention.

In a further aspect the invention provides the pharmaceutical preparation of the invention for use as a medicament.

DESCRIPTION OF DRAWINGS AND FIGURES

FIG. 1 depicts the early flavonoid biosynthetic pathway, from the amino acids phenylalanine or tyrosine to the common flavanones, shown with the various hydroxylation patterns of the B-ring (ring names indicated for naringenin): pinocembrin with no hydroxylation of B-ring, naringenin with one hydroxylation (4'), eriodictyol with two hydroxylations (3',4'), and pentahydroxyflavanone with three (3'4'5'), respectively. All flavanones further have hydroxylations at the A-ring (3,5). The number of hydroxylations on the B-ring depends on the starter molecule, cinnamic acid or p-coumaric acid, and the P450 enzymes F3'H and F3'5'H. Bold arrows indicate the most common plant pathway to naringenin, the precursor of most other flavonoids. Names of enzymes are indicated as abbreviations, with corresponding full names as provided in list of SEQ IDs.

Figure 2:
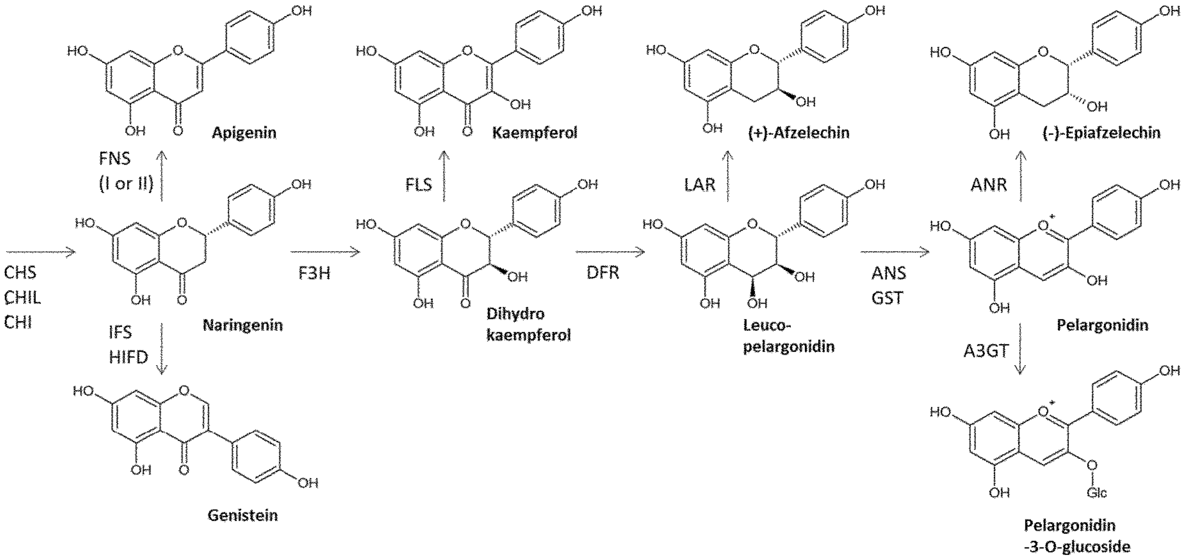

FIG. 2 depicts examples of flavonoid biosynthetic pathways derived from the common flavanone precursor. For simplicity, only the most common flavanone, naringenin, with a single B-ring hydroxylation is shown. Abbreviated enzyme names correspond to full names as provided in the list of SEQ IDs.

Figure 3:
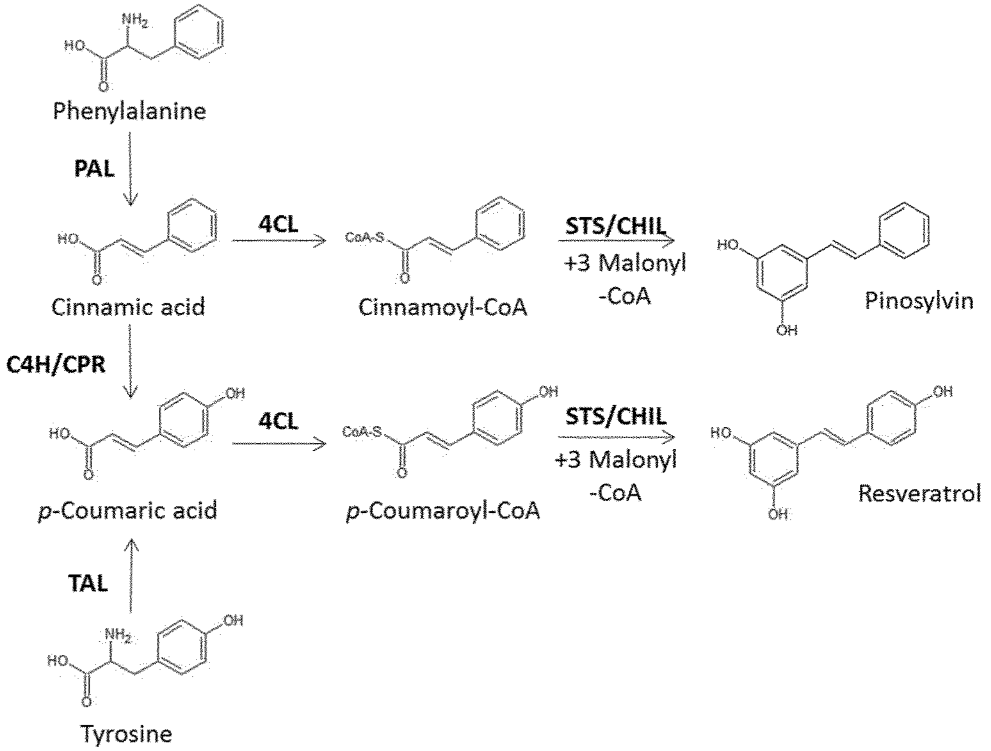

FIG. 3 depicts examples of stilbene biosynthetic pathways derived from cinnamic acid and p-coumaric acid, respectively. Abbreviated enzyme names correspond to full names as provided in the list of SEQ IDs.

Figure 4:
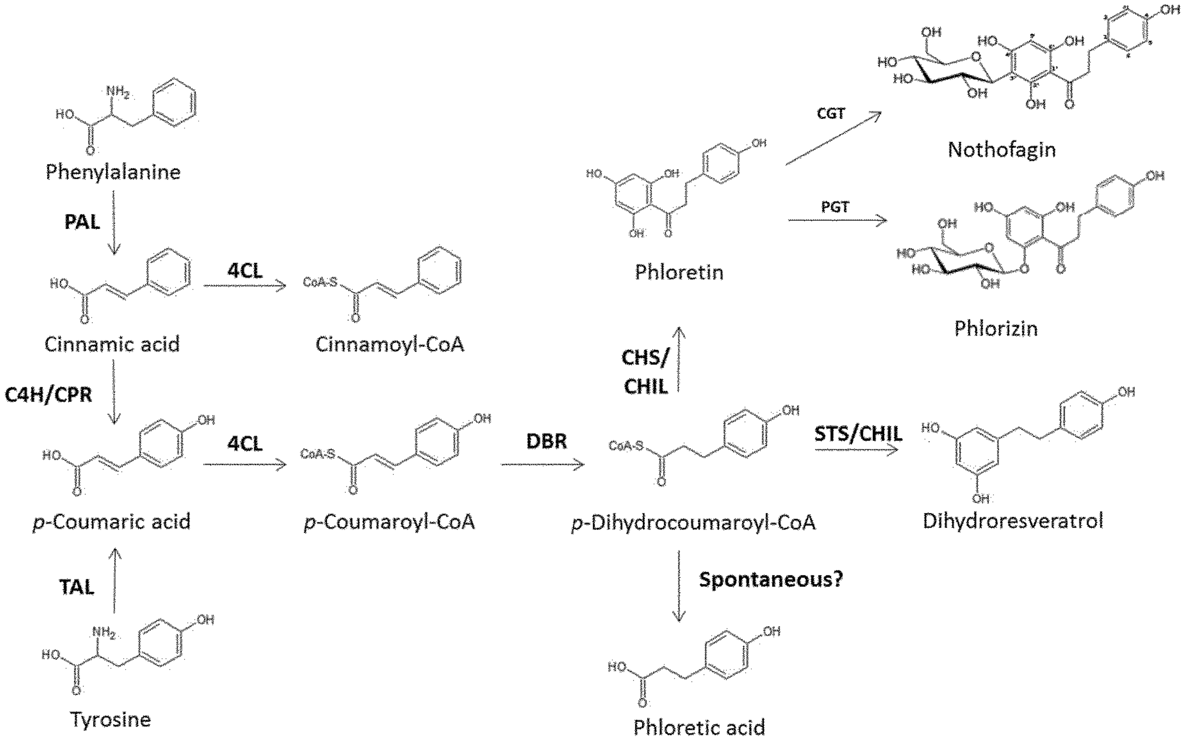

FIG. 4 depicts examples of dihydrochalcone and dihydrostilbene biosynthetic pathways derived from p-coumaric acid by including a DBR. Similar types of compounds can be derived from cinnamoyl-CoA (not shown). Abbreviated enzyme names correspond to full names as provided in the list of SEQ IDs.

Figure 5:
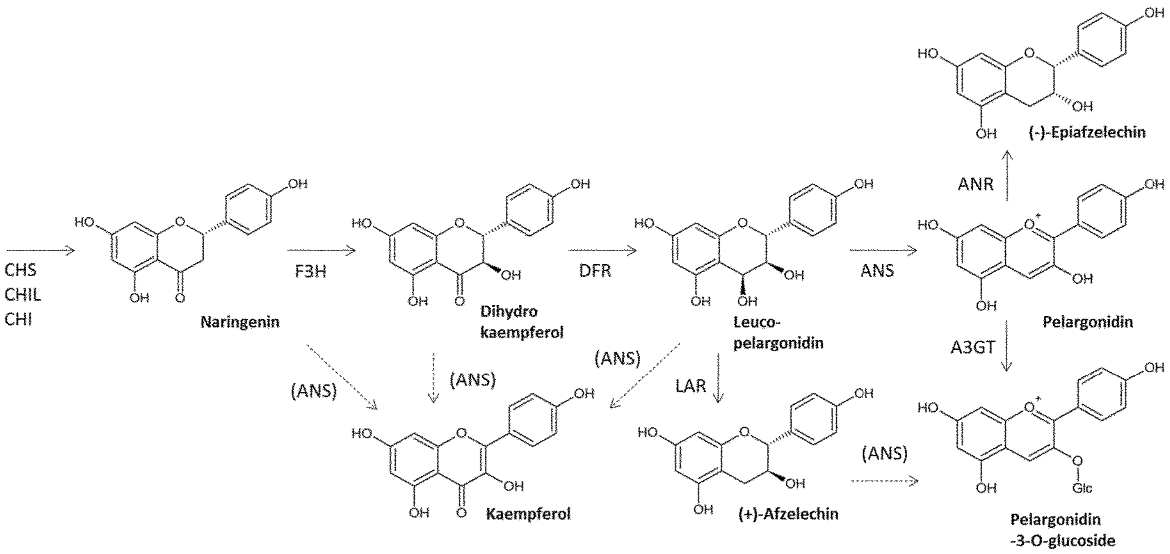

FIG. 5 depicts the biosynthetic pathway from flavanones to flavanols (aka flavan-3-ols) and anthocyanins. For simplicity, only derivatives with a single B-ring hydroxylation is shown. In planta, the pathway from naringenin normally leads to derivatives such as (−)-epiafzelechin and pelargonidin-3-O-glucoside. However, ex planta a number of side activities of ANS have been reported, as indicated by dashed lined arrows. Abbreviated enzyme names correspond to full names as provided in the list of SEQ IDs.

Figure 6:
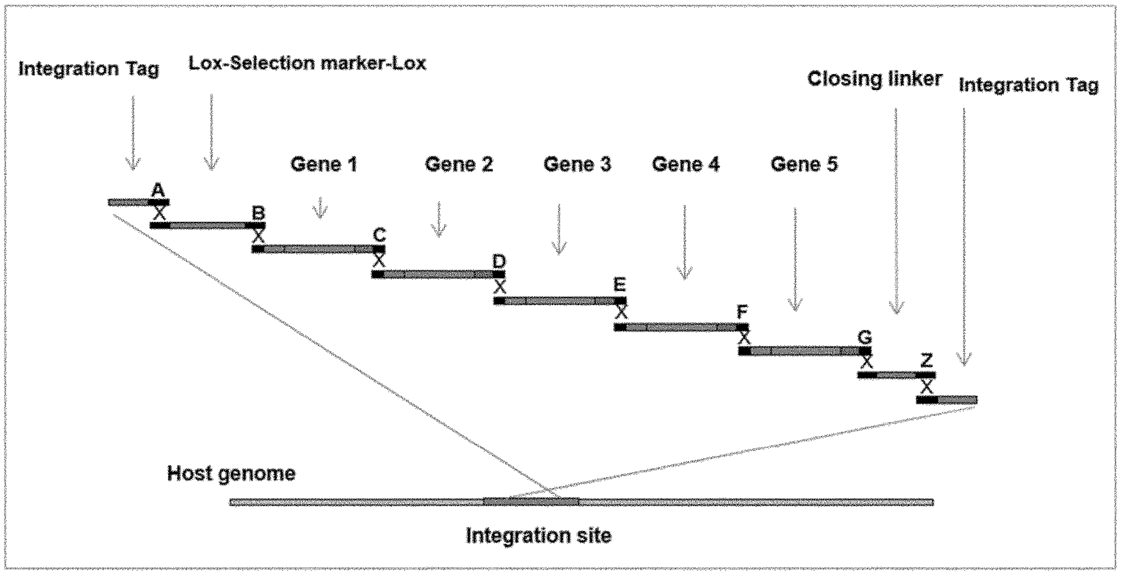

FIG. 6 depicts a graphic representation of the integration constructs used to integrate multiple genes into the genome of the host, *S. cerevisiae*, via in vivo homologous recombination (see Eichenberger et al., Met. Eng., 2017, 39: 80-89 for details). Each DNA fragment, comprising a gene expression cassette (promoter-gene-terminator), or a specific helper fragment (see Example no. 2) is nested between homologous recombination tags (HRT), i.e 60 base pair sequences indicated with a letter, in which the preceding fragment has a sequence that is identical to the next fragment and so forth. All fragments have been excised from the backbone of the plasmid, in which they are maintained and amplified, by a restriction enzyme digest, using the Asc I recognition sites flanking each fragment. One fragment comprises two parts, separated by Asc I, which has homology to the intended genomic target sequence, allowing concomitant in vivo integration, by homologous recombination, of all fragments after a single host transformation event (see Shao 2009, Nucl. Acids Res., 37 (2) e16 for details).

Figure 7:
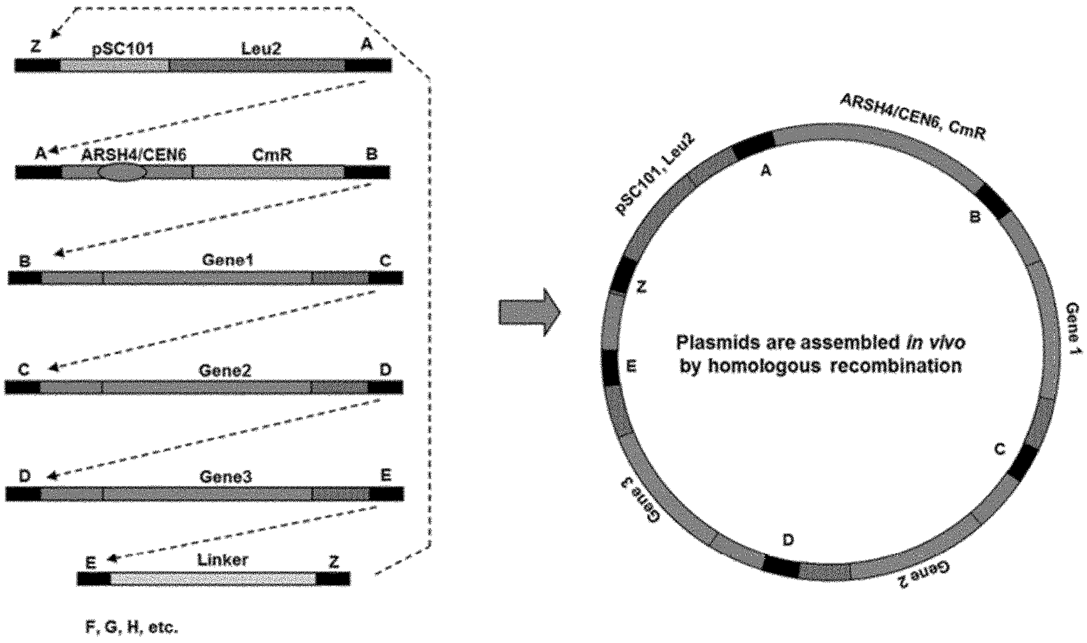

FIG. 7 depicts a schematic representation of the HRT in vivo plasmid assembly. Shown is an example of the fragments needed for in vivo assembly, in *S. cerevisae*, of a multi gene expression plasmid. Each fragment comprises either a gene expression cassette, or the elements required for stable maintenance and replication in yeast. The gene expression cassettes comprise a yeast promoter, a gene encoding sequence, and a yeast terminator sequence. Each fragment is flanked by homologous recombination tags (HRTs) as described in FIG. 6, and by restriction enzyme recognition sites for Asc I. This restriction enzyme is used to release each fragment form the backbone of the plasmid used to maintain and amplify the fragment (typically a bacterial pUC based plasmid). After a single transformation of yeast with a mixture of the relevant fragments, these are in vivo assembled into a single copy plasmid, by way of the host's DNA repair system, allowing stable expression of the heterologous genes comprised in the expression cassettes.

INCORPORATION BY REFERENCE

All publications, patents, and patent applications referred to herein are incorporated by reference to the same extent as if each individual publication, patent, or patent application was specifically and individually indicated to be incorporated by reference. In the event of a conflict between a term herein and a term in an incorporated reference, the term herein prevails and controls.

DETAILED DESCRIPTION OF THE INVENTION

In this section the invention is described in further detailed embodiments.

Definitions

The terms "polypeptide" and "protein" are used herein interchangeably. Proteins with catalytic function are referred to as "enzymes".

The term "PAL" as used herein refers to phenylalanine ammonia lyase, an EC4.3.1.24 enzyme capable of catalyzing conversion of phenylalanine to cinnamic acid.

The term "C4H" as used herein refers to the enzyme trans-cinnamate 4-monooxygenase also known as cinnamate 4-hydroxylase, an EC1.14.14.91 CYP450 enzyme capable of catalyzing conversion of cinnamic acid to p-coumaric acid.

The term "CYP450 as used herein" refers to an enzyme of the Cytochrome P450 family, capable of oxidizing a range of substrates. Upon acting on a substrate, CYP450 must be reduced by its cognate reductase (CPR) to regain catalytic capacity.

The term "CPR" as used herein refers to cytochrome P450 reductase, an EC1.6.2.4 enzyme catalyzing the reduction of CYP450 enzymes.

The term "TAL" as used herein refers to tyrosine ammonia lyase or a PAL enzyme with TAL activity, an EC4.3.1.25 enzyme capable of catalyzing conversion of tyrosine to p-coumaric acid.

The term "C3H" as used herein refers to coumarate 3-hydroxylase, an EC1.14.13 enzyme catalyzing conversion of p-coumaric acid to caffeic acid.

The term "4CL" as used herein refers to 4-coumarate-CoA-ligase, an EC6.2.1.12 enzyme capable of catalyzing conversion of the ligation of CoA to various phenylpropanoic acids.

The term "COMT" as used herein refers to caffeic acid 3-O-methyltransferase, an EC2.1.1.68 enzyme capable of catalyzing conversion of caffeic acid to ferulic acid.

The term "CCOMT" as used herein refers to caffeoyl-CoA-O-methyltransferase, an EC2.1.1.104 enzyme capable of catalyzing conversion of caffeoyl-CoA to feruloyl-CoA.

The term "HCT" as used herein refers to shikimate O-hydroxycinnamoyltransferase, an EC2.3.1.133 enzyme capable of ligating shikimate to various CoA-activated phenylpropanoic acids.

The term "C3'H" as used herein refers to 5-O-(4-coumaroyl)-D-quinate 3'-monooxygenase, an EC1.14.14.96 enzyme capable of catalyzing conversion of trans-5-O-(4-coumaroyl)-D-quinate or trans-5-O-(4-coumaroyl)-shikimate to trans-5-O-caffeoyl-D-quinate trans-5-O-caffeoyl-D-shikimate, respectively.

The term "Type 3 PKS" or "type 3 polyketide synthase" as used herein refers to polyketide synthase, an enzyme capable of catalyzing the condensation of a CoA-activated substrate with one or more malonyl-CoA units.

The term "CHIL" as used herein refers to chalcone isomerase-like protein, a polypeptide also known as the non-catalytic type IV CHI.

The term "CHS" as used herein refers to chalcone synthase, a type 3 polyketide synthase enzyme capable of synthesizing a chalcone by condensing 3 molecules of malonyl-CoA with a phenylpropanoyl CoA (aka (hydroxy)-cinnamoyl-CoA), such as a naringenin chalcone from one molecule of p-coumaroyl CoA and three molecules of malonyl CoA.

The term "CHI" as used herein refers to chalcone isomerase, an enzyme capable of stereospecifically isomerizing naringenin chalcone to (2S)-naringenin.

The term "STS" as used herein refers to a stilbene synthase, a type 3 polyketide synthase enzyme capable of catalyzing the formation of a stilbene or dihydrostilbene from one molecule of cinnamoyl CoA or p-coumaroyl CoA and three molecules of malonyl CoA.

The term "FH" as used herein refers to flavonoid hydroxylase, an enzyme capable of hydroxylating flavonoids.

The term "F3H" as used herein refers to the enzyme flavanone 3-hydroxylase, an enzyme capable of hydroxylating (2S)-Naringenin at the 3-position to (2R,3R)-dihydrokaempferol, a dihydroflavonol. F3H belongs to the 2-oxoglutarate-dependent dioxygenase (2ODD) family.

The terms "F3'H" and "F3'5'H" as used herein refers to flavonoid 3'-hydroxylase and flavonoid 3',5'-hydroxylase respectively, which are CYP450 enzymes capable of catalyzing hydroxylation of naringenin to form eriodictyol and 5,7,3'4'5'-pentahydroxyflavanone, respectively, or of catalyzing hydroxylation of dihydrokaempferol (DHK) to form (2R,3R)-dihydroquercetin and dihydromyricetin, respectively.

The term "DFR" as used herein refers to dihydroflavonol 4-reductase, an enzyme capable of reducing dihydroflavonols to the corresponding 3,4-cis leucoanthocyanidins.

The term "LAR" as used herein refers to leucoanthocyanidin reductase, an enzyme capable of catalyzing conversion of leucoanthocyanidins into flavan-3-ols, such as catechins.

The term "ANS as used herein" refers to anthocyanidin synthase (also known as leucoanthocyanidin dioxygenase or LDOX), an enzyme capable of synthesizing anthocyanidins from 3,4-cis leucoanthocyanidin. ANS belongs to the 2ODD family The term "GST" as used herein refers to glutathione-S-transferase, a class of enzymes best known for their ability to catalyze the conjugation of the reduced form of glutathione (GSH) to xenobiotic substrates for the purpose of detoxificationan. It should be noted, however, that GSTs may have a range of other functions, some of which might have not yet been fully elucidated.

The term "ANR" as used herein refers to anthocyanidin reductase, an enzyme capable of catalyzing conversion of anthocyanidin into epicatechins, such as (−)-epicatechin (2R,3R).

The term "UGT" as used herein refers to UDP-dependent glycosyltransferase, an enzyme capable of catalyzing conversion of anthocyanidins into anthocyanins.

The term "UDP-glucose" as used herein refers to uridine diphosphate glucose.

The term "A3GT" as used herein refers to anthocyanidin 3-O-glycosyltransferase, an enzyme capable of catalyzing glycosylation of anthocyanidins and/or other flavonoids at its 3-O position using UDP-glucose.

The term "A3'GT" as used herein refers to anthocyanin 3'-O-glycosyl transferase, an enzyme capable of catalyzing glycosylation of anthocyanidins and/or other flavonoids at its 3'-O position using an UDP-sugar, such as UDP-glucose.

The term "A5GT" as used herein refers to anthocyanin-5-O-glycosyl transferase, an enzyme capable of catalyzing glycosylation of anthocyanidins and/or other flavonoids at its 5-O position using an UDP-sugar, such as UDP-glucose.

The term "A7GT" as used herein refers to anthocyanin-7-O-glycosyl transferase, an enzyme capable of catalyzing glycosylation of anthocyanidins and/or other flavonoids at its 7-O position using an UDP-sugar, such as UDP-glucose.

The term "A3'5'GT" as used herein refers to anthocyanin 3'5'-di-O-glycosyl transferase, an enzyme capable of catalyzing glycosylation of anthocyanidins and/or other flavonoids at its 3'-O and its 5'-0 position using an UDP-sugar, such as UDP-glucose.

The term "IFS" as used herein refers to an enzyme capable of catalyzing conversion of flavanones into isoflavones, a conversion normally assisted by a dehydratase, such as the 2-hydroxy-isoflavanone dehydratase (EC4.2.1.105).

The term "HIFD" as used herein refers to Hydroxy isoflavanone dehydratase (EC4.2.1.105) an enzyme capable of catalyzing XXcapable of catalyzing the loss of a hydroxy group during the conversion of 2-hydroxy-isoflavones to isoflavones The term "FNS" as used herein refers to, an enzyme capable of catalyzing conversion of a flavanone to a flavone, whether as the sole catalyst or assisted by a dehydratase.

The term "FLS" as used herein refers to, an enzyme capable of catalyzing conversion of dihydroflavonols (flavanonols) to flavonols.

The term "AOMT" as used herein refers to, an enzyme capable of methylating anthocyanins at one or more of the B-ring hydroxyl groups.

The term "AAT" as used herein refers to, an enzyme capable of transferring an acyl group to an anthocyanin, in particular to sugar moieties of anthocyanins.

The term "AAroAT" as used herein refers to anthocyanin aromatic acyl transferase, an enzyme capable of transferring an aromatic acyl group to an anthocyanin, in particular to sugar moieties of anthocyanins.

The term "AAliAT" as used herein refers to anthocyanin aliphatic acyl transferase, an enzyme capable of transferring an aliphatic acyl group to an anthocyanin, in particular to sugar moieties of anthocyanins.

The term "functional homolog" refers to a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs may be designated in the art as homologs, or orthologs, or paralogs. Variants of a naturally occurring functional homologues, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. Functional homolog is sometimes applied to the polynucleotide that encodes a functionally homologous polypeptide.

The term "substrate" or "precursor", as used herein refers to any compound that can be converted into a different compound. For example, XX can be a substrate for YY and can be converted into ZZ. For clarity, substrates and/or precursors include both compounds generated in situ by an enzymatic reaction in a cell or exogenously provided compounds, such as exogenously provided organic carbon molecules which the host cell can metabolize into a desired compound.

The term "Chalcone" as used herein refers to a molecule of the general formula:

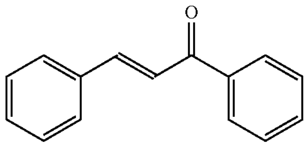

The term "flavonoid precursor" as used herein refers to intermediate compounds relevant for the pathways in a cell for producing flavonoids. These include the CHS starter molecules selected from acetyl-CoA, malonyl-CoA, cinnamic acid, cinnamoyl-CoA, p-coumaric acid, p-coumaroyl-CoA, benzoate, benzoyl-CoA, hydroxybenzoate, p-hydroxybenzoyl-CoA, sinapate, sinapoyl-CoA, ferulate, feruloyl-CoA, caffeate, caffeoyl-CoA, and intermediates from the groups of chalcones, flavanones, dihydroflavonols, leucoanthocyanidins, and anthocyanidins. Flavonoid precursors can be used to feed the recombinant host to achieve increased production of the end product. As will be known in the art, the same can be achieved by feeding the recombinant host with an excess of host molecules, such as aromatic amino acids.

The term "flavonoid" refers to molecules that have the general structure of a 15-carbon skeleton, which consists of two phenyl rings (A and B) and a heterocyclic ring (C). This carbon structure can be abbreviated C6-C3-C6. They are the result of sequential condensation reaction between phenylpropanoyl-CoA and 3 molecules of malonyl-CoA. The ring names as well as the conventional numbering of carbon atoms in flavonoids follows from:

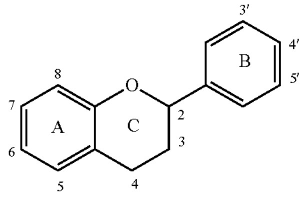

Flavonoids includes the non-ketone compounds which are more specifically termed flavanoids. Hence, the term "flavonoid" includes flavanones, flavones, isoflavones, flavanonols (dihydroflavonols), flavonols, flavans (flavan-3-ols, flavan-4-ols, and flavan-3,4-ols), and anthocyanidins, and refers to compounds of the formula I or II:

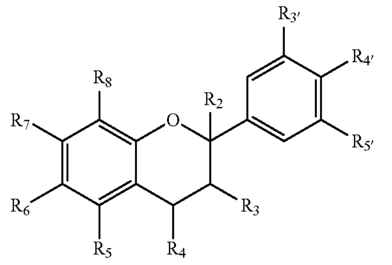

wherein (a) the bond between C2 and C3 can be a single bond or a double bond, (b) the B-ring phenyl group can be a C2-phenyl- or C3-phenyl-group, (c) the configuration at C2 and C3 can be either R or S, (d) R2, R3, R5, R6, R7, R8, R3', R4', and R5' are selected from the group consisting of —H, and —OH; and (e) R4 is selected from the group consisting of —H, =O, and —OH;

(f) R6 and R8 are selected from the group consisting of —H, and —OH, and -glycosyl, and prenyl; and (g) any of the hydroxyl groups (—OH) can be further modified by single or multiple additions of methyl groups, and/or one or more sugar groups, and/or acyl groups (aliphatic or aromatic), and/or prenyl groups, and/or any combination of said groups.

(II)

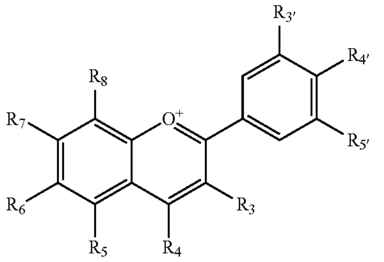

wherein (a) R3, R5, R6, R7, R8, R3', R4', and R5' are selected from the group consisting of —H, and —OH; and (b) any of the hydroxyl groups (—OH) can be further modified by single or multiple additions of methyl groups, and/or one or more sugar groups, and/or acyl groups (aliphatic or aromatic), and/or prenyl groups, and/or any combination of said groups.

One or more hydroxyl groups of the flavonoid can be substituted with residues such as methyl, acyl, and glycosyl residues. The hydroxyl groups can be methylated at one or more positions. One or more hydroxyl groups can also be glycosylated with one or more sugar residues, the sugar residues being selected from the group consisting of glucose, rhamnose, xylose, galactose, and arabinose. The sugar residue can also be the sugar acid derivative, such as glucuronic acid. The residues consisting of one or more glycosides can be, for example, a monosaccharide, disaccharide, or a trisaccharide. The monosaccharide, disaccharide, and the trisaccharide can, for example, consist of sugar residues selected from the group consisting of glucose, rhamnose, xylose, galactose, and arabinose, and any combination thereof. One or more hydroxyl groups of the flavonoid can also be acylated, for example a flavonoid glycoside can be acylated, at one or more positions, on one or more of the sugar residues. Acyl residues can be selected from the group consisting of cinnamoyl, coumaroyl, caffeoyl, sinapoyl, feruloyl, malonyl, benzoyl, and hydroxybenzoyl. Further, acylated flavonoid glycoside, can be glycosylated on the acyl residue. Preferably, the flavonoid is glycosylated at one or more hydroxyl group, these primary glycosyl residues being further glycosylated and/or acylated. Optionally, these secondary glycosyl and/or acyl residues can be further substituted with sugar and/or acyl groups. It will be understood by a person skilled in the art, that glycosyl residues can be derivatized at one or more positions, whereas acyl groups are rarely derivatized at more than one position.

The term "anthocyanin" as used herein refers to any anthocyanidin comprising at least one glycosylation. Base anthocyanin structure is represented by molecules, including but not limited to those selected from pelargonidin, cyanidin, delphinidin, malvidin, peonidin, petunidin and their derivatives. It also includes chemical compounds belonging to the 3-deoxyanthocyanidins such as luteolinidin or diosmetinidin.

The term "Dihydrochalcone" as used herein refers to a molecule of the general formula:

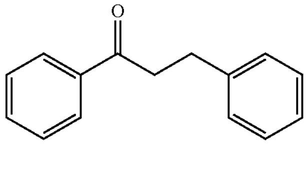

The term "Stilbene" as used herein refers to cis or trans molecules of the general formula:

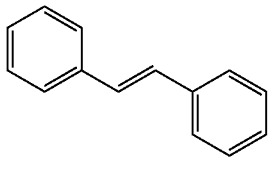

The term "Dihydrostilbene" as used herein refers to a molecule of the general formula:

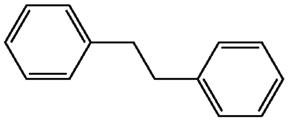

The term "microorganism" or "microbial cell" as used herein refers to a microscopic live organism, which may exist in its single-celled form, or in a colony of cells. Microbials comprise prokaryotes and some eukaryotes such as fungi, yeast, and molds. In one aspect microbials includes cells of higher organisms such as plants and animals unless the cells are isolated or cultured. In another aspect microbials excludes cells of higher organisms such as plants and animals unless the cells are isolated or cultured. Microorganism, host, host cell, recombinant host, and recombinant host cell are terms which are used interchangeably.

The term "host cell" refers to any cell type that is susceptible to transformation, transfection, transduction, or the like with a polynucleotide construct or expression vector comprising a polynucleotide of the present invention. The term "host cell" encompasses any progeny of a parent cell that is not identical to the parent cell due to mutations that occur during replication.

The term "recombinant host cell" is intended to refer to a host cell, wherein at least one DNA sequence has been modified, deleted from, or added to the genome, thereby augmenting or altering the genome. Such DNA sequences include but are not limited to genes that are not naturally present, DNA sequences that are not normally transcribed into RNA or translated into a protein ("expressed"), and other genes or DNA sequences which one desires to introduce into the non-recombinant host cell. Typically, the genome of a recombinant host cell described herein is augmented through stable introduction of one or more recombinant genes that may be inserted into the host cell genome and/or by way of an episomal vector (e.g., plasmid, YAC, etc.). Generally, introduced DNA is not originally resident in the host cell that is the recipient of the DNA, but it is within the scope of this disclosure to isolate a DNA segment from a given host cell, and to subsequently introduce one or more additional copies of that DNA into the same host cell, e.g., to enhance production of the product of a gene or alter the expression pattern of a gene. In some instances, the introduced DNA may modify or even replace an endogenous gene or DNA sequence by, e.g., homologous recombination or site-directed mutagenesis. In one embodiment the recombinant host cell is a host cell comprising and expressing heterologous or recombinant polynucleotide genes.

The term "in vivo", as used herein refers to within a living cell, including, for example, a microorganism or a plant cell.

The term "in vitro", as used herein refers to outside a living cell, including, without limitation, for example, in a microwell plate, a tube, a flask, a beaker, a tank, a reactor and the like.

The terms "polynucleotide," "nucleotide," "oligonucleotide," and "nucleic acid" can be used interchangeably to refer to nucleotide sequence comprising DNA, RNA, derivatives thereof, or combinations thereof.

The term "polynucletide construct" refers to a polynucleotide molecule, either single- or double stranded, which is isolated from a naturally occurring gene or is modified to contain segments of polynucleotides in a manner that would not otherwise exist in nature or which is synthetic, and which comprises one or more control sequences.

The term "structural gene" as used herein refers to genes that encode enzymes that are directly involved in the conversion of a chemical substrate into the next chemical intermediate of a biosynthetic pathway, where "intermediate" can mean a chemical compound, which is the product of one catalytic conversion, or the substrate of the next catalytic conversion in the pathway.

The term "non-structural gene" as used herein refers to genes encoding a peptide or protein which is not itself catalytically active, but which can act, in a variety of ways, to support and enhance the function of enzymes encoded by the structural genes.

The term "gene" as used herein refers here to the expressible, polypeptide-encoding DNA sequence, corresponding to the RNA sequence found in the mature messenger RNA (mRNA) transcript. The DNA sequence corresponding to the RNA sequence is known as copyDNA or simply cDNA, and typically comprises at least the part of the mRNA that encodes a polypeptide, also known as the "coding sequence" or the "open reading frame" (ORF). Genes can be codon optimized for the intended host organism, using standard methods in the art, or can be prepared by reverse transcription of the mRNA, followed by PCR amplification to prepare cDNA. The polypeptide encoded by the ORF can be a functional protein, with or without catalytic function. The former are normally considered to be enzymes. Although the term "gene" normally refers to a DNA sequence encoding a known polypeptide, it is known from the art that DNA sequences of genes can be changed (mutated, truncated, extended, fused) while retaining the desired function of the polypeptide.

The term "cDNA" refers to a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" refers to a nucleotide sequence, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequence", "regulatory sequence" "control region" and "regulatory region" as used herein interchangeably (prokaryotic and eukaryotic) refers to nucleotide sequences (control sequence) that influence transcription or translation initiation rate, or the stability of a transcript or the resulting translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also can include at least one control element, such as an enhancer sequence, an upstream enhancer element, or an upstream activation region (UAR). A regulatory region is operably linked to a coding sequence by positioning the regulatory region and the coding sequence so that the regulatory region is effective for regulating transcription or translation of the coding sequence. For example, to operably link a coding sequence and a promoter sequence, the translation initiation site of the translational reading frame of the coding sequence is typically positioned between one and about fifty nucleotides downstream of the promoter. A regulatory region can however be positioned as much as about 5,000 nucleotides upstream of the translation initiation site or about 2,000 nucleotides upstream of the transcription start site. The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region can be present, e.g., introns, enhancers, upstream activation regions, transcription terminators, and inducible elements. One or more genes can be combined in a recombinant nucleic acid construct under the influence of common regulatory sequences. Combining a plurality of genes into such modules, particularly a polycistronic module, facilitates the expression of genes in a variety of species.

The term "expression vector" refers to a linear or circular DNA molecule that comprises a polynucleotide sequence encoding a polypeptide, and which is operably linked to control sequences that provide for its expression.

The term "operably linked" refers to a configuration in which a control sequence is placed at an appropriate position relative to the coding polynucleotide such that the control sequence directs expression of the coding polynucleotide.

The term "recombinant" as used herein, refers to any polynucleotide sequence that has been modified, mutated, truncated, or fused to another polynucleotide, in order to modify the function or expression of the sequence. The term "recombinant host" refers to any microorganisms comprising recombinant polynucleotide sequences, either by mutation or by intentional introduction of a polynucleotide sequence, or any other re-arrangement of its native polynucleotide sequence.

The term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species, or can be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed. For any recombinant gene, one or more additional copies of the DNA can be introduced, to thereby permit overexpression or modified expression of the gene product of that DNA. A recombinant gene encoding a polypeptide described herein comprises the coding sequence for that polypeptide, operably linked in sense orientation to one or more control sequences suitable for expressing the polypeptide. Because many microorganisms are capable of expressing multiple gene products from a polycistronic mRNA, multiple polypeptides can be expressed under the control of a single regulatory sequence for those microorganisms, if desired. A coding sequence and a regulatory region are considered to be operably linked when control sequences within the regulatory region are positioned so that the regulatory region is effective for regulating transcription or translation of the sequence.

The terms "heterologous sequence," "heterologous coding sequence," and "heterologous gene" are used to describe a sequence or gene derived from a species other than the recombinant host. For example, if the recombinant host is an *S. cerevisiae* cell, then the cell would include a heterologous sequence derived from an organism other than *S. cerevisiae*. A heterologous coding sequence or gene, for example, can be from a prokaryotic microorganism, a eukaryotic microorganism, a plant, an animal, an insect, or from a fungus different to the recombinant host expressing the heterologous sequence.

In some aspects the coding sequence for a polypeptide described herein originates from a species other than the recombinant host, i.e., is a heterologous gene. In some of these aspects the coding sequence can be a chimaera, consisting of domains or regions from various organisms, or can be completely synthetic based on in silico modelling. Thus, if the recombinant host is a microorganism, the coding sequence can be from other prokaryotic or eukaryotic microorganisms, from plants or from animals. In many cases, the coding sequence for a polypeptide described herein is identified in a species other than the recombinant host, i.e., is a heterologous nucleic acid. In some cases, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant gene construct. Further, a native coding sequence can be operably linked to a native regulatory sequence, in a non-native manner. When such native regulatory sequences are used to control expression of a coding sequence other than its natural cognate coding sequence, the regulatory sequence is said to be heterologous to this native coding sequence. In addition, stably transformed exogenous genes typically are integrated at positions other than the position where the native sequence is found.

The terms "codon optimization" and "codon optimized" as used herein refer to a technique to maximize protein expression in fast-growing microorganisms such as *E. coli* or *S. cerevisiae* by increasing the translation efficiency of a particular gene. Codon optimization can be achieved, for example, by converting a nucleotide sequence of one species into a genetic sequence, which better reflects the translation machinery of a different, host species. Optimal codons help to achieve faster translation rates and high accuracy.

The term "metabolic pathway" as used herein is intended to mean two or more enzymes acting sequentially to convert chemical substrate(s) into chemical product(s). Enzymes are characterized by having catalytic activity, which can change the chemical structure of the substrate(s). An enzyme may have more than one substrate and produce more than one product. The enzyme may also depend on co-factors, which can be chemical compounds or can be a protein or enzyme. The CPR that reduces the Cytochrome P450 is an example of an enzymatic co-factor. The term "operative biosynthetic metabolic pathway" refers to a metabolic pathway that occurs in a live recombinant host, as described herein, and does not naturally occur in the host.

The term "engineered microorganism" refers to a recombinant host that contains an engineered biosynthetic pathway or operative metabolic pathway. Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, CA).

The term "expression" includes any step involved in the production of a polypeptide including, but not limited to, transcription, post-transcriptional modification, translation, post-translational modification, and secretion. "Functional expression" implies that a recombinant polynucleotide or its encoded polypeptide retains an activity similar to the expected and intended activity The term "cell culture" as used herein refers to a culture medium comprising a plurality of recombinant host cells of the invention. A cell culture may comprise a single strain of recombinant host or may comprise two or more distinct host strains. The culture medium may be any medium that may comprise a recombinant host, e.g., a liquid medium (i.e., a culture broth) or a semi-solid medium, and may comprise additional components, e.g., a carbon source such as dextrose, sucrose, glycerol, or acetate; a nitrogen source such as ammonium sulfate, urea, or amino acids; a phosphate source; vitamins; trace elements; salts; amino acids; nucleobases; yeast extract; aminoglycoside antibiotics such as G418 and hygromycin B.

The term "conditions" as used herein for culturing cell cultures of the invention is intended to mean physico-chemical condition for the culturing of host cells allowing the culture to propagate and to express enzymes of the operative biosynthetic metabolic pathway in an active form and for these enzymes to operate effectively to produce a desired product of the pathway.

The terms "substantially" or "approximately" or "about", as used herein refers to a reasonable deviation around a value or parameter such that the value or parameter is not significantly changed. These terms of deviation from a value should be construed as including a deviation of the value where the deviation would not negate the meaning of the value deviated from. For example, in relation to a reference numerical value the terms of degree can include a range of values plus or minus 10% from that value. For example, using these deviating terms can also include a range deviation plus or minus such as plus or minus 9%, 8%, 7%, 6%, 5%, 4%, 3%, 2%, or 1% from a specified value.

The term "and/or" as used herein is intended to represent an inclusive "or". The wording X and/or Y is meant to mean both X or Y and X and Y. Further the wording X, Y and/or Z is intended to mean X, Y and Z alone or any combination of X, Y, and Z.

The term "isolated" as used herein about a compound, refers to any compound, which by means of human intervention, has been put in a form or environment that differs from the form or environment in which it is found in nature. Isolated compounds include but is not limited to compounds of the invention for which the ratio of the compounds relative to other constituents with which they are associated in nature is increased or decreased. In an important embodiment the amount of compound is increased relative to other constituents with which the compound is associated in nature. In an embodiment the compound of the invention may be isolated into a pure or substantially pure form. In this context a substantially pure compound means that the compound is separated from other extraneous or unwanted material present from the onset of producing the compound or generated in the manufacturing process. Such a substantially pure compound preparation contains less than 10%, such as less than 8%, such as less than 6%, such as less than 5%, such as less than 4%, such as less than 3%, such as less than 2%, such as less than 1%, such as less than 0.5% by weight of other extraneous or unwanted material usually associated with the compound when expressed natively or recombinantly. In an embodiment the isolated compound is at least 90% pure, such as at least 91% pure, such as at least 92% pure, such as at least 93% pure, such as at least 94% pure, such as at least 95% pure, such as at least 96% pure, such as at least 97% pure, such as at least 98% pure, such as at least 99% pure, such as at least 99.5% pure, such as 100% pure by weight.

The term "non-naturally occurring" as used herein about a substance, refers to any substance that is not normally found in nature or natural biological systems. In this context the term "found in nature or in natural biological systems" does not include the finding of a substance in nature resulting from releasing the substance to nature by deliberate or accidental human intervention. Non-naturally occurring substances may include substances completely or partially synthetized by human intervention and/or substances prepared by human modification of a natural substance.

The term "% identity" as used herein about polynucleotide or polypeptide sequences refers to the degree of identity in percent between two sequences. The term "% identity" for any polynucleotide or polypeptide relative to a reference polynucleotide or polypeptide is to be understood and determined as follows. A reference sequence (e.g. a polynucleotide or polypeptide sequence) is aligned to one or more candidate sequences using the computer program ClustalW (version 1.83, default parameters), which allows alignments of polynucleotide or polypeptide sequences to be carried out across their entire length (global alignment). See Chenna et al., Nucleic Acids Res., 31 (13):3497-500 (2003). ClustalW calculates the best match between a reference and one or more candidate sequences, and aligns them so that identities, similarities, and differences can be determined. Gaps of one or more residues can be inserted into a reference sequence, a candidate sequence, or both, to maximize sequence alignments. For fast pairwise alignment of polynucleotide sequences, the following default parameters are used: word size: 2; window size: 4; scoring method: percentage; number of top diagonals: 4; and gap penalty: 5. For multiple alignment of polynucleotide sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gin, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw). To determine % identity of a candidate polynucleotide or amino acid sequence to a reference sequence, the sequences are aligned using ClustalW, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2. It will be appreciated that polynucleotides or polypeptides described herein can include additional nucleotides encoding additional amino acids that are not involved in polypeptide function (such as enzymatic activity), and thus such a polypeptide can be longer than would otherwise be the case. For example, a polypeptide can include a purification tag (e.g., HIS tag or GST tag), a chloroplast transit peptide, a mitochondrial transit peptide, an amyloplast peptide, signal peptide, or a secretion tag added to the amino or carboxy terminus. In some aspects, a polypeptide includes an amino acid sequence that functions as a reporter, e.g., a green fluorescent protein or yellow fluorescent protein. It will be appreciated that because of the degeneracy of the genetic code, a number of different polynucleotides can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated polynucleotides, these modified sequences can exist as purified molecules and can be incorporated into a vector or a virus for use in constructing modules for recombinant polynucleotide constructs.

The term "comprise" and "include" as used throughout the specification and the accompanying claims as well as variations such as "comprises", "comprising", "includes" and "including" are to be interpreted inclusively. These words are intended to convey the possible inclusion of other elements or integers not specifically recited, where the context allows.

The articles "a" and "an" as used herein refers to one or to more than one (i.e. to one or at least one) of the grammatical object of the article. By way of example, "an element" may mean one element or more than one element.

Terms like "preferably", "commonly", "particularly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

The term "product ratio" as used herein about enzymes refers to the ratio of products produced by an enzyme from a substrate. For example, ANS in the anthocyanin pathway will under different conditions covert leucoanthocyanidins into flavonol and anthocyanidin in various product ratios depending on the conditions.

The term "detectable concentration" refers to a level of tetraketides or derivatives thereof or other measured compounds measured in mg/L, nM, μM, or mM. Tetraketides or derivatives thereof can be detected and/or analyzed by techniques generally available to one skilled in the art, for example, but not limited to, thin layer chromatography (TLC), high-performance liquid chromatography (HPLC), ultraviolet-visible spectroscopy/spectrophotometry (UV- Vis), mass spectrometry (MS), nuclear magnetic resonance spectroscopy (NMR) or any combination thereof such as LC-MS.

Term "endogenous" or "native" as used herein refers to a gene or a polypepetide in a host cell which originates from the same host cell.

The term "deletion" as used herein refers to manipulation of a gene so that it is no longer expressed in a host cell.

The term "disruption" as used herein refers to manipulation of a gene or any of the machinery participating in the expression the gene, so that it is no longer expressed in a host cell.

The term "attenuation" as used herein refers to manipulation of a gene or any of the machinery participating in the expression the gene, so that it the expression of the gene is reduced as compared to expression without the manipulation.

Recombinant Microbial Host Cells

The invention provides in a first aspect a recombinant microbial host cell producing a tetraketide or derivatives thereof from one or more substrates selected from cinnamoyl-CoA, p-Coumaroyl-CoA, Caffeoyl-CoA, Feruloyl-CoA, and dihydro derivatives thereof, comprising an operative biosynthetic metabolic pathway for the tetraketide or derivatives thereof comprising a chalcone isomerase-like (CHIL) polypeptide heterologous to the host cell and a Type 3 polyketide synthase (PKS). Further, the one or more substrates may also include malonyl-CoA and/or sinapoyl-CoA. It has been found that CHIL improves the function of PKS, so in a further embodiment the CHIL polypeptide increases PKS conversion of the one or more substrates into the respective tetraketide or derivatives thereof in the host cell of the invention compared to a recombinant host cell absent of the CHIL polypeptide. The CHIL enhance the catalytic efficiency of the PKS at least 1.25 fold, such as at least 1.5 fold, such as at least 1.75 fold, such as at least 2 fold, such as at least 3 fold, such as at least 5 fold, such as at least 10 fold, such as at least 50 fold, such as at least 100 fold, such as at least 500 fold, such as at least 1000 fold. In a still further embodiment the CHIL polypeptide of the invention has at least 80% identity to the CHIL polypeptide encoded by the sequence set forth in SEQ ID NO: 13, SEQ ID NO: 15, SEQ ID NO: 17, SEQ ID NO: 19, and/or SEQ ID NO: 21. More particularly in this embodiment the % sequence identity for the mentioned sequences may be at least 85%, such as at least 90%, such as at least 92%, such as at least 94%, such as at least 96%, such as at least 98%, such as at least 99%, such as at least 99.5%, such as at least 99.8%, such as at least 99.9%, such as 100% identity. The CHIL or the PKS or both the CHIL and the PKS are heterologous to the host cell of the invention.

In the initial tetraketide operative biosynthetic metabolic pathway (see FIG. 1) intermediate p-coumaroyl-CoA is produced via the phenylpropanoid pathway. In plants, the starting molecule is typically phenylalanine, which is deaminated by the action of PAL type enzymes to form cinnamic acid. Cinnamic acid is then hydroxylated to p-coumaric acid (also called 4-coumaric acid) e.g. by C4H. Alternatively, p-coumaric acid is formed directly from tyrosine by the action of TAL type enzymes. Some enzymes have both PAL and TAL activity. The enzyme 4CL activates p-coumaric acid to p-coumaroyl-CoA by attachment of a CoA group.

Accordingly, the host cell of the invention comprises in a further embodiment an operative biosynthetic metabolic pathway capable of producing the one or more substrates of the invention comprising one or more polypeptides selected from:

a) phenylalanine ammonia lyase (PAL/EC 4.3.1.24);
b) tyrosine ammonia lyase (TAL/EC 4.3.1.25);
c) CYP450 reductase (CPR/EC 1.6.2.4);
d) cinnamate 4-hydroxylase (C4H/EC 1.14.14.91);
e) Coumarate 3-hydroxylase (C3H/EC 1.14.13);
f) 4-coumaric acid-CoA ligase (4CL/EC 6.2.1.12);
g) caffeic acid 3-O-methyltransferase (COMT/EC 2.1.1.68);
h) caffeoyl-CoA-O-methyltransferase (CCOMT/EC 2.1.1.104);
i) shikimate O-hydroxycinnamoyltransferase (HCT/EC 2.3.1.133);
j) 5-O-(4-coumaroyl)-D-quinate 3'-monooxygenase (C3'H/EC 1.14.14.96); and
k) double bond reductase (DBR).

Among these pathway enzymes the host cell of the invention can in one embodiment comprise:

a) one or more polypeptides selected from phenylalanine ammonia lyase (PAL); tyrosine ammonia lyase (TAL), cinnamate 4-hydroxylase (C4H), coumarate 3-hydroxylase (C3H), caffeic acid 3-O-methyltransferase (COMT); shikimate O-hydroxycinnamoyltransferase (HCT); and 5-O-(4-coumaroyl)-D-quinate 3'-monooxygenase (C3'H); capable of producing one or more compounds selected from cinnamic acid, p-coumaric acid, caffeic acid and ferulic acid;
b) 4-coumaric acid-CoA ligase (4CL); and caffeoyl-CoA O-methyltransferase (CCOMT); capable of converting the one or more compounds selected from cinnamic acid; cinnamoyl-CoA; p-coumaric acid; p-coumaroyl-CoA; caffeic acid; caffeoyl-CoA caffeic acid; and ferulic acid; into one or more compounds selected from cinnamoyl-CoA; p-Coumaroyl-CoA; Caffeoyl-CoA; and Feruloyl-CoA; and
c) optionally double bond reductase (DBR).

In one embodiment the CYP450 reductase (CPR) is native to the host cell. However, one or more heterologous CPRs may be co-expressed to regenerate the CYP450 enzymes. Further, in certain embodiments it may be advantageous to express or overexpress the *Saccharomyces cerevisiae* ICE2 gene (NM_001179438) or homologues thereof, which may improve the stability of the Cytochrome P450 reductase (CPR) and thereby the efficiency of the CYP450 enzyme reaction (see e.g. Emmerstorfer A et al., 2015, Biotechnol. J., 10: 623-35). Similarly, it may be advantageous to express or overexpress a CytB5 enzyme, such as the CytB5 from *Petunia* x *hybrida* (acc. no. AF098510) or a homologue thereof, which may enhance the function of CYP450 enzymes (see e.g. De Vetten N et al., 1999, Proc. Natl. Acad. Sci. USA, 96:778-783).

For a host cell comprising an initial tetraketide operative biosynthetic metabolic pathway the corresponding:

a) phenylalanine ammonia lyase (PAL) has at least 80% identity to the phenylalanine ammonia lyase encoded by the sequence set forth in SEQ ID NO: 1;
b) tyrosine ammonia lyase (TAL) has at least 80% identity to the tyrosine ammonia lyase encoded by the sequence set forth in SEQ ID NO: 3;
c) CYP450 reductase (CPR) has at least 80% identity to a CYP450 reductases encoded by a sequence set forth in SEQ ID NO: 23 or SEQ ID NO: 25;
d) trans-cinnamate 4-monooxygenase (C4H) has at least 80% identity to the trans-cinnamate 4-monooxygenase encoded by the sequence set forth in SEQ ID NO: 5;
e) 4-coumaric acid-CoA ligase (4CL) has at least 80% identity to the 4-coumaric acid-CoA ligase encoded by the sequence set forth in SEQ ID NO: 7;

f) caffeic acid 3-O-methyltransferase (COMT) has at least 80% identity to the caffeic acid 3-O-methyltransferase encoded by the sequence set forth in SEQ ID NO: 61;
g) caffeoyl-CoA-O-methyltransferase (CCOMT) has at least 80% identity to the caffeoyl-CoA-O-methyltransferase (CCOMT) encoded by the sequence set forth in SEQ ID NO: 63;
h) shikimate O-hydroxycinnamoyltransferase (HCT) has at least 80% identity to the shikimate O-hydroxycinnamoyltransferase encoded by the sequence set forth in SEQ ID NO: 67;
i) 5-O-(4-coumaroyl)-D-quinate 3'-monooxygenase (C3'H) has at least 80% identity to the 5-O-(4-coumaroyl)-D-quinate 3'-monooxygenase encoded by the sequence set forth in SEQ ID NO: 65; and/or
j) double bond reductase (DBR) has at least 80% identity to the double bond reductase (DBR) encoded by the sequence set forth in SEQ ID NO: 91.

More particularly in this embodiment the % sequence identity for the mentioned sequences may be at least 85%, such as at least 90%, such as at least 92%, such as at least 94%, such as at least 96%, such as at least 98%, such as at least 99%, such as at least 99.5%, such as at least 99.8%, such as at least 99.9%, such as 100% identity.

The tetraketide derivative of the invention is preferably selected from chalcones, dihydrochalcones, stilbenes and dihydrostilbenes or derivatives thereof.

In a particular embodiment involving metabolome formation and/or other stabilizing effects, the initial tetraketide operative biosynthetic metabolic pathway of the invention may further benefit from also including CHI in addition to CHIL.

Flavonoid Tetraketide Derivatives

In the flavonoid pathway (see FIG. 1), CHS is the first committed enzyme and, although CHS in some cases accepts a variety of cinnamoyl- and hydroxycinnamoyl-CoA substrates, it normally catalyzes synthesis of naringenin chalcone from one molecule of p-coumaroyl-CoA and three molecules of malonyl-CoA. Naringenin chalcone is stereospecifically isomerized to the colorless (2S)-naringenin, a flavanone, by CHI. (2S)-Naringenin is hydroxylated at the 3-position by F3H to yield (2R,3R)-dihydrokaempferol, a dihydroflavonol. Alternatively, the flavanones are turned into flavones by two different types of flavone synthase enzymes, either a 2-oxoglutarate-dependent dioxygenase (FNS I) or an NADPH-dependent cytochrome P450 monooxygenase (FNS II). The dihydroflavonols can be branched into flavonols by the action of flavonol synthase (FLS). F3'H and F3'5'H catalyze hydroxylation of naringenin or dihydrokaempferol (DHK) to form eriodictyol and pentahydroxyflavanone, or (2R,3R)-dihydroquercetin and dihydromyricetin, respectively. F3'H and F3'5'H determine the hydroxylation pattern of the B-ring of flavonoids and anthocyanins and are necessary for cyanidin and delphinidin production, respectively. They are key enzymes that determine the structures of flavonoids and anthocyanins. Dihydroflavonols are reduced to leucoanthocyanidins by DFR. Leucoanthocyanidins can be turned into catechins by the action of leucoanthocyanidin reductase (LAR). Alternatively, anthocyanidin synthase (ANS) catalyzes the synthesis of corresponding, colored anthocyanidins. Additionally, in order to form more stable anthocyanins, anthocyanidins can be 3-glucosylated by the action of A3GT. Alternatively, the anthocyanidins can be converted to epicatechins by the action of anthocyanidin reductase (ANR).

Accordingly, the polyketide synthase (PKS) of the invention may be a chalcone synthase (CHS) capable of converting the substrates into a chalcone and the operative biosynthetic metabolic pathway further comprises a chalcone isomerase (CHI) capable of converting the chalcone into a flavanone. Preferably the chalcone synthase (CHS) has at least 80% identity to the chalcone synthase (CHS) encoded by the sequence set forth in SEQ ID NO: 9 and/or the chalcone isomerase (CHI) has at least 80% identity to the chalcone isomerase encoded by the sequence set forth in SEQ ID NO: 11. More particularly in this embodiment the % sequence identity for the mentioned sequences may be at least 85%, such as at least 90%, such as at least 92%, such as at least 94%, such as at least 96%, such as at least 98%, such as at least 99%, such as at least 99.5%, such as at least 99.8%, such as at least 99.9%, such as 100% identity.

Further, the flavanone is preferably selected from one of naringenin, pinocembrin, and eriodictyol. Further the host cell of the invention can comprise polypeptides of an operative biosynthetic metabolic pathway capable of converting the flavanone into a flavonoid which is not a flavanone. Particular non-flavanone flavonoids include those selected from one or more of flavone, isoflavone, flavanonols, flavonol, flavans, anthocyanidins, and derivatives thereof.

In a particular embodiment the isoflavone is selected from genistein and daidzein and in another embodiment the flavonol is selected from quercetin, kaempferol and myricetin.

In particular, the non-flavanone flavonoid is selected from one or more of flavans, anthocyanidins and derivatives thereof. The anthocyanidin can be selected from anyone of pelargonidin, cyanidin, delphinidin, peonidin, petunidin, and malvidin.

The flavan can be a flavanol or derivatives thereof, such as a flavanol selected from one or more of flavan-3-ol, flavan-4-ol, flavan-3,4-diol and derivatives thereof. The flavan-3-ol can be selected from one or more of afzelechin, catechin, gallocatechin, catechin 3-gallate, Gallocatechin 3-gallate, epiafzelechin, Epicatechin, Epigallocatechin, Epicatechin 3-gallate, Epigallocatechin 3-gallate and any isomers thereof.

The host cell of the invention may comprise in the operative biosynthetic metabolic pathway one or more polypeptides of a flavonoid pathway selected from a) flavonoid hydroxylase (FH);
b) dihydroflavonol-4-reductase (DFR);
c) leucoanthocyanidin reductase (LAR);
d) anthocyanidin synthase (ANS);
e) glutathione-S-transferase (GST);
f) anthocyanidin reductase (ANR);
g) UDP-dependent glycosyltransferase (UGT);
h) Isoflavone synthase (IFS);
i) Hydroxy isoflavanone dehydratase (HIFD);
j) Flavone synthase (FNS);
k) Flavonol synthase (FLS);
l) anthocyanin-O-methyl transferase (AOMT); and
m) anthocyanin acyl transferase (AAT).

The UDP-dependent glycosyltransferase (UGT) in this flavonoid pathway can be selected from one or more of:

a) anthocyanidin 3-O-glycosyltransferase (A3GT);
b) anthocyanin 3'-O-glycosyl transferase (A3'GT);
c) anthocyanin-5-O-glycosyl transferase (A5GT); and
d) anthocyanin 3'5'-di-O-glycosyl transferase (A3'5'GT).

In particular, the UDP-dependent glycosyltransferase (UGT) is anthocyanidin 3-O-glycosyltransferase (A3GT).

The flavonoid hydrolase (FH) in this flavonoid pathway can be selected from one or more of:

a) Flavonoid 3-hydroxylase (F3H);
b) flavonoid 3'-hydroxylase (F3'H); and
c) flavonoid 3'-5'-hydroxylase (F3'5'H).

The anthocyanin acyl transferase (AAT) in this flavonoid pathway can be selected from one or more of: anthocyanin aromatic acyl transferase (AAroAT); and anthocyanin aliphatic acyl transferase (AAliAT).

In a particular embodiment the flavanone is naringenin, the flavonoid is an anthocyanin and the operative biosynthetic metabolic pathway comprises, in addition to CHIL and CHS:

a) chalcone isomerase (CHI);
b) one or more polypeptides selected from flavanone 3-hydroxylase (F3H); flavonoid 3'-hydroxylase (F3'H) and Flavonoid 3'-5'-hydroxylase (F3'5'H);
c) dihydroflavonol-4-reductase (DFR);
d) anthocyanidin synthase (ANS); and
e) one or more polypeptides selected from anthocyanidin 3-O-glycosyltransferase (A3GT); anthocyanin 3'-O-glycosyl transferase (A3'GT); anthocyanin-5-O-glycosyl transferase (A5GT); anthocyanin-7-O-glycosyl transferase (A7GT); anthocyanin 3'5'-di-O-glycosyl transferase (A3'5'GT); anthocyanin acyl transferase (AAT); and anthocyanin-O-methyl transferase (AOMT).

In this particular embodiment the operative biosynthetic metabolic flavonoid pathway may also comprise a glutathione-S-transferase (GST); which modifies the product ratio of the anthocyanidin synthase (ANS) by decreasing ANS formation of flavanol or derivatives thereof and increasing ANS formation of anthocyanidin or derivatives thereof when converting leucoanthocyanidin. The product ratio is preferably modified by an at least 1.25 fold increase in formation of anthocyanidin or derivatives thereof, such as at least 1.5 fold, such as at least 1.75 fold, such as at least 2 fold, such as at least 3 fold, such as at least 5 fold, such as at least 10 fold, such as at least 50 fold, such as at least 100 fold, such as at least 500 fold, such as at least 1000 fold. Further, the glutathione-S-transferase (GST) may be expressed in the host cell of the invention as a fused polypeptide with the anthocyanidin synthase (ANS). Still further the glutathione-S-transferase (GST) may be co-expressed with the anthocyanidin synthase (ANS) in the host cell of the invention. In an embodiment the glutathione-S-transferase (GST) is heterologous to the host cell.

In certain embodiments of the invention, in which the flavonoid or anthocyanin is further derivatized by acylation, the host cell may comprise further enzymes that allow the production of CoA activated phenylpropanoid acyl-donor molecules. For example, the bacterial enzymes HpaB and HpaC, such as the HpaB from *Pseudomonas aeruginosa* (acc. no. PKG21040) or its homologues, and the HpaC from *Salmonella enterica* (acc. no. GAR62209) or ist homologues, may be included for the conversion of p-coumarate to caffeate. Any combination of HpaB and HpaC homologs may have the desired effect of hydroxylating the 3-position of p-coumarate (see e.g. Liu L et al., Engineering 2019, 5: 287-295). Further, the caffeate, or the caffeoyl-CoA, may be further hydroxylated and/or methylated by expressing, in the host cell, an O-methyl transferase (OMT) such as the OMT1 from *Arabidopsis thaliana* (acc. no. AED96460 and with the function EC 2.1.1.68 or EC 2.1.1.42) or a homologue thereof, and/or a ferulate 5-hydroxylase (F5H) sauch as the *Arabidopsis thaliana* FAH1 (acc. no. NM_119790) or a homologue thereof. Combinations of these enzymes, together with the 4CL described above (with the function EC 6.2.1.12) will enable the production of the various CoA-activated phenylpropanoids, such as CoA esters of caffeate, ferulate, and sinapate. Similarly, the host cell may comprise heterologous nucleic acid sequences encoding one or more enzymes for the biosynthesis of benzoyl-CoA and/or p-hydroxybenzoyl-CoA. The anthocyanin is preferably selected from one or more of pelargonidin-3-O-glycoside (P3G), cyanidin-3-O-glycoside (C3G) delphinidin-3-O-glycoside (D3G); peonidin-3-O-glycoside, petunidin-3-O-glycoside, malvidin-3-O-glycoside; and derivatives thereof. A particularly interesting anthocyanin is selected from one or more of Petunidin 3-p-coumaroylrutinoside-5-glucoside; petunidin 3-feruloylrutinoside-5-glucoside; malvidin 3-p-coumaroylrutinoside-5-glucoside; pelargonidin 3-feruloylrutinoside-5-glucoside; pelargonidin rutinoside; pelargonidin 3-rutinoside-5-glucoside; pelargonidin 3-p-coumaroylrutinoside-5-glucoside; petunidin 3-rutinoside-5-glucoside; pelargonidin 3-rutinoside-5-glucoside; peonidin 3-rutinoside-5-glucoside; malvidin 3-rutinoside-5-glucoside; petunidin 3-rutinoside; pelargonidin 3-rutinoside; malvidin 3-rutinoside; petunidin 3-caffeoylrutinoside-5-glucoside; delphinidin 3-p-coumaroylrutinoside-5-glucoside; pelargonidin feruloyl-xylosyl-glucosylgalactoside; cyanidin 3-p-coumaroylrutinoside-5-glucoside; petunidin 3-p-coumaroylrutinoside-5-glucoside; petunidin 3-feruloylrutinoside-5-glucoside; pelargonidin 3-p-coumaroylrutinoside-5-glucoside; peonidin 3-p-coumaroylrutinoside-5-glucoside; malvidin 3-p-coumaroylrutinoside-5-glucoside; pelargonidin 3-feruloylrutinoside-5-glucoside; peonidin 3-feruloylrutinoside-5-glucoside; malvidin 3-feruloylrutinoside-5-glucoside; petunidin 3-p-coumaroylrutinoside; pelargonidin 3-p-coumaroylrutinoside; Cyanidin 3-O-glucoside; cyanidin 3;7-O-diglucoside; cyanidin 3-O-(3";6"-O-dimalonyl)-glucoside; cyanidin 3-O-6"-O-malonylglucoside; delphinidin 3-O-glucoside; delphinidin 3;5;3'-O-triglucoside; delphinidin 3-O-(3";6"-O-dimalonyl)-glucoside; delphinidin 3-O-6"-O-malonylglucoside; delphinidin 3-O-rutinoside; delphinidin 3-O-rutinoside 7-O-glucoside; delphinidin 3-O-rutinoside 7-O-(6"-O-p-hydroxybenzoyl)-glucoside; pelargonidin 3-O-glucoside; Cyanidin 3-(6";6'"-di-p-coumarylsophoroside)-5-(6-malonylglucoside); Cyanidin 3-(6";6'"-dicaffeylsophoroside)-5-glucoside; Cyanidin 3-(6";6"-disinapylsophoroside)-5-glucoside; Cyanidin 3-(6"-caffeyl-6"-ferulylsophoroside)-5-glucoside; Cyanidin 3-(6"-ferulyl-2"-sinapylsambubioside)-5-glucoside; Cyanidin 3-(6"-ferulyl-2'"-sinapylsophoroside)-5-glucoside; Cyanidin 3-(6"-p-coumaryl-2"-sinapylsophoroside)-5-glucoside; Cyanidin 3-(6-malonylglucoside)-7;3'-di-(6-feruloylglucoside); Cyanidin 3-(6-malonylglucoside)-7-(6-feruloylglucoside)-3'-glucoside; Cyanidin 3-[2-(6-p-coumarylglucosyl)-6-caffeoylglucoside]-5-glucoside; Cyanidin 3-[2-(6-p-coumarylglucosyl)-6-p-coumarylglucoside)]-5-glucoside; Cyanidin 3-[6"-(4-glucosylcaffeyl isophoroside]-5-glucoside; Cyanidin 3-O-[2"-O-(2'"-O-(sinapoyl) xylosyl) 6"-O-(p-coumaroyl) glucoside] 5-O-glucoside; Cyanidin 3-O-[beta-D-glucopyranoside]-7;3'-di-O-[6-O-(sinapyl)-beta-D-glucopyranoside]; Delphinidin 3-(6";6"-di-p-coumarylsophoroside)-5-(6-malonylglucoside); Delphinidin 3-(6-malonylglucoside)-3';5'-di-(6-p-coumaroylglucoside); Delphinidin 3-(diferuloyl)sophoroside-5-glucoside; Delphinidin 3-[2-(6-(feruloylglucoside)-6-feruloylglucoside]-5-(6-malonylglucoside); Delphinidin 3-[2-(6-feruloylglucoside)-6-p-coumaroylglucoside]-5-(6-malonylglucoside); Delphinidin 3-glucoside-5-(6-caffeoylglucoside)-3'-(6-(E)-p-coumaroylglucoside); Delphinidin 3-glucoside-7;3'-di-(6-(E)-sinapoylglucoside); Delphinidin 3-rutinoside-7-(6-p- coumaroylglucoside)-3'-glucoside; Cyanidin 3-glucoside-5; 3'-di-(caffeoylglucoside); Malvidin 3-O-[6-O-(4-O-(4-O-(6-O-(trans-caffeoyl)-beta-D-glucopyranosyl)-trans-p-coumaroyl)-alpha-L-rhamnopyranosyl)-beta-D-glucopyranoside]; Pelargonidin 3-(6";2"-diferulylsambubioside)-5-(6-malonylglucoside); Pelargonidin 3-(6"-ferulyl-2'"-sinapylsambubioside)-5-(6-malonylglucoside); Pelargonidin 3-(6"-ferulyl-2'"-sinapyl-sambubioside)-5-glucoside; Pelargonidin 3-(6"-p-coumaryl-2'"-sinapyl-sambubioside)-5-(6-malonylglucoside); Pelargonidin 3-(6"-p-coumaryl-2"-sinapylsambubioside)-5-glucoside; Pelargonidin 3-[6"-(3-glucosylcaffeyl)sophoroside]-5-glucoside; Pelargonidin 3-O-(6-O-malonyl-beta-D-glucopyranoside)-7-O-(6-O-(4-O-(trans-caffeyl)-beta-D-glucopyranosyl)-trans-caffeyl)-beta-D-glucopyranoside); Pelargonidin 3-O-[2-O-(2-(E)-feruloyl-beta-D-glucopyranosyl)-6-O-(E)-feruloyl-beta-D-glucopyranoside]-5-O-(beta-D-glucopyranoside); Pelargonidin 3-(2-(2-ferulylglucosyl)-6-ferulylglucoside)-5-glucoside; Pelargonidin 3-O-[2-O-(6-(E)-caffeoyl-beta-D-glucopyranosyl)-6-O-(E)-caffeoyl-beta-D-glucopyranoside]-5-O-(beta-D-glucopyranoside); Pelargonidin 3-(2-(6-caffeylglucosyl)-6-caffeylglucoside)-5-glucoside; Pelargonidin 3-O-[2-O-(6-(E)-caffeoyl-beta-D-glucopyranosyl)-6-O-(E)-feruloyl-beta-D-glucopyranoside]-5-O-(beta-D-glucopyranoside); Pelargonidin 3-(2-(6-caffeylglucosyl)-6-ferulylglucoside)-5-glucoside; Pelargonidin 3-O-[2-O-(6-(E)-caffeoyl-beta-D-glucopyranosyl)-6-O-(E)-p-coumaroyl-beta-D-glucopyranoside]-5-O-(beta-D-glucopyranoside); Pelargonidin 3-(2-(6-caffeylglucosyl)-6-p-coumarylglucoside)-5-glucoside; Pelargonidin 3-O-[2-O-(6-(E)-feruloyl-beta-D-glucopyranosyl)-6-O-(E)-caffeoyl-beta-D-glucopyranoside]-5-O-(beta-D-glucopyranoside); Pelargonidin 3-(2-(6-ferulylglucosyl)-6-caffeylglucoside)-5-glucoside; Pelargonidin 3-O-[2-O-(6-(E)-feruloyl-beta-D-glucopyranosyl)-6-O-(E)-feruloyl-beta-D-glucopyranoside]-5-O-(beta-D-glucopyranoside); Pelargonidin 3-(2-(6-ferulylglucosyl)-6-ferulylglucoside)-5-glucoside; Pelargonidin 3-O-[2-O-(6-(E)-feruloyl-beta-D-glucopyranosyl)-6-O-(E)-p-coumaroyl-beta-D-glucopyranoside]-5-O-(beta-D-glucopyranoside); Pelargonidin 3-(2-(6-ferulylglucosyl)-6-p-coumarylglucoside)-5-glucoside; Peonidin 3-[6"-(4-glucosylcaffeyl) sophoroside]-5-glucoside; Petunidin 3-O-[6-O-(4-O-(4-O-(beta-D-glucopyranosyl)-trans-p-coumaroyl)-alpha-L-rhamnopyranosyl)-beta-D-glucopyranoside]-5-O-[beta-D-glucopyranoside].

Alternatively, the selection of anthocyanin can be based on specific parameters, such as colour and/or stability of the molecule under various conditions, such as different pH, temperature, oxygen level, etc. In this embodiment, a host cell producing a basic anthocyanin scaffold, such as Pelargonidin-3-O-glucoside, Cyanidin-3-O-glucoside, or Delphinidin-3-O-glucoside, further expresses one or more randomly introduced genes encoding one or more of an O-methyl transferase, a glycosyl transferase, and an acyl transferase, plus any necessary accessory genes, e.g. those for producing various activated sugar- and acyl-donors. Assay conditions can thus be varied to allow selection of the molecules with desired properties, produced by the random combination of such modifying enzymes. In certain embodiments the assay conditions can be such as to include the presence of metal ions, or flavonoids which together with anthocyanins are able to result in co-pigmentation. In the case of flavonoids for co-pigmentation, these flavonoids may be added directly to the assay system, or they may be co-produced, together with anthocyanin, by the host itself or by co-cultivation with a secondary host.

In an alternative embodiment the flavonoid is a flavan-3-ol selected from (−)-epiafzelechin; (−)-epicatechin; and (−)-epigallocatechin and the operative biosynthetic metabolic pathway comprises:

a) chalcone isomerase (CHI);
b) one or more polypeptides selected from flavanone 3-hydroxylase (F3H); flavonoid 3'-hydroxylase (F3'H) and Flavonoid 3'-5'-hydroxylase (F3'5'H);
c) dihydroflavonol-4-reductase (DFR);
d) anthocyanidin synthase (ANS); and
e) anthocyanidin reductase (ANR).

Also, in this embodiment the operative biosynthetic metabolic flavonoid pathway may advantageously comprise glutathione-S-transferase (GST) which modifies the product ratio of the anthocyanidin synthase (ANS) by decreasing ANS formation of flavanol or derivatives thereof and increasing ANS formation of anthocyanidin or derivatives thereof when converting leucoanthocyanidin. The product ratio is preferably modified by an at least 1.25 fold increase in formation of anthocyanidin or derivatives thereof, such as at least 1.5 fold, such as at least 1.75 fold, such as at least 2 fold, such as at least 3 fold, such as at least 5 fold, such as at least 10 fold, such as at least 50 fold, such as at least 100 fold, such as at least 500 fold, such as at least 1000 fold. Further, the glutathione-S-transferase (GST) may be expressed in the host cell of the invention as a fused polypeptide with the anthocyanidin synthase (ANS). Still further the glutathione-S-transferase (GST) may be co-expressed with the anthocyanidin synthase (ANS) in the host cell of the invention. In an embodiment, the glutathione-S-transferase (GST) is heterologous to the host cell.

For a host cell comprising a flavonoid operative biosynthetic metabolic pathway the corresponding:

a) flavanone 3-hydroxylase (F3H) has at least 80% identity to the flavanone 3-hydroxylase encoded by the sequence set forth in SEQ ID NO: 39;
b) flavonoid 3'-hydroxylase (F3'H) has at least 80% identity to the flavonoid 3'-hydroxylase encoded by the sequence set forth in SEQ ID NO: 27;
c) flavonoid 3',5'-hydroxylase (F3'5'H) has at least 80% identity to the flavonoid 3',5'-hydroxylase encoded by the sequence set forth in SEQ ID NO: 29;
d) isoflavone synthase (IFS) has at least 80% identity to the isoflavone synthase encoded by the sequence set forth in SEQ ID NO: 35;
e) Hydroxy isoflavanone dehydratase (HIFD) has at least 80% identity to the isoflavone synthase encoded by the sequence set forth in SEQ ID NO: 37
f) flavone synthase (FNS) has at least 80% identity to the flavone synthase encoded by the sequence set forth in SEQ ID NO: 31, or SEQ ID NO:33
g) flavonol synthase (FLS) has at least 80% identity to the flavonol synthase encoded by the sequence set forth in SEQ ID NO: 41;
h) dihydroflavonol-4-reductase (DFR) has at least 80% identity to the dihydroflavonol-4-reductase encoded by the sequence set forth in SEQ ID NO: 43, SEQ ID NO: 45, or SEQ ID NO: 47;
i) anthocyanidin synthase (ANS) has at least 80% identity to an anthocyanidin synthase (ANS) encoded by the sequence set forth in SEQ ID NO: 53;
j) glutathione-S-transferase (GST) has at least 80% identity to the glutathione-S-transferase (GST) encoded by the sequence set forth in SEQ ID NO: 55;
k) leucoanthocyanidin reductase (LAR) has at least 80% identity to the leucoanthocyanidin reductase (LAR) encoded by the sequence set forth in SEQ ID NO: 49;

l) anthocyanidin reductase (ANR) has at least 80% identity to an anthocyanidin reductase (ANR) encoded by the sequence set forth in SEQ ID NO: 51;
m) anthocyanidin 3-O-glycosyltransferase (A3GT) has at least 80% identity to an anthocyanidin 3-O-glycosyltransferase encoded by the sequence set forth in SEQ ID NO: 57 or SEQ ID NO: 59;
n) anthocyanidin 3'-O-glycosyltransferase (A3'GT) has at least 80% identity to an anthocyanidin 3-O-glycosyltransferase encoded by the sequence set forth in SEQ ID NO: 87;
o) anthocyanin-5-O-glycosyl transferase (A5GT) has at least 80% identity to the anthocyanin-5-O-glycosyl transferase encoded by the sequence set forth in SEQ ID NO: 81;
p) anthocyanin-7-O-glycosyl transferase (A7GT) has at least 80% identity to the anthocyanin-7-O-glycosyl transferase encoded by the sequence set forth in SEQ ID NO: 69;
q) anthocyanin 3'5'-O-di-glycosyl transferase (A3'5'GT) has at least 80% identity to the anthocyanin 3'5'-di-O-glycosyl transferase (A3'5'GT) encoded by the sequence set forth in SEQ ID NO: 85;
r) anthocyanin aromatic acyl transferase (AAroAT) has at least 80% identity to the anthocyanin aromatic acyl transferase encoded by the sequence set forth in SEQ ID NO: 79;
s) anthocyanin aliphatic acyl transferase (AAliAT) has at least 80% identity to the anthocyanin aliphatic acyl transferase encoded by the sequence set forth in SEQ ID NO: 77; and/or
t) anthocyanidin O-methyl transferase (AOMT) has at least 80% identity to the anthocyanin O-methyl transferase encoded by the sequence set forth in SEQ ID NO: 97.

More particularly in this embodiment the % sequence identity for the mentioned sequences may be at least 85%, such as at least 90%, such as at least 92%, such as at least 94%, such as at least 96%, such as at least 98%, such as at least 99%, such as at least 99.5%, such as at least 99.8%, such as at least 99.9%, such as 100% identity.

Stilbenes and Derivatives

In the Stilbene pathway (see FIG. 3), Stilbene Synthase (STS) is the first committed enzyme and catalyzes synthesis of pinosylvin from cinnamoyl-CoA, and resveratrol from p-coumaroyl-CoA. These products may be further modified by hydroxylations, methylations, and/or prenylations.

Accordingly, the polyketide synthase (PKS) may also be a stilbene synthase (STS), capable of converting the substrates into a stilbene or a dihydrostilbene derivative. Preferably the stilbene synthase (STS) has at least 80% identity to the stilbene synthase (STS) encoded by the sequence set forth in SEQ ID NO: 71 or SEQ ID NO: 73. Further, the operative biosynthetic metabolic pathway may comprise trans-resveratrol di-O-methyltransferase (ROMT/EC 2.1.1.240).

The stilbene may be selected from one or more of 3,5-dihydroxystilbene (pinosylvin); 3,4',5-trihydroxystilbene (resveratrol); 3,3',4',5-tetrahydroxy stilbene (piceatannol); and 3,5-dimethoxy-4'-hydroxystilbene (pterostilbene); and the operative biosynthetic metabolic pathway may comprise one or more polypeptides capable of hydroxylating and/or methylating stilbenes and/or dihydrostilbenes.

Dihydrochalcones, Dihydrostilbenes, and Derivatives

For making tetraketide derivatives, such as dihydrochalcone and dihydrostilbene and further derivatives thereof the host cell of the invention may also comprises a Double Bond Reductase (DBR) capable of converting the one or more substrates selected from cinnamoyl-CoA, p-Coumaroyl-CoA, Caffeoyl-CoA, Feruoyl-CoA into the respective dihydrocinnamoyl-CoA, p-dihydrocoumaroyl-CoA, dihydrocaffeoyl-CoA and dihydroferuloyl-CoA which can then be converted to the further dihydro-derivatives by the Type 3 Polyketide Synthase (PKS). If the PKS is CHS the dihydrosubstrates may be converted into dihydrochalcones, while if the PKS is STS the dihydro-substrates may be converted into dihydro-stilbenes. The dihydrochalcones and/or dihydrostilbenes may then be further derivatized upon including into the host cell further enzymes of the flavonoid and/or the stilbene operative biosynthetic metabolic pathway. The Double Bond Reductase (DBR) is in one embodiment native to the host cell, while in another embodiment it is heterologous to the host cell. The Double Bond Reductase (DBR) may be TSC13. Preferably, Double Bond Reductase (DBR) has at least 80% identity to the Double Bond Reductase (DBR) encoded by the sequence set forth in SEQ ID NO: 91; the chalcone synthase (CHS) has at least 80% identity to the chalcone synthase (CHS) encoded by the sequence set forth in SEQ ID NO: 9 and/or the stilbene synthase (STS) has at least 80% identity to the stilbene synthase (STS) encoded by the sequence set forth in SEQ ID NO: 71 or SEQ ID NO: 73. More particularly in this embodiment the % sequence identity for the mentioned sequences may be at least 85%, such as at least 90%, such as at least 92%, such as at least 94%, such as at least 96%, such as at least 98%, such as at least 99%, such as at least 99.5%, such as at least 99.8%, such as at least 99.9%, such as 100% identity.

The dihydrochalcone can be pinocembrin dihydrochalcone or naringenin dihydrochalcone (phloretin) or derivatives thereof, most preferably phloretin. The derivatives are preferably Phlorizin or Nothofagin.

For the operative biosynthetic metabolic pathway of the invention a singularity or a plurality of polypeptides, i.e. at least one, are heterologous to the host cell, i.e. they are encoded by genes that are heterologous to the host cell, and particularly a plurality of polypeptides are heterologous such as 2, 3, 4, 5, 6, 7, 8, 9, 10, 11, 12, 13, 14, 15 or all of the pathway polypeptides are heterologous to the host cell.

Recombinant Host Cells with Improved ANS Function

The invention provides in a further aspect a separate microbial recombinant host cell, comprising a glutathione-S-transferase (GST) and an operative biosynthetic metabolic pathway capable of producing an anthocyanidin comprising an anthocyanidin synthase (ANS) capable of converting a leucoanthocyanidin and/or a flavanol substrate into an anthocyanidin. The glutathione-S-transferase (GST) can modify the product specificity of the anthocyanidin synthase (ANS) by lowering formation of flavonol or derivatives thereof and increasing formation of anthocyanidin or derivatives thereof in the second host cell compared to a host cell wherein the is no glutathione-S-transferase (GST) present.

The glutathione-S-transferase (GST) preferably increases the anthocyanidin synthase (ANS) product ratio towards formation of anthocyanidin or derivatives thereof by at least 1.25 fold, such as at least 1.5 fold, such as at least 1.75 fold, such as at least 2 fold, such as at least 3 fold, such as at least 5 fold, such as at least 10 fold, such as at least 50 fold, such as at least 100 fold, such as at least 500 fold, such as at least 1000 fold.

The glutathione-S-transferase (GST) may in the second host cell be expressed as fused polypeptides with the anthocyanidin synthase (ANS) or it may be co-expressed with the anthocyanidin synthase (ANS).

The second host cell of the invention may further comprise a second operative biosynthetic metabolic pathway comprising one or more polypeptides of a flavonoid pathway selected from:

a) phenylalanine ammonia lyase (PAL);
b) tyrosine ammonia lyase (TAL);
c) CYP450 reductase (CPR);
d) cinnamate 4-hydroxylase(C4H);
e) cinnamate 3-hydroxylase(C3H);
f) 4-coumaric acid-CoA ligase (4CL);
g) Caffeic acid —O-methyl transferase (COMT);
h) chalcone isomerase-like (CHIL);
i) chalcone synthase (CHS);
j) chalcone isomerase (CHI);
k) flavonoid hydroxylase (FH);
l) dihydroflavonol-4-reductase (DFR);
m) leucoanthocyanidin reductase (LAR);
n) anthocyanidin reductase (ANR);
o) UDP-dependent glycosyltransferase (UGT);
p) anthocyanin-O-methyl transferase (AOMT); and
q) anthocyanin acyl transferase (AAT).

The UDP-dependent glycosyltransferase (UGT) in this flavonoid pathway can be selected from one or more of:

e) anthocyanidin 3-O-glycosyltransferase (A3GT);
f) anthocyanin 3'-O-glycosyl transferase (A3'GT);
g) anthocyanin-5-O-glycosyl transferase (A5GT); and
h) anthocyanin 3'5'-di-O-glycosyl transferase (A3'5'GT).

The flavonoid hydroxylase (FH) in this flavonoid pathway can be selected from one or more of:

d) Flavonoid 3-hydroxylase (F3H);
e) flavonoid 3'-hydroxylase (F3'H); and
f) flavonoid 3'-5'-hydroxylase (F3'5'H).

The anthocyanin acyl transferase (AAT) in this flavonoid pathway can be selected from one or more of: anthocyanin aromatic acyl transferase (AAroAT); and anthocyanin aliphatic acyl transferase (AAliAT). In a particular embodiment the second operative biosynthetic metabolic pathway comprises:

a) chalcone isomerase (CHI);
b) one or more polypeptides selected from flavanone 3-hydroxylase (F3H); flavonoid 3'-hydroxylase (F3'H) and Flavonoid 3'-5'-hydroxylase (F3'5'H); and
c) dihydroflavonol-4-reductase (DFR).

In particular, the anthocyanidin can be selected from anyone of pelargonidin, cyanidin, delphinidin, peonidin, petunidin, and malvidin.

The second operative biosynthetic metabolic pathway comprises in an embodiment one or more polypeptides capable of further modifying the anthocyanidin into an anthocyanin, said polypeptides selected from:

a) anthocyanidin 3-O-glycosyltransferase (A3GT);
b) anthocyanin 3'-O-glycosyl transferase (A3'GT);
c) anthocyanin-5-O-glycosyl transferase (A5GT);
d) anthocyanin-7-O-glycosyl transferase (A7GT);
e) anthocyanin 3'5'-di-O-glycosyl transferase (A3'5'GT);
f) anthocyanin acyl transferase (AAT);
g) anthocyanin-O-methyl transferase (AOMT).

Particularly, the second operative biosynthetic metabolic pathway comprises anthocyanidin 3-O-glycosyltransferase (A3GT).

The anthocyanin is particularly selected from one or more of pelargonidin-3-O-glucoside (P3G), cyanidin-3-O-glucoside (C3G), or delphinidin-3-O-glucoside (D3G) or derivatives thereof. The anthocyanin can more specifically be one or more of Petunidin 3-p-coumaroylrutinoside-5-glucoside; petunidin 3-feruloylrutinoside-5-glucoside; malvidin 3-p-coumaroylrutinoside-5-glucoside; pelargonidin 3-feruloylrutinoside-5-glucoside; pelargonidin rutinoside; pelargonidin 3-rutinoside-5-glucoside; pelargonidin 3-p-coumaroylrutinoside-5-glucoside; petunidin 3-rutinoside-5-glucoside; pelargonidin 3-rutinoside-5-glucoside; peonidin 3-rutinoside-5-glucoside; malvidin 3-rutinoside-5-glucoside; petunidin 3-rutinoside; pelargonidin 3-rutinoside; malvidin 3-rutinoside; petunidin 3-caffeoylrutinoside-5-glucoside; delphinidin 3-p-coumaroylrutinoside-5-glucoside; pelargonidin feruloyl-xylosyl-glucosylgalactoside; cyanidin 3-p-coumaroylrutinoside-5-glucoside; petunidin 3-p-coumaroylrutinoside-5-glucoside; petunidin 3-feruloylrutinoside-5-glucoside; pelargonidin 3-p-coumaroylrutinoside-5-glucoside; peonidin 3-p-coumaroylrutinoside-5-glucoside; malvidin 3-p-coumaroylrutinoside-5-glucoside; pelargonidin 3-feruloylrutinoside-5-glucoside; peonidin 3-feruloylrutinoside-5-glucoside; malvidin 3-feruloylrutinoside-5-glucoside; petunidin 3-p-coumaroylrutinoside; pelargonidin 3-p-coumaroylrutinoside; Cyanidin 3-O-glucoside; cyanidin 3;7-O-diglucoside; cyanidin 3-O-(3";6"-O-dimalonyl)-glucoside; cyanidin 3-O-6"-O-malonylglucoside; delphinidin 3-O-glucoside; delphinidin 3;5;3'-O-triglucoside; delphinidin 3-O-(3";6"-O-dimalonyl)-glucoside; delphinidin 3-O-6"-O-malonylglucoside; delphinidin 3-O-rutinoside; delphinidin 3-O-rutinoside 7-O-glucoside; delphinidin 3-O-rutinoside 7-O-(6"-O-p-hydroxybenzoyl)-glucoside; pelargonidin 3-O-glucoside; Cyanidin 3-(6";6'''-di-p-coumarylsophoroside)-5-(6-malonylglucoside); Cyanidin 3-(6";6'''-dicaffeylsophoroside)-5-glucoside; Cyanidin 3-(6";6"-disinapylsophoroside)-5-glucoside; Cyanidin 3-(6"-caffeyl-6"-ferulylsophoroside)-5-glucoside; Cyanidin 3-(6"-ferulyl-2'''-sinapylsambubioside)-5-glucoside; Cyanidin 3-(6"-ferulyl-2"-sinapylsophoroside)-5-glucoside; Cyanidin 3-(6"-p-coumaryl-2"-sinapylsophoroside)-5-glucoside; Cyanidin 3-(6-malonylglucoside)-7;3'-di-(6-feruloylglucoside); Cyanidin 3-(6-malonylglucoside)-7-(6-feruloylglucoside)-3'-glucoside; Cyanidin 3-[2-(6-p-coumarylglucosyl)-6-caffeoylglucoside]-5-glucoside; Cyanidin 3-[2-(6-p-coumarylglucosyl)-6-p-coumarylglucoside)]-5-glucoside; Cyanidin 3-[6"-(4-glucosylcaffeyl isophoroside]-5-glucoside; Cyanidin 3-O-[2"-O-(2"-O-(sinapoyl) xylosyl) 6"-O-(p-coumaroyl) glucoside] 5-O-glucoside; Cyanidin 3-O-[beta-D-glucopyranoside]-7;3'-di-O-[6-O-(sinapyl)-beta-D-glucopyranoside]; Delphinidin 3-(6";6"-di-p-coumarylsophoroside)-5-(6-malonylglucoside); Delphinidin 3-(6-malonylglucoside)-3';5'-di-(6-p-coumaroylglucoside); Delphinidin 3-(diferuloyl)sophoroside-5-glucoside; Delphinidin 3-[2-(6-(feruloylglucoside)-6-feruloylglucoside]-5-(6-malonylglucoside); Delphinidin 3-[2-(6-feruloylglucoside)-6-p-coumaroylglucoside]-5-(6-malonylglucoside); Delphinidin 3-glucoside-5-(6-caffeoylglucoside)-3'-(6-(E)-p-coumaroylglucoside); Delphinidin 3-glucoside-7;3'-di-(6-(E)-sinapoylglucoside); Delphinidin 3-rutinoside-7-(6-p-coumaroylglucoside)-3'-glucoside; Cyanidin 3-glucoside-5;3'-di-(caffeoylglucoside); Malvidin 3-O-[6-O-(4-O-(4-O-(6-O-(trans-caffeoyl)-beta-D-glucopyranosyl)-trans-p-coumaroyl)-alpha-L-rhamnopyranosyl)-beta-D-glucopyranoside]; Pelargonidin 3-(6";2'''-diferulylsambubioside)-5-(6-malonylglucoside); Pelargonidin 3-(6"-ferulyl-2"-sinapylsambubioside)-5-(6-malonylglucoside); Pelargonidin 3-(6"-ferulyl-2'''-sinapylsambubioside)-5-glucoside; Pelargonidin 3-(6"-p-coumaryl-2'''-sinapyl-sambubioside)-5-(6-malonylglucoside); Pelargonidin 3-(6"-p-coumaryl-2'''-sinapylsambubioside)-5-glucoside; Pelargonidin 3-[6'''-(3-glucosylcaffeyl)sophoroside]-5-glucoside; Pelargonidin 3-O-(6-O-malonyl-beta-D-glucopyranoside)-7-O-(6-O-(4-O-(trans-caffeyl)-beta-D-glucopyranosyl)-trans-caffeyl)-beta-D-glucopyranoside);

Pelargonidin 3-O-[2-O-(2-(E)-feruloyl-beta-D-glucopyranosyl)-6-O-(E)-feruloyl-beta-D-glucopyranoside]-5-O-(beta-D-glucopyranoside); Pelargonidin 3-(2-(2-ferulylglucosyl)-6-ferulylglucoside)-5-glucoside; Pelargonidin 3-O-[2-O-(6-(E)-caffeoyl-beta-D-glucopyranosyl)-6-O-(E)-caffeoyl-beta-D-glucopyranoside]-5-O-(beta-D-glucopyranoside); Pelargonidin 3-(2-(6-caffeylglucosyl)-6-caffeylglucoside)-5-glucoside; Pelargonidin 3-O-[2-O-(6-(E)-caffeoyl-beta-D-glucopyranosyl)-6-O-(E)-feruloyl-beta-D-glucopyranoside]-5-O-(beta-D-glucopyranoside); Pelargonidin 3-(2-(6-caffeylglucosyl)-6-ferulylglucoside)-5-glucoside; Pelargonidin 3-O-[2-O-(6-(E)-caffeoyl-beta-D-glucopyranosyl)-6-O-(E)-p-coumaroyl-beta-D-glucopyranoside]-5-O-(beta-D-glucopyranoside); Pelargonidin 3-(2-(6-caffeylglucosyl)-6-p-coumarylglucoside)-5-glucoside; Pelargonidin 3-O-[2-O-(6-(E)-feruloyl-beta-D-glucopyranosyl)-6-O-(E)-caffeoyl-beta-D-glucopyranoside]-5-O-(beta-D-glucopyranoside); Pelargonidin 3-(2-(6-ferulylglucosyl)-6-caffeylglucoside)-5-glucoside; Pelargonidin 3-O-[2-O-(6-(E)-feruloyl-beta-D-glucopyranosyl)-6-O-(E)-feruloyl-beta-D-glucopyranoside]-5-O-(beta-D-glucopyranoside); Pelargonidin 3-(2-(6-ferulylglucosyl)-6-ferulylglucoside)-5-glucoside; Pelargonidin 3-O-[2-O-(6-(E)-feruloyl-beta-D-glucopyranosyl)-6-O-(E)-p-coumaroyl-beta-D-glucopyranoside]-5-O-(beta-D-glucopyranoside); Pelargonidin 3-(2-(6-ferulylglucosyl)-6-p-coumarylglucoside)-5-glucoside; Peonidin 3-[6"-(4-glucosylcaffeyl) sophoroside]-5-glucoside; Petunidin 3-O-[6-O-(4-O-(4-O-(beta-D-glucopyranosyl)-trans-p-coumaroyl)-alpha-L-rhamnopyranosyl)-beta-D-glucopyranoside]-5-O-[beta-D-glucopyranoside].

The second operative biosynthetic metabolic pathway may further comprise anthocyanidin reductase (ANR) capable of converting the anthocyanidin into one or more flavan-3-ols selected from (−)-epicatechin; (−)-epiafzelechin; and (−)-epigallocatechin.

For a host cell comprising the second operative biosynthetic metabolic pathway the corresponding:

a) phenylalanine ammonia lyase (PAL) has at least 80% identity to the phenylalanine ammonia lyase encoded by the sequence set forth in SEQ ID NO: 1;
b) tyrosine ammonia lyase (TAL) has at least 80% identity to the tyrosine ammonia lyase encoded by the sequence set forth in SEQ ID NO: 3;
c) CYP450 reductase (CPR) has at least 80% identity to a CYP450 reductases encoded by a sequence set forth in SEQ ID NO: 23 or SEQ ID NO: 25;
d) trans-cinnamate 4-monooxygenase (C4H) has at least 80% identity to the trans-cinnamate 4-monooxygenase encoded by the sequence set forth in SEQ ID NO: 5;
e) 4-coumaric acid-CoA ligase (4CL) has at least 80% identity to the 4-coumaric acid-CoA ligase encoded by the sequence set forth in SEQ ID NO: 7;
f) chalcone synthase (CHS) has at least 80% identity to the chalcone synthase (CHS) encoded by the sequence set forth in SEQ ID NO: 9;
g) caffeic acid 3-O-methyltransferase (COMT) has at least 80% identity to the caffeic acid 3-O-methyltransferase encoded by the sequence set forth in SEQ ID NO: 61;
h) chalcone isomerase-like (CHIL) polypeptide has at least 80% identity to the chalcone isomerase-like (CHIL) polypeptide encoded by the sequence set forth in SEQ ID NO: 13, SEQ ID NO: 15, SEQ ID NO: 17, SEQ ID NO: 19, and/or SEQ ID NO: 21;
i) the chalcone isomerase (CHI) has at least 80% identity to the chalcone isomerase encoded by the sequence set forth in SEQ ID NO: 11;
j) the flavanone 3-hydroxylase (F3H) has at least 80% identity to the flavanone 3-hydroxylase encoded by the sequence set forth in SEQ ID NO: 39;
k) the flavonoid 3'-hydroxylase (F3'H) has at least 80% identity to a flavonoid 3'-hydroxylase encoded by a sequence set forth in SEQ ID NO: 27;
l) the flavonoid 3',5'-hydroxylase (F3'5'H) has at least 80% identity to a flavonoid 3',5'-hydroxylase encoded by a sequence set forth in SEQ ID NO: 29;
m) the dihydroflavonol-4-reductase (DFR) has at least 80% identity to a dihydroflavonol-4-reductase encoded by a sequence set forth in SEQ ID NO: 43, SEQ ID NO: 45, or SEQ ID NO: 47;
n) the anthocyanidin synthase (ANS) has at least 80% identity to an anthocyanidin synthase (ANS) encoded by a sequence set forth in SEQ ID NO: 53;
o) glutathione-S-transferase (GST) has at least 80% identity to an glutathione-S-transferase (GST) encoded by a sequence set forth in SEQ ID NO: 55;
p) the leucoanthocyanidin reductase (LAR) has at least 80% identity to a leucoanthocyanidin reductase (LAR) encoded by a sequence set forth in SEQ ID NO: 49;
q) the anthocyanidin reductase (ANR) has at least 80% identity to an anthocyanidin reductase (ANR) encoded by a sequence set forth in SEQ ID NO: 51
r) the anthocyanidin 3-O-glycosyltransferase (A3GT) has at least 80% identity to an anthocyanidin 3-O-glycosyltransferase encoded by a sequence set forth in SEQ ID NO: 57 or SEQ ID NO: 59;
s) anthocyanidin 3'-O-glycosyltransferase (A3'GT) has at least 80% identity to an anthocyanidin 3-O-glycosyltransferase encoded by a sequence set forth in SEQ ID NO: 87;
t) the anthocyanin-5-O-glycosyl transferase (A5GT) has at least 80% identity to the anthocyanin-5-O-glycosyl transferase encoded by the sequence set forth in SEQ ID NO: 81;
u) anthocyanin-7-O-glycosyl transferase (A7GT) has at least 80% identity to the anthocyanin-7-O-glycosyl transferase encoded by the sequence set forth in SEQ ID NO: 69;
v) anthocyanin 3'5'-O-di-glycosyl transferase (A3'5'GT) has at least 80% identity to the anthocyanin 3'5'-di-O-glycosyl transferase (A3'5'GT) encoded by the sequence set forth in SEQ ID NO: 85;
w) anthocyanin aromatic acyl transferase (AAroAT) has at least 80% identity to the anthocyanin aromatic acyl transferase encoded by the sequence set forth in SEQ ID NO: 79;
x) anthocyanin aliphatic acyl transferase (AAliAT) has at least 80% identity to the anthocyanin aliphatic acyl transferase encoded by the sequence set forth in SEQ ID NO: 77; and/or
y) anthocyanidin O-methyl transferase (AOMT) has at least 80% identity to the anthocyanin O-methyl transferase encoded by the sequence set forth in SEQ ID NO: 97.

For the second operative biosynthetic metabolic pathway a singularity or a plurality of polypeptides, i.e. at least one, are heterologous to the second host cell, i.e. they are encoded by genes that are heterologous to the second host cell, and particularly a plurality of polypeptides are heterologous such as 2, 3, 4, 5, 6, 7, 8, 9, 10, 11, 12, 13, 14, 15 or all of the pathway polypeptides are heterologous to the second host cell. In an embodiment one or more of the glutathione-S-transferase (GST) and the anthocyanidin synthase (ANS) is heterologous to the second host cell.

Sources of Pathway Enzymes

In the operative biosynthetic metabolic pathways of the invention a singularity or a plurality of polypeptides/enzymes (i.e. at least one) and genes encoding them are heterologous to the host cell. Depending on the host cell the heterologous enzymes/polypeptides may be sourced from various sources. For example, in the case of a yeast host, the genes may be derived from plants, archaea, bacteria, animals, and other fungi. In an embodiment, at least one heterologous gene is derived from a plant. In certain embodiments, the heterologous genes can be selected from any one or a combination of organisms. For example, organisms which can be the source of heterologous genes for use in the host cell of the invention include species from one or more of the following plant genera: *Petunia, Malus, Anthurium, Zea, Arabidopsis, Ammi, Glycine, Hordeum, Medicago, Populus, Fragaria, Dianthus*, and the like. Representative species from these genera that may be used include *Petunia* x *hybrida, Malus domestica, Anthurium andraeanum, Arabidopsis thaliana, Ammi majus, Hordeum vulgare, Medicago sativa, Populus trichocarpa, Fragaria* x *ananassa*, and *Dianthus caryuphyllus*. In a further embodiment, genes encoding orthogonal enzymes from other organisms may also be included. Hence, there may be many options for constructing operational biosynthetic metabolic pathways by identifying a set of genes/enzymes that will work well together in a given microorganism.

Host optimization to improve expression of the heterologous pathways described is also possible. This may for example be done in such a way as to improve the ability of the host to provide higher levels of precursor molecules, tolerate higher levels of product, or to eliminate unwanted host enzyme activity, which interferes with the heterologous flavonoid-producing pathway. It may be advantageous to include transporter polypeptides, to facilitate transport of intermediates or end products of the heterologous biosynthic pathway across cell membranes, such as cell or vacuolar membranes. Such transporters are well known in the art, and may facilitate uptake of precursor molecules or the secretion of end products, sometimes increasing the overall production of end product. As will be understood by a skilled person, any enzyme of the operative biosynthetic metabolic pathway can be a target for optimization by genetic modifications, such as specific deletions, insertions, alterations, e.g., by mutagenesis, to improve both the specificity and turn-over rate of that enzyme. It will also be understood that the operational biosynthetic metabolic pathway may be constructed in such a way that, for each biosynthetic step, one or more genes is included. The one or more gene may be orthologs, carrying out the same biosynthetic reaction, or they be multiple copies of the same gene. Moreover, while specific enzymes are disclosed herein, the skilled person will appreciate that each disclosed enzyme represents its enzymatic function not only the listed enzyme and the disclosure should not be considered to be limited to the particular enzyme exemplified herein by name or sequence.

Host Cells

Host cells of the invention (including both host cells and second host cells) may be eukaryotic cells selected from the group consisting of mammalian, amphibian, insect, plant, or fungal cells. The host cells may be a fungal cell selected from phylas consisting of Ascomycota, Basidiomycota, Neocallimastigomycota, Glomeromycota, Blastocladiomycota, Chytridiomycota, Zygomycota, Oomycota and Microsporidia. In particular the host cell is a yeast cell selected from the group consisting of ascosporogenous yeast (Endomycetales), basidiosporogenous yeast, and Fungi Imperfecti yeast (Blastomycetes), particularly a yeast cell is selected from the genera consisting of *Saccharomyces, Kluveromyces, Candida, Pichia, Debaromyces, Hansenula, Yarrowia, Zygosaccharomyces, Arxula, Cyberlindnera, Xanthophyllomyces* and *Schizosaccharomyces*. For specific species the yeast host cell may be selected from the species consisting of *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Schizosaccharomyces pombe, Candida glabrata, Cyberlindnera jadinii, Pichia pastoris, Kluyveromyces lactis, Hansenula polymorpha, Candida boidinii, Arxula adeninivorans, Xanthophyllomyces dendrorhous, Candida albicans*, and *Yarrowia lipolytica*. In another embodiment the host cell is filamentous fungus. Suitable filamentous fungal host cell may be selected among the phylas consisting of Ascomycota, Eumycota and Oomycota, particularly selected from the genera of *Acremonium, Aspergillus, Ashbya, Aureobasidium, Bjerkandera, Ceriporiopsis, Chrysosporium, Coprinus*, Corio/us, *Cryptococcus, Filibasidium, Fusarium, Gibberella, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, and *Trichoderma*.

More specially a filamentous fungal host cell may be selected among the species of *Aspergillus awamori, Aspergillus foetidus, Aspergillus fumigatus, Aspergillus japonicus, Aspergillus nidulans, Aspergillus niger, Aspergillus oryzae, Ashbya gossypii, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora*, Chrysosporiuminops, Chrysosporiumkeratinophilum, *Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Gibberella fujikuroi, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, and *Trichoderma viride*.

In a particular embodiment the host cell of the invention is a yeast, particularly a yeast which belongs to the genus *Saccharomyces, Klyuveromyces, Candida, Pichia, Debaromyces, Hansenula, Yarrowia, Zygosaccharomyces*, or *Schizosaccharomyces*; such as the yeast *Saccharomyces cerevisiae*.

Host cells of the invention (including both host cells and second host cells) may also be prokaryotic cells, such as bacteria. Accordingly, the host cell of the invention may be a bacterium of a genera selected from *Escherichia, Lactobacillus, Lactococcus, Corynebacterium, Bacillus, Acetobacter, Acinetobacter, Pseudomonas* or *Rhodobacter*. In particular the host cell may be selected from the species of *Escherichia coli, Corynebacterium glutamicum, Bacillus*

*subtilus, Rhodobacter sphaeroides, Rhodobacter capsulatus*, or *Rhodotorula* toruloides. In one embodiment the bacterium is *Escherichia coli.*

In a further alternative embodiment, the host cell of the invention may be an algae such as algaes of the species *Blakeslea trispora, Dunaliella salina, Haematococcus pluvialis, Chlorella* sp., *Undaria pinnatifida, Sargassum, Laminaria japonica*, or *Scenedesmus almeriensis* species. In a further alternative embodiment, the host cell of the invention is a cyanobacterium such as cyanobacteria selected from the species *Blakeslea trispora, Dunaliella salina, Haematococcus pluvialis, Chlorella* sp., *Undaria pinnatifida, Sargassum, Laminaria japonica*, or *Scenedesmus almeriensis.*

Alternative host cells of the invention may be plant cells for example of the genus *Physcomitrella*. In addition to plant cells the invention also provides an isolated plant, e.g., a transgenic plant, plant part, or plant cell culture comprising the operative biosynthetic metabolic pathway of the invention and producing the tetraketide or derivatives thereof in useful quantities. The tetraketide or derivatives thereof may be recovered from the plant or plant part or cell. The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn). Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*. Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats. Also included within the scope of the present invention are the progeny of such plants, plant parts, and plant cells. The transgenic plant or plant cells comprising the operative pathway of the invention and produce the tetraketide or derivatives thereof may be constructed in accordance with methods known in the art. In short, the plant or plant cell is constructed by incorporating one or more expression vectors of the invention into the plant host genome or chloroplast genome and propagating the resulting modified plant or plant cell into a transgenic plant or plant cell.

The host cell of the invention may further be modified to provide an increased amount of a substrate for at least one polypeptide of the operative biosynthetic metabolic pathway and/or the host cell of the invention may be even further genetically modified to exhibit increased tolerance towards one or more substrates, intermediates, or product molecules from the operative biosynthetic metabolic pathway. Moreover, the host cell of the invention may comprise one or more native genes which have been attenuated, disrupted and/or deleted using method known in the art.

Nucleotide Constructs

The invention also provides a recombinant polynucleotide construct comprising a nucleotide encoding the chalcone isomerase-like (CHIL) polypeptide and/or the Type 3 polyketide synthase (PKS) of the invention, operably linked to one or more control sequences, such as a promotor which is heterologous to the CHIL and/or type 3 PKS encoding polynucleotide.

Polynucleotides may be manipulated in a variety of ways to enable or optimize expression. Manipulation of the polynucleotide prior to its insertion into an expression vector may be desirable or necessary depending on the expression vector. The techniques for modifying polynucleotides utilizing recombinant DNA methods are well known in the art.

The control sequence may be a promoter, which is a polynucleotide sequence that is recognized by a host cell for expression of a polynucleotide. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either native or heterologous to the host cell. The promoter may be an inducible promoter.

Examples of suitable promoters for directing transcription of the polynucleotide construct of the invention in a yeast host are listed as SEQ ID NOS: 101-108. They also include promoters obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound.

A CHIL encoding polynucleotide in the polynucleotide construct of the invention has in one embodiment at least 70%, such at least 75%, such as at least 80%, such as at least 90%, such as at least 95%, such as at least 99%, such as at least 100% identity to SEQ ID NO: 13, SEQ ID NO: 15, SEQ ID NO: 17, SEQ ID NO: 19, and/or SEQ ID NO: 21. The PKS encoding polynucleotide in the polynucleotide construct of the invention encodes in another embodiment a chalcone synthase (CHS) which has at least 70%, such at least 75%, such as at least 80%, such as at least 90%, such as at least 95%, such as at least 99%, such as at least 100% identity to SEQ ID NO: 9. The PKS encoding polynucleotide in the polynucleotide construct of the invention encodes in a further embodiment a stilbene synthase (STS) which has at least 70%, such at least 75%, such as at least 80%, such as at least 90%, such as at least 95%, such as at least 99%, such as at least 100% identity to SEQ ID NO: 71 or SEQ ID NO: 73.

A GST encoding polynucleotide construct of the invention has in one embodiment at least 70%, such at least 75%, such as at least 80%, such as at least 90%, such as at least 95%, such as at least 99%, such as at least 100% identity to SEQ ID NO: 55.

The transcriptional control sequences of the regulatory region controls can thus be a promoter, transcription terminator, mRNA stabilizer region, a leader, and/or a polyadenylation sequence and it can be either native or heterologous to the host cell. In one embodiment the control sequence is a promoter which is native to *S. cerevisiae* and has at least 70%, such at least 75%, such as at least 80%, such as at least 90%, such as at least 95%, such as at least 99%, such as at least 100% identity to a sequence selected from the groups consisting of SEQ ID NO: 101, SEQ ID NO: 102; SEQ ID NO: 103; SEQ ID NO: 104; SEQ ID NO: 105; SEQ ID NO: 106; SEQ ID NO: 107 and SEQ ID NO: 108.

Further the invention provides an expression vector comprising a polynucleotide construct of the invention.

Accordingly, in a special embodiment the host cell of the invention comprises an integrated polynucleotide construct of the invention and/or the expression vector of the invention.

The host cell may be further manipulated to contain a plurality of copies of any native or heterologous genes in the operative biosynthetic metabolic pathway producing tertraketide or derivatives thereof. For example, the host cell of the invention may include at least 2 copies of genes encoding the CHIL and/or type 3 PKS and/or the GST.

In a further embodiment the host cell has been further modified by introducing one or more heterologous genes, or by modifying one or more native genes, encoding a transporter, e.g. of the multidrug and toxic compound extrusion (MATE)-type or the ATP-binding cassettes (ABC)-type (reviewed by Zhao, 2015). Although GST has previously been contemplated to be associated with transport, the current application demonstrates that GST is involved in anthocyanidin production, independent of transporters. However, it is contemplated herein that the combination of GST and transporters for metabolites of the pathway and/or target molecule would have a beneficial impact on the final compound yield. This includes the engineering of host native transporters, e.g. transporter overexpression or engineering of native transporter specificity in order to facilitate transport of flavonoids and anthocyanins.

Although certain flavonoids are known to be secreted from plant roots, most flavonoids and anthocyanins are predominantly stored in the plant vacuole, and hence, the transport into the vacuole is the normal function of most flavonoid and anthocyanin transporters. However, it is conceivable that engineering transporters to relocate them to the host plasma membrane, as opposed to the tonoplast of vacuoles, would increase transport out of the cell, thereby increasing overall yield. This could happen by relieving internal stress from accumulating compounds, relieving unknown feedback inhibition, or by creating a sink for the pool of product molecules. Such engineering of transporters, in order to relocate them to the plasma membrane, is known in the art and can be applied to both C-terminal localization signals (Wolfenstetter et al. 2012) or N-terminal localization signals (Wang 2014). Transporters that could possibly be re-engineered includes, but are not limited to, ABC type transporters and MATE-type transporters. Some examples of ABC-type transporters are the ABCCs or ABCGs from *Zea mays* (Goodman et al. 2004; Badone et al. 2010), *Vitis vinifera* (Francisco et al. 2013), *Homo sapiens* (Chowdhurry et al. 2014), *Arabidopsis thaliana* (Liu et al. 2001; Francisco et al. 2013), or *Medicago truncatula* (Banasiak et al. 2013). Examples of suitable MATE-type transporters are MATEs from *Solanum lycopersicum* (Mathews et al. 2003), *Arabidopsis thaliana* (Debeaujon et al. 2001; Marinova et al. 2007; Zhao & Dixon, 2009), *Vitis viniferas* (Gomez et al. 2009), *Medicago truncatula* (Zhao & Dixon 2009; Zhao et al. 2011), *Malus domestica* (Frank et al. 2011), *Brassica napus* (Chai et al. 2009), *Gossypium hirsitum* (Gao et al. 2016) and *Vaccinium corymbosum* (Chen et al. 2015). In addition, the host may have both ABC-type and MATE-type transporters suitable for engineering towards enhanced transport out of the cell.

Cultures

The invention further provides a cell culture, comprising the host cells of the invention and a growth medium. The invention also provides a second cell culture, comprising the second host cell of the invention and a growth medium.

Methods of Producing Tetraketide or Derivatives Thereof.

In a separate aspect the invention provides a method for producing a tetraketide derivative comprising:

a) culturing the cell culture of the invention at conditions allowing the host cell to convert the one or more substrates into the tetraketide derivative; and
b) optionally recovering and/or isolating the tetraketide derivative.

In the method of the invention the recovering step may comprise separating a liquid phase of the host cell or cell culture from a solid phase of the host cell or cell culture to obtain a supernatant comprising the tetraketide derivative by one or more steps selected from:

a) contacting the supernatant with one or more adsorbent resins in order to obtain at least a portion of the produced tetraketide derivative;
b) contacting the supernatant with one or more ion exchange or reversed-phase chromatography columns in order to obtain at least a portion of the tetraketide derivative;
c) crystallizing or extracting the tetraketide derivative; and
d) evaporating the solvent of the liquid phase to concentrate the tetraketide derivative;

thereby recovering the tetraketide derivative.

In an embodiment the method of the invention further comprises one or more elements selected from:

a) culturing the cell culture in a nutrient medium comprising vitamins, trace elements, salts, amino acids, nitrogen, and a carbon source;
b) culturing the cell culture under aerobic or anaerobic conditions
c) culturing the cell culture under agitation;
d) culturing the cell culture at a temperature of between 20-50° C.;
e) culturing the cell culture at a pH of between 3-9; and
f) culturing the cell culture for between 20 to 120 hours.

The method of the invention may further comprise at least one step of producing the tetraketide derivative, which is performed in vitro.

In a further aspect, the invention provides a method for increasing the catalytic activity of CHS and/or STS by co-expression of CHIL and optionally CHI, thereby increasing overall productivity and, hence, production of tetraketide derivatives. The co-expression of CHIL, with CHS and/or STS and optionally CHI, allows in vivo association of the proteins to enhance the overall productivity over the method not employing CHIL. In this embodiment the relative production of tetraketide derivatives may be increased at least 1.25 fold, such as at least 1.5 fold, such as at least 1.75 fold, such as at least 2 fold, such as at least 3 fold, such as at least 5 fold, such as at least 10 fold, such as at least 50 fold, such as at least 100 fold, such as at least 500 fold, such as at least 1000 fold.

In a still further aspect the invention provides a method for producing epicatechin or anthocyanin or a derivative thereof comprising incorporating a heterologous glutathione-S-transferase (GST) in a recombinant host cell of the invention comprising an operative biosynthetic metabolic pathway capable of producing said epicatechin or anthocyanin or a derivative thereof and culturing said host cell to produce said epicatechin or anthocyanin or a derivative thereof.

In a still further aspect, the invention provides a method for converting a leucoanthocyanidin into an anthocyanidin comprising contacting in a host cell of the invention the leucoanthocyanidin with an anthocyanidin synthase (ANS) in combination with a glutathione-S-transferase (GST).

In a still further aspect, the invention provides a method of modifying the product ratio of an anthocyanidin synthase (ANS) by decreasing ANS formation of flavonol or derivatives thereof and increasing ANS formation of anthocyanidin or derivatives thereof when converting leucoanthocyanidin, comprising contacting in a host cell of the invention the ANS with a glutathione-S-transferase (GST) in a reaction medium. In this embodiment the product ratio is preferably modified by an at least 1.25 fold increase in formation of anthocyanidin or derivatives thereof, such as at least 1.5 fold, such as at least 1.75 fold, such as at least 2 fold, such as at least 3 fold, such as at least 5 fold, such as at least 10 fold, such as at least 50 fold, such as at least 100 fold, such as at least 500 fold, such as at least 1000 fold.

It is appreciated by a person skilled in the art, that host cells and cultures of the invention can be cultivated using conventional cell culture or fermentation processes, including, inter alia, chemostat, batch, fed-batch cultivations, continuous perfusion fermentation, and continuous perfusion cell culture.

The skilled person will also appreciate that after the host cells have been grown in culture for a desired period of time, the tertraketide derivatives can then be recovered from the culture or culture medium using standard techniques known in the art.

Fermentation Liquids

In a still further aspect, the invention provides a fermentation liquid comprising the cell culture of the invention and its contents of tetraketide derivatives. In the fermentation liquid of the invention at least 50% of the host cells may be lysed such as at least 75%, such as at least 95%, such as at least 99%. Also, in the fermentation liquid of the invention at least 50% (w/w) of solid cellular material may have been removed such as at least 75% (w/w), such as at least 95% (w/w), such as at least 99% (w/w). In the fermentation liquid of the invention the tetraketide derivative is in an embodiment a flavan-3-ol selected from one or more of (−)-epiafzelechin; (−)-epicatechin; and (−)-epigallocatechin, while in another embodiment the tetraketide derivative is an anthocyanin selected from one or more of pelargonidin-3-O-glycoside (P3G), cyanidin-3-O-glycoside (C3G) delphinidin-3-O-glycoside (D3G); peonidin-3-O-glycoside, petunidin-3-O-glycoside, malvidin-3-O-glycoside, and derivatives thereof. Still further in the fermentation liquid of the invention the tetraketide derivative may be a stilbene selected from one or more of pinosylvin; resveratrol; piceatannol; and pterostilbene. In the fermentation liquid of the invention the tetraketide derivative may also be a dihydrochalcone selected from one or more of pinocembrin dihydrochalcone or naringenin dihydrochalcone (phloretin).

Preferably, the tetraketide derivative concentration in the fermentation liquid is at least 5 mg/L, such as at least 10 mg/L, such as at least 20 mg/l, such as at least 50 mg/L, such as at least 100 mg/L, such as at least 500 mg/L, such as at least 1000 mg/L, such as at least 5000 mg/L, such as at least 10000 mg/L, such as at least 50000 mg/L.

Compositions

In a further aspect the invention provides a composition comprising the fermentation liquid of the invention and one or more agents, additives and/or excipients. Agents, additives and/or excipients includes formulation additives, stabilising agent and fillers.

The composition may contain one or more co-pigments, which can affect stability, color, and hue of the tetraketide derivatives such as anthocyanins. This can be an intramolecular interaction e.g. of the acyl group with the rest of the tetraketide derivative, but it can also be an intermolecular interaction with other molecules in the composition. For processing, formulation and storage of products containing tetraketide derivatives, stabilization of the intact tetraketide derivatives may be desired. However, e.g. in vivo therapeutic effects of tetraketide derivatives can also be due to one or more of native degradation products or metabolites, in which case certain instability of the tetraketide derivatives in the composition may be desired for some applications. Notably, the amount of for example native anthocyanin in plasma has been quoted as less than 1% of the consumed quantities. This has been due to limited intestinal absorption, high rates of cellular uptake, metabolism and excretion. Therefore, for therapeutic applications of tetraketide derivatives, it can be advantageous to use tetraketide derivatives with instability at the relevant stage of the digestive tract, or further derivatization for maximum adsorption at the relevant stage of the digestive tract. Colonic metabolism of tetraketide derivatives can also be considered. Therefore, in some instances "improved stability" of tetraketide derivatives may actually be a decrease in stability for delivery to a specific stage of the digestive tract or colon. The chemical forms of tetraketide derivatives ingested in the diet may not be the ones that reach a specific target in the body instead it may be their respective metabolites as they are formed through metabolism.

The composition of the invention may be formulated into a dry solid form by using methods known in the art. Further, the composition may be in dry form such as a spray dried, spray cooled, lyophilized, flash frozen, granular, microgranular, capsule or microcapsule form made using methods known in the art.

The composition of the invention may also be formulated into liquid stabilized form using methods known in the art. Further, the composition may be in liquid form such as a stabilized liquid comprising one or more stabilizers such as sugars and/or polyols (e.g. sugar alcohols) and/or organic acids (e.g. lactic acid).

The composition of the invention may further be characterised by being a food product, a dietary supplement, a pharmaceutical product, a cosmetic product.

Pharmaceutical Preparations

The invention further provides a method for preparing a pharmaceutical preparation comprising subjecting the composition of the invention to one or more steps transforming the composition and its contents of tetraketide derivatives into a therapeutically relevant mixture further comprising one or more pharmaceutical grade additives and/or adjuvants.

The invention also provides a pharmaceutical preparation obtained or obtainable from the method for preparing the pharmaceutical preparation.

Use of Tetraketide Derivatives of the Invention

A composition of the invention may be used for non-therapeutic purposes for example as a dye, colorant or pigment, as pH indicators, as food additives, as antioxidants, in cosmetics, or as non-therapeutic food and nutritional supplements.

Further, the pharmaceutical preparation of the invention can be used as a medicament. Tetraketide derivatives of the invention are known to be active in the prevention and/or treatment of a range of disorders linked to human metabolic syndrome, including obesity, diabetes, insulin resistance, hyperglycemia, and neuropathy. Further, tetraketide derivatives of the invention are known to be active in the prevention and/or treatment of cardiovascular diseases, including inflammations, atherosclerosis, hypercholesterolemia, and hypertension; in the prevention and/or treatment of neurodegenerative disorders, such as cognitive disorders, memory loss, alzheimer's disease, depressions, and anxiety; in the prevention and/or treatment of cancers, such as renal and colorectal cancers, or cancers of colon, liver, pancreas, or prostate cancer; in the prevention and/or treatment of skin disorders, including atopic dermatitis, eye care, venous diseases, fatigues, hormonal disruptions, and viral or bacterial infections; for the use in hormonal replacement therapy. Accordingly, the invention provides the pharmaceutical preparation of the invention for use in the prevention and/or treatment of a disease selected from:

a) metabolic syndrome, including obesity, diabetes, insulin resistance, hyperglycemia, and neuropathy;
b) cardiovascular diseases, including inflammations, atherosclerosis, hypercholesterolemia, and hypertension;
c) neurodegenerative disorders, such as cognitive disorders, memory loss, alzheimer's disease, depressions, and anxiety;
d) cancers, such as renal and colorectal cancers, or cancers of colon, liver, pancreas, or prostate;
e) skin disorders, including atopic dermatitis;
f) ophthalmic disorders;
g) venous diseases;
h) fatigue;
i) endocrine disorders, including hormonal disruptions; and
j) infections, including viral or bacterial infections.

Further, in an embodiment the pharmaceutical preparation of the invention can be used in a method of treating a disease in a mammal in need thereof comprising administering a therapeutically effective amount of the pharmaceutical preparation of the invention to the mammal.

REFERENCE TO SEQUENCE LISTING

The present application includes a Sequence Listing for the sequences of table A, titled 17420990 Sequence Listing ST25, and 318,546 bytes in size, with a creation date of Apr. 7, 2022, prepared in PatentIn version 3.5.1, which is submitted electronically in ST25 format which is hereby incorporated by reference in its entirety.

TABLE A

| SEQ ID NO | | | | Species |
|---|---|---|---|---|
| SEQ ID NO: 1 | DNA coding sequence of | PAL | from | *Arabidopsis thaliana* |
| SEQ ID NO: 2 | Polypeptide sequence of | PAL | from | *Arabidopsis thaliana* |
| SEQ ID NO: 3 | DNA coding sequence of | TA | from | *Zea mays* |
| SEQ ID NO: 4 | Polypeptide sequence of | TA | from | *Zea mays* |
| SEQ ID NO: 5 | DNA coding sequence of | C4H | from | *Ammi majus* |
| SEQ ID NO: 6 | Polypeptide sequence of | C4H | from | *Ammi majus* |
| SEQ ID NO: 7 | DNA coding sequence of | 4CL | from | *Arabidopsis thaliana* |
| SEQ ID NO: 8 | Polypeptide sequence of | 4CL | from | *Arabidopsis thaliana* |
| SEQ ID NO: 9 | DNA coding sequence of | CHS | from | *Hypericum androsaemum* |
| SEQ ID NO: 10 | Polypeptide sequence of | CHS | from | *Hypericum androsaemum* |
| SEQ ID NO: 11 | DNA coding sequence of | CHI | from | *Medicago sativa* |
| SEQ ID NO: 12 | Polypeptide sequence of | CHI | from | *Medicago sativa* |
| SEQ ID NO: 13 | DNA coding sequence of | CHIL | from | *Petunia × hybrida* |
| SEQ ID NO: 14 | Polypeptide sequence of | CHIL | from | *Petunia × hybrida* |
| SEQ ID NO: 15 | DNA coding sequence of | CHIL | from | *Arabidopsis thaliana* |
| SEQ ID NO: 16 | Polypeptide sequence of | CHIL | from | *Arabidopsis thaliana* |
| SEQ ID NO: 17 | DNA coding sequence of | CHIL | from | *Ipomoea nil* |
| SEQ ID NO: 18 | Polypeptide sequence of | CHIL | from | *Ipomoea nil* |
| SEQ ID NO: 19 | DNA coding sequence of | CHIL | from | *Antirrhinum majus* |
| SEQ ID NO: 20 | Polypeptide sequence of | CHIL | from | *Antirrhinum majus* |
| SEQ ID NO: 21 | DNA coding sequence of | CHIL | from | *Glycine max* |
| SEQ ID NO: 22 | Polypeptide sequence of | CHIL | from | *Glycine max* |
| SEQ ID NO: 23 | DNA coding sequence of | CPR | from | *Saccharomyces cerevisiae* |
| SEQ ID NO: 24 | Polypeptide sequence of | CPR | from | *Saccharomyces cerevisiae* |
| SEQ ID NO: 25 | DNA coding sequence of | CPR | from | *Arabidopsis thaliana* |
| SEQ ID NO: 26 | Polypeptide sequence of | CPR | from | *Arabidopsis thaliana* |
| SEQ ID NO: 27 | DNA coding sequence of | F3'H | from | *Petunia × hybrida* |
| SEQ ID NO: 28 | Polypeptide sequence of | F3'H | from | *Petunia × hybrida* |
| SEQ ID NO: 29 | DNA coding sequence of | F3'5'H | from | *Petunia × hybrida* |
| SEQ ID NO: 30 | Polypeptide sequence of | F3'5'H | from | *Petunia × hybrida* |
| SEQ ID NO: 31 | DNA coding sequence of | FNS I | from | *Petroselinum crispum* |
| SEQ ID NO: 32 | Polypeptide sequence of | FNS I | from | *Petroselinum crispum* |
| SEQ ID NO: 33 | DNA coding sequence of | FNS II | from | *Antirrhinum majus* |

TABLE A-continued

| SEQ ID NO | | | | Species |
|---|---|---|---|---|
| SEQ ID NO: 34 | Polypeptide sequence of | FNS II | from | *Antirrhinum majus* |
| SEQ ID NO: 35 | DNA coding sequence of | IFS | from | *Glycine max* |
| SEQ ID NO: 36 | Polypeptide sequence of | IFS | from | *Glycine max* |
| SEQ ID NO: 37 | DNA coding sequence of | HIFD | from | *Glycine max* |
| SEQ ID NO: 38 | Polypeptide sequence of | HIFD | from | *Glycine max* |
| SEQ ID NO: 39 | DNA coding sequence of | F3H | from | *Malus domestica* |
| SEQ ID NO: 40 | Polypeptide sequence of | F3H | from | *Malus domestica* |
| SEQ ID NO: 41 | DNA coding sequence of | FLS | from | *Citrus unshiu* |
| SEQ ID NO: 42 | Polypeptide sequence of | FLS | from | *Citrus unshiu* |
| SEQ ID NO: 43 | DNA coding sequence of | DFR | from | *Anthurium andraeanum* |
| SEQ ID NO: 44 | Polypeptide sequence of | DFR | from | *Anthurium andraeanum* |
| SEQ ID NO: 45 | DNA coding sequence of | DFR | from | *Populus trichocarpa* |
| SEQ ID NO: 46 | Polypeptide sequence of | DFR | from | *Populus trichocarpa* |
| SEQ ID NO: 47 | DNA coding sequence of | DFR | from | *Iris × hollandica* |
| SEQ ID NO: 48 | Polypeptide sequence of | DFR | from | *Iris × hollandica* |
| SEQ ID NO: 49 | DNA coding sequence of | LAR | from | *Vitis vinifera* |
| SEQ ID NO: 50 | Polypeptide sequence of | LAR | from | *Vitis vinifera* |
| SEQ ID NO: 51 | DNA coding sequence of | ANR | from | *Lotus corniculatus* |
| SEQ ID NO: 52 | Polypeptide sequence of | ANR | from | *Lotus corniculatus* |
| SEQ ID NO: 53 | DNA coding sequence of | ANS | from | *Petunia × hybrida* |
| SEQ ID NO: 54 | Polypeptide sequence of | ANS | from | *Petunia × hybrida* |
| SEQ ID NO: 55 | DNA coding sequence of | GST | from | *Petunia × hybrida* |
| SEQ ID NO: 56 | Polypeptide sequence of | GST | from | *Petunia × hybrida* |
| SEQ ID NO: 57 | DNA coding sequence of | A3GT | from | *Dianthus caryophyllus* |
| SEQ ID NO: 58 | Polypeptide sequence of | A3GT | from | *Dianthus caryophyllus* |
| SEQ ID NO: 59 | DNA coding sequence of | A3GT | from | *Fragaria × ananassa* |
| SEQ ID NO: 60 | Polypeptide sequence of | A3GT | from | *Fragaria × ananassa* |
| SEQ ID NO: 61 | DNA coding sequence of | COMT | from | *Medicago sativa* |
| SEQ ID NO: 62 | Polypeptide sequence of | COMT | from | *Medicago sativa* |
| SEQ ID NO: 63 | DNA coding sequence of | CCOMT | from | *Arabidopsis thaliana* |
| SEQ ID NO: 64 | Polypeptide sequence of | CCOMT | from | *Arabidopsis thaliana* |
| SEQ ID NO: 65 | DNA coding sequence of | C3'H | from | *Arabidopsis thaliana* |
| SEQ ID NO: 66 | Polypeptide sequence of | C3'H | from | *Arabidopsis thaliana* |
| SEQ ID NO: 67 | DNA coding sequence of | HCT | from | *Arabidopsis thaliana* |
| SEQ ID NO: 68 | Polypeptide sequence of | HCT | from | *Arabidopsis thaliana* |
| SEQ ID NO: 69 | DNA coding sequence of | C3H | from | N/A |
| SEQ ID NO: 70 | Polypeptide sequence of | C3H | from | N/A |
| SEQ ID NO: 71 | DNA coding sequence of | STS | from | *Pinus densiflora* |
| SEQ ID NO: 72 | Polypeptide sequence of | STS | from | *Pinus densiflora* |
| SEQ ID NO: 73 | DNA coding sequence of | STS | from | *Vitis vinifera* |
| SEQ ID NO: 74 | Polypeptide sequence of | STS | from | *Vitis vinifera* |
| SEQ ID NO: 75 | DNA coding sequence of | ROMT | from | *Sorghum bicolor* |
| SEQ ID NO: 76 | Polypeptide sequence of | ROMT | from | *Sorghum bicolor* |
| SEQ ID NO: 77 | DNA coding sequence of | AAliAT | from | *Dahlia variabilis* |
| SEQ ID NO: 78 | Polypeptide sequence of | AAliAT | from | *Dahlia variabilis* |
| SEQ ID NO: 79 | DNA coding sequence of | AAroAT | from | *Arabidopsis thaliana* |
| SEQ ID NO: 80 | Polypeptide sequence of | AAroAT | from | *Arabidopsis thaliana* |
| SEQ ID NO: 81 | DNA coding sequence of | A5GT | from | *Vitis amurensis* |
| SEQ ID NO: 82 | Polypeptide sequence of | A5GT | from | *Vitis amurensis* |
| SEQ ID NO: 83 | DNA coding sequence of | A3GRhaT | from | *Nierembergia* sp. NB17 |
| SEQ ID NO: 84 | Polypeptide sequence of | A3GRhaT | from | *Nierembergia* sp. NB17 |
| SEQ ID NO: 85 | DNA coding sequence of | A3'5'GT | from | *Clitoria ternatea* |
| SEQ ID NO: 86 | Polypeptide sequence of | A3'5'GT | from | *Clitoria ternatea* |
| SEQ ID NO: 87 | DNA coding sequence of | A3'GT | from | *Gentiana triflora* |
| SEQ ID NO: 88 | Polypeptide sequence of | A3'GT | from | *Gentiana triflora* |
| SEQ ID NO: 89 | DNA coding sequence of | AAroAT | from | *Gentiana triflora* |
| SEQ ID NO: 90 | Polypeptide sequence of | AAroAT | from | *Gentiana triflora* |
| SEQ ID NO: 91 | DNA coding sequence of | DBR | from | *Saccharomyces cerevisiae* |
| SEQ ID NO: 92 | Polypeptide sequence of | DBR | from | *Saccharomyces cerevisiae* |
| SEQ ID NO: 93 | DNA coding sequence of | PGT | from | *Pyrus communis* |
| SEQ ID NO: 94 | Polypeptide sequence of | PGT | from | *Pyrus communis* |
| SEQ ID NO: 95 | DNA coding sequence of | CGT | from | *Oryza sativa* |
| SEQ ID NO: 96 | Polypeptide sequence of | CGT | from | *Oryza sativa* |
| SEQ ID NO: 97 | DNA coding sequence of | AOMT | from | *Vitis vinifera* |
| SEQ ID NO: 98 | Polypeptide sequence of | AOMT | from | *Vitis vinifera* |
| SEQ ID NO: 99 | DNA coding sequence of | RHM2 | from | *Arabidopsis thaliana* |
| SEQ ID NO: 100 | Polypeptide sequence of | RHM2 | from | *Arabidopsis thaliana* |
| SEQ ID NO: 101 | DNA promoter sequence | FBA1 | from | *Saccharomyces cerevisiae* |
| SEQ ID NO: 102 | DNA promoter sequence | GPD1 | from | *Saccharomyces cerevisiae* |
| SEQ ID NO: 103 | DNA promoter sequence | PGK1 | from | *Saccharomyces cerevisiae* |
| SEQ ID NO: 104 | DNA promoter sequence | PDC1 | from | *Saccharomyces cerevisiae* |
| SEQ ID NO: 105 | DNA promoter sequence | PYK1 | from | *Saccharomyces cerevisiae* |
| SEQ ID NO: 106 | DNA promoter sequence | TEF1 | from | *Saccharomyces cerevisiae* |
| SEQ ID NO: 107 | DNA promoter sequence | TEF2 | from | *Saccharomyces cerevisiae* |
| SEQ ID NO: 108 | DNA promoter sequence | TPI1 | from | *Saccharomyces cerevisiae* |

Further, the sequence listing include the following sequences

SEQ ID NO: 109 DNA ZA helper construct for integration into host genome locus XI-3
SEQ ID NO: 110 DNA ZA helper construct for integration into host genome locus XI-2
SEQ ID NO: 111 DNA AB helper construct, comprising the URA3 auxotrophic marker
SEQ ID NO: 112 DNA ZA helper construct for plasmids, comprising the LEU2 auxotrophic marker
SEQ ID NO: 113 DNA ZA helper construct for plasmids, comprising the HIS3 auxotrophic marker
SEQ ID NO: 114 DNA AB helper construct for plasmids, comprising ARS/CEN
SEQ ID NO: 115 DNA DZ linker fragment
SEQ ID NO: 116 DNA EZ linker fragment
SEQ ID NO: 117 DNA FZ linker fragment
SEQ ID NO: 118 DNA GZ linker fragment
SEQ ID NO: 119 DNA HZ linker fragment
SEQ ID NO: 120 DNA BC tags flanking promoter/terminator cassette Gpd1/Cyc1
SEQ ID NO: 121 DNA CD tags flanking promoter/terminator cassette Pgk1/Adh2
SEQ ID NO: 122 DNA DE tags flanking promoter/terminator cassette Tef1/Eno2
SEQ ID NO: 123 DNA EF tags flanking promoter/terminator cassette Pdc1/Fba1
SEQ ID NO: 124 DNA FG tags flanking promoter/terminator cassette Tef2/Pgi1
SEQ ID NO: 125 DNA GH tags flanking promoter/terminator cassette Pyk1/Adh1

LIST OF REFERENCES

Akita et al., Planta 2011, 234 (6): 1127-36
Arend et al., Biotech. & Bioeng, 2001, 78: 126-131
Ausubel et al., 1989, Current protocols in molecular biology, Greene Publishing Associates and Wiley Interscience, New York, USA
Ban et al., PNAS, 2018, 115(22): E5223-32.
Chenna et al., Nucleic Acids Res., 2003, 31 (13):3497-500.
De Vetten N. Et al., 1999, Proc. Natl. Acad. Sci. USA, 96:778-783
Eichenberger et al., FEMS Yeast Res. 2018, 1: 18(4)
Eichenberger et al., Met. Eng., 2017, 39: 80-89
Eichenberger, Michael; Biosynthesis of plant polyketides in yeast. Technische Universität, Darmstadt [Ph.D. Thesis], (2019) Darmstadt University, 3 Apr. 2019 10:27
Emmerstorfer A et al., 2015, Biotechnol. J., 10: 623-35
Fujino et al., Plant Biotechnol 2014, 31: 105-14.
Gietz et al., Nat. Protoc. 2007, 2(1): 35-7
Green & Sambrook, 2012, Molecular cloning: A laboratory Manual, Fourth Edition, Cold Spring Harbor Laboratory, New York, USA
Hugueney et al., Plant Physiol. 2009, 150 (4): 2057-70
Innis et al.; 1990, PCR Protocols: A Guide to Methods and Applications, Acad. Press, San Diego, CA, USA.
Jiang et al., J. Exp. Bot. 2015, 66, 22: 7165-79
Jiang H et al., Appl Environ Microbiol. 2005, 71(6): 2962-9
Koopman et al., Microb Cell Fact 2012, 11:155.
Lehka et al. FEMS Yeast Res. 2017, 17(1).
Leonard E et al., Appl Environ Microbiol. 2007, 73(12): 3877-86
Liu L et al., Engineering 2019, 5: 287-295
Mikkelsen et al., Met. Eng., 2012, 14: 104-11
Morita et al. The Plant Journal, 2014, 78: 294-304
Paquette et al., Phytochemistry, 2003, 62: 399-413
Roldan et al., Plant J. 2014, 80(4): 695-708
Sasaki et al., Molecules, 2014, 19: 18747-66
Shao et al., Nucl. Acids Res. 2009, 37(2):e16
Sikorski and Hieter 1989, Genetics 122: 19-27
Turnbull et al., Bioorg. Med. Chem. Lett., 2003, 13: 3853-57
Turnbull et al., Chem. Commun., 2000, 2473-74
Turnbull et al., J. Biol. Chem. 2004, 279: 1206-16
Welford et al., Chem. Commun., 2001, 1828-29.
Yan Y et al., Appl Environ Microbiol. 2005, 71(9):5610-3
Yin et al., PLOS One, 2011, 6(11): e27995
Zhao J; Trends Plant Sci.; 2015; vol. 20(9); pp 576-85.
Wolfenstetter S et al.; Plant Cell; 2012; vol. 24(1); pp 215-32.
Wang X et al.; Plant Cell; 2014; vol. 26(10); pp 4102-18.
Goodman C D et al.; Plant Cell; 2004; vol. 16(7); pp 1812-26.
Badone F C et al.; Planta; 2010; vol. 231(5); pp 1189-99.
Francisco R M et al.; Plant Cell; 2013; vol. 25(5); pp 1840-54.
Chowdhury S et al.; J. Biol. Chem.; 2014; vol. 289(23); pp 16129-47.
Liu G et al.; J. Biol. Chem.; 2001; vol. 276(12); pp 8648-56.
Banasiak J et al.; J. Exp. Bot.; 2013; vol. 64(4); pp 1005-15.
Mathews H et al; Plant Cell; 2003; vol. 15(8); pp 1689-703.
Debeaujon I et al.; Plant Cell; 2001; vol. 13(4); pp 853-71.
Marinova K. et al.; Plant Cell; 2007; vol. 19(6); pp 2023-38.
Zhao J et al.; Plant Cell; 2009; vol. 21(8); pp 2323-40. Erratum in: Plant Cell; 2010; vol. 22(3); p 991.
Gomez C et al.; Plant Physiol.; 2009; vol. 150(1); pp 402-15.
Zhao J et al.; Plant Cell; 2011; vol. 23(4); pp 1536-55.
Frank S et al.; Plant Biol. (Stuttg); 2011; vol. 13(1); pp 42-50.
Chai Y R et al.; Mol. Genet. Genomics; 2009; vol. 281(1); pp 109-23.
Gao J S et al.; Gene; 2016; vol. 576(2 Pt 2); pp 763-9.
Chen L et al.; PLOS One; 2015; vol. 10(3); e0118578; doi: 10.1371/journal.pone.0118578; eCollection 2015; PubMed PMID: 25781331; PubMed Central PMCID: PMC4363705.

EXAMPLES

The invention will be further described in the following examples, which do not limit the scope of the invention described in the claims.

Materials and Methods

Materials

Chemicals used in the examples herein e.g. for buffers and substrates are commercial products of at least reagent grade.

Strains and Genes

For demonstrating production of tetraketide derivatives a base *S. cerevisiae* strain, S288c, is engineered to integrate the genes of the pathways of the invention. The *S. cerevisiae* S288C, strain NCYC 3608, is obtained from the National Collection of Yeast Cultures (NCYC), Norwich, U.K.

All pathway genes/polynucleotides referred to and disclosed herein (SEQ ID NOS: 1-100) encoding the enzymes and proteins used, are manufactured synthetically by a commercial supplier using codons optimized for expression in yeast, *S. cerevisiae*, except for ScCPR1 (SEQ ID NO: 23), which is amplified by PCR from yeast genomic DNA. During synthesis, all genes are appended with the DNA sequence AAGCTTAAA at the 5'-end, including a Hind III restriction recognition site and a Kozak sequence, and with the DNA sequence CCGCGG at the 3'-end, including a Sac II recognition site.

Assays and Reagents

Tetraketide derivatives are analyzed using liquid-chromatography coupled to mass spectrometry (LC/MS). An HSS T3 column (Waters AG, Baden-Dättwil, Switzerland), 130 Å, 1.7 μm, 2.1 mm×100 mm is employed using the conditions indicated in table 1 below.

The following solution are used:

Solution A=0.1% aqueous solution of formic acid,

Solution B=0.1% solution of formic acid in acetonitrile.

TABLE 1

Chromatographic gradient for LCMS analysis of flavonoids and anthocyanins.

| Time (min) | Flow (mL/min) | % A | % B |
|---|---|---|---|
| Initial | 0.400 | 95.0 | 5.0 |
| 3.00 | 0.400 | 80.0 | 20.0 |
| 4.30 | 0.400 | 80.0 | 20.0 |
| 9.00 | 0.400 | 55.0 | 45.0 |
| 11.00 | 0.400 | 0.0 | 100.0 |
| 13.00 | 0.400 | 0.0 | 100.0 |
| 13.01 | 0.400 | 95.0 | 5.0 |
| 15.00 | 0.400 | 95.0 | 5.0 |

For mass spectrum (MS) analysis, full scan spectrum data are recorded using a Xevo® G2-XS Mass spectrometer (Waters Cooperation, Milford, US) with the parameters indicated in table 2, below.

TABLE 2

Mass spectrometry parameters.

| Source Parameter | Value |
|---|---|
| Ion Source | Electrospray Positive Mode (ESI−) |
| Capillary Voltage | 2.0 kV |
| Sampling Cone | 40 V |
| Source Offset | 80 V |
| Source Temperature | 150° C. |
| Desolvation Temperature | 500° C. |
| Cone gas flow | 100 L/h |
| Desolvation gas flow | 1000 L/h |
| Mass Range | From 50 to 1200 m/z |
| Lock Mass | Leucin Enkephalin (ESI+) |

For each compound, an extracted ion chromatogram within a mass window of 0.01 Da is calculated. Peak areas and compound quantities are calculated according to the retention time and linear calibration curve of the respective standard compounds (obtained from Sigma-Aldrich, Switzerland and/or Extrasynthese, Genay, France) where ever available.

Example 1—Culturing Recombinant Host Cells to Produce the Tetraketide Derivatives of the Invention For demonstrating successful tetraketide derivative production in engineered yeast via heterologous full-length biosynthetic pathways, genes encoding highly efficient recombinant enzymes were integrated and expressed in the base yeast strain under near optimal conditions to achieve sufficient flow through the pathway to produce useful amounts of the tetraketide derivative.

For culturing the engineered yeast strain, cultures of the strain are grown in 96 well, deep well plates (DWP) at 30° C., using 5 cm shaking diameter, and 300 rpm. Pre-cultures are grown for 24 hours from single colonies in 300 μL SC dropout medium (Formedium, Hunstanton, UK), as required for auxotrophic selection. The SC dropout medium contained:

1.47 g/L Synthetic Complete (Kaiser) Drop Out: Leu, His, Ura (Formedium, Hunstanton, UK), 6.7 g/L Yeast Nitrogen Base without Amino Acids, 20 g/L D-(+)-Glucose, 76 mg/L histidine, and/or 380 mg/L leucine, and/or 76 mg/L uracil depending on the auxotrophies of the strains.

pH of the medium is adjusted to 5.8 with hydrochloric acid.

Main cultures are inoculated in 300 μl of the same medium to a 1:100 dilution of the pre-culture and cultured for 72 hours at 30° C., in 96 well, 1.1 mL deep well plates (DWP) as described by Eichenberger et al. (FEMS Yeast Res. 2018, 1: 18(4)). After 72 hours all cultures had reached essentially the same final optical density (OD) at 600 nm. It is contemplated that all tetraketide derivatives of interest are located both intra- and extracellularly, and product titers are calculated based on extraction of total culture volumes.

For extraction and stabilization of tetraketide derivatives, 150 μL culture broth is mixed with 150 μL acidified methanol (1% hydrochloric acid) and incubated for 30 min in a 96 well DWP at 30° C., 5 cm shaking diameter, and 300 rpm and subsequently clarified by centrifugation at 4000 g for 5 min. The clarified lysates are analyzed by LC-MS.

Example 2—Engineering of Base Yeast Strain to Produce Tetraketide Derivative Naringenin The naringenin structural pathway is assembled by in vivo homologous recombination and simultaneous integration (Eichenberger et al., FEMS Yeast Res. 2018, 1: 18(4)) into the base *S. cerevisiae* strain to create a naringenin producing strain, marked BG1.

The genes listed in table 3) below are used for constructing the naringenin pathway. For generating the naringenin metabolic precursor, p-coumaric acid (see the pathway of FIG. 1), as alternative to or in addition to PAL and C4H a tyrosine ammonia lyase (TAL), such as the one specified by SEQ ID NO: 3 and 4 could have been used. The genes are cloned into expression cassettes, comprising native promoters and terminators, which by Asc I digestion are released as individual DNA fragments (Eichenberger et al., Met. Eng., 2017, 39: 80-89). The expression cassettes, into which the genes are cloned, are constructed in such a way that the Gpd1/Cyc1 promoter/terminator pair is flanked by HRT tags B and C (SEQ ID NO: 120), the Pgk1/Adh2 pair by C and D (SEQ ID NO: 121), the Tef1/Eno2 pair by D and E (SEQ ID NO: 122), the Pdc1/Fba1 pair by E and F (SEQ ID NO: 123), the Tef2/Pgi1 pair by F and G (SEQ ID NO: 124), and the Pyk1/Adh1 pair by G and H (SEQ ID NO: 125), respectively. All cassettes comprise an approx. 650 bps spacer fragment, that is excised and replaced, during cloning, by the genes intended for expression. Hence, after excision of the cassettes, by Asc I digestion, these fragments are autonomously assembled by homologous recombination after introduction into yeast. Table 3) also lists some additional DNA fragments, which are used to assemble the integration construct. At both ends each DNA fragment comprised so-called Homologous Recombination Tags (HRTs) that allow in vivo assembly and integration into the genome in a single step process (see below or Eichenberger et al. FEMS Yeast Res. 2018 Jun. 1; 18(4))

TABLE 3

| Naringenin pathway genes used in Example No. 2. | | | |
|---|---|---|---|
| Cassette | Content | SEQ ID NO | Species |
| ZA | Integration tag for XI-3 | 109 | N/A |
| AB | URA3 and LoxP | 111 | N/A |
| BC | AtPAL2 | 1 | *Arabidopsis thaliana* |
| CD | AmC4H | 5 | *Ammi majus* |
| DE | At4CL2 | 7 | *Arabidopsis thaliana* |
| EF | HaCHS | 9 | *Hypericum androsaemum* |
| FG | MsCHI | 11 | *Medicago sativa* |
| GH | ScCPR1 | 23 | *Saccharomyces cerevisiae* |
| HZ | Linker | 119 | N/A |

All genes are cloned into Hind III and Sac II of pUC18 based vectors containing yeast expression cassettes, said cassettes comprising the native yeast promoter and terminator sequences, separated by a spacer and multi-cloning sequence, comprising the Hind III and Sac II sites. Promoters (SEQ ID Nos: 101-108) and terminators, are previously described by Shao et al. (Nucl. Acids Res. 2009, 37(2):e16). Each expression cassette is flanked at both ends by 60 bp Homologous Recombination Tag (HRT) sequences, which are, in turn, flanked by Asc I restriction enzyme recognition sites (FIGS. 6 and 7). The HRTs, named A, B, C, D, E, F, G, H, and Z, are designed such that the 3'-end HRT of the first expression cassette fragment is identical to the 5'-end HRT of the second expression cassette fragment, and so forth. Three helper fragments are used to integrate multiple expression cassettes into the yeast genome by homologous recombination. One helper fragment (ZA, SEQ ID NO: 109), included the two recombination tags for integration into the site XI-3, described by Mikkelsen et al. (Met. Eng., 2012, 14:104-11), each tag having homology to sequences in the yeast genome. The integration tags are both flanked by HRTs and separated by an Asc I site. The second helper fragment (AB, SEQ ID NO: 111) included a yeast auxotrophic marker gene (URA3) flanked by LoxP sites. This fragment also had flanking HRTs. The third helper fragment (HZ, SEQ ID NO: 119) is designed only with HRTs, separated by a short 650 bp spacer sequence. All helper fragments had been cloned in the Asc I site of a pUC18 based plasmid backbone for amplification in *E. coli*.. FIGS. 6 and 7 depicts how the DNA assembler technology, based on Shao et al. (Nucl. Acids Res. 2009, 37(2):e16) is used to assemble biosynthetic pathways by homologous recombination, either for stable maintenance on a plasmid (FIG. 7) or after integration into the host genome (FIG. 6).

To integrate the naringenin pathway into the base yeast strain, plasmid DNA from the three helper plasmids (SEQ ID NOS: 109, 111, and 119) is mixed with plasmid DNA from each of the plasmids containing the expression cassettes. The mix of plasmid DNA is digested with Asc I. This treatment released all fragments from the plasmid backbone and created fragments with HRTs at the ends, these being sequentially overlapping with the HRT of the next fragment.

The base yeast strain is transformed with the digested mix, and the naringenin pathway is self-assembled and integrated by in vivo homologous recombination as described by Shao et al. 2009. Following integration the URA3 marker is excised by standard procedures, using the Cre recombinase.

Following integration, the genes are transcribed and translated into the enzymes of the naringenin biosynthetic pathway, plus the additional polypeptide ScCPR1, known to improve the activity of C4H. Successful naringenin production is confirmed by LC/MS.

Example 3—Boosting Naringenin Production by Chalcone Isomerase-Like Protein (CHIL)

To further improve the production of naringenin, the gene encoding a *P. hybrida* chalcone isomerase-like protein (PhCHIL; SEQ ID NO. 13) is introduced into the naringenin producing strain, BG1 of example 2, on a single copy plasmid. This plasmid is based on the pRS413 (Sikorski R. S. and Hieter P. 1989, Genetics 122:19-27), and comprised the expression cassette of the GPD1 promoter (SEQ ID NO: 102) and the ADH1 terminator. A control strain is also created, comprising the pRS413 plasmid with an empty expression cassette, introduced into the naringenin producing BG1 strain. This control strain is cultured alongside the strain comprising the PhCHIL gene, and the production of naringenin is analysed. Compared to the control strain, the strain comprising the PhCHIL gene exhibited a more than 1.5 fold increase in naringenin production.

Example 4—Engineering of Base Yeast Strain to Produce Naringenin, Eriodictyol, and Pentahydroxyflavanone Using CHIL Strains producing naringenin, eriodictyol, and 5,7,3',4',5'-pentahydroxyflavanone are created by assembly of HRT plasmids into the naringenin producing strain BG1 of example 2 according to Table 4 below. Five different CHIL enzymes are tested for their ability to increase flavanone production. Hence, the BC cassette is either empty, or carries one of the five CHIL enzymes: 1) *Petunia* x *hybrida* PhCHIL (SEQ ID NO: 13), 2) *Arabidopsis thaliana* AtCHIL (SEQ ID NO: 15), 3) *Ipomoea nil* InCHIL (SEQ ID NO: 17), 4) *Antirrhinum majus* AmCHIL (SEQ ID NO: 19), or 5) *Glycine max* GmCHIL (SEQ ID NO: 21). The CD cassette carried the *Arabidopsis thaliana* AtCPR (SEQ ID NO: 25), and the DE cassette is either empty, or comprised a flavonoid-3'-hydroxylase (PhF3'H; SEQ ID NO: 27) or a flavonoid-3'5'-hydroxylase (PhF3'5'H; SEQ ID NO: 29), both from *Petunia* X *hybrida*. FIG. 7 depicts pathway assembly on HRT plasmids.

The backbone of the HRT vectors is formed by the DNA fragments ZA (SEQ ID NO: 112), AB (SEQ ID NO: 114), and EZ (SEQ ID NO: 116), which contained a yeast selection marker gene (LEU2), an autonomously replicating sequence (ARSH4) and a yeast centromere (CEN6), and a 650 bp stuffer sequence, respectively (see Table 4 below). The ZA fragment further comprised a bacterial origin of replication (pSC101), and the AB fragment further comprised the chloramphenicol resistance marker gene (CmR), but none of these two functionalities are used in the current embodiment. Expression of each gene is driven by a yeast native promoter as described in example 2 above. The DNA helper fragments, as well as the gene expression cassettes, are flanked by 60 bp homologous recombination tags (HRT), where each terminal tag is identical to the first tag of the following cassette. Each HRT cassette included terminal Asc I restriction sites to allow excision from the donor plasmid backbone.

TABLE 4

Pathway gene cassettes for production of naringenin, eriodictyol, and pentahydroxy-flavanone in BG1 strain

| Cassette | Content | SEQ ID NO | Species |
|---|---|---|---|
| ZA | LEU2, pSC101 | 112 | N/A |
| AB | ARSH4/CEN6, CmR | 114 | N/A |
| BC | Empty or CHIL | 13, 15, 17, 19, or 21 | *Petunia* × *hybrida*, *Arabidopsis thaliana*, *Ipomoea nil*, *Antirrhinum majus*, or *Glycine max* |
| CD | AtCPR | 25 | *Arabidopsis thaliana* |
| DE | Empty, PhF3'H, or PhF3'5'H | 27 or 29 | *Petunia* × *hybrida* |
| EZ | Linker | 116 | N/A |

The CHIL enzymes in the BC cassette are from various plant species as listed in the Table 4).

Plasmids containing the described helper fragments and gene expression cassettes of Table 4) are combined into 18 different reaction mixtures and digested with Asc I in a 20 μl reaction volume. The digest is performed for 2 h at 37° C. The entire volume of each reaction is used to transform yeast strain BG1, creating 18 new strains.

After transformation, using the LiAC/SS carrier DNA/PEG method (see e.g., Gietz et al., Nat Protoc. 2007; 2(1): 35-7), cells are grown at 30° C. for 72 h. Next, four clones from each of the 18 resulting transformations are re-streaked onto fresh plates and grown for 48 h at 30° C.

All clones are then grown in 2 mL liquid cultures for 72 hours. Subsequently, 1 volume of acidified methanol is added, and after ½ hour of shaking at 30° C., cell debris are spun down by centrifugation and the cleared supernatants are collected for analysis by LC/MS. Naringenin, eriodictyol, and pentahydroxyflavanone production is markedly higher, approx. 30-70%, in strains co-expressing a CHIL protein, compared to control strains with no CHIL. The PhCHIL is chosen for further experiments.

Example 5—Engineering of Base Yeast Strain to Produce Apigenin, Luteolin, and Genistein Strains producing flavones and isoflavones are created by assembly of HRT plasmids into strain BG1 of example 2 according to table 5 below. The BC cassette is either empty, or carries the *Petunia* x *hybrida* PhCHIL (SEQ ID NO: 13), the CD cassette carried the AtCPR1 (SEQ ID NO: 25), the DE cassette is either empty (for apigenin), or carried the PhF3'H (SEQ ID NO: 27) for luteolin, or the 2-hydroxy-isoflavanone dehydratase (GmHIFD; SEQ ID NO: 37) from *Glycine max* for genistein, and the EF cassette carried the *Antirrhinum majus* flavone synthase (AmFNSII; SEQ ID NO: 33) or the *Glycine max* isoflavone synthase (GmIFS; SEQ ID NO: 35), for flavone and isoflavone synthesis, respectively. Hence, one set of fragments included the combination of FNS II with an empty cassette, or the combination of FNS II together with F3'H, in order to produce apigenin and luteolin, respectively. Another set included the combination of IFS and HIFD, for production of genistein.

The backbone of the HRT vectors is formed by the DNA fragments ZA (SEQ ID NO: 112), AB (SEQ ID NO: 114), and FZ (SEQ ID NO: 117), which contained a yeast selection marker gene (LEU2), an autonomously replicating sequence (ARSH4) and a yeast centromere (CEN6), and a 650 bp stuffer sequence, respectively (see table 5 below). Expression of each gene is driven by a yeast native promoter as described in example 2 above. The DNA helper fragments, as well as the gene expression cassettes, are flanked by 60 bp homologous recombination tags (HRT), where each terminal tag is identical to the first tag of the following cassette. Each HRT cassette included terminal Asc I restriction sites to allow excision from the donor plasmid backbone.

TABLE 5

Pathway gene cassettes for production of apigenin, luteolin, and genistein in BG1 strain

| Cassette | Content | SEQ ID NO | Species |
|---|---|---|---|
| ZA | LEU2, pSC101 | 112 | N/A |
| AB | ARSH4/CEN6, CmR | 114 | N/A |
| BC | Empty or PhCHIL | 13 | *Petunia* × *hybrida* |
| CD | AtCPR | 25 | *Arabidopsis thaliana* |
| DE | Empty, PhF3'H or GmHIFD | 27 or 37 | *Petunia* × *hybrida* *Glycine max* |
| EF | AmFNSII or GmIFS | 33 or 35 | *Antirrhinum majus* *Glycine max* |
| FZ | Linker | 117 | N/A |

DNA fragments listed in table 5. are prepared as described above and used to transform strain BG1. The resulting strains are grown and analyzed, as described above in example 4 for production of flavones and isoflavones.

Production of apigenin and luteolin is markedly higher, more than 50%, in strains expressing the PhCHIL, compared to control strains with no PhCHIL. The production of genistein is approx. 60% higher in the strain expressing PhCHIL.

Example 6—Engineering of Base Yeast Strain to Produce Dihydroflavonols (Flavanonols)

The three dihydroflavonols (DHF), dihydrokaempferol (DHK), dihydroquercetin (DHQ), and dihydromyricetin (DHM) are intermediates for flavonols, but also for the extended flavonoid pathway towards catechins and anthocyanins. In order to demonstrate the effects of chalcone isomerase-like protein on these extended pathways, a set of strains are first prepared, comprising the three DHF pathways, with or without co-expression of PhCHIL. These six strains are prepared by transforming the strain BG1 of example 2 with HRT plasmids comprising the genes listed in table 6. Hence, the BC cassette is either empty, or carried the *Petunia* x *hybrida* PhCHIL (SEQ ID NO: 13), the CD cassette carried the AtCPR1 (SEQ ID NO: 25), the DE cassette is either empty (for DHK), or carried the PhF3'H (SEQ ID NO: 27) for DHQ, or the PhF3'5'H (SEQ ID NO: 29) for DHM, and the EF cassette carried the *Malus domestica* flavonoid-3-O-hydroxylase (F3H; SEQ ID NO: 39).

The backbone of the HRT vectors is formed by the DNA fragments ZA (SEQ ID NO: 112), AB (SEQ ID NO: 114), and FZ (SEQ ID NO: 117), which contained a yeast selection marker gene (LEU2), an autonomously replicating sequence (ARSH4) and a yeast centromere (CEN6), and a 650 bp stuffer sequence, respectively (see table 6 below). Expression of each gene is driven by a yeast native promoter as described in example 2, above. The DNA helper fragments, as well as the gene expression cassettes, are flanked by 60 bp homologous recombination tags (HRT), where each terminal tag is identical to the first tag of the following cassette. Each HRT cassette included terminal Asc I restriction sites to allow excision from the donor plasmid backbone.

TABLE 6

| Pathway gene cassettes for production of dihydroflavonols in BG1 strain | | | |
|---|---|---|---|
| Cassette | Content | SEQ ID NO | Species |
| ZA | LEU2, pSC101 | 112 | N/A |
| AB | ARSH4/CEN6, CmR | 114 | N/A |
| BC | PhCHIL or empty | 13 | *Petunia × hybrida* |
| CD | AtCPR | 25 | *Arabidopsis thaliana* |
| DE | Empty, PhF3'H or PhF3'5'H | 27 or 29 | *Petunia × hybrida* |
| EF | MdF3H | 39 | *Malus domestica* |
| FZ | Linker | 117 | N/A |

DNA fragments listed in table 6 are prepared as described above and used to transform strain BG1. The resulting strains are grown and analyzed, as described above in example 4, confirming production of the expected DHFs. The strains producing dihydrokaempferol (DHK) are named BG5_DHK and BG5_DHKc, including or missing the PhCHIL, respectively. Similarly, the strains producing dihydroquercetin (DHQ) are named BG5_DHQ and BG5_DHQc, including or missing the PhCHIL, respectively, and the strains producing dihydromyricetin (DHM) are named BG5_DHM and BG5_DHMc, including or missing the PhCHIL, respectively. Production of dihydroflavonols is markedly higher, more than 50%, in strains expressing the PhCHIL compared to control strains with no PhCHIL.

Example 7—Engineering of Base Yeast Strain to Produce Flavonols

In order to demonstrate the effect of co-expression of CHIL on production of flavonols, all six BG5 strains of example 6 are transformed with an additional plasmid, based on pRS413 (see example 2), comprising the Citrus unshiu flavonol synthase (CuFLS; SEQ ID NO: 41). The strains are cultured and analysed as described above, and production of kaempferol, quercetin, and myricetin, respectively, is confirmed. Production of flavonols is markedly higher, more than 50%, in strains expressing the PhCHIL compared to control strains with no PhCHIL.

Example 8—Engineering of Base Yeast Strain to Produce Afzelechin and (+)-Catechin In order to study the effect of CHIL expression on production of catechins, four BG5 strains, the BG5_DHK, BG5_DHKc, BG5_DHQ, and BG5DHQc (see example 6) are transformed with an additional HRT plasmid, comprising the dihydroflavonol reductase (DFR) and leucoanthocyanidin reductase (LAR). Hence, the second HRT plasmid comprised the *Anthurium andraeanum* DFR (AaDFR; SEQ ID NO: 43) in the BC cassette, and the *Vitis vinifera* LAR (VvLAR; SEQ ID NO: 49) in the CD cassette, as listed in Table No. 7 below. The backbone of the second HRT vectors is formed by the DNA fragments ZA (SEQ ID NO: 113), AB (SEQ ID NO: 114), and DZ (SEQ ID NO: 115), which contained a yeast selection marker gene (HIS3), an autonomously replicating sequence (ARSH4) and a yeast centromere (CEN6), and a 650 bp stuffer sequence, respectively (see table 7 below).

TABLE 7

| Pathway gene cassettes for production of afzelechin and catechin | | | |
|---|---|---|---|
| Cassette | Content | SEQ ID NO | Species |
| ZA | HIS3, pSC101 | 113 | N/A |
| AB | ARSH4/CEN6, CmR | 114 | N/A |
| BC | AaDFR | 43 | *Anthurium andraeanum* |
| CD | VvLAR | 49 | *Vitis vinifera* |
| DZ | Linker | 115 | N/A |

The strains are cultured and analyzed as described above and production of afzelechin and (+)-catechin, respectively, is confirmed. Production of catechins is markedly higher, more than 50%, in strains expressing the PhCHIL compared to control strains with no PhCHIL.

Example 9—Engineering of Yeast Strain to Produce Epi-Afzelechin and (−)-Epicatechin In order to study the effect of CHIL expression on production of epicatechins, four BG5 strains, the BG5_DHK, BG5_DHKc, BG5_DHQ, and BG5DHQc (see example 6) are transformed with a second HRT plasmid, comprising the dihydroflavonol reductase (DFR), the anthocyanidin synthase (ANS), and the anthocyanidin reductase (ANR). In addition, and in order to also study the effect of co-expressing a glutathione-S-reductase (GST) together with the ANS enzyme, the GST gene is introduced, together with DFR, ANS, and ANR, into the same four BG5 strains. The four strains BG5_DHK, BG5_DHKc, BG5_DHQ, and BG5DHQc are, thus, transformed with HRT plasmids, comprising the DFR, ANS, ANR, and either an empty cassette, or a cassette comprising the GST, resulting in a total of eight strains.

Specifically, the second HRT plasmid in those strains comprised the *Anthurium andraeanum* DFR (AaDFR; SEQ ID NO: 43) in the BC cassette, the *Petunia* x *hybrida* GST (PhGST; SEQ ID NO: 55) or an empty cassette in the CD cassette, the *Petunia* x *hybrida* ANS (PhANS; SEQ ID NO: 53) in the DE cassette, and the *Lotus corniculatus* ANR (LcANR; SEQ ID NO: 51) in the EF cassette, as listed in table 8, below. The backbone of the second HRT vectors is formed by the DNA fragments ZA (SEQ ID NO: 113), AB (SEQ ID NO: 114), and FZ (SEQ ID NO: 117), which contained a yeast selection marker gene (HIS3), an autonomously replicating sequence (ARSH4) and a yeast centromere (CEN6), and a 650 bp stuffer sequence, respectively (see table 8, below).

TABLE 8

| Pathway gene cassettes for production of epi-afzelechin and (—)-epicatechin | | | |
|---|---|---|---|
| Cassette | Content | SEQ ID NO | Species |
| ZA | HIS3, pSC101 | 113 | N/A |
| AB | ARSH4/CEN6, CmR | 114 | N/A |
| BC | AaDFR | 43 | *Anthurium andraeanum* |
| CD | Empty or PhGST | 55 | *Petunia × hybrida* |
| DE | PhANS | 53 | *Petunia × hybrida* |
| EF | LcANR | 51 | *Lotus corniculatus* |
| FZ | Linker | 117 | N/A |

The strains are cultured and analyzed as described above and production of epi-afzelechin and (−)-epicatechin, respectively, is confirmed. Production of both catechins is markedly higher, more than 50%, in strains expressing the PhCHIL compared to control strains with no PhCHIL. Remarkably, the production of catechins increased more than 20-fold after co-expression of PhGST. Moreover, the strains co-expressing the GST exhibited a significant reduction in the levels of flavonols. This is remarkable since, in the absence of GST, the ANS enzyme is reported to produce flavonols as an undesired side-product (see Eichenberger et al. 2018 above).

Example 10—Engineering of Yeast Strain to Produce Pelargonidin-3-O-Glucoside, Cyanidin-3-O-Glucoside, and Delphinidin-3-O-Glucoside In order to study the effect of CHIL expression on production of anthocyanins, all six BG5 strains (see example 6) are transformed with an additional HRT plasmid, comprising the dihydroflavonol reductase (DFR), the anthocyanidin synthase (ANS), and the anthocyanidin-3-O-glycosyl transferase (A3GT). In addition, and in order to also study the effect of co-expressing a glutathione-S-reductase (GST) together with the ANS enzyme, the GST is introduced, together with DFR, ANS, and A3GT, into the same six BG5 strains. The six BG5 strains are, thus, transformed with HRT plasmids, comprising the DFR, ANS, A3GT, and either an empty cassette, or a cassette comprising the GST, resulting in a total of twelve strains. Because DFRs and A3GTs exhibit specific substrate preferences, depending on the number of B-ring hydroxylations, various enzymes are used, reflecting those preferences (see Eichenberger et al. 2018 above).

Specifically, the second HRT plasmid in strains for production of pelargonidin-3-O-glucoside (P3G) comprised the *Anthurium andraeanum* DFR (AaDFR; SEQ ID NO: 43) in the BC cassette, the *Petunia* x *hybrida* GST (PhGST; SEQ ID NO: 55) or an empty cassette in the CD cassette, the *Petunia* x *hybrida* ANS (PhANS; SEQ ID NO: 53) in the DE cassette, and the *Dianthus* caryophyllus A3GT (DcA3GT; SEQ ID NO: 57) in the EF cassette, as listed in table 9, below.

Similarly, the second HRT plasmid in strains for cyanidin-3-O-glucoside (C3G) production comprised the *Populus trichocarpa* DFR (PtDFR; SEQ ID NO: 45) in the BC cassette, the *Petunia* x *hybrida* GST (PhGST; SEQ ID NO: 55) or an empty cassette in the CD cassette, the *Petunia* x *hybrida* ANS (PhANS; SEQ ID NO: 53) in the DE cassette, and the *Fragaria* x *ananassa* A3GT (FaA3GT; SEQ ID NO: 59) in the EF cassette, as listed in table 9, below.

Finally, the second HRT plasmid in strains for delphinidin-3-O-glucoside (D3G) production comprised the *Iris* x *hollandica* DFR (IhDFR; SEQ ID NO: 47) in the BC cassette, the *Petunia* x *hybrida* GST (PhGST; SEQ ID NO: 55) or an empty cassette in the CD cassette, the *Petunia* x *hybrida* ANS (PhANS; SEQ ID NO: 53) in the DE cassette, and the *Fragaria* x *ananassa* A3GT (FaA3GT; SEQ ID NO: 59) in the EF cassette, as listed in table 9, below.

The backbone of the second HRT vectors is formed by the DNA fragments ZA (SEQ ID NO: 113), AB (SEQ ID NO: 114), and FZ (SEQ ID NO: 117), which contained a yeast selection marker gene (HIS3), an autonomously replicating sequence (ARSH4) and a yeast centromere (CEN6), and a 650 bp stuffer sequence, respectively (see table 9, below).

TABLE 9

Pathway gene cassettes for production of P3G, C3G, and D3G

| Cassette | Content | SEQ ID NO | Species |
|---|---|---|---|
| ZA | HIS3, pSC101 | 113 | N/A |
| AB | ARSH4/CEN6, CmR | 114 | N/A |
| BC | AaDFR (P3G), PtDFR (C3G), or lhDFR (D3G) | 43, 45, or 47 | *Anthurium andraeanum*, *Populus trichocarpa*, or *Iris × hollandica* |
| CD | Empty or PhGST | 55 | *Petunia × hybrida* |
| DE | PhANS | 53 | *Petunia × hybrida* |
| EF | DcA3GT (P3G) or FaA3GT (C3G and D3G) | 57 or 59 | *Dianthus caryophyllus* *Fragaria × ananassa* |
| FZ | Linker | 117 | N/A |

The strains are cultured and analysed as described above and production of P3G, C3G, and D3G, respectively, is confirmed. Production of anthocyanins is markedly higher, more than 50%, in strains expressing the PhCHIL compared to control strains with no PhCHIL. Remarkably, the production of anthocyanin increased more than 20-fold after co-expression of PhGST. Moreover, the strains co-expressing the PhGST exhibited a significant reduction in the levels of flavonols, including their glucosides. This is remarkable since, in the absence of GST, the ANS enzyme is reported to produce flavonols as an undesired side-product (see Eichenberger et al. 2018 above).

Example 11—Engineering of Yeast Strain to Produce Anthocyanidins

The anthocyanidins pelargonidin (Pg), cyanidin (Cy), and delphinidin (Dp) are unstable intermediates in the biosynthetic pathways to anthocyanins and epicatechins. However, in order to extend the biosynthetic pathways beyond the 3 basic anthocyanins (see example 10) the pathway from naringenin to anthocyanidin is first integrated into strain BG1 of example 2.

Integration is done into the site XI-2, described by Mikkelsen et al. (Metabolic Engineering 2012, 14:104-11), as described in example 2 for integration into XI-3. The plasmids used are listed in table 10. Hence, for pelargonidin (Pg) production the second integration comprised the genes MdF3H (SEQ ID NO: 39), AtCPR1 (SEQ ID NO: 25), AaDFR (SEQ ID NO: 43), and PhANS (SEQ ID NO: 53). For cyanidin (Cy) production the second integration comprised the genes PhF3'H (SEQ ID NO: 27), AtCPR1 (SEQ ID NO: 25), MdF3H (SEQ ID NO: 39), PtDFR (SEQ ID NO: 45), and PhANS (SEQ ID NO: 53). For delphinidin (Dp) production the second integration comprised the genes PhF3'5'H (SEQ ID NO: 29), AtCPR1 (SEQ ID NO: 25), MdF3H (SEQ ID NO: 39), IhDFR (SEQ ID NO: 47), and PhANS (SEQ ID NO: 53) as listed in table 10, below.

As described in Example 2, integration is done using three helper fragments, the ZA (SEQ ID NO: 110), which included the two recombination tags for integration into the site XI-2, (described by Mikkelsen et al. Met. Eng., 2012, 14:104-11), the AB (SEQ ID NO: 111) which included a yeast auxotrophic marker gene (URA3) flanked by LoxP sites, and the linker fragment GZ (SEQ ID NO: 118).

TABLE 10

Plasmids used for integrating, into yeast, the pathways to pelagonidin (Pg), cyanidin (Cy), and delphinidin (Dp).

| Cassette | Content | SEQ ID NO | Species |
|---|---|---|---|
| ZA | Integration tag for XI-2 | 110 | N/A |
| AB | URA3 and LoxP | 111 | N/A |
| BC | PhANS | 53 | *Petunia × hybrida* |
| CD | Empty (Pg) | N/A | N/A |
| | PhF3'H (Cy) | 27 | *Petunia × hybrida* |
| | PhF3'5'H (Dp) | 29 | *Petunia × hybrida* |
| DE | MdF3H | 39 | *Malus domestica* |
| EF | AaDFR (Pg) | 43 | *Anthurium andraeanum* |
| | PtDFR (Cy) | 45 | *Populus trichocarpa* |
| | IhDFR (Dp) | 47 | *Iris × hollandica* |
| FG | AtCPR1 | 25 | *Arabidopsis thaliana* |
| GZ | Linker | 118 | N/A |

Following transformation, single colonies are selected and cultured. Crude DNA preparations are prepared and used as template for PCR, using standard techniques, to confirm correct integrations into the XI-2 site. For each anthocyanidin a clone with the expected PCR profile is chosen, and the strains are named BG6_Pg (pelargonidin), BG6_Cy (cyanidin), and BG6_Dp (delphinidin), respectively. The URA3 marker gene is subsequently excised, by standard procedures, using the Cre recombinase.

Example 12—Engineering of Yeast Strain to Produce Modified Anthocyanins

The three strains constructed in example 11, comprising the pathways to pelargonidin, cyanidin, and delphinidin, respectively, are used to test various secondary modifications of the central scaffold of anthocyanins. As described in example 11, each of these strains had the full-length pathway to the respective anthocyanidin integrated into the yeast genome via two integrations. Each strain is then provided with two HRT plasmids, assembled in vivo as described above, comprising various modifying genes.

A first HRT plasmid is assembled with PhCHIL (SEQ ID NO: 13), PhGST (SEQ ID NO: 55), and either DcA3GT (SEQ ID NO: 57) for pelargonidin-3-O-glucoside (P3G), or FaA3GT (SEQ ID NO: 59) for cyanidin-3-O-glucoside (C3G) and delphinidin-3-O-glucoside (D3G) production (table 11). Helper fragments ZA (SEQ ID NO: 112), AB (SEQ ID NO: 114), and FZ (SEQ ID NO: 117) are used, as described above, for the in vivo assembly of plasmids.

TABLE 11

Cassettes used to assemble HRT plasmid for P3G, C3G, and D3G production

| Cassette | Content | SEQ ID NO | Species |
|---|---|---|---|
| ZA | LEU2, pSC101 | 112 | N/A |
| AB | ARSH4/CEN6, CmR | 114 | N/A |
| BC | PhCHIL | 13 | *Petunia × hybrida* |
| CD | PhGST | 55 | *Petunia × hybrida* |
| DE | Empty | N/A | N/A |
| EF | DcA3GT (P3G) | 57 | *Dianthus caryophyllus* |
| | FaA3GT(C3G and D3G) | 59 | *Fragaria × ananassa* |
| FZ | Linker | 117 | N/A |

Following transformation, single colonies are selected, grown, and analyzed as described above. Production of P3G, C3G, and D3G, respectively, is verified.

A second HRT plasmid comprised the anthocyanin aliphatic acyl transferase (AAliAT) from *Dahlia variabilis*, i.e. the anthocyanidin-3-O-glucoside-6"-malonyl-transferase gene (Dv3MAT, SEQ ID NO. 77) in combination with the *Fragaria* x *ananassa* FaA3GT (SEQ ID NO: 59) (table 12) to produce anthocyanidin-3-O-(6"-malonyl)-glucosides. The inclusion of an additional A3GT is assumed to improve the 3-O-glycosylation.

Helper fragments ZA (SEQ ID NO: 113), AB (SEQ ID NO: 114), and EZ (SEQ ID NO: 116) are used, as described above, for the in vivo assembly of plasmids.

TABLE NO. 12

Cassettes used to assemble HRT plasmid for aliphatic acylation of P3G, C3G, and D3G.

| Cassette | Content | SEQ ID NO | Species |
|---|---|---|---|
| ZA | HIS3, pSC101 | 113 | N/A |
| AB | ARSH4/CEN6, CmR | 114 | N/A |
| BC | Dv3MAT | 77 | *Dahlia variabilis* |
| CD | FaA3GT | 59 | *Fragaria × ananassa* |
| DE | Empty | N/A | N/A |
| EZ | Linker | 116 | N/A |

Strains BG6_Pg (pelargonidin), BG6_Cy (cyanidin), and BG6_Dp (delphinidin), described in example 11, are thus transformed with a first and a second HRT plasmid, according to tables 11 and 12, respectively.

Resulting strains are grown in appropriate culture medium and analyzed as described above. As predicted, strains derived from BG6_Pg are shown to produce pelargonidin-3-O-(6"-malonyl)-glucoside, whereas strains derived from BG6_Cy are shown to produce cyanidin-3-O-(6"-malonyl)-glucoside, and strains derived from BG6_Dp are shown to produce delphinidin-3-O-(6"-malonyl)-glucoside Another second HRT plasmid comprised an anthocyanin aromatic acyl transferase (AAroAT) from *Arabidopsis thaliana*, i.e. the anthocyanin-3-O-glucoside-6"-O-p-coumaroyl-transferase (At3AT1; SEQ ID NO. 79) in combination with the *Fragaria* x *ananassa* FaA3GT (SEQ ID NO: 59) (table 13) for production of anthocyanidin-3-O-(6"-O-coumarate)-glucosides.

Helper fragments ZA (SEQ ID NO: 113), AB (SEQ ID NO: 114), and EZ (SEQ ID NO: 116) are used, as described above, for the in vivo assembly of plasmids.

TABLE 13

Cassettes used to assemble HRT plasmid for aromatic acylation of P3G, C3G, and D3G.

| Cassette | Content | SEQ ID NO | Species |
|---|---|---|---|
| ZA | HIS3, pSC101 | 113 | N/A |
| AB | ARSH4/CEN6, CmR | 114 | N/A |
| BC | Empty | N/A | N/A |
| CD | FaA3GT | 59 | *Fragaria × ananassa* |
| DE | At3AT1 | 79 | *Arabidopsis thaliana* |
| EZ | Linker | 116 | N/A |

Strains BG6_Pg (pelargonidin), BG6_Cy (cyanidin), and BG6_Dp (delphinidin), described in example 11, are thus transformed with a first and a second HRT plasmid, according to tables 11 and 13, respectively.

Resulting strains are grown in appropriate culture medium and analyzed as described above. As predicted, strains derived from BG6_Pg are shown to produce pelargonidin-3-O-(6"-coumaroyl)-glucoside, whereas strains derived from BG6_Cy are shown to produce cyanidin-3-O-(6"-coumaroyl)-glucoside, and strains derived from BG6_Dp are shown to produce delphinidin-3-O-(6"-coumaroyl)-glucoside.

Another second HRT plasmid comprised the *Vitis amurensis* anthocyanidin-3-O-glucoside-5-O-glycosyltransferase (VaA5GT, SEQ ID NO. 81) in combination with the *Fragaria* x *ananassa* FaA3GT (SEQ ID NO: 59) (table 14) for production of anthocyanidin-3,5-di-O-glucosides.

Helper fragments ZA (SEQ ID NO: 113), AB (SEQ ID NO: 114), and EZ (SEQ ID NO: 116) are used, as described above, for the in vivo assembly of plasmids.

TABLE NO. 14

Cassettes used to assemble HRT plasmid for 5-O-glycosylation of P3G, C3G, and D3G.

| Cassette | Content | SEQ ID NO | Species |
|---|---|---|---|
| ZA | HIS3, pSC101 | 113 | N/A |
| AB | ARSH4/CEN6, CmR | 114 | N/A |
| BC | Empty | N/A | N/A |
| CD | FaA3GT | 59 | *Fragaria ananassa* |
| DE | VaA5GT | 81 | *Vitis amurensis* |
| EZ | Linker | 116 | N/A |

Strains BG6_Pg (pelargonidin), BG6_Cy (cyanidin), and BG6_Dp (delphinidin), described in Example No. 11, are thus transformed with a first and a second HRT plasmid, according to Tables No. 11 and 14, respectively.

Resulting strains are grown in appropriate culture medium, and analysed as described above. As predicted, strains derived from BG6_Pg are shown to produce pelargonidin-3,5-di-O-glucoside, whereas strains derived from BG6_Cy are shown to produce cyanidin-3,5-di-O-glucoside, and strains derived from BG6_Dp are shown to produce delphinidin-3,5-di-O-glucoside Another second HRT plasmid comprised the *Nierenbergia* ssp. anthocyanidin-3-O-glucoside-6"-O-rhamnosyltransferase (NsA3GRhaT, SEQ ID NO. 83) and the *Arabidopsis thaliana* NDP-rhamnose synthase (AtRHM2, SEQ ID NO. 99) in combination with the *Fragaria* x *ananassa* FaA3GT (SEQ ID NO: 59) (table 15) for production of anthocyanidin-3-O-rutinosides.

Helper fragments ZA (SEQ ID NO: 113), AB (SEQ ID NO: 114), and EZ (SEQ ID NO: 116) are used, as described above, for the in vivo assembly of plasmids.

TABLE 15

Cassettes used to assemble HRT plasmid for production of anthocyanidin 3-O-rutinosides.

| Cassette | Content | SEQ ID NO | Species |
|---|---|---|---|
| ZA | HIS3, pSC101 | 113 | N/A |
| AB | ARSH4/CEN6, CmR | 114 | N/A |
| BC | AtRHM2 | 99 | *Arabidopsis thaliana* |
| CD | FaA3GT | 59 | *Fragaria ananassa* |
| DE | NsA3GRhaT | 83 | *Nierenbergia* ssp |
| EZ | Linker | 116 | N/A |

Strains BG6_Pg (pelargonidin), BG6_Cy (cyanidin), and BG6_Dp (delphinidin), described in example 11, are thus transformed with a first and a second HRT plasmid, according to Tables No. 11 and 15, respectively.

Resulting strains are grown in appropriate culture medium, and analysed as described above. As predicted, strains derived from BG6_Pg are shown to produce pelargonidin-3-O-rutinoside, whereas strains derived from BG6_Cy are shown to produce cyanidin-3-O-rutinoside, and strains derived from BG6_Dp are shown to produce delphinidin-3-O-rutinoside.

Another second HRT plasmid comprised the *Clitoria ternatea* anthocyanidin-3-O-glucoside-3',5'-O-glycosyltransferase (CtA3'5'GT, SEQ ID NO. 85) in combination with the *Fragaria* x *ananassa* FaA3GT (SEQ ID NO: 59) (table 16) for production of cyanidin-3,3'-di-O-glucoside and delphinidin-3,3',5'-tri-O-glucoside.

Helper fragments ZA (SEQ ID NO: 113), AB (SEQ ID NO: 114), and EZ (SEQ ID NO: 116) are used, as described above, for the in vivo assembly of plasmids.

TABLE 16

Cassettes used to assemble HRT plasmid for production of cyanidin-3,3'-di-O-glucoside and delphinidin-3,3',5'-tri-O-glucoside

| Cassette | Content | SEQ ID NO | Species |
|---|---|---|---|
| ZA | HIS3, pSC101 | 113 | N/A |
| AB | ARSH4/CEN6, CmR | 114 | N/A |
| BC | Empty | N/A | N/A |
| CD | FaA3GT | 59 | *Fragaria ananassa* |
| DE | CtA3'5'GT | 85 | *Clitoria ternatea* |
| EZ | Linker | 116 | N/A |

Strains BG6_Pg (pelargonidin), BG6_Cy (cyanidin), and BG6_Dp (delphinidin), described in example 11, are thus transformed with a first and a second HRT plasmid, according to Tables No. 11 and 16, respectively.

Resulting strains are grown in appropriate culture medium and analyzed as described above. As predicted, strains derived from BG6_Pg produced no new compounds, whereas strains derived from BG6_Cy are shown to produce cyanidin-3,3'-di-O-glucoside, and strains derived from BG6_Dp are shown to produce delphinidin-3,3',5'-tri-O-glucoside.

Another second HRT plasmid comprised the *Clitoria ternatea* anthocyanidin-3-O-glucoside-3',5'-O-glycosyltransferase (CtA3'5'GT, SEQ ID NO. 85) in combination with the anthocyanin aliphatic acyl transferase (AAliAT) from *Dahlia variabilis*, i.e. the anthocyanidin-3-O-glucoside-6"-malonyl-transferase gene (Dv3MAT, SEQ ID NO. 77) and the *Fragaria* x *ananassa* FaA3GT (SEQ ID NO: 59) (table 17) for production of malonylated cyanidin-3,3'-di-O-glucoside and delphinidin-3,3',5'-tri-O-glucoside, respectively.

Helper fragments ZA (SEQ ID NO: 113), AB (SEQ ID NO: 114), and EZ (SEQ ID NO: 116) are used, as described above, for the in vivo assembly of plasmids.

TABLE NO. 17

Cassettes used to assemble HRT plasmid for production of malonylated cyanidin-3,3'-di-O-glucoside and delphinidin-3,3',5'-tri-O-glucoside.

| Cassette | Content | SEQ ID NO | Species |
|---|---|---|---|
| ZA | HIS3, pSC101 | 113 | N/A |
| AB | ARSH4/CEN6, CmR | 114 | N/A |
| BO | Dv3MAT | 77 | *Dahlia variabilis* |
| CD | FaA3GT | 59 | *Fragaria ananassa* |
| DE | CtA3'5'GT | 85 | *Clitoria ternatea* |
| EZ | Linker | 116 | N/A |

Strains BG6_Pg (pelargonidin), BG6_Cy (cyanidin), and BG6_Dp (delphinidin), described in example 11, are thus transformed with a first and a second HRT plasmid, according to Tables No. 11 and 17, respectively.

Resulting strains are grown in appropriate culture medium, and analysed as described above. As predicted, strains derived from BG6_Pg are shown to produce pelargonidin-3-O-(6"-malonyl)-glucoside, whereas strains derived from BG6_Cy are shown to produce cyanidin-3-O-(6"-malonyl)-glucosyl-3'-O-glucoside, and strains derived from BG6_Dp are shown to produce delphinidin-3-O-(6"-malonyl)-glucosyl-3',5'-di-O-glucoside Another second HRT plasmid comprised the *Vitis amurensis* anthocyanidin-3-O-glucoside-5-O-glycosyltransferase (VaA5GT, SEQ ID NO. 81) in combination with the *Gentiana triflora* anthocyanin 3'-glucosyltransferase (GtA3'GT, SEQ ID NO. 87) and the the *Gentiana triflora* anthocyanin 5-aromatic acyltransferase (GtGAT4, SEQ ID NO: 89), an enzyme reported to transfer caffeoyl to both the 5- and 3'-glucose (U.S. Pat. No. 8,053,648). The DNA fragments used for production of delphinidin 3-O-glucosyl-5-O-(6-O-caffeoyl-glucosyl)-3'-O-(6-O-caffeoyl-glucoside) (gentiodelphin) are shown in table 18.

Helper fragments ZA (SEQ ID NO: 113), AB (SEQ ID NO: 114), and EZ (SEQ ID NO: 116) are used, as described above, for the in vivo assembly of plasmids.

TABLE 18

Cassettes used to assemble HRT plasmid for production of gentiodelphin

| Cassette | Content | SEQ ID NO | Species |
|---|---|---|---|
| ZA | HIS3, pSC101 | 113 | N/A |
| AB | ARSH4/CEN6, CmR | 114 | N/A |
| BC | GtA3'GT | 87 | *Gentiana triflora* |
| CD | GtpGAT4 | 89 | *Gentiana triflora* |
| DE | VaA5GT | 81 | *Vitis amurensis* |
| EZ | Linker | 116 | N/A |

Strain BG6_Dp (delphinidin), described in Example No. 10, is thus transformed with a first and a second HRT plasmid, according to Tables No. 11 and 18, respectively.

A resulting strain is grown in medium as described in Example No 1, except that caffeic acid is added to the medium at a starting concentration of 20 mg/L. The strain is grown for 72 hours and analyzed as described above. Two compounds with molecular masses corresponding to delphinidin 3-O-glucosyl-5-O-(6"-caffeoyl)-glucoside-3'-O-glucoside, and delphinidin 3-O-glucosyl-5-O-(6-O-caffeoyl-glucosyl)-3'-O-(6-O-caffeoyl-glucoside) (gentiodelphin), respectively, are detected in the medium, and the extract showed a distinct blue colour corresponding to the blue colour associated with gentiodelphin.

In summary, all secondary HRT plasmids (tables 12-18) are assembled in vivo, in yeast strains already comprising the full length integrated pathways to pelargonidin, cyanidin, and delphinidin, respectively, as well as the first HRT plasmid (table 11) comprising the PhCHIL (SEQ ID NO: 13), PhGST (SEQ ID NO: 55), and either DcA3GT (SEQ ID NO: 57) for pelargonidin derivatives or FaA3GT (SEQ ID NO: 59) for cyanidin and delphinidin derivatives, as described above. It is noted that, as a result, several strains would have two copies of A3GTs. Resulting strains are grown in liquid cultures for 72 hours with the appropriate selection, and with sugar as the sole carbon source (except for caffeic acid in one experiment). Production of modified anthocyanins is confirmed by LC-MS as described above.

Example 13—Engineering of Yeast Strain to Produce Dihydrochalcones

A basic yeast strain, *Saccharomyces cerevisiae* S288C as described in Eichenberger et al. (Met. Eng., 2017, 39: 80-89), is used to construct the biosynthetic pathways to phlorizin and nothofagin (FIG. 4), either with or without co-expression of the *Petunia* x *hybrida* CHIL gene (SEQ ID NO: 13). The pathways are assembled, in vivo, on two HRT plasmids.

A first plasmid is assembled using the genes listed in table 19, to generate a strain producing phloretin. Hence, the plasmid comprised the pathway structural genes phenylalanine ammonia lyase (PAL) from *A. thaliana* (SEQ ID NO: 1), the cinnamate-4-hydroxylase (C4H) from *Ammi majus* (SEQ ID NO: 5), the 4-coumarate-CoA ligase (4CL) from *A. thaliana* (SEQ ID NO: 7), and the chalcone synthase (CHS) from *Hypericum androsaemum* (SEQ ID NO: 9). In addition, it comprised an additional copy of the native genes ScCPR1 (SEQ ID NO: 23), for regenerating the activity of C4H, and ScTSC13 (SEQ ID NO: 91), a double bond reductase (DBR) known to increase the amount of dihydrocoumaroyl-CoA needed for phloretin and phlorizin production (see Eichenberger et al., Met. Eng., 2017, 39: 80-89).

Helper fragments ZA (SEQ ID NO: 112), AB (SEQ ID NO: 114), and HZ (SEQ ID NO: 119) are used, as described above, for the in vivo assembly of plasmids. After transformation of the yeast, production of phloretin is verified.

A second plasmid is assembled, using the genes listed in table 20, comprising the *Pyrus communis* UDP-dependent glycosyl transferase (PGT; SEQ ID NO: 93) or the UDP dependent C-glycosyl transferase (CGT) from *Oryza sativa* (SEQ ID NO: 95) in the CD cassette. The BC cassette is either empty (control) or comprised the gene encoding CHIL from *Petunia* x *hybrida* (SEQ ID NO: 13).

Helper fragments ZA (SEQ ID NO: 112), AB (SEQ ID NO: 114), and DZ (SEQ ID NO: 115) are used, as described above, for the in vivo assembly of plasmids.

The resulting strains are grown and analysed as described above. Surprisingly, the strains co-expressing PhCHIL produced more phlorizin and nothofagin, compared to the control strains without PhCHIL.

TABLE 19

Cassettes used to assemble HRT plasmid for phloretin production

| Cassette | Content | SEQ ID NO | Species |
|---|---|---|---|
| ZA | LEU2, pSC101 | 112 | N/A |
| AB | ARSH4/CEN6, CmR | 114 | N/A |
| BC | AtPAL | 1 | *Arabidopsis thaliana* |
| CD | AmC4H | 5 | *Ammi majus* |
| DE | At4CL | 7 | *Arabidopsis thaliana* |
| EF | HaCHS | 9 | *Hypericum androsaemum* |
| FG | ScTSC13 | 91 | *Saccharomyces cerevisiae* |
| GH | ScCPR1 | 23 | *Saccharomyces cerevisiae* |
| HZ | Linker | 119 | N/A |

TABLE 20

Cassettes used to assemble HRT plasmid for phlorizin and nothofagin production

| Cassette | Content | SEQ ID NO | Species |
|---|---|---|---|
| ZA | HIS3, pSC101 | 113 | N/A |
| AB | ARSH4/CEN6, CmR | 114 | N/A |
| BC | Empty or PhCHIL | 13 | *Petunia × hybrida* |
| CD | PcPGT or OsCGT | 93 or 95 | *Pyrus communis, Oryza sativa* |
| DZ | Linker | 115 | N/A |

Example 14—Engineering of Yeast Strain to Produce Resveratrol

A basic yeast strain *Saccharomyces cerevisiae* S288C as described in Eichenberger et al. (Met. Eng., 2017, 39: 80-89), is used to construct the biosynthetic pathway to resveratrol, either with or without co-expression of the *Petunia* x *hybrida* CHIL gene (SEQ ID NO: 13). The pathway is assembled, in vivo, onto an HRT plasmid.

The HRT plasmid is assembled, using the genes listed in table 21. Hence, the plasmid comprised the pathway structural genes phenylalanine ammonia lyase (PAL) from *A. thaliana* (SEQ ID NO: 1), the cinnamate-4-hydroxylase (C4H) from *Ammi majus* (SEQ ID NO: 5), the 4-coumarate-CoA ligase (4CL) from *A. thaliana* (SEQ ID NO: 7), and the stilbene synthase (STS) from *Pinus densiflora* (SEQ ID NO: 71) or from *Vitis vinifera* (SEQ ID NO: 73). In addition, it comprised an additional copy of the native genes ScCPR1 (SEQ ID NO: 23), for regenerating the C4H, and either an empty gene cassette (control) or the *Petunia* x *hybrida* CHIL gene (SEQ ID NO: 13).

Helper fragments ZA (SEQ ID NO: 112), AB (SEQ ID NO: 114), and HZ (SEQ ID NO: 119) are used, as described above, for the in vivo assembly of plasmids.

After transformation of yeast, the resulting strains are grown and analyzed as described above. The strains co-expressing STS from *Pinus densiflora* (SEQ ID NO: 71) are shown to produce pinosylvin, and the strains co-expressing STS from *Vitis vinifera* (SEQ ID NO: 73) are shown to produce resveratrol. Surprisingly, all strains co-expressing PhCHIL produced more stilbenes, compared to the control strain without PhCHIL.

TABLE 21

Cassettes used to assemble HRT plasmid for resveratrol production

| Cassette | Content | SEQ ID NO | Species |
|---|---|---|---|
| ZA | LEU2, pSC101 | 112 | N/A |
| AB | ARSH4/CEN6, CmR | 114 | N/A |
| BC | AtPAL | 1 | *Arabidopsis thaliana* |
| CD | AmC4H | 5 | *Ammi majus* |
| DE | At4CL | 7 | *Arabidopsis thaliana* |
| EF | PdSTS, or<br>VvSTS | 71<br>73 | *Pinus densiflora*<br>*Vitis vinifera* |
| FG | Empty or PhCHIL | 13 | *Petunia* × *hybrida* |
| GH | ScCPR1 | 82 | *Saccharomyces cerevisiae* |
| HZ | Linker | 119 | N/A |

Example 15—Methylation to Produce Peonidin, Petunidin, and Malvidin

Several naturally occurring anthocyanins are methylated at one or more hydroxyl group on the B-ring of the basic scaffold, as found for example in the cyanin derivative peonidin, and the delphinidin derivatives petunidin and malvidin. A small number of O-methyl transferases (OMT) have been characterized, which exhibit specificity for anthocyanins, such as the VvAOMT from *Vitis vinifera* (Hugueney et al., Plant Physiol. 2009, 150 (4): 2057-70), the CkmAOMT2 from a cyclamen hybrid (Akita et al., Planta 2011, 234 (6): 1127-36), and the SIAOMT from *Solanum lycopersicum* (Roldan et al., Plant J. 2014, 80(4): 695-708). In order to demonstrate production of methylated anthocyanins in yeast we chose the VvAOMT (SEQ ID NO: 97) and co-expressed this enzyme in strains comprising the full-length pathways to C3G or D3G, respectively. The strains are based on the cyanidin and delphinidin producing strains described above in example 11, and an HRT plasmid is assembled in these two strains according to table 22, below. Hence, this plasmid comprised the PhCHIL (SEQ ID NO: 13), the PhGST (SEQ ID NO: 55), The FaA3GT (SEQ ID NO: 59), and the VvAOMT (SEQ ID NO: 97).

Helper fragments ZA (SEQ ID NO: 112), AB (SEQ ID NO: 114), and FZ (SEQ ID NO: 117) are used, as described above, for the in vivo assembly of plasmids.

TABLE 22

Cassettes used to assemble HRT plasmid peonidin, petunidin, and malvidin production

| Cassette | Content | SEQ ID NO | Species |
|---|---|---|---|
| ZA | LEU2, pSC101 | 112 | N/A |
| AB | ARSH4/CEN6, CmR | 114 | N/A |
| BC | PhCHIL | 13 | *Petunia* × *hybrida* |
| CD | PhGST | 55 | *Petunia* × *hybrida* |
| DE | VvAOMT | 97 | *Vitis vinifera* |
| EF | FaA3GT | 59 | *Fragaria* × *ananassa* |
| FZ | Linker | 117 | N/A |

After transformation of yeast, the resulting strains are grown and analyzed as described above. The strain originally producing cyanidin are shown to produce peonidin, the 3'-O-methylated derivative of C3G, and the strain originally producing delphinidin is shown to produce both petunidin, the 3'-O-methylated derivative of D3G, and malvidin, the 3'5'-O-di-methylated derivative of D3G.

The invention claimed is:

1. A recombinant microbial host cell producing a naringenin from one or more substrates selected from cinnamoyl CoA and p-Coumaroyl-CoA, the recombinant microbial host cell further comprising an operative biosynthetic metabolic pathway for the naringenin comprising a chalcone isomerase-like (CHIL) polypeptide heterologous to the host cell, a chalcone isomerase (CHI) heterologous to the host cell, and a chalcone synthase (CHS) heterologous to the host cell, wherein the CHIL polypeptide has at least 80% identity to a CHIL polypeptide of SEQ ID NO: 14, 16, 18, or 20, the CHI has at least 80% identity to the CHI of SEQ ID NO:12, and the CHS has at least 80% identity to the CHS of SEQ ID NO: 10, and wherein the recombinant microbial host cell produces more naringenin compared to an unmodified microbial host cell.

2. The host cell of claim 1, further comprising an operative biosynthetic metabolic pathway capable of producing naringenin, the operative biosynthetic metabolic pathway comprising one or more polypeptides selected from:

a) phenylalanine ammonia lyase (PAL/EC 4.3.1.24);
b) tyrosine ammonia lyase (TAL/EC 4.3.1.25);
c) CYP450 reductase (CPR/EC 1.6.2.4);
d) cinnamate 4-hydroxylase (C4H/EC 1.14.14.91);
e) Coumarate 3-hydroxylase (C3H/EC 1.14.13);
f) 4-coumaric acid-CoA ligase (4CL/EC 6.2.1.12);
g) caffeic acid 3-O-methyltransferase (COMT/EC 2.1.1.68);
h) caffeoyl-CoA-O-methyltransferase (CCOMT/EC 2.1.1.104);
i) shikimate O-hydroxycinnamoyltransferase (HCT/EC 2.3.1.133);
j) 5-O-(4-coumaroyl)-D-quinate 3'-monooxygenase (C3'H/EC 1.14.14.96);
k) double bond reductase (DBR);
l) Flavonoid hydroxylase (FH);
m) dihydroflavonol-4-reductase (DFR);
n) leucoanthocyanidin reductase (LAR);
o) anthocyanidin synthase (ANS);
p) glutathione-S-transferase (GST);
q) anthocyanidin reductase (ANR);
r) UDP-dependent glycosyltransferase (UGT);
s) isoflavone synthase (IFS);
t) hydroxy isoflavanone dehydratase (HIFD);
u) flavone synthase (FNS);
v) flavonol synthase (FLS);
w) anthocyanin acyl transferase (AAT); and
x) trans-resveratrol di-O-methyltransferase (ROMT/EC 2.1.1.240).

3. The host cell of claim 2, wherein the corresponding a) phenylalanine ammonia lyase (PAL) has at least 80% identity to the phenylalanine ammonia lyase encoded by the sequence set forth in SEQ ID NO: 1;
b) tyrosine ammonia lyase (TAL) has at least 80% identity to the tyrosine ammonia lyase encoded by the sequence set forth in SEQ ID NO: 3;
c) CYP450 reductase (CPR) has at least 80% identity to a CYP450 reductases encoded by a sequence set forth in SEQ ID NO: 23 or SEQ ID NO: 25;
d) trans-cinnamate 4-monooxygenase (C4H) has at least 80% identity to the trans-cinnamate 4-monooxygenase encoded by the sequence set forth in SEQ ID NO: 5;

e) coumarate 3-hydroxylase (C3H) has at least 80% identity to the coumarate 3-hydroxylase encoded by the sequence set forth in SEQ ID NO: 69;

f) 4-coumaric acid-CoA ligase (4CL) has at least 80% identity to the 4-coumaric acid-CoA ligase encoded by the sequence set forth in SEQ ID NO: 7;

g) caffeic acid 3-O-methyltransferase (COMT) has at least 80% identity to the caffeic acid 3-O-methyltransferase encoded by the sequence set forth in SEQ ID NO: 61;

h) caffeoyl-CoA-O-methyltransferase (CCOMT) has at least 80% identity to the caffeoyl-CoA-O-methyltransferase (CCOMT) encoded by the sequence set forth in SEQ ID NO: 63;

i) shikimate O-hydroxycinnamoyltransferase (HCT) has at least 80% identity to the shikimate O-hydroxycinnamoyltransferase encoded by the sequence set forth in SEQ ID NO: 67;

j) 5-O-(4-coumaroyl)-D-quinate 3'-monooxygenase (C3'H) has at least 80% identity to the 5-O-(4-coumaroyl)-D-quinate 3'-monooxygenase encoded by the sequence set forth in SEQ ID NO: 65; and/or k) double bond reductase (DBR) has at least 80% identity to the double bond reductase (DBR) encoded by the sequence set forth in SEQ ID NO: 91;

l) Flavonoid hydroxylase (FH) has at least 80% identity to the flavanone 3-hydroxylase (F3H) encoded by the sequence set forth in SEQ ID NO: 39 or the flavonoid 3'-hydroxylase encoded by the sequence set forth in SEQ ID NO: 27, or the flavonoid 3',5'-hydroxylase encoded by the sequence set forth in SEQ ID NO: 29;

m) dihydroflavonol-4-reductase (DFR) has at least 80% identity to the dihydroflavonol-4-reductase encoded by the sequence set forth in SEQ ID NO: 43, SEQ ID NO: 45, or SEQ ID NO: 47;

n) leucoanthocyanidin reductase (LAR) has at least 80% identity to the leucoanthocyanidin reductase (LAR) encoded by the sequence set forth in SEQ ID NO: 49;

o) anthocyanidin synthase (ANS) has at least 80% identity to the anthocyanidin synthase (ANS) encoded by the sequence set forth in SEQ ID NO: 53;

p) glutathione-S-transferase (GST) has at least 80% identity to the glutathione-S-transferase (GST) encoded by the sequence set forth in SEQ ID NO: 55;

q) anthocyanidin reductase (ANR) has at least 80% identity to the anthocyanidin reductase (ANR) encoded by the sequence set forth in SEQ ID NO: 51;

r) UDP-dependent glycosyltransferase (UGT) has at least 80% identity to the anthocyanidin 3-O-glycosyltransferase (A3GT) encoded by the sequence set forth in SEQ ID NO: 57 or SEQ ID NO: 59, or the anthocyanidin 3'-O-glycosyltransferase (A3'GT) encoded by the sequence set forth in SEQ ID NO: 87, or the anthocyanin-5-O-glycosyl transferase (A5GT) encoded by the sequence set forth in SEQ ID NO: 81, or the anthocyanin-7-O-glycosyl transferase (A7GT) encoded by the sequence set forth in SEQ ID NO: 69, or the anthocyanin 3'5'-O-di-glycosyl transferase (A3'5'GT) encoded by the sequence set forth in SEQ ID NO: 85;

s) isoflavone synthase (IFS) has at least 80% identity to the isoflavone synthase encoded by the sequence set forth in SEQ ID NO: 35;

t) hydroxy isoflavanone dehydratase (HIFD) has at least 80% identity to the isoflavone synthase encoded by the sequence set forth in SEQ ID NO: 37;

u) flavone synthase (FNS) has at least 80% identity to the flavone synthase encoded by the sequence set forth in SEQ ID NO: 31, or SEQ ID NO:33 v) flavonol synthase (FLS) has at least 80% identity to the flavonol synthase encoded by the sequence set forth in SEQ ID NO: 41;

w) anthocyanin acyl transferase (AAT) has at least 80% identity to the anthocyanin aromatic acyl transferase (AAroAT) encoded by the sequence set forth in SEQ ID NO: 79, or the anthocyanin aliphatic acyl transferase (AAliAT) encoded by the sequence set forth in SEQ ID NO: 77, or the anthocyanidin O-methyl transferase (AOMT) encoded by the sequence set forth in SEQ ID NO: 97; and/or x) trans-resveratrol di-O-methyltransferase (ROMT) has at least 80% identity to the trans-resveratrol di-O-methyltransferase (ROMT) encoded by the sequence set forth in SEQ ID NO: 75.

4. The host cell of claim 1, wherein the recombinant microbial host cell further produces compounds from naringenin selected from;

a) flavanones comprising eriodictyol;

b) flavones comprising apigenin;

c) isoflavones comprising genistein;

d) flavanonols comprising dihydrokaempferol;

e) flavanols comprising kaempferol;

f) flavans optionally selected from flavan-3-ol, flavan-4-ol, and flavan-3,4-diol;

g) anthocyanidins optionally selected from pelargonidin, cyanidin, delphinidin, peonidin, petunidin, and malvidin;

h) anthocyanins optionally selected from pelargonidin-3-O-glycoside (P3G), cyanidin-3-O-glycoside (C3G), delphinidin-3-O-glycoside (D3G), peonidin-3-O-glycoside, petunidin-3-O-glycoside, and malvidin-3-O-glycoside.

5. The host cell of claim 4, wherein the anthocyanin is selected from one or more of Petunidin 3-p-coumaroylrutinoside-5-glucoside; petunidin 3-feruloylrutinoside-5-glucoside; malvidin 3-p-coumaroylrutinoside-5-glucoside; pelargonidin 3-feruloylrutinoside-5-glucoside; pelargonidin rutinoside; pelargonidin 3-rutinoside-5-glucoside; pelargonidin 3-p-coumaroylrutinoside-5-glucoside; petunidin 3-rutinoside-5-glucoside; pelargonidin 3-rutinoside-5-glucoside; peonidin 3-rutinoside-5-glucoside; malvidin 3-rutinoside-5-glucoside; petunidin 3-rutinoside; pelargonidin 3-rutinoside; malvidin 3-rutinoside; petunidin 3-caffeoylrutinoside-5-glucoside; delphinidin 3-p-coumaroylrutinoside-5-glucoside; pelargonidin feruloyl-xylosyl-glucosylgalactoside; cyanidin 3-p-coumaroylrutinoside-5-glucoside; petunidin 3-p-coumaroylrutinoside-5-glucoside; petunidin 3-feruloylrutinoside-5-glucoside; pelargonidin 3-p-coumaroylrutinoside-5-glucoside; peonidin 3-p-coumaroylrutinoside-5-glucoside; malvidin 3-p-coumaroylrutinoside-5-glucoside; pelargonidin 3-feruloylrutinoside-5-glucoside; peonidin 3-feruloylrutinoside-5-glucoside; malvidin 3-feruloylrutinoside-5-glucoside; petunidin 3-p-coumaroylrutinoside; pelargonidin 3-p-coumaroylrutinoside; Cyanidin 3-O-glucoside; cyanidin 3;7-O-diglucoside; cyanidin 3-O-(3";6"-O-dimalonyl)-glucoside; cyanidin 3-O-6"-O-malonylglucoside; delphinidin 3-O-glucoside; delphinidin 3;5;3'-O-triglucoside; delphinidin 3-O-(3";6"-O-dimalonyl)-glucoside; delphinidin 3-O-6"-O-malonylglucoside; delphinidin 3-O-rutinoside; delphinidin 3-O-rutinoside 7-O-glucoside; delphinidin 3-O-rutinoside 7-O-(6"-O-p-hydroxybenzoyl)-glucoside; pelargonidin 3-O-glucoside; Cyanidin 3-(6";6'-di-p-coumarylsophoroside)-5-(6-malonylglucoside); Cyanidin 3-(6";6'"-dicaffeylsophoroside)-5-glucoside; Cyanidin 3-(6";6'"-disinapylsophoroside)-5-glucoside; Cyanidin 3-(6"-caffeyl-6'"-ferulylsophoroside)-5-glucoside; Cyanidin 3-(6"-ferulyl-2'"-sinapylsambubioside)-5-glucoside; Cyanidin 3-(6"-ferulyl-2'"-sinapylsophoroside)-5-glucoside; Cyanidin 3-(6"-p-coumaryl-2"-sinapylsophoroside)-5-glucoside; Cyanidin 3-(6-malonylglucoside)-7;3'-di-(6-feruloylglucoside); Cyanidin 3-(6-malonylglucoside)-7-(6-feruloylglucoside)-3'-glucoside; Cyanidin 3-[2-(6-p-coumarylglucosyl)-6-caffeoylglucoside]-5-glucoside; Cyanidin 3-[2-(6-p-coumarylglucosyl)-6-p-coumarylglucoside)]-5-glucoside; Cyanidin 3-[6"-(4-glucosylcaffeyl isophoroside]-5-glucoside; Cyanidin 3-O-[2"-O-(2'"-O-(sinapoyl) xylosyl) 6"-O-(p-coumaroyl) glucoside] 5-O-glucoside; Cyanidin 3-O-[beta-D-glucopyranoside]-7;3'-di-O-[6-O-(sinapyl)-beta-D-glucopyranoside]; Delphinidin 3-(6";6'"-di-p-coumarylsophoroside)-5-(6-malonylglucoside); Delphinidin 3-(6-malonylglucoside)-3';5'-di-(6-p-coumaroylglucoside); Delphinidin 3-(diferuloyl) sophoroside-5-glucoside; Delphinidin 3-[2-(6-(feruloylglucoside)-6-feruloylglucoside]-5-(6-malonylglucoside); Delphinidin 3-[2-(6-feruloylglucoside)-6-p-coumaroylglucoside]-5-(6-malonylglucoside); Delphinidin 3-glucoside-5-(6-caffeoylglucoside)-3'-(6-(E)-p-coumaroylglucoside); Delphinidin 3-glucoside-7;3'-di-(6-(E)-sinapoylglucoside); Delphinidin 3-rutinoside-7-(6-p-coumaroylglucoside)-3'-glucoside; Cyanidin 3-glucoside-5; 3'-di-(caffeoylglucoside); Malvidin 3-O-[6-O-(4-O-(4-O-(6-O-(trans-caffeoyl)-beta-D-glucopyranosyl)-trans-p-coumaroyl)-alpha-L-rhamnopyranosyl)-beta-D-glucopyranoside]; Pelargonidin 3-(6";2"-diferulylsambubioside)-5-(6-malonylglucoside); Pelargonidin 3-(6"-ferulyl-2'-sinapylsambubioside)-5-(6-malonylglucoside); Pelargonidin 3-(6"-ferulyl-2'-sinapylsambubioside)-5-glucoside; Pelargonidin 3-(6"-p-coumaryl-2'"-sinapyl-sambubioside)-5-(6-malonylglucoside); Pelargonidin 3-(6"-p-coumaryl-2'-sinapylsambubioside)-5-glucoside; Pelargonidin 3-[6"-(3-glucosylcaffeyl) sophoroside]-5-glucoside; Pelargonidin 3-O-(6-O-malonyl-beta-D-glucopyranoside)-7-O-(6-O-(4-O-(trans-caffeyl)-beta-D-glucopyranosyl)-trans-caffeyl)-beta-D-glucopyranoside); Pelargonidin 3-O-[2-O-(2-(E)-feruloyl-beta-D-glucopyranosyl)-6-O-(E)-feruloyl-beta-D-glucopyranoside]-5-O-(beta-D-glucopyranoside); Pelargonidin 3-(2-(2-ferulylglucosyl)-6-ferulylglucoside)-5-glucoside; Pelargonidin 3-O-[2-O-(6-(E)-caffeoyl-beta-D-glucopyranosyl)-6-O-(E)-caffeoyl-beta-D-glucopyranoside]-5-O-(beta-D-glucopyranoside); Pelargonidin 3-(2-(6-caffeylglucosyl)-6-caffeylglucoside)-5-glucoside; Pelargonidin 3-O-[2-O-(6-(E)-caffeoyl-beta-D-glucopyranosyl)-6-O-(E)-feruloyl-beta-D-glucopyranoside]-5-O-(beta-D-glucopyranoside); Pelargonidin 3-(2-(6-caffeylglucosyl)-6-ferulylglucoside)-5-glucoside; Pelargonidin 3-O-[2-O-(6-(E)-caffeoyl-beta-D-glucopyranosyl)-6-O-(E)-p-coumaroyl-beta-D-glucopyranoside]-5-O-(beta-D-glucopyranoside); Pelargonidin 3-(2-(6-caffeylglucosyl)-6-p-coumarylglucoside)-5-glucoside; Pelargonidin 3-O-[2-O-(6-(E)-feruloyl-beta-D-glucopyranosyl)-6-O-(E)-caffeoyl-beta-D-glucopyranoside]-5-O-(beta-D-glucopyranoside); Pelargonidin 3-(2-(6-ferulylglucosyl)-6-caffeylglucoside)-5-glucoside; Pelargonidin 3-O-[2-O-(6-(E)-feruloyl-beta-D-glucopyranosyl)-6-O-(E)-feruloyl-beta-D-glucopyranoside]-5-O-(beta-D-glucopyranoside); Pelargonidin 3-(2-(6-ferulylglucosyl)-6-ferulylglucoside)-5-glucoside; Pelargonidin 3-O-[2-O-(6-(E)-feruloyl-beta-D-glucopyranosyl)-6-O-(E)-p-coumaroyl-beta-D-glucopyranoside]-5-O-(beta-D-glucopyranoside); Pelargonidin 3-(2-(6-ferulylglucosyl)-6-p-coumarylglucoside)-5-glucoside; Peonidin 3-[6"-(4-glucosylcaffeyl) sophoroside]-5-glucoside; Petunidin 3-O-[6-O-(4-O-(4-O-(beta-D-glucopyranosyl)-trans-p-coumaroyl)-alpha-L-rhamnopyranosyl)-beta-D-glucopyranoside]-5-O-[beta-D-glucopyranoside].

6. The host cell of claim 4, wherein the flavonoid is a flavan-3-ol selected from (−) epiafzelechin; (−)-epicatechin; and (−)-epigallocatechin and the operative biosynthetic metabolic pathway comprises:

a) one or more polypeptides selected from flavanone 3-hydroxylase (F3H); flavonoid 3'-hydroxylase (F3'H) and Flavonoid 3'-5'-hydroxylase (F3'5'H);
b) dihydroflavonol-4-reductase (DFR);
c) anthocyanidin synthase (ANS); and
d) anthocyanidin reductase (ANR).

7. The host cell of claim 1, wherein the host cell is a yeast.

8. The host cell of claim 7, wherein the yeast belongs to the genus *Saccharomyces, Kluyveromyces, Candida, Pichia*, Debaryomyces, *Hansenula, Yarrowia, Zygosaccharomyces*, or *Schizosaccharomyces*.

9. A cell culture, comprising the host cell of claim 1 and a growth medium.

10. A method for producing a naringenin comprising a) culturing the cell culture of claim 9 at conditions allowing the host cell to convert the one or more substrates into the naringenin; and
b) optionally recovering and/or isolating the naringenin.

11. The method of claim 10, wherein the recovering step comprises separating a liquid phase of the host cell or cell culture from a solid phase of the host cell or cell culture to obtain a supernatant comprising the tetraketide derivative by one or more steps selected from:

a) contacting the supernatant with one or more adsorbent resins in order to obtain at least a portion of the produced tetraketide derivative;
b) contacting the supernatant with one or more ion exchange or reversed-phase chromatography columns in order to obtain at least a portion of the tetraketide derivative;
c) crystallizing or extracting the tetraketide derivative; and
d) evaporating the solvent of the liquid phase to concentrate the tetraketide derivative;

thereby recovering the tetraketide derivative.

12. The method of claim 10, further comprising one or more elements selected from:

a) culturing the cell culture in a nutrient medium comprising vitamins, trace elements, salts, amino acids, nitrogen, and a carbon source;
b) culturing the cell culture under aerobic or anaerobic conditions
c) culturing the cell culture under agitation;
d) culturing the cell culture at a temperature of between 20-50° C.;
e) culturing the cell culture at a pH of between 3-9; and
f) culturing the cell culture for between 20 to 120 hours.

13. The method of claim 10, further comprising the step of producing the tetraketide derivative which is performed in vitro.

14. A fermentation liquid comprising the cell culture of claim 9.

15. The fermentation liquid of claim 14 wherein at least 99% of the host cells are lysed and at least 99% of solid cellular material has been removed.

16. A composition comprising the fermentation liquid of claim 14 and one or more agents, additives and/or excipients.

17. The composition of claim 16, wherein the fermentation liquid and the one or more agents, additives and/or excipients are converted into in a dry solid form.

18. The composition of claim 16, wherein the fermentation liquid and the one or more agents, additives and/or excipients are in a liquid stabilized form.

19. The composition of claim 16, wherein the composition is a food product, a dietary supplement, a pharmaceutical product, or a cosmetic.

* * * * *